United States Patent
Schann et al.

(10) Patent No.: US 10,221,179 B2
(45) Date of Patent: Mar. 5, 2019

(54) SUBSTITUTED PYRAZOLOQUINAZOLINONES AND PYRROLOQUINAZOLINONES AS ALLOSTERIC MODULATORS OF GROUP II METABOTROPIC GLUTAMATE RECEPTORS

(71) Applicant: DOMAIN THERAPEUTICS, Illkirch, Graffenstaden (FR)

(72) Inventors: Stephan Schann, Illkirch Graffenstaden (FR); Stanislas Mayer, Eschau (FR); Baptiste Manteau, Lingolsheim (FR)

(73) Assignee: DOMAIN THERAPEUTICS, Illkirch Graffenstaden (FR)

( * ) Notice: Subject to any disclaimer, the term of this patent is extended or adjusted under 35 U.S.C. 154(b) by 0 days.

(21) Appl. No.: 15/514,431

(22) PCT Filed: Sep. 25, 2015

(86) PCT No.: PCT/EP2015/072178
§ 371 (c)(1),
(2) Date: Mar. 24, 2017

(87) PCT Pub. No.: WO2016/046404
PCT Pub. Date: Mar. 31, 2016

(65) Prior Publication Data
US 2017/0305913 A1    Oct. 26, 2017

(30) Foreign Application Priority Data
Sep. 26, 2014 (EP) ..................................... 14186711

(51) Int. Cl.
*C07D 487/04* (2006.01)
(52) U.S. Cl.
CPC .................. *C07D 487/04* (2013.01)
(58) Field of Classification Search
CPC .................................................. C07D 487/04
See application file for complete search history.

(56) References Cited

U.S. PATENT DOCUMENTS

2015/0105381 A1    4/2015   Mayer et al.

FOREIGN PATENT DOCUMENTS

| EP | 2 666 775 A1 | 11/2013 |
|----|----|----|
| WO | WO 2007/144669 | 12/2007 |
| WO | WO 2013/174822 | * 11/2013 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
West, Anthony R., Solid State Chemistry and Its Applications, Wiley, New York, 1988, 358.*
International Search Report (PCT/ISA/210) dated Dec. 10, 2015, by the European Patent Office as the International Searching Authority for International Application No. PCT/EP2015/072178.
Written Opinion (PCT/ISA/237) dated Dec. 10, 2015, by the European Patent Office as the International Searching Authority for International Application No. PCT/EP2015/072178.
Wenthur, Cody J., "Synthesis and SAR of substituted pyrazolo [1,5-a]quinazolines as dual mGlu2/mGlu3 NAMs", Bioorganic & Medical Chemistry Letters, vol. 24, No. 12, Jun. 16, 2014, pp. 2693-2698, Nashville, TN United States.
C. Loschen et al., "Computational Screening of Drug Solvates", Pharm Res., 33(11), pp. 2794-2804, Nov. 2016 (abstract only).
C. Loschen et al., "Solubility prediction, solvate and cocrystal screening as tools for rational crystal engineering", J Pharm Pharmacol., 67(6), pp. 803-811, Jun. 2015 (abstract only).
B. Rodriguez-Spong et al., "General principles of pharmaceutical solid polymorphism: a supramolecular perspective", Advanced Drug Delivery Reviews, 56, pp. 241-274, 2004.

* cited by examiner

*Primary Examiner* — Erich A Leeser
(74) *Attorney, Agent, or Firm* — Buchanan Ingersoll & Rooney PC

(57) ABSTRACT

The present invention provides pyrazoloquinazolinone and pyrroloquinazolinone derivatives of the general formula (I) and pharmaceutical compositions containing them. Moreover, the compounds of formula (I) and the compositions containing them are provided for use in the treatment and/or prophylaxis of conditions associated with altered glutamatergic signalling and/or functions, and/or conditions which can be affected by alteration of glutamate level or signalling in mammals. These pyrazoloquinazolinone and pyrroloquinazolinone derivatives of the general formula (I) can act as modulators of nervous system receptors sensitive to glutamate, in particular as modulators of metabotropic glutamate receptors (mGluRs), which makes them particularly suitable for the treatment and/or prophylaxis of acute and chronic neurological and/or psychiatric disorders.

21 Claims, No Drawings

SUBSTITUTED PYRAZOLOQUINAZOLINONES AND PYRROLOQUINAZOLINONES AS ALLOSTERIC MODULATORS OF GROUP II METABOTROPIC GLUTAMATE RECEPTORS

The present invention provides pyrazoloquinazolinone and pyrroloquinazolinone derivatives of the general formula (I) and pharmaceutical compositions containing them. Moreover, the compounds of formula (I) and the compositions containing them are provided for use in the treatment and/or prophylaxis of conditions associated with altered glutamatergic signalling and/or functions, and/or conditions which can be affected by alteration of glutamate level or signalling in mammals. These pyrazoloquinazolinone and pyrroloquinazolinone derivatives of the general formula (I) can act as modulators of nervous system receptors sensitive to glutamate, in particular as modulators of metabotropic glutamate receptors (mGluRs), which makes them particularly suitable for the treatment and/or prophylaxis of acute and chronic neurological and/or psychiatric disorders.

Glutamatergic pathways have been shown to be clearly involved in the physiopathology of a number of neuronal damages and injuries. Many nervous system disorders including epilepsy and chronic or acute degenerative processes, such as for example Alzheimer's disease, Huntington's disease, Parkinson's disease and amyotrophic lateral sclerosis (Mattson M P., *Neuromolecular Med.*, 3(2), 65-94, 2003), but also AIDS-induced dementia, multiple sclerosis, spinal muscular atrophy, retinopathy, stroke, ischemia, hypoxia, hypoglycaemia and various traumatic brain injuries, involve neuronal cell death caused by imbalanced levels of glutamate. It has also been shown that drug-induced neurotoxicity, for example neurotoxic effects of methamphetamine (METH) on striatel dopaminergic neurons, could actually be mediated by over-stimulation of the glutamate receptors (Stephans S E and Yamamoto B K, *Synapse* 17(3), 203-9, 1994). Antidepressant and anxiolytic-like effects of compounds acting on glutamate have also been observed in mice, suggesting that glutamatergic transmission is implicated in the pathophysiology of affective disorders such as major depression, schizophrenia and anxiety (Palucha A et al., *Pharmacol. Ther.* 115(1), 116-47, 2007; Cryan J F et al., *Eur. J. Neurosc.* 17(11), 2409-17, 2003; Conn P J et al., Trends Pharmacol. Sci. 30(1), 25-31, 2009). Consequently, any compound able to modulate glutamatergic signalling or function would constitute a promising therapeutic compound for many disorders of the nervous system.

Moreover, compounds modulating glutamate level or signalling may be of great therapeutic value for diseases and/or disorders not directly mediated by glutamate levels and/or glutamate receptor malfunctioning, but which could be affected by alteration of glutamate levels or signalling.

In the central nervous system (CNS), L-glutamate (Glu) is the main excitatory neurotransmitter and is referred to as an excitatory amino-acid (EAA), and gamma-aminobutyric acid (GABA) is the main inhibitory neurotransmitter. The balance between excitation and inhibition is of utmost importance to CNS functions, and dysfunctions of either of the two can be related to various neurodegenerative or neurological disorders.

Glutamate is ubiquitously distributed in the nervous system in high concentrations, especially in the brain and spinal cord of mammals, where it is working at a variety of excitatory synapses being thereby involved in virtually all physiological functions such as motor control, vision, central control of heart, processes of learning and memory. However, a large number of studies have established that cellular communication involving glutamate can also lead to a mechanism of cell destruction. This combination of neuroexcitatory activities and neurotoxic properties is called excitotoxicity.

Glutamate operates through two classes of receptors (Brauner-Osborne H et al., *J. Med. Chem.* 43(14), 2609-45, 2000). The first class of glutamate receptors is directly coupled to the opening of cation channels in the cellular membrane of the neurons. Therefore they are called ionotropic glutamate receptors (IGluRs). The IGluRs are divided in three subtypes, which are named according to the depolarizing action of their selective agonists: N-methyl-D-aspartate (NMDA), α-amino-3-hydroxy-5-methylisoxazole-4-propionic acid (AMPA), and kainic acid (KA). The second class of glutamate receptor consists of G-protein coupled receptors (GPCRs) called metabotropic glutamate receptors (mGluRs). These mGluRs are localized both pre- and post-synaptically. They are coupled to multiple second messenger systems and their role is to regulate the activity of the ionic channels or enzymes producing second messengers via G-proteins binding the GTP (Nicoletti F et al.; *Neuropharmacol.*, 60(7-8), 1017-41, 2011). Although they are generally not directly involved in rapid synaptic transmission, the mGluRs modulate the efficacy of the synapses by regulating either the post-synaptic channels and their receptors, or the pre-synaptic release or recapture of glutamate. Therefore, mGluRs play an important role in a variety of physiological processes such as long-term potentiation and long-term depression of synaptic transmission, regulation of baroreceptive reflexes, spatial learning, motor learning, and postural and kinetic integration.

To date, eight mGluRs have been cloned and classified in three groups according to their sequence homologies, pharmacological properties and signal transduction mechanisms. Group I is constituted of mGluR1 and mGluR5, group II of mGluR2 and mGluR3 and group III of mGluR4, mGluR6, mGluR7 and mGluR8 (Schoepp D D et al., *Neuropharmacology*, 38(10), 1431-76, 1999).

mGluR modulators can be classified into two families depending on their site of interaction with the receptor (see Brauner-Osborne H et al., *J. Med. Chem.* 43(14), 2609-45, 2000 for review). The first family consists in orthosteric modulators (or competitive modulators) able to interact with the glutamate binding-site of the mGluRs, which is localized in the large extra-cellular N-terminal part of the receptor (about 560 amino acids). Therefore, they are glutamate analogs and constitute a highly polar family of ligand. Examples of orthosteric modulators are S-DHPG or LY-367385 for group I mGluRs, LY-354740 or LY-379268 for group II mGluRs and ACPT-I or L-AP4 for group III mGluRs. The second family of mGluR modulators consists in allosteric modulators that interact with a different site from the extracellular active site of the receptor (see Bridges T M et al., *ACS Chem Biol*, 3(9), 530-41, 2008 for review). Their action results in a modulation of the effects induced by the endogenous ligand glutamate. Examples of such allosteric modulators are Ro-674853, MPEP or JNJ16259685 for group I mGluRs and CBiPES, BINA, LY487379 or RO4491533 for group II mGluRs and PHCCC, VU0155041 or VU0359516 for group III mGluRs.

By interacting with allosteric binding sites, mGluR allosteric modulators stabilize a receptor conformation and equilibrium shift that increases or decreases the affinity and/or efficacy of an orthosteric agonist of the receptor, without activating the receptor on its own (Bridges T M et al., *ACS Chem Biol*, 3(9), 530-41, 2008). Such modulators are respectively termed positive allosteric modulators (PAMs) and negative allosteric modulators (NAMs).

Group II mGluR activation or potentiation has been shown to be associated with positive effects in animal models of anxiety (Swanson C J.; *Nat Rev Drug Discov*, 4, 131-44, 2005), schizophrenia (Conn P J et al.; *Trends in Pharmacol Sci*, 30, 25-31, 2009), drug-addiction (Adewale A S et al.; *J Pharmacol Exp Ther*, 318, 922-31, 2006) or chronic pain (Jones C K et al.; *Neuropharmacology*, 49 (Suppl 1), 206-18, 2005).

Antagonists and NAMs of group II mGluRs have been shown to exert antidepressant-like and cognitive enhancing properties (Chaki S et al.; *Neuropharmacology*, 46, 457-67, 2004-Higgins G A et al.; *Neuropharmacology*, 46, 907-17, 2004-Yoshimizu T and Shaki S.; *Biochem Biophys Res Commun*, 315, 493-6, 2004-Knoflach F et al.; 5*th* *International Meeting on Metabotropic Glutamate Receptors*, Taormina Italy, 2005-Yoshimizu T et al.; *Psychopharmacology (Berl)*, 183, 587-93, 2006-Campo B et al.; *Annual Meeting of the Society for Neuroscience*, Chicago Ill., 2009, 343.8-Kalinichev M et al.; *Annual Meeting of the Society for Neuroscience*, San Diego Calif., 2010, 406.9-Kalinichev M et al.; *Annual Meeting of the Society for Neuroscience*, San Diego Calif., 2010, 886.14-Lambeng N et al.; *Annual Meeting of the Society for Neuroscience*, San Diego Calif., 2010, 651.15-Lambeng N et al.; 3*rd* *RSC/SCI Symposium on GPCRs in Medicinal Chemistry*, Oss The Netherlands, 2010-Woltering T J, et al.; *Bioorg Med Chem Lett*, 20, 6969-74, 2010), cytotoxic properties against colorectal cancer cell lines and human glioblastoma stem cells (Mosillo P et al.; *Annual Meeting of the Society for Neuroscience*, San Diego Calif., 2010, 642.28-Bonelli M et al.; *Annual Meeting of the Society for Neuroscience*, San Diego Calif., 2010, 642.29-Ciceroni C, et al.; *Cell Death and Differentiation*, 20(3), 396-407, 2013), sleep/wake disorders (Feinberg I, et al.; *J Pharmacol Exp Ther*, 312(2), 826-33, 2005-Ahnaou A, et al.; *Behav Brain Res*, 270, 56-67, 2014-WO2012068041-WO2012068067) and autism spectrum disorders such as Fragile X syndrome and Rett syndrome (WO2014064028).

Numerous examples of group II mGluR PAMs have already been described in research articles and patent literature (see Trabanco A A, et al.; *Curr Med Chem*, 18(1), 47-68, 2011 for review). However, less information is available regarding group II mGluR NAMs. Benzodiazepinone derivatives (Woltering T J, et al.; *Bioorg Med Chem Lett*, 17, 6811-5, 2007-Woltering T J, et al.; *Bioorg Med Chem Lett*, 18, 1091-5, 2008; Woltering T J, et al., *Bioorg Med Chem Lett*, 18, 2725-9, 2008; Woltering T J, et al., *Bioorg Med Chem Lett*, 20, 6969-74, 2010; and WO 2013/033246), pyrazolopyrimidine derivatives (WO 2005/040171, WO 2005/123738, WO 2006/084634, WO 2006/099072 and WO2007/039439), pyridine/pyrimidine derivatives (WO 2007/110337 and WO 2007/119689), pyrazoloquinazolinone and pyrroloquinazolinone derivatives (WO 2013/174822; EP-A-2666775), heteroaryl-pyrazole derivatives (WO 2012/020820, WO 2012/015024, WO 2012/099200 and WO 2013/111796) and quinoline derivatives (WO 2013/066736) have been disclosed as group II mGluR NAMs.

Little information is available with regard to the selectivity of group II mGluR NAMs for either mGluR2 or mGluR3. Some of the group II mGluR NAMs mentioned in the previous paragraph, like RO4491533, RO4988546, RO5488608 or certain pyrazoloquinazolinone derivatives, have been described as non-selective group II NAMs blocking both mGluR2 and mGluR3 with similar potency and efficacy (Woltering T J, et al., *Bioorg Med Chem Lett*, 20, 6969-74, 2010; Lundström L, et al., *British Journal of Pharmacology*, 164, 521-37, 2011; Wenthur C J, et al., *Bioorg Med Chem Lett*, 24, 2693-98, 2014). The specific mGluR3 NAM LY2389575 was previously reported as amplifying neurotoxicity induced by Aβ amyloid (Caraci F, et al., *Molecular Pharmacology*, 79(3), 618-26, 2011). It would therefore be advantageous to develop group II mGluR NAMs that are selective for mGluR2 over mGluR3 for the treatment of CNS disorders, and more particularly for the treatment of neurodegenerative disorders like Alzheimer's disease.

In the context of the present invention, it has surprisingly been found that compounds of formula (I) constitute potent NAMs of the mGluR2 subtype, showing an advantageous selectivity for mGluR2 over mGluR3. This can be illustrated with reference to the compounds of examples 1 and 9 according to the invention, which show $IC_{50}<100$ nM for human mGluR2 and $IC_{50}>1$ μM for human mGluR3, resulting in a ratio $[IC_{50}\ hmGluR3]/[IC_{50}\ hmGluR2]>10$, i.e., a more than ten-fold greater negative allosteric modulator activity on mGluR2 than on mGluR3.

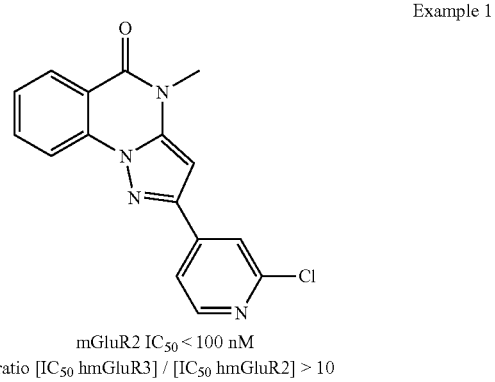

Example 1 mGluR2 $IC_{50}<100$ nM
ratio $[IC_{50}\ hmGluR3]/[IC_{50}\ hmGluR2]>10$

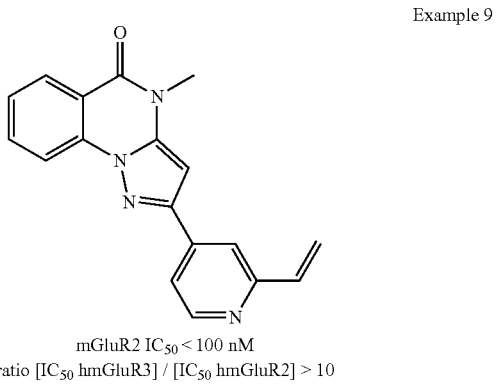

Example 9 mGluR2 $IC_{50}<100$ nM
ratio $[IC_{50}\ hmGluR3]/[IC_{50}\ hmGluR2]>10$

The compounds of the present invention are thus highly advantageous in terms of their mGluR2/3 selectivity. In comparison thereto, structurally related compounds disclosed in WO 2013/174822 and EP-A-2666775, such as the compounds A and B shown below, have a similar potency on mGluR2 ($IC_{50}<100$ nM) but lack selectivity for mGluR2 over mGluR3 (ratio $[IC_{50}\ hmGluR3]/[IC_{50}\ hmGluR2]<1$).

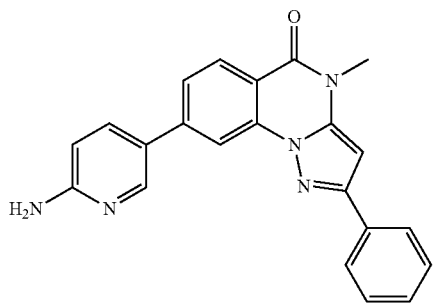

Compound A (Example 2 of WO 2013/174822)
mGluR2 IC$_{50}$ < 100 nM
ratio [IC$_{50}$ hmGluR3]/[IC$_{50}$ hmGluR2] < 1

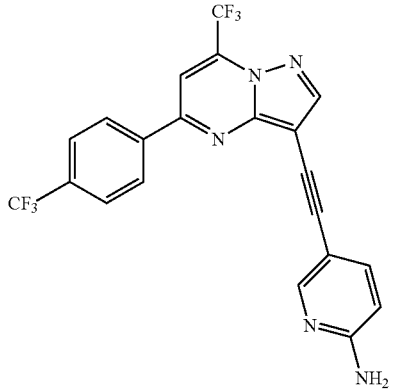

Decoglurant (RG1578)

mGluR2 IC$_{50}$ = 19.5 nM
ratio [IC$_{50}$ hmGluR3]/[IC$_{50}$ hmGluR2] = 0.66

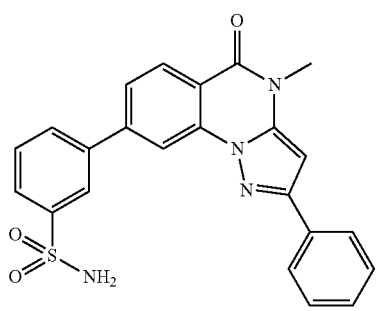

Compound B (Example 1 of WO 2013/174822)
mGluR2 IC$_{50}$ < 100 nM
ratio [IC$_{50}$ hmGluR3]/[IC$_{50}$ hmGluR2] < 1

Moreover, the two reference drugs RO4491533 and decoglurant (RG1578), which are known group II mGluR NAMs, also display a ratio [IC$_{50}$ hmGluR3]/[IC$_{50}$ hmGluR2]<1 when tested under the same conditions, and thus likewise lack selectivity for mGluR2 over mGluR3.

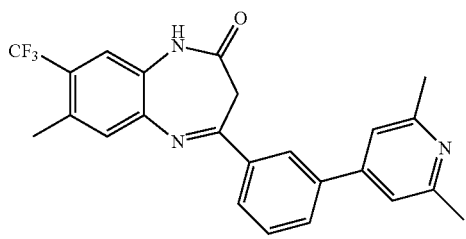

RO4491533 mGluR2 IC$_{50}$ = 60 nM
ratio [IC$_{50}$ hmGluR3]/[IC$_{50}$ hmGluR2] = 0.62

Pyrazoloquinazolinone structures have further been described as poly(ADP-ribose)polymerase (PARP) inhibitors in Orvieto F, et al., *Bioorg Med Chem Lett,* 2009, 19(15):4196-4200 and also in the patent applications WO 2007/144669, WO 2007/149907 and WO 2008/090379. These pyrazoloquinazolinones mimick the nicotinamide moiety of NAD$^+$, the cofactor of PARP, and therefore invariably comprise an unsubstituted lactam nitrogen, i.e. a hydrogen in position 4 of the pyrazoloquinazolinone scaffold, as an essential feature. In contrast thereto, the compounds of the present invention are substituted at position 4 of the pyrazoloquinazolinone ring and thus form a different class of therapeutic agents.

Pyrazoloquinazolinone compounds and their microwave-assisted preparations were described in Vasquez T E et al., *Mol Divers,* 7(2-4), 161-4, 2003. However, all the compounds disclosed in this publication differ structurally from those of the present invention, e.g., due to a hydrogen atom on position 4 of the pyrazoloquinazolinone scaffold and due to the lack of an aromatic ring group in position 8 of the pyrazoloquinazolinone scaffold.

Pyrazoloquinazolinone structures were also described as anti-secretory, anti-inflammatory, anti-allergic and anti-parasitic agents in patent documents U.S. Pat. No. 4,105,764 and U.S. Pat. No. 4,105,766 or as photographic material in patent applications such as EP0374781, JP4003154, JP4003155, JP4009050, JP4039656, JP4037741 or JP4037748.

Pyrroloquinazolinone compounds and their preparations were described in Volovenko Y M et al., *Chemistry of Heterocyclic Compounds,* 38(3), 324-30, 2002. The pyrroloquinazolin-2,5-diones disclosed in this publication differ structurally from the compounds of the present invention, e.g., since they have a carbonyl on position 2, a thiazole substituent in position 3, and an unsubstituted lactam nitrogen in position 4.

The present invention thus provides compounds which are potent mGluR2 negative allosteric modulators, showing selectivity for mGluR2 over mGluR3, which renders them particularly suitable as medicaments. The invention hence solves the problem of providing improved means and methods for the medical intervention in diseases, disorders and conditions associated with altered glutamatergic signalling and/or functions as well as conditions which can be affected by alteration of glutamate level or signalling in mammals, in particular for the treatment and/or prophylaxis of acute and chronic neurological and/or psychiatric disorders.

Accordingly, in a first aspect the present invention relates to a compound of the general formula (I):

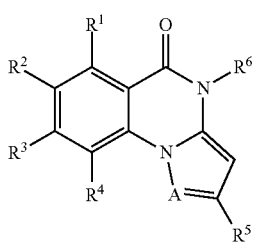

or a pharmaceutically acceptable salt, solvate or prodrug thereof for use as a medicament.

In formula (I), A represents N or —CH.

$R^1$, $R^2$ and $R^4$ are each independently selected from $R^7$, halogen, —CN, —$OR^7$, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, —$NR^7COOR^8$, aryl, or heteroaryl, wherein said aryl and said heteroaryl are each substituted with one or more groups independently selected from $R^7$, halogen, —CN, —$OR^7$, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, or —$NR^7COOR^8$.

$R^3$ is selected from hydrogen, halogen, —CN, —$OR^7$, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, —$NR^7COOR^8$, $C_1$-$C_4$ alkyl, $C_2$-$C_4$ alkenyl, cycloalkyl or heterocycloalkyl, wherein said $C_1$-$C_4$ alkyl and said $C_2$-$C_4$ alkenyl are each optionally substituted with one or more groups independently selected from halogen, —$CF_3$, —CN, —OH, —$O(C_1$-$C_4$ alkyl), —$NH_2$, —$NH(C_1$-$C_4$ alkyl) or —$N(C_1$-$C_4$ alkyl)($C_1$-$C_4$ alkyl), and further wherein said cycloalkyl and said heterocycloalkyl are each optionally substituted with one or more groups independently selected from: $C_1$-$C_4$ alkyl; halogen; —$CF_3$; —CN; —OH; —$O(C_1$-$C_4$ alkyl); $C_1$-$C_4$ alkyl substituted with one or more —OH groups; —$NH_2$; —$NH(C_1$-$C_4$ alkyl); or —$N(C_1$-$C_4$ alkyl)($C_1$-$C_4$ alkyl).

$R^5$ is heteroaryl which is optionally substituted with one or more groups independently selected from $R^7$, halogen, —CN, —$NR^7R^8$, —$CONR^7R^8$, —$COR^7$, —$OR^7$, —$SR^7$, —$SOR^7$, —$SO_2R^7$, —$SO_2NR^7R^8$, —$NR^7COR^8$, —$NR^7SO_2R^8$, —$OCOR^7$, or —$COOR^7$.

$R^6$ is selected from $C_1$-$C_4$ alkyl, cycloalkyl, or heterocycloalkyl, wherein said $C_1$-$C_4$ alkyl is optionally substituted with one or more groups independently selected from cycloalkyl, halogen, —$CF_3$, —CN, —OH or —$O(C_1$-$C_4$ alkyl), and further wherein, if $R^6$ is cycloalkyl or heterocycloalkyl, then said cycloalkyl and said heterocycloalkyl are each optionally substituted with one or more groups independently selected from $C_1$-$C_4$ alkyl, cycloalkyl, halogen, —$CF_3$, —CN, —OH or —$O(C_1$-$C_4$ alkyl).

Each $R^7$, $R^8$ and $R^9$ is independently selected from hydrogen, $C_1$-$C_4$ alkyl, $C_2$-$C_4$ alkenyl, cycloalkyl, cycloalkenyl, heterocycloalkyl, heterocycloalkenyl, aryl or heteroaryl, wherein said $C_1$-$C_4$ alkyl and said $C_2$-$C_4$ alkenyl are each optionally substituted with one or more groups independently selected from halogen, —$CF_3$, —CN, cycloalkyl, cycloalkenyl, heterocycloalkyl, heterocycloalkenyl, aryl, heteroaryl, —OH, —$O(C_1$-$C_4$ alkyl), —$NH_2$, —$NH(C_1$-$C_4$ alkyl) or —$N(C_1$-$C_4$ alkyl)($C_1$-$C_4$ alkyl), and further wherein, if $R^7$, $R^8$ or $R^9$ is cycloalkyl, cycloalkenyl, heterocycloalkyl, heterocycloalkenyl, aryl or heteroaryl, then said cycloalkyl, said cycloalkenyl, said heterocycloalkyl, said heterocycloalkenyl, said aryl and said heteroaryl are each optionally substituted with one or more groups independently selected from: $C_1$-$C_4$ alkyl; halogen; —$CF_3$; —CN; —OH; —$O(C_1$-$C_4$ alkyl); $C_1$-$C_4$ alkyl substituted with one or more —OH groups; —$NH_2$; —$NH(C_1$-$C_4$ alkyl); or —$N(C_1$-$C_4$ alkyl)($C_1$-$C_4$ alkyl).

The present invention further provides novel compounds. In particlar, in a second aspect, the invention relates to a compound of formula (I) or a pharmaceutically acceptable salt, solvate or prodrug thereof as described and defined in the first aspect of the invention, with the proviso that the following compounds are excluded:

8-bromo-2-furan-2-yl-4-methyl-4H-pyrazolo[1,5-a]quinazolin-5-one;

8-bromo-2-(2,6-dimethyl-pyridin-4-yl)-4-methyl-4H-pyrazolo[1,5-a]quinazolin-5-one;

8-bromo-4-methyl-2-(1-methyl-1H-pyrazol-4-yl)-4H-pyrazolo[1,5-a]quinazolin-5-one;

8-bromo-4-methyl-2-(1-ethyl-1H-pyrazol-4-yl)-4H-pyrazolo[1,5-a]quinazolin-5-one;

8-bromo-2-(2-methyl-pyridin-4-yl)-4-methyl-4H-pyrazolo[1,5-a]quinazolin-5-one;

8-bromo-4-methyl-2-pyridin-3-yl-4H-pyrazolo[1,5-a]quinazolin-5-one; and 8-bromo-4-methyl-2-(2-trifluoromethyl-pyridin-4-yl)-4H-pyrazolo[1,5-a]quinazolin-5-one.

In a third aspect, the invention relates to a compound of formula (I) or a pharmaceutically acceptable salt, solvate or prodrug thereof as described and defined in the first aspect of the invention, wherein the groups/variables A, $R^1$, $R^2$ and $R^4$ to $R^9$ have the same meanings as defined in the first aspect of the invention, and wherein the group $R^3$ is selected from hydrogen, —F, —Cl, —I, —CN, —$OR^7$, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, —$NR^7COOR^8$, $C_1$-$C_4$ alkyl, $C_2$-$C_4$ alkenyl, cycloalkyl or heterocycloalkyl, wherein said $C_1$-$C_4$ alkyl and said $C_2$-$C_4$ alkenyl are each optionally substituted with one or more groups independently selected from halogen, —$CF_3$, —CN, —OH, —$O(C_1$-$C_4$ alkyl), —$NH_2$, —$NH(C_1$-$C_4$ alkyl) or —$N(C_1$-$C_4$ alkyl)($C_1$-$C_4$ alkyl), and further wherein said cycloalkyl and said heterocycloalkyl are each optionally substituted with one or more groups independently selected from: $C_1$-$C_4$ alkyl; halogen; —$CF_3$; —CN; —OH; —$O(C_1$-$C_4$ alkyl); $C_1$-$C_4$ alkyl substituted with one or more —OH groups; —$NH_2$; —$NH(C_1$-$C_4$ alkyl); or —$N(C_1$-$C_4$ alkyl)($C_1$-$C_4$ alkyl).

Moreover, the present invention provides a pharmaceutical composition containing a compound of formula (I) as defined in the first, second or third aspect of the invention, or a pharmaceutically acceptable salt, solvate or prodrug thereof, and optionally a pharmaceutically acceptable excipient.

The invention further relates to the compounds of formula (I) as well as their pharmaceutically acceptable salts, solvates and prodrugs as defined in the first, second or third aspect for use in the treatment and/or prophylaxis of conditions associated with altered glutamatergic signalling and/ or functions, and/or conditions which can be affected by alteration of glutamate level or signalling. The invention likewise relates to a pharmaceutical composition containing a compound of formula (I) as defined in the first, second or third aspect of the invention, or a pharmaceutically acceptable salt, solvate or prodrug thereof, and optionally a pharmaceutically acceptable excipient, for use in the treatment and/or prophylaxis of conditions associated with altered glutamatergic signalling and/or functions, and/or conditions which can be affected by alteration of glutamate level or signalling.

The present invention also relates to the use of a compound of formula (I) as defined in the first, second or third aspect of the invention, or a pharmaceutically acceptable salt, solvate or prodrug thereof, for the preparation of a medicament for the treatment and/or prophylaxis of conditions associated with altered glutamatergic signalling and/or functions, and/or conditions which can be affected by alteration of glutamate level or signalling.

The invention further provides a method of treating and/or preventing conditions associated with altered glutamatergic signalling and/or functions, and/or conditions which can be affected by alteration of glutamate level or signalling in a mammal. Accordingly, the invention relates to a method of treating and/or preventing a disease or disorder, in particular a condition associated with altered glutamatergic signalling and/or functions, and/or a condition which can be affected by alteration of glutamate level or signalling, the method comprising the administration of a compound of formula (I) as defined in the first, second or third aspect of the invention, or a pharmaceutically acceptable salt, solvate or prodrug thereof, or a pharmaceutical composition comprising any of the aforementioned entities and optionally a pharmaceutically acceptable excipient, to a subject (preferably a mammal, more preferably a human) in need of such treatment or prevention.

The compounds of formula (I) as defined in the first, second or third aspect of the invention can be used as modulators of mGluRs of the nervous system, preferably as allosteric modulators of the mGluRs, more preferably as negative allosteric modulators (NAMs) of group II mGluRs, even more preferably as NAMs of mGluR2, and yet even more preferably as NAMs of mGluR2 that are selective for mGluR2 over mGluR3. It is preferred that such NAMs that are selective for mGluR2 over mGluR3 have a ratio of [$IC_{50}$ mGluR3]/[$IC_{50}$ mGluR2]>3, more preferably >5, and even more preferably >10. The ratio [$IC_{50}$ mGluR3]/[$IC_{50}$ mGluR2] can be determined as described in Example 127.

As noted above, the invention relates to the compounds of formula (I) as defined in the first, second or third aspect, their pharmaceutically acceptable salts, solvates and prodrugs, as well as pharmaceutical compositions comprising any of the aforementioned entities and optionally a pharmaceutically acceptable excipient, for use in the treatment and/or prophylaxis of conditions associated with altered glutamatergic signalling and/or functions, and/or conditions which can be affected by alteration of glutamate level or signalling.

The conditions associated with altered glutamatergic signalling and/or functions, and/or conditions which can be affected by alteration of glutamate level or signalling, to be treated and/or prevented with the compounds or the pharmaceutical compositions according to the invention, include in particular: epilepsy, including newborn, infantile, childhood and adult syndromes, partial (localization-related) and generalized epilepsies, with partial and generalized, convulsive and non-convulsive seizures, with and without impairment of consciousness, and status epilepticus; Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Motor neuron disease or amyotrophic lateral sclerosis (ALS); Other neurodegenerative and/or hereditary disorders of the nervous system, including spinocerebrellar degenerations such as Friedrich's ataxia and other hereditary cerebellar ataxias, predominantly spinal muscular atrophies, hereditary neuropathies, and phakomatoses; Disorders of the peripheral nervous system, including trigeminal neuralgia, facial nerve disorders, disorders of the other cranial nerves, nerve root and plexus disorders, mononeuritis such as carpal tunnel syndrome and sciatica, hereditary and idiopathic peripheral neuropathies, inflammatory and toxic neuropathies; Multiple sclerosis and other demyelinating diseases of the nervous system; Infantile cerebral palsy (spastic), monoplegic, paraplegic or tetraplegic; Hemiplegia and hemiparesis, flaccid or spastic, and other paralytic syndromes; Cerebrovascular disorders, including subarachnoid hemorrhage, intracerebral hemorrhage, occlusion and stenosis of precerebral arteries, occlusion of cerebral arteries including thrombosis and embolism, brain ischemia, stroke, transient ischemic attacks, atherosclerosis, cerebrovascular dementias, aneurysms, cerebral deficits due to cardiac bypass surgery and grafting; Migraine, including classical migraine and variants such as cluster headache; Headache; Myoneural disorders including myasthenia gravis, acute muscle spasms, myopathies including muscular dystrophies, mytotonias and familial periodic paralysis; Disorders of the eye and visual pathways, including retinal disorders, and visual disturbances; Intracranial trauma/injury and their sequels; Trauma/injury to nerves and spinal cord and their sequels; Poisoning and toxic effects of nonmedicinal substances; Accidental poisoning by drugs, medicinal substances and biologicals acting on the central, peripheral and autonomic system; Neurological and psychiatric adverse effects of drugs, medicinal and biological substances; Disturbance of sphincter control and sexual function; Mental disorders usually diagnosed in infancy, childhood or adolescence, including: mental retardation, learning disorders, motor skill disorders, communication disorders, pervasive developmental disorders, attention deficit and disruptive behaviour disorders, feeding and eating disorders, TIC disorders, elimination disorders; Delirium and other cognitive disorders; Substance related disorders including: alcohol-related disorders, nicotine-related disorders, disorders related to cocaine, opioids, cannabis, hallucinogens and other drugs; Schizophrenia and other psychotic disorders; Mood disorders, including depressive disorders and bipolar disorders; Anxiety disorders, including panic disorders, phobias, obsessive-compulsive disorders, stress disorders, generalized anxiety disorders; Eating disorders, including anorexia and bulimia; Sleep disorders and sleep/wake disorders, including dyssomnias (e.g., insomnia, hypersomnia, idiopathic hypersomnolence, narcolepsy, hypersomnia associated with obstructive sleep apnea or narcolepsy, or breathing related sleep disorder), parasomnias, excessive daytime sleepiness (EDS), circadian rhythm sleep disorders (e.g., shift work sleep disorder, jet lag disorder, delayed sleep phase disorder, advanced phase sleep disorder, or non-24 hour sleep-wake syndrome), and excessive sleepiness associated with non-restorative sleep (NRS); Medication-induced movement disorders (including neuroleptic-induced parkinsonism and tardive dyskinesia); Endocrine and metabolic diseases including diabetes, disorders of the endocrine glands, hypoglycaemia; Acute and chronic pain; Nausea and vomiting; Irritable bowel syndrome; cancers, including gliomas, colorectal cancer, melanoma, prostate cancer; or autism spectrum disorders, including autism, Asperger syndrome, Fragile X syndrome, Rett syndrome, childhood disintegrative disorder, or pervasive developmental disorder not otherwise specified (PDD-NOS). Accordingly, the present invention relates to a compound of formula (I), as described and defined in the first, second or third aspect of the invention, or a pharmaceutically acceptable salt, solvate or prodrug thereof, or a pharmaceutical composition containing any of the aforementioned entities and optionally a pharmaceutically acceptable excipient, for use in the treatment and/or prophylaxis of any of the above-mentioned diseases, disorders or conditions. The invention also encompasses methods for the treatment and/or prophylaxis of any of the above-mentioned diseases, disorders or conditions, comprising administering an effective amount of a compound of formula (I), as defined in the first, second or third aspect, or a pharmaceutically acceptable salt, solvate or prodrug thereof, or a pharmaceutical composition containing any of the aforementioned entities and optionally a pharmaceutically acceptable excipient, to a subject in need thereof (preferably a mammal, more preferably a human).

In particular, the conditions associated with altered glutamatergic signalling and/or functions, and/or conditions which can be affected by alteration of glutamate level or signalling, to be treated and/or prevented by the compounds or the pharmaceutical compositions according to the invention, include: Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Acute and chronic pain; Anxiety disorders, including panic disorders, phobias, obsessive-compulsive disorders, stress disorders and generalized anxiety disorders; Schizophrenia and other psychotic disorders; Mood disorders, including depressive disorders and bipolar disorders; Endocrine and metabolic diseases including diabetes, disorders of the endocrine glands and hypoglycaemia; or cancers, including gliomas, colorectal cancer, melanoma, prostate cancer.

The compounds and the pharmaceutical compositions according to the invention are envisaged to be used particularly in the treatment or prevention/prophylaxis of the following conditions/diseases/disorders: Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Mood disorders, including depressive disorders and bipolar disorders; Endocrine and metabolic diseases including diabetes, disorders of the endocrine glands and hypoglycaemia; or cancers, including gliomas, colorectal cancer, melanoma, prostate cancer. Accordingly, the present invention relates to the compounds of formula (I), as defined in the first, second or third aspect, their pharmaceutically acceptable salts, solvates and prodrugs, as well as pharmaceutical compositions comprising any of the aforementioned entities and optionally a pharmaceutically acceptable excipient, for use in the treatment or prevention/prophylaxis of any of the above-mentioned conditions/diseases/disorders. In particular, the invention relates to a compound of formula (I) as defined in the first, second or third aspect, or a pharmaceutically acceptable salt, solvate or prodrug thereof, or a pharmaceutical composition comprising any of the aforementioned entities and optionally a pharmaceutically acceptable excipient, for use in the treatment or prevention/prophylaxis of Alzheimer's disease.

In a preferred embodiment, the present invention thus provides a compound of formula (I) as defined in the first, second or third aspect, or a pharmaceutically acceptable salt, solvate or prodrug thereof, or a pharmaceutical composition comprising any of the aforementioned entities and optionally a pharmaceutically acceptable excipient, for use in the treatment or prophylaxis of a neurodegenerative disorder (particularly Alzheimer's disease).

The present invention furthermore provides a method for identifying an agent that binds to metabotropic glutamate receptor 2 (mGluR2), or in other words for determining the capability of one or more test agent(s) to bind to mGluR2, comprising the following steps: (a) contacting mGluR2 with a compound of the present invention (i.e., a compound of formula (I) as defined in the first, second or third aspect of the invention, or a pharmaceutically acceptable salt, solvate or prodrug thereof) which is labeled, preferably radiolabeled or fluorescence-labeled, under conditions that permit binding of the compound to mGluR2, thereby generating a bound, labeled compound; (b) detecting a signal that corresponds to the amount of the bound, labeled compound in the absence of test agent; (c) contacting the bound, labeled compound with a test agent; (d) detecting a signal that corresponds to the amount of the bound labeled compound in the presence of test agent; and (e) comparing the signal detected in step (d) to the signal detected in step (b) to determine whether the test agent binds to mGluR2. As will be understood, a substantially unchanged signal detected in step (d) in comparison with the signal detected in step (b) indicates that the test agent does not bind to the receptor, or binds to the receptor less strongly than the compound according to the invention. A decreased or increased signal detected in step (d) in comparison with the signal detected in step (b) indicates that the test agent binds to the receptor. Thus, agents that bind to mGluR2 can be identified among the test agents employed in this method. It will further be understood that it is preferred to remove unbound labeled compounds, e.g. in a washing step, before carrying out steps (b) and (d). The method may be carried out in any suitable in vitro environment, e.g., in an aqueous solution which may be provided, e.g., in a flask, a test tube, a Petri dish, or a microtiter plate.

The mGluR2 that is used in the above method may be a human form (Flor P J, et al. *Eur J Neurosci*. 1995. 7(4): 622-629), e.g., a protein of the accession number NP_000830.2, or a protein having at least 80% (preferably at least 90%, more preferably at least 95%, even more preferably at least 99%) amino acid identity to said protein of the accession number NP_000830.2, or a non-human form, including e.g. a mouse form or a homolog thereof found in a different species (e.g. in a different mammalian species), or a mutein of any of the aforementioned entities wherein the mutein retains the mGluR2 activity. Said mutein can preferably be obtained by substitution, insertion, addition and/or deletion of one or more (such as, e.g., 1 to 20, including 1 to 10 or 1 to 3) amino acid residues of said aforementioned entities. The mGluR2 to be used in the above method may also be a functional fragment of any of the aforementioned entities (including said muteins), i.e. a fragment which retains the mGluR2 activity of the respective aforementioned entity or, in other words, a fragment having essentially the same biological activity (i.e., at least about 60% activity, preferably at least about 70% activity, more preferably at least about 80% activity, even more preferably at least about 90% activity) as the respective aforementioned entity. A skilled person is readily in a position to determine whether mGluR2 activity is retained using techniques known in the art, e.g., knock-out and rescue experiments. Furthermore, the mGluR2 to be used in the above method may also be a compound comprising any one or more of the aforementioned entities (including, without limitation, a protein of the accession number NP_000830.2, a protein having at least 80% amino acid identity to said protein of the accession number NP_000830.2, or a functional fragment thereof), wherein the mGluR2 activity is retained. Preferably, the mGluR2 to be used in the above method is human mGluR2.

The compounds of formula (I) according to the first and the second aspect of the invention will be described in more detail in the following:

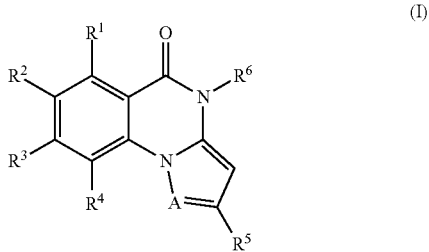

(I)

A represents N or —CH. Preferably, A is N.

$R^1$, $R^2$ and $R^4$ are each independently selected from $R^7$, halogen, —CN, —$OR^7$, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, —$NR^7COOR^8$, aryl, or heteroaryl, wherein said aryl and said heteroaryl are each substituted with one or more groups (preferably with one, two or three groups; more preferably with one or two groups; even more preferably with one group) independently selected from $R^7$, halogen, —CN, —$OR^7$, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, or —$NR^7COOR^8$.

Preferably, $R^1$, $R^2$ and $R^4$ are each independently selected from $R^7$, halogen, —CN, —$OR^7$, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, or —$NR^7COOR^8$. More preferably, $R^1$, $R^2$ and $R^4$ are each independently selected from $R^7$, halogen, —CN, —$OR^7$, —$NR^7R^8$, —$CONR^7R^8$, —$COR^7$, or —$NR^7COOR^8$. Even more preferably, $R^1$, $R^2$ and $R^4$ are each independently selected from hydrogen, halogen (e.g., —F, —Cl or —Br), $C_1$-$C_4$ haloalkyl (e.g., —$CF_3$), $C_1$-$C_4$ haloalkoxy (e.g., —$OCF_3$), —CN, $C_1$-$C_4$ alkyl, $C_2$-$C_4$ alkenyl, cycloalkyl, heterocycloalkyl, aryl, heteroaryl, —OH, —O($C_1$-$C_4$ alkyl), —O—($C_1$-$C_4$ alkylene)-OH, —O—($C_1$-$C_4$ alkylene)-O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —O-aryl, —O—($C_1$-$C_4$ alkylene)-aryl, —O-heteroaryl, —O—($C_1$-$C_4$ alkylene)-heteroaryl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —NH-aryl, —N($C_1$-$C_4$ alkyl)-aryl, —NH-heteroaryl, —N($C_1$-$C_4$ alkyl)-heteroaryl, —NH—($C_1$-$C_4$ alkylene)-aryl, —N($C_1$-$C_4$ alkyl)-($C_1$-$C_4$ alkylene)-aryl, —NH—($C_1$-$C_4$ alkylene)-heteroaryl, —N($C_1$-$C_4$ alkyl)-($C_1$-$C_4$ alkylene)-heteroaryl, —CO—($C_1$-$C_4$ alkyl), —CO-cycloalkyl, —CO-heterocycloalkyl, —CO—($C_1$-$C_4$ alkylene)-cycloalkyl, —CO—($C_1$-$C_4$ alkylene)-heterocycloalkyl, —CO-aryl, —CO-heteroaryl, —CO—($C_1$-$C_4$ alkylene)-aryl, —CO—($C_1$-$C_4$ alkylene)-heteroaryl, —CO—$NH_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH—($C_1$-$C_4$ alkylene)-cycloalkyl, —CO—N($C_1$-$C_4$ alkyl)-($C_1$-$C_4$ alkylene)-cycloalkyl, —CO—NH-heterocycloalkyl, —CO—N($C_1$-$C_4$ alkyl)-heterocycloalkyl, —CO—NH—($C_1$-$C_4$ alkylene)-heterocycloalkyl, —CO—N($C_1$-$C_4$ alkyl)-($C_1$-$C_4$ alkylene)-heterocycloalkyl, —CO—NH-aryl, —CO—N($C_1$-$C_4$ alkyl)-aryl, —CO—NH—($C_1$-$C_4$ alkylene)-aryl, —CO—N($C_1$-$C_4$ alkyl)-($C_1$-$C_4$ alkylene)-aryl, —CO—NH-heteroaryl, —CO—N($C_1$-$C_4$ alkyl)-heteroaryl, —CO—NH—($C_1$-$C_4$ alkylene)-heteroaryl, —CO—N($C_1$-$C_4$ alkyl)-($C_1$-$C_4$ alkylene)-heteroaryl, —NH—CHO, —N($C_1$-$C_4$ alkyl)-CHO, —NH—CO($C_1$-$C_4$ alkyl), —N($C_1$-$C_4$ alkyl)-CO($C_1$-$C_4$ alkyl), —NH—CO-cycloalkyl, —N($C_1$-$C_4$ alkyl)-CO-cycloalkyl, —NH—CO—($C_1$-$C_4$ alkylene)-cycloalkyl, —N($C_1$-$C_4$ alkyl)-CO—($C_1$-$C_4$ alkylene)-cycloalkyl, —NH—CO-heterocycloalkyl, —N($C_1$-$C_4$ alkyl)-CO-heterocycloalkyl, —NH—CO—($C_1$-$C_4$ alkylene)-heterocycloalkyl, —N($C_1$-$C_4$ alkyl)-CO—($C_1$-$C_4$ alkylene)-heterocycloalkyl, —NH—CO-aryl, —N($C_1$-$C_4$ alkyl)-CO-aryl, —NH—CO—($C_1$-$C_4$ alkylene)-aryl, —N($C_1$-$C_4$ alkyl)-CO—($C_1$-$C_4$ alkylene)-aryl, —NH—CO-heteroaryl, —N($C_1$-$C_4$ alkyl)-CO-heteroaryl, —NH—CO—($C_1$-$C_4$ alkylene)-heteroaryl, or —N($C_1$-$C_4$ alkyl)-CO—($C_1$-$C_4$ alkylene)-heteroaryl, wherein said cycloalkyl, said heterocycloalkyl, said aryl, said heteroaryl, the cycloalkyl moiety comprised in any of the aforementioned groups (i.e., the cycloalkyl moiety comprised in said —O-cycloalkyl, said —O—($C_1$-$C_4$ alkylene)-cycloalkyl, said —NH-cycloalkyl, said —N($C_1$-$C_4$ alkyl)-cycloalkyl, said —NH—($C_1$-$C_4$ alkylene)-cycloalkyl, said —N($C_1$-$C_4$ alkyl)-($C_1$-$C_4$ alkylene)-cycloalkyl, said —CO-cycloalkyl, said —CO—($C_1$-$C_4$ alkylene)-cycloalkyl, said —CO—NH-cycloalkyl, said —CO—

N($C_1$-$C_4$ alkyl)-cycloalkyl, said —CO—NH—($C_1$-$C_4$ alkylene)-cycloalkyl, said —CO—N($C_1$-$C_4$ alkyl)-($C_1$-$C_4$ alkylene)-cycloalkyl, said —NH—CO-cycloalkyl, said —N($C_1$-$C_4$ alkyl)-CO-cycloalkyl, said —NH—CO—($C_1$-$C_4$ alkylene)-cycloalkyl, or said —N($C_1$-$C_4$ alkyl)-CO—($C_1$-$C_4$ alkylene)-cycloalkyl), the heterocycloalkyl moiety comprised in any of the aforementioned groups (i.e., the heterocycloalkyl moiety comprised in said —O-heterocycloalkyl, said —O—($C_1$-$C_4$ alkylene)-heterocycloalkyl, said —NH-heterocycloalkyl, said —N($C_1$-$C_4$ alkyl)-heterocycloalkyl, said —NH—($C_1$-$C_4$ alkylene)-heterocycloalkyl, said —N($C_1$-$C_4$ alkyl)-($C_1$-$C_4$ alkylene)-heterocycloalkyl, said —CO-heterocycloalkyl, said —CO—($C_1$-$C_4$ alkylene)-heterocycloalkyl, said —CO—NH-heterocycloalkyl, said —CO—N($C_1$-$C_4$ alkyl)-heterocycloalkyl, said —CO—NH—($C_1$-$C_4$ alkylene)-heterocycloalkyl, said —CO—N($C_1$-$C_4$ alkyl)-($C_1$-$C_4$ alkylene)-heterocycloalkyl, said —NH—CO-heterocycloalkyl, said —N($C_1$-$C_4$ alkyl)-CO-heterocycloalkyl, said —NH—CO—($C_1$-$C_4$ alkylene)-heterocycloalkyl, or said —N($C_1$-$C_4$ alkyl)-CO—($C_1$-$C_4$ alkylene)-heterocycloalkyl), the aryl moiety comprised in any of the aforementioned groups (i.e., the aryl moiety comprised in said —O-aryl, said —O—($C_1$-$C_4$ alkylene)-aryl, said —NH-aryl, said —N($C_1$-$C_4$ alkyl)-aryl, said —NH—($C_1$-$C_4$ alkylene)-aryl, said —N($C_1$-$C_4$ alkyl)-($C_1$-$C_4$ alkylene)-aryl, said —CO-aryl, said —CO—($C_1$-$C_4$ alkylene)-aryl, said —CO—NH-aryl, said —CO—N($C_1$-$C_4$ alkyl)-aryl, said —CO—NH—($C_1$-$C_4$ alkylene)-aryl, said —CO—N($C_1$-$C_4$ alkyl)-($C_1$-$C_4$ alkylene)-aryl, said —NH—CO-aryl, said —N($C_1$-$C_4$ alkyl)-CO-aryl, said —NH—CO—($C_1$-$C_4$ alkylene)-aryl, or said —N($C_1$-$C_4$ alkyl)-CO—($C_1$-$C_4$ alkylene)-aryl), and the heteroaryl moiety comprised in any of the aforementioned groups (i.e., the heteroaryl moiety comprised in said —O-heteroaryl, said —O—($C_1$-$C_4$ alkylene)-heteroaryl, said —NH-heteroaryl, said —N($C_1$-$C_4$ alkyl)-heteroaryl, said —NH—($C_1$-$C_4$ alkylene)-heteroaryl, said —N($C_1$-$C_4$ alkyl)-($C_1$-$C_4$ alkylene)-heteroaryl, said —CO-heteroaryl, said —CO—($C_1$-$C_4$ alkylene)-heteroaryl, said —CO—NH-heteroaryl, said —CO—N($C_1$-$C_4$ alkyl)-heteroaryl, said —CO—NH—($C_1$-$C_4$ alkylene)-heteroaryl, said —CO—N($C_1$-$C_4$ alkyl)-($C_1$-$C_4$ alkylene)-heteroaryl, said —NH—CO-heteroaryl, said —N($C_1$-$C_4$ alkyl)-CO-heteroaryl, said —NH—CO—($C_1$-$C_4$ alkylene)-heteroaryl, or said —N($C_1$-$C_4$ alkyl)-CO—($C_1$-$C_4$ alkylene)-heteroaryl) are each optionally substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Even more preferably, $R^1$, $R^2$ and $R^4$ are each independently selected from hydrogen, halogen, $C_1$-$C_4$ haloalkyl, $C_1$-$C_4$ haloalkoxy, —CN, $C_1$-$C_4$ alkyl, $C_2$-$C_4$ alkenyl, cycloalkyl, heterocycloalkyl, aryl, heteroaryl, —OH, —O($C_1$-$C_4$ alkyl), —O—($C_1$-$C_4$ alkylene)-OH, —O—($C_1$-$C_4$ alkylene)-O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —O-aryl, —O—($C_1$-$C_4$ alkylene)-aryl, —O-heteroaryl, —O—($C_1$-$C_4$ alkylene)-heteroaryl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —NH-aryl, —N($C_1$-$C_4$ alkyl)-aryl, —NH—($C_1$-$C_4$ alkylene)-aryl, —N($C_1$-$C_4$ alkyl)-($C_1$-$C_4$ alkylene)-aryl, —NH-heteroaryl, —N($C_1$-$C_4$ alkyl)-heteroaryl, —NH—($C_1$-$C_4$ alkylene)-heteroaryl, —N($C_1$-$C_4$ alkyl)-($C_1$-$C_4$ alkylene)-heteroaryl, —CO—($C_1$-$C_4$ alkyl), —CO-cycloalkyl, —CO-heterocycloalkyl, —CO—($C_1$-$C_4$ alkylene)-cycloalkyl, —CO—($C_1$-$C_4$ alkylene)-heterocycloalkyl, —CO-aryl, —CO-heteroaryl, —CO—($C_1$-$C_4$ alkylene)-aryl, —CO—($C_1$-$C_4$ alkylene)-heteroaryl, —CO—$NH_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH—($C_1$-$C_4$ alkylene)-cycloalkyl, —CO—N($C_1$-$C_4$ alkyl)-($C_1$-$C_4$ alkylene)-cycloalkyl, —CO—NH-heterocycloalkyl, —CO—N($C_1$-$C_4$ alkyl)-heterocycloalkyl, —CO—NH—($C_1$-$C_4$ alkylene)-heterocycloalkyl, —CO—N($C_1$-$C_4$ alkyl)-($C_1$-$C_4$ alkylene)-heterocycloalkyl, —CO—NH-aryl, —CO—N($C_1$-$C_4$ alkyl)-aryl, —CO—NH—($C_1$-$C_4$ alkylene)-aryl, —CO—N($C_1$-$C_4$ alkyl)-($C_1$-$C_4$ alkylene)-aryl, —CO—NH-heteroaryl, —CO—N($C_1$-$C_4$ alkyl)-heteroaryl, —CO—NH—($C_1$-$C_4$ alkylene)-heteroaryl, —CO—N($C_1$-$C_4$ alkyl)-($C_1$-$C_4$ alkylene)-heteroaryl, —NH—CHO, —N($C_1$-$C_4$ alkyl)-CHO, —NH—CO($C_1$-$C_4$ alkyl), —N($C_1$-$C_4$ alkyl)-CO($C_1$-$C_4$ alkyl), —NH—CO-cycloalkyl, —N($C_1$-$C_4$ alkyl)-CO-cycloalkyl, —NH—CO—($C_1$-$C_4$ alkylene)-cycloalkyl, —N($C_1$-$C_4$ alkyl)-CO—($C_1$-$C_4$ alkylene)-cycloalkyl, —NH—CO-heterocycloalkyl, —N($C_1$-$C_4$ alkyl)-CO-heterocycloalkyl, —NH—CO—($C_1$-$C_4$ alkylene)-heterocycloalkyl, —N($C_1$-$C_4$ alkyl)-CO—($C_1$-$C_4$ alkylene)-heterocycloalkyl, —NH—CO-aryl, —N($C_1$-$C_4$ alkyl)-CO-aryl, —NH—CO—($C_1$-$C_4$ alkylene)-aryl, —N($C_1$-$C_4$ alkyl)-CO—($C_1$-$C_4$ alkylene)-aryl, —NH—CO-heteroaryl, —N($C_1$-$C_4$ alkyl)-CO-heteroaryl, —NH—CO—($C_1$-$C_4$ alkylene)-heteroaryl, or —N($C_1$-$C_4$ alkyl)-CO—($C_1$-$C_4$ alkylene)-heteroaryl, wherein said aryl, said heteroaryl, the aryl moiety comprised in any of the aforementioned groups, and the heteroaryl moiety comprised in any of the aforementioned groups are each optionally substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Even more preferably, $R^1$, $R^2$ and $R^4$ are each independently selected from hydrogen, halogen, $C_1$-$C_4$ haloalkyl, $C_1$-$C_4$ haloalkoxy, —CN, $C_1$-$C_4$ alkyl, $C_2$-$C_4$ alkenyl, cycloalkyl, heterocycloalkyl, —OH, —O($C_1$-$C_4$ alkyl), —O—($C_1$-$C_4$ alkylene)-OH, —O—($C_1$-$C_4$ alkylene)-O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—$NH_2$, —CO—NH($C_1$-$C_4$ alkyl), —CO—N($C_1$-$C_4$ alkyl)($C_1$-$C_4$ alkyl), —NH—CHO, —N($C_1$-$C_4$ alkyl)-CHO, —NH—CO($C_1$—$C_4$ alkyl), or —N($C_1$-$C_4$ alkyl)-CO($C_1$-$C_4$ alkyl). Even more preferably, $R^1$, $R^2$ and $R^4$ are each independently selected from hydrogen, halogen, $C_1$-$C_4$ haloalkyl, $C_1$-$C_4$ haloalkoxy, $C_1$-$C_4$ alkyl, —OH, —O($C_1$-$C_4$ alkyl), —NH($C_1$-$C_4$ alkyl), or —N($C_1$-$C_4$ alkyl)($C_1$-$C_4$ alkyl). Yet even more preferably, $R^1$, $R^2$ and $R^4$ are each independently selected from hydrogen, halogen (e.g., —F or —Cl), —$CF_3$, methyl, —$OCH_3$, or —$NH(CH_3)$.

It is particularly preferred that $R^1$ and $R^4$ are each hydrogen and $R^2$ is selected from hydrogen, halogen (e.g., —F, —Cl or —Br), $C_1$-$C_4$ haloalkyl (e.g., —$CF_3$), $C_1$-$C_4$ haloalkoxy (e.g., —$OCF_3$), —CN, $C_1$-$C_4$ alkyl, $C_2$-$C_4$ alkenyl, cycloalkyl, heterocycloalkyl, aryl, heteroaryl, —OH, —O($C_1$-$C_4$ alkyl), —O—($C_1$-$C_4$ alkylene)-OH, —O—($C_1$-$C_4$ alkylene)-O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —O-aryl, —O—($C_1$-$C_4$ alkylene)-aryl, —O-heteroaryl, —O—($C_1$-$C_4$ alkylene)-heteroaryl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —NH-aryl, —N($C_1$-$C_4$ alkyl)-aryl, —NH-heteroaryl, —N($C_1$-$C_4$ alkyl)-heteroaryl, —NH—($C_1$-$C_4$ alkylene)-aryl, —N($C_1$-$C_4$ alkyl)-($C_1$-$C_4$ alkylene)-aryl, —NH—($C_1$-$C_4$ alkylene)-heteroaryl, —N($C_1$-$C_4$ alkyl)-($C_1$-$C_4$ alkylene)-heteroaryl, —CO—($C_1$-$C_4$ alkyl), —CO-cycloalkyl, —CO-heterocycloalkyl, —CO—($C_1$-$C_4$ alkylene)-cycloalkyl, —CO—($C_1$-$C_4$ alkylene)-heterocycloalkyl, —CO-aryl, —CO-heteroaryl, —CO—($C_1$-$C_4$ alkylene)-aryl, —CO—($C_1$-$C_4$ alkylene)-heteroaryl, —CO—NH$_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH—($C_1$-$C_4$ alkylene)-cycloalkyl, —CO—N($C_1$-$C_4$ alkyl)-($C_1$-$C_4$ alkylene)-cycloalkyl, —CO—NH-heterocycloalkyl, —CO—N($C_1$-$C_4$ alkyl)-heterocycloalkyl, —CO—NH—($C_1$-$C_4$ alkylene)-heterocycloalkyl, —CO—N($C_1$-$C_4$ alkyl)-($C_1$-$C_4$ alkylene)-heterocycloalkyl, —CO—NH-aryl, —CO—N($C_1$-$C_4$ alkyl)-aryl, —CO—NH—($C_1$-$C_4$ alkylene)-aryl, —CO—N($C_1$-$C_4$ alkyl)-($C_1$-$C_4$ alkylene)-aryl, —CO—NH-heteroaryl, —CO—N($C_1$-$C_4$ alkyl)-heteroaryl, —CO—NH—($C_1$-$C_4$ alkylene)-heteroaryl, —CO—N($C_1$-$C_4$ alkyl)-($C_1$-$C_4$ alkylene)-heteroaryl, —NH—CHO, —N($C_1$-$C_4$ alkyl)-CHO, —NH—CO($C_1$-$C_4$ alkyl), —N($C_1$-$C_4$ alkyl)-CO($C_1$-$C_4$ alkyl), —NH—CO-cycloalkyl, —N($C_1$-$C_4$ alkyl)-CO-cycloalkyl, —NH—CO—($C_1$-$C_4$ alkylene)-cycloalkyl, —N($C_1$-$C_4$ alkyl)-CO—($C_1$-$C_4$ alkylene)-cycloalkyl, —NH—CO-heterocycloalkyl, —N($C_1$-$C_4$ alkyl)-CO-heterocycloalkyl, —NH—CO—($C_1$-$C_4$ alkylene)-heterocycloalkyl, —N($C_1$-$C_4$ alkyl)-CO—($C_1$-$C_4$ alkylene)-heterocycloalkyl, —NH—CO-aryl, —N($C_1$-$C_4$ alkyl)-CO-aryl, —NH—CO—($C_1$-$C_4$ alkylene)-aryl, —N($C_1$-$C_4$ alkyl)-CO—($C_1$-$C_4$ alkylene)-aryl, —NH—CO-heteroaryl, —N($C_1$-$C_4$ alkyl)-CO-heteroaryl, —NH—CO—($C_1$-$C_4$ alkylene)-heteroaryl, or —N($C_1$-$C_4$ alkyl)-CO—($C_1$-$C_4$ alkylene)-heteroaryl, wherein said cycloalkyl, said heterocycloalkyl, said aryl, said heteroaryl, the cycloalkyl moiety comprised in any of the aforementioned groups, the heterocycloalkyl moiety comprised in any of the aforementioned groups, the aryl moiety comprised in any of the aforementioned groups, and the heteroaryl moiety comprised in any of the aforementioned groups are each optionally substituted with one or more groups (e.g., one, two or three groups) independently selected from $C_1$-$C_4$ alkyl, halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl). More preferably, $R^1$ and $R^4$ are each hydrogen and $R^2$ is selected from hydrogen, halogen, $C_1$-$C_4$ haloalkyl, $C_1$-$C_4$ haloalkoxy, —CN, $C_1$-$C_4$ alkyl, $C_2$-$C_4$ alkenyl, cycloalkyl, heterocycloalkyl, —OH, —O($C_1$-$C_4$ alkyl), —O—($C_1$-$C_4$ alkylene)-OH, —O—($C_1$-$C_4$ alkylene)-O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—NH$_2$, —CO—NH($C_1$-$C_4$ alkyl), —CO—N($C_1$-$C_4$ alkyl)($C_1$-$C_4$ alkyl), —NH—CHO, —N($C_1$-$C_4$ alkyl)-CHO, —NH—CO($C_1$-$C_4$ alkyl), or —N($C_1$-$C_4$ alkyl)-CO($C_1$-$C_4$ alkyl). Even more preferably, $R^1$ and $R^4$ are each hydrogen and $R^2$ is selected from hydrogen, halogen, $C_1$-$C_4$ haloalkyl, $C_1$-$C_4$ haloalkoxy, $C_1$-$C_4$ alkyl, —OH, —O($C_1$-$C_4$ alkyl), —NH($C_1$-$C_4$ alkyl), or —N($C_1$-$C_4$ alkyl)($C_1$-$C_4$ alkyl). Yet even more preferably, $R^1$ and $R^4$ are each hydrogen and $R^2$ is selected from hydrogen, —F, —Cl, —CF$_3$, methyl, —OCH$_3$, or —NH (CH$_3$). Still more preferably, $R^1$ and $R^4$ are each hydrogen and $R^2$ is hydrogen or —F. Most preferably, $R^1$, $R^2$ and $R^4$ are each hydrogen.

$R^3$ is selected from hydrogen, halogen, —CN, —OR$^7$, —NR$^7$R$^8$, —COOR$^7$, —SO$_3$H, —B(OH)$_2$, —CONR$^7$R$^8$, —COR$^7$, —SR$^7$, —R$^7$, —SO$_2$R$^7$, —SO$_2$NR$^7$R$^8$, —NR$^7$COR$^8$, —NR$^7$SO$_2$R$^8$, —OCOR$^7$, —NR$^7$C(O)NR$^8$R$^9$, —NR$^7$C(S)NR$^8$R$^9$, —NR$^7$COOR$^8$, $C_1$-$C_4$ alkyl, $C_2$-$C_4$ alkenyl, cycloalkyl or heterocycloalkyl, wherein said $C_1$-$C_4$ alkyl and said $C_2$-$C_4$ alkenyl are each optionally substituted with one or more groups (e.g., one, two or three groups) independently selected from halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more groups (e.g., one, two or three groups) independently selected from: $C_1$-$C_4$ alkyl; halogen; —CF$_3$; —CN; —OH; —O($C_1$-$C_4$ alkyl); $C_1$-$C_4$ alkyl substituted with one or more (e.g., one, two or three) —OH groups; —NH$_2$; —NH($C_1$-$C_4$ alkyl); or —N($C_1$-$C_4$ alkyl)($C_1$-$C_4$ alkyl).

Preferably, $R^3$ is selected from hydrogen, halogen, —CN, —OR$^7$, —NR$^7$R$^8$, —COOR$^7$, —CONR$^7$R$^8$, —COR$^7$, —NR$^7$COR$^8$, $C_1$-$C_4$ alkyl, $C_2$-$C_4$ alkenyl, cycloalkyl or heterocycloalkyl, wherein said $C_1$-$C_4$ alkyl and said $C_2$-$C_4$ alkenyl are each optionally substituted with one or more groups (e.g., one, two or three groups) independently selected from halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more groups (e.g., one, two or three groups) independently selected from: $C_1$-$C_4$ alkyl; halogen; —CF$_3$; —CN; —OH; —O($C_1$-$C_4$ alkyl); $C_1$-$C_4$ alkyl substituted with one or more —OH groups; —NH$_2$; —NH($C_1$-$C_4$ alkyl); or —N($C_1$-$C_4$ alkyl)($C_1$-$C_4$ alkyl). More preferably, $R^3$ is selected from hydrogen, halogen (e.g., —F, —Cl or —Br), $C_1$-$C_4$ haloalkyl (e.g., —CF$_3$), $C_1$-$C_4$ haloalkoxy (e.g., —OCF$_3$), —CN, $C_1$-$C_4$ alkyl, $C_2$-$C_4$ alkenyl, cycloalkyl, heterocycloalkyl, —OH, —O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, —CO—($C_1$-$C_4$ alkylene)-heterocycloalkyl, —CO—NH$_2$, —CO—NH ($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH—($C_1$-$C_4$ alkylene)-cycloalkyl, —CO—N($C_1$-$C_4$ alkyl)-($C_1$-$C_4$ alkylene)-cycloalkyl, —CO—NH-heterocycloalkyl, —CO—N($C_1$-$C_4$ alkyl)-heterocycloalkyl, —CO—NH—($C_1$-$C_4$ alkylene)-heterocycloalkyl, —CO—N($C_1$-$C_4$ alkyl)-($C_1$-$C_4$ alkylene)-heterocycloalkyl, —NH—CO-cycloalkyl, —N($C_1$-$C_4$ alkyl)-CO-cycloalkyl, —NH—CO—($C_1$-$C_4$ alkylene)-cycloalkyl, —N($C_1$-$C_4$ alkyl)-CO—($C_1$-$C_4$ alkylene)-cycloalkyl, —NH—CO-heterocycloalkyl, —N($C_1$-$C_4$ alkyl)-CO-heterocycloalkyl, —NH—CO—($C_1$-$C_4$ alkylene)-heterocycloalkyl, —N($C_1$-$C_4$ alkyl)-CO—($C_1$-$C_4$ alkylene)-heterocycloalkyl, or —COOH, wherein said cycloalkyl, said heterocycloalkyl, the cycloalkyl moiety comprised in any of the aforementioned groups (i.e., the cycloalkyl moiety comprised in said —O-cycloalkyl, said —O—($C_1$-$C_4$ alkylene)-cycloalkyl, said —NH-cycloalkyl, said —N($C_1$-$C_4$ alkyl)-cycloalkyl, said —NH—($C_1$-$C_4$ alkylene)-cycloalkyl, said —N($C_1$-$C_4$ alkyl)-($C_1$-$C_4$ alkylene)-cycloalkyl, said —CO-cycloalkyl, said —CO—($C_1$-$C_4$ alkylene)-cycloalkyl, said —CO—NH-cycloalkyl, said —CO—N($C_1$-$C_4$ alkyl)-cycloalkyl, said —CO—NH—($C_1$-$C_4$ alkylene)-cycloalkyl, said —CO—N($C_1$-$C_4$ alkyl)-($C_1$-$C_4$ alkylene)-cycloalkyl, said —NH—CO-cycloalkyl, said —N($C_1$-$C_4$ alkyl)-CO-cycloalkyl, said —NH—CO—($C_1$-$C_4$ alkylene)-cycloalkyl, or said —N($C_1$-$C_4$ alkyl)-CO—($C_1$-$C_4$ alkylene)-cycloalkyl), and the heterocycloalkyl moiety comprised in any of the aforementioned groups (i.e., the heterocycloalkyl moiety comprised in said —O-heterocycloalkyl, said —O—($C_1$-$C_4$ alkylene)-heterocycloalkyl, said —NH-heterocycloalkyl, said —N($C_1$-$C_4$ alkyl)-heterocycloalkyl, said —NH—($C_1$-$C_4$ alkylene)-heterocycloalkyl, said —N($C_1$-$C_4$ alkyl)-($C_1$-$C_4$ alkylene)-heterocycloalkyl, said —CO-heterocycloalkyl, said —CO—($C_1$-$C_4$ alkylene)-heterocycloalkyl, said —CO—NH-heterocycloalkyl, said —CO—N($C_1$-$C_4$ alkyl)-heterocycloalkyl, said —CO—NH—($C_1$-$C_4$ alkylene)-heterocycloalkyl, said —CO—N($C_1$-$C_4$ alkyl)-($C_1$-$C_4$ alkylene)-heterocycloalkyl, said —NH—CO-heterocycloalkyl, said —N($C_1$-$C_4$ alkyl)-CO-heterocycloalkyl, said —NH—CO—($C_1$-$C_4$ alkylene)-heterocycloalkyl, or said —N($C_1$-$C_4$ alkyl)-CO—($C_1$-$C_4$ alkylene)-heterocycloalkyl) are each optionally substituted with one or more groups (e.g., one, two or three groups) independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl). Even more preferably, $R^3$ is selected from hydrogen, halogen, $C_1$-$C_4$ haloalkyl, $C_1$-$C_4$ haloalkoxy, —CN, $C_1$-$C_4$ alkyl, cycloalkyl, heterocycloalkyl, —OH, —O($C_1$-$C_4$ alkyl), —O-cycloalkyl, —O-heterocycloalkyl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —CO-cycloalkyl, —CO-heterocycloalkyl, —CO—$NH_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH-heterocycloalkyl, —CO—N($C_1$-$C_4$ alkyl)-heterocycloalkyl, —NH—CO-cycloalkyl, —N($C_1$-$C_4$ alkyl)-CO-cycloalkyl, —NH—CO-heterocycloalkyl, or —N($C_1$-$C_4$ alkyl)-CO-heterocycloalkyl, wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups (e.g., one, two or three groups) independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl). Even more preferably, $R^3$ is selected from hydrogen, halogen, $C_1$-$C_4$ haloalkyl, $C_1$-$C_4$ haloalkoxy, —CN, $C_1$-$C_4$ alkyl, cycloalkyl, heterocycloalkyl, —OH, —O($C_1$-$C_4$ alkyl), —O-cycloalkyl, —O-heterocycloalkyl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —CO-cycloalkyl, —CO-heterocycloalkyl, —CO—$NH_2$, —CO—NH($C_1$-$C_4$ alkyl), or —CO—N($C_1$-$C_4$ alkyl)($C_1$-$C_4$ alkyl), wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups (e.g., one, two or three groups) independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl). Even more preferably, $R^3$ is selected from hydrogen, halogen (e.g., —F or —Cl), $C_1$-$C_4$ haloalkyl (e.g., —$CF_3$), —CN, heterocycloalkyl (e.g., azetidinyl, pyrrolidinyl, piperidinyl, piperazinyl, or morpholinyl), —O($C_1$-$C_4$ alkyl), —NH($C_1$-$C_4$ alkyl), or —CO—N($C_1$-$C_4$ alkyl)($C_1$-$C_4$ alkyl), wherein said heterocycloalkyl is optionally substituted with one or more groups (e.g., one or two groups) independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups (e.g., —$(CH_2)_{1-4}$—OH); —$NH_2$; —NH($C_1$-$C_4$ alkyl); or —N($C_1$-$C_4$ alkyl)($C_1$-$C_4$ alkyl). Yet even more preferably, $R^3$ is selected from hydrogen, —F, —Cl, —$CF_3$, —CN, 3-hydroxyazetidin-1-yl, 4-hydroxypiperidin-1-yl, morpholin-4-yl, —$OCH_3$, —$NHCH_3$, —CO—N($CH_3$)$_2$, or —CO—N($CH_2CH_3$)$_2$. Most preferably, $R^3$ is hydrogen.

$R^5$ is heteroaryl which is optionally substituted with one or more groups (e.g., one, two or three groups; preferably one or two groups; more preferably one group) independently selected from $R^7$, halogen, —CN, —$NR^7R^8$, —$CONR^7R^8$, —$COR^7$, —$OR^7$, —$SR^7$, —$SOR^7$, —$SO_2R^7$, —$SO_2NR^7R^8$, —$NR^7COR^8$, —$NR^7SO_2R^8$, —$OCOR^7$, or —$COOR^7$.

Said heteroaryl is preferably a heteroaryl having 5 to 14 ring members and comprising one or more (preferably one, two, three or four) ring heteroatoms independently selected from O, S or N; more preferably, said heteroaryl is a heteroaryl having 5 or 6 ring members and comprising one or more (preferably one, two or three) ring heteroatoms independently selected from O, S or N (wherein the 5- to 14-membered heteroaryl and the 5- or 6-membered heteroaryl are optionally substituted, as defined for said heteroaryl). Even more preferably, said heteroaryl is pyridinyl, pyrazolyl, oxazolyl, isoxazolyl, thiazolyl, isothiazolyl, pyrrolyl, furanyl, thienyl, pyridazinyl, pyrimidinyl or pyrazinyl (wherein these specific groups are optionally substituted, as defined for said heteroaryl). Yet even more preferably, said heteroaryl is pyridinyl or pyrazolyl, yet even more preferably pyridinyl (such as, e.g., pyridin-4-yl, pyridin-3-yl or pyridin-2-yl), and most preferably pyridin-4-yl (wherein the aforementioned specific heteroaryl groups are optionally substituted, as defined for said heteroaryl).

Said heteroaryl (including any of the above-mentioned specific heteroaryl groups) is preferably unsubstituted or substituted with one, two or three groups, more preferably it is substituted with one or two groups, and even more preferably it is substituted with one group. If said heteroaryl is pyridin-4-yl substituted with one group, it is preferred that this one substituent group is attached to the pyridin-4-yl group in position 2. If said heteroaryl is pyridin-4-yl substituted with two groups, it is preferred that these two substituent groups are attached to the pyridin-4-yl group in positions 2 and 6, respectively.

The optional substituent groups with which the heteroaryl as $R^5$ (including any of the aforementioned specific heteroaryl groups) may be substituted are independently selected from $R^7$, halogen, —CN, —NR$^7$R$^8$, —CONR$^7$R$^8$, —COR$^7$, —OR$^7$, —SR$^7$, —R$^7$, —SO$_2$R$^7$, —SO$_2$NR$^7$R$^8$, —NR$^7$COR$^8$, —NR$^7$SO$_2$R$^8$, —OCOR$^7$, or —COOR$^7$. Preferably, these optional substituent groups are independently selected from $R^7$, halogen, —CN, —NR$^7$R$^8$, —CONR$^7$R$^8$, —COR$^7$, —OR$^7$, or —NR$^7$COR$^8$, more preferably from $R^7$, halogen, —CN, —NR$^7$R$^8$, —COR$^7$, or —OR$^7$. Even more preferably, these optional substituent groups are independently selected from $C_1$-$C_4$ alkyl, $C_2$-$C_4$ alkenyl, halogen (e.g., —F, —Cl or —Br), $C_1$-$C_4$ haloalkyl (e.g., —CF$_3$, —CHF$_2$, or —CF$_2$—CH$_3$), $C_1$-$C_4$ haloalkoxy (e.g., —O—CH$_2$—CF$_3$, —O—CH$_2$—CHF$_2$, —O—CH$_2$—CF$_2$—CH$_3$, —O—CH$_2$—CF$_2$—CF$_3$, —O—CH(CF$_3$)$_2$, or —OCF$_3$), —CN, cycloalkyl, heterocycloalkyl, aryl (e.g., phenyl), heteroaryl, —OH, —O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, or —CO—($C_1$-$C_4$ alkylene)-heterocycloalkyl, wherein said aryl, said heteroaryl, said cycloalkyl, said heterocycloalkyl, the cycloalkyl moiety comprised in any of the aforementioned groups (i.e., the cycloalkyl moiety comprised in said —O-cycloalkyl, the cycloalkyl moiety comprised in said —O—($C_1$-$C_4$ alkylene)-cycloalkyl, the cycloalkyl moiety comprised in said —NH-cycloalkyl, the cycloalkyl moiety comprised in said —N($C_1$-$C_4$ alkyl)-cycloalkyl, the cycloalkyl moiety comprised in said —NH—($C_1$-$C_4$ alkylene)-cycloalkyl, the cycloalkyl moiety comprised in said —N($C_1$-$C_4$ alkyl)-($C_1$-$C_4$ alkylene)-cycloalkyl, the cycloalkyl moiety comprised in said —CO-cycloalkyl, or the cycloalkyl moiety comprised in said —CO—($C_1$-$C_4$ alkylene)-cycloalkyl), and the heterocycloalkyl moiety comprised in any of the aforementioned groups (i.e., the heterocycloalkyl moiety comprised in said —O-heterocycloalkyl, the heterocycloalkyl moiety comprised in said —O—($C_1$-$C_4$ alkylene)-heterocycloalkyl, the heterocycloalkyl moiety comprised in said —NH-heterocycloalkyl, the heterocycloalkyl moiety comprised in said —N($C_1$-$C_4$ alkyl)-heterocycloalkyl, the heterocycloalkyl moiety comprised in said —NH—($C_1$-$C_4$ alkylene)-heterocycloalkyl, the heterocycloalkyl moiety comprised in said —N($C_1$-$C_4$ alkyl)-($C_1$-$C_4$ alkylene)-heterocycloalkyl, the heterocycloalkyl moiety comprised in said —CO-heterocycloalkyl, or the heterocycloalkyl moiety comprised in said —CO—($C_1$-$C_4$ alkylene)-heterocycloalkyl) are each optionally substituted with one or more groups (e.g., one, two or three groups) independently selected from $C_1$-$C_4$ alkyl, halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl). Yet even more preferably, the optional substituent groups with which the heteroaryl as $R^5$ may be substituted are independently selected from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, —O($C_1$-$C_4$ alkyl), —O-cycloalkyl, or —O-heterocycloalkyl. Still more preferably, these optional substituent groups are independently selected from methyl, vinyl, propenyl (e.g., propen-2-yl), —F, —Cl, —CF$_3$, —O—CH$_2$—CF$_3$, —CN, cyclopropyl, or pyrrolidinyl (e.g., pyrrolidin-1-yl).

Accordingly, it is particularly preferred that $R^5$ is heteroaryl having 5 or 6 ring members and comprising one or more (preferably one, two or three) ring heteroatoms independently selected from O, S or N, wherein said heteroaryl having 5 or 6 ring members is optionally substituted with one or more groups (preferably one or two groups; more preferably one group) independently selected from $C_1$-$C_4$ alkyl, $C_2$-$C_4$ alkenyl, halogen (e.g., —F, —Cl or —Br), $C_1$-$C_4$ haloalkyl (e.g., —CF$_3$, —CHF$_2$, or —CF$_2$—CH$_3$), $C_1$-$C_4$ haloalkoxy (e.g., —O—CH$_2$—CF$_3$, —O—CH$_2$—CHF$_2$, —O—CH$_2$—CF$_2$—CH$_3$, —O—CH$_2$—CF$_2$—CF$_3$, —O—CH(CF$_3$)$_2$, or —OCF$_3$), —CN, cycloalkyl, heterocycloalkyl, aryl, heteroaryl, —OH, —O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, or —CO—($C_1$-$C_4$ alkylene)-heterocycloalkyl, wherein said aryl, said heteroaryl, said cycloalkyl, said heterocycloalkyl, the cycloalkyl moiety comprised in any of the aforementioned groups (i.e., the cycloalkyl moiety comprised in said —O-cycloalkyl, the cycloalkyl moiety comprised in said —O—($C_1$-$C_4$ alkylene)-cycloalkyl, the cycloalkyl moiety comprised in said —NH-cycloalkyl, the cycloalkyl moiety comprised in said —N($C_1$-$C_4$ alkyl)-cycloalkyl, the cycloalkyl moiety comprised in said —NH—($C_1$-$C_4$ alkylene)-cycloalkyl, the cycloalkyl moiety comprised in said —N($C_1$-$C_4$ alkyl)-($C_1$-$C_4$ alkylene)-cycloalkyl, the cycloalkyl moiety comprised in said —CO-cycloalkyl, or the cycloalkyl moiety comprised in said —CO—($C_1$-$C_4$ alkylene)-cycloalkyl), and the heterocycloalkyl moiety comprised in any of the aforementioned groups (i.e., the heterocycloalkyl moiety comprised in said —O-heterocycloalkyl, the heterocycloalkyl moiety comprised in said —O—($C_1$-$C_4$ alkylene)-heterocycloalkyl, the heterocycloalkyl moiety comprised in said —NH-heterocycloalkyl, the heterocycloalkyl moiety comprised in said —N($C_1$-$C_4$ alkyl)-heterocycloalkyl, the heterocycloalkyl moiety comprised in said —NH—($C_1$-$C_4$ alkylene)-heterocycloalkyl, the heterocycloalkyl moiety comprised in said —N($C_1$-$C_4$ alkyl)-($C_1$-$C_4$ alkylene)-heterocycloalkyl, the heterocycloalkyl moiety comprised in said —CO-heterocycloalkyl, or the heterocycloalkyl moiety comprised in said —CO—($C_1$-$C_4$ alkylene)-heterocycloalkyl) are each optionally substituted with one or more groups (e.g., one, two or three groups) independently selected from $C_1$-$C_4$ alkyl, halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl). More preferably, $R^5$ is heteroaryl having 5 or 6 ring members and comprising one or more (preferably one, two or three) ring heteroatoms independently selected from O, S or N (e.g., pyridinyl, pyrazolyl, oxazolyl, isoxazolyl, thiazolyl, isothiazolyl, pyrrolyl, furanyl, thienyl, pyridazinyl, pyrimidinyl or pyrazinyl), wherein said heteroaryl having 5 or 6 ring members is optionally substituted with one or more substituent groups (preferably one or two substituent groups; more preferably one substituent group) independently selected from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, —O($C_1$-$C_4$ alkyl), —O-cycloalkyl, or —O-heterocycloalkyl, wherein it is furthermore preferred that said substituent group(s) is/are selected independently from methyl, vinyl, propenyl (e.g., propen-2-yl), —F, —Cl, —CF$_3$, —O—CH$_2$—CF$_3$, —CN, cyclopropyl, or pyrrolidinyl (e.g., pyrrolidin-1-yl). Even more preferably, $R^5$ is pyridinyl (particularly pyridin-4-yl) which is optionally substituted with one or more groups (preferably one or two groups; more preferably one group) independently selected from $C_1$-$C_4$ alkyl, $C_2$-$C_4$ alkenyl, halogen (e.g., —F, —Cl or —Br), $C_1$-$C_4$ haloalkyl (e.g., —CF$_3$, —CHF$_2$, or —CF$_2$—CH$_3$), $C_1$-$C_4$ haloalkoxy (e.g., —O—CH$_2$—CF$_3$, —O—CH$_2$—CHF$_2$, —O—CH$_2$—CF$_2$—CH$_3$, —O—CH$_2$—CF$_2$—CF$_3$, or —O—CH(CF$_3$)$_2$), —CN, cycloalkyl, heterocycloalkyl, aryl, heteroaryl, —OH, —O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, or —CO—($C_1$-$C_4$ alkylene)-heterocycloalkyl, wherein said aryl, said heteroaryl, said cycloalkyl, said heterocycloalkyl, the cycloalkyl moiety comprised in any of the aforementioned groups (i.e., the cycloalkyl moiety comprised in said —O-cycloalkyl, the cycloalkyl moiety comprised in said —O—($C_1$-$C_4$ alkylene)-cycloalkyl, the cycloalkyl moiety comprised in said —NH-cycloalkyl, the cycloalkyl moiety comprised in said —N($C_1$-$C_4$ alkyl)-cycloalkyl, the cycloalkyl moiety comprised in said —NH—($C_1$-$C_4$ alkylene)-cycloalkyl, the cycloalkyl moiety comprised in said —N($C_1$-$C_4$ alkyl)-($C_1$-$C_4$ alkylene)-cycloalkyl, the cycloalkyl moiety comprised in said —CO-cycloalkyl, or the cycloalkyl moiety comprised in said —CO—($C_1$-$C_4$ alkylene)-cycloalkyl), and the heterocycloalkyl moiety comprised in any of the aforementioned groups (i.e., the heterocycloalkyl moiety comprised in said —O-heterocycloalkyl, the heterocycloalkyl moiety comprised in said —O—($C_1$-$C_4$ alkylene)-heterocycloalkyl, the heterocycloalkyl moiety comprised in said —NH-heterocycloalkyl, the heterocycloalkyl moiety comprised in said —N($C_1$-$C_4$ alkyl)-heterocycloalkyl, the heterocycloalkyl moiety comprised in said —NH—($C_1$-$C_4$ alkylene)-heterocycloalkyl, the heterocycloalkyl moiety comprised in said —N($C_1$-$C_4$ alkyl)-($C_1$-$C_4$ alkylene)-heterocycloalkyl, the heterocycloalkyl moiety comprised in said —CO-heterocycloalkyl, or the heterocycloalkyl moiety comprised in said —CO—($C_1$-$C_4$ alkylene)-heterocycloalkyl) are each optionally substituted with one or more groups (e.g., one, two or three groups) independently selected from $C_1$-$C_4$ alkyl, halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl). Yet even more preferably, $R^5$ is pyridinyl (particularly pyridin-4-yl) which is optionally substituted with one or more substituent groups (preferably one or two substituent groups; more preferably one substituent group) independently selected from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, —O($C_1$-$C_4$ alkyl), —O-cycloalkyl, or —O-heterocycloalkyl, wherein it is furthermore preferred that said substituent group(s) is/are selected independently from methyl, vinyl, propenyl (e.g., propen-2-yl), —F, —Cl, —CF$_3$, —O—CH$_2$—CF$_3$, —CN, cyclopropyl, or pyrrolidinyl (e.g., pyrrolidin-1-yl). Still more preferably, $R^5$ is pyridin-4-yl which is substituted with one substituent group at position 2 of said pyridin-4-yl or with two substituent groups at position 2 and 6 of said pyridin-4-yl, wherein said one or two substituent group(s) is/are selected independently from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, —O($C_1$-$C_4$ alkyl), —O-cycloalkyl, or —O-heterocycloalkyl, and wherein it is furthermore preferred that said one or two substituent group(s) is/are selected independently from methyl, vinyl, propenyl (e.g., propen-2-yl), —F, —Cl, —CF$_3$, —O—CH$_2$—CF$_3$, —CN, cyclopropyl, or pyrrolidinyl (e.g., pyrrolidin-1-yl). Most preferably, $R^5$ is pyridin-4-yl which is substituted with one substituent group at position 2 of said pyridin-4-yl, wherein said substituent group is selected from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, —O($C_1$-$C_4$ alkyl), —O-cycloalkyl, or —O-heterocycloalkyl, preferably said substituent group is selected from methyl, vinyl, propenyl (e.g., propen-2-yl), —F, —Cl, —CF$_3$, —O—CH$_2$—CF$_3$, —CN, cyclopropyl, or pyrrolidinyl (e.g., pyrrolidin-1-yl), more preferably said substituent group is —CF$_3$ or vinyl, and even more preferably said substituent group is —CF$_3$. Accordingly, it is most preferred that $R^5$ is 2-trifluoromethyl-pyridin-4-yl.

$R^6$ is selected from $C_1$-$C_4$ alkyl, cycloalkyl (e.g., cyclopropyl), or heterocycloalkyl, wherein said $C_1$-$C_4$ alkyl is optionally substituted with one or more groups (e.g., one, two or three groups) independently selected from cycloalkyl (e.g., cyclopropyl), halogen, —CF$_3$, —CN, —OH or —O($C_1$-$C_4$ alkyl), and further wherein, if $R^6$ is cycloalkyl or heterocycloalkyl, then said cycloalkyl and said heterocycloalkyl are each optionally substituted with one or more groups (e.g., one, two or three groups) independently selected from $C_1$-$C_4$ alkyl, cycloalkyl, halogen, —CF$_3$, —CN, —OH or —O($C_1$-$C_4$ alkyl).

Preferably, $R^6$ is $C_1$-$C_4$ alkyl which is optionally substituted with one or more groups (e.g., one, two or three groups) independently selected from cycloalkyl, halogen, —CF$_3$, —CN, —OH or —O($C_1$-$C_4$ alkyl). More preferably, $R^6$ is $C_1$-$C_4$ alkyl which is optionally substituted with one or more fluoro atoms (such as, e.g., —($C_1$-$C_3$ alkylene)-CF$_3$ or —($C_1$-$C_3$ alkylene)-CHF$_2$). Even more preferably, $R^6$ is $C_1$-$C_4$ alkyl, and yet even more preferably $R^6$ is methyl (e.g., deuterium-enriched methyl, —CD$_3$; or —C($^1$H)$_3$) or ethyl. Most preferably, $R^6$ is methyl.

Each $R^7$, $R^8$ and $R^9$ is independently selected from hydrogen, $C_1$-$C_4$ alkyl, $C_2$-$C_4$ alkenyl, cycloalkyl, cycloalkenyl, heterocycloalkyl, heterocycloalkenyl, aryl or heteroaryl, wherein said $C_1$-$C_4$ alkyl and said $C_2$-$C_4$ alkenyl are each optionally substituted with one or more groups (e.g., one, two or three groups) independently selected from halogen, —CF$_3$, —CN, cycloalkyl, cycloalkenyl, heterocycloalkyl, heterocycloalkenyl, aryl, heteroaryl, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein, if $R^7$, $R^8$ or $R^9$ is cycloalkyl, cycloalkenyl, heterocycloalkyl, heterocycloalkenyl, aryl or heteroaryl, then said cycloalkyl, said cycloalkenyl, said heterocycloalkyl, said heterocycloalkenyl, said aryl and said heteroaryl are each optionally substituted with one or more groups (e.g., one, two or three groups) independently selected from: $C_1$-$C_4$ alkyl; halogen; —CF$_3$; —CN; —OH; —O($C_1$-$C_4$ alkyl); $C_1$-$C_4$ alkyl substituted with one or more (e.g., one, two or three) —OH groups (such as, e.g., —(CH$_2$)$_{1-4}$—OH); —NH$_2$; —NH($C_1$-$C_4$ alkyl); or —N($C_1$-$C_4$ alkyl)($C_1$-$C_4$ alkyl).

The above detailed description of the compounds of formula (I) according to the first and the second aspect of the invention, including in particular the description and definition of the preferred meanings of the groups/variables A, $R^1$, $R^2$ and $R^4$ to $R^9$ also applies to the compounds of formula (I) according to the third aspect of the invention.

In accordance with the third aspect of the invention, the group $R^3$ is selected from hydrogen, —F, —Cl, —I, —CN, —OR$^7$, —NR$^7$R$^8$, —COOR$^7$, —SO$_3$H, —B(OH)$_2$, —CONR$^7$R$^8$, —COR$^7$, —SR$^7$, —SOR$^7$, —SO$_2$R$^7$, —SO$_2$NR$^7$R$^8$, —NR$^7$COR$^8$, —NR$^7$SO$_2$R$^8$, —OCOR$^7$, —NR$^7$C(O)NR$^8$R$^9$, —NR$^7$C(S)NR$^8$R$^9$, —NR$^7$COOR$^8$, $C_1$-$C_4$ alkyl, $C_2$-$C_4$ alkenyl, cycloalkyl or heterocycloalkyl, wherein said $C_1$-$C_4$ alkyl and said $C_2$-$C_4$ alkenyl are each optionally substituted with one or more groups independently selected from halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more groups independently selected from: $C_1$-$C_4$ alkyl; halogen; —CF$_3$; —CN; —OH; —O($C_1$-$C_4$ alkyl); $C_1$-$C_4$ alkyl substituted with one or more —OH groups; —NH$_2$; —NH($C_1$-$C_4$ alkyl); or —N($C_1$-$C_4$ alkyl)($C_1$-$C_4$ alkyl).

In this third aspect, $R^3$ is preferably selected from hydrogen, —F, —Cl, —I, —CN, —OR$^7$, —NR$^7$R$^8$, —COOR$^7$, —CONR$^7$R$^8$, —COR$^7$, —NR$^7$COR$^8$, $C_1$-$C_4$ alkyl, $C_2$-$C_4$ alkenyl, cycloalkyl or heterocycloalkyl, wherein said $C_1$-$C_4$ alkyl and said $C_2$-$C_4$ alkenyl are each optionally substituted with one or more (e.g., one, two or three groups) independently selected from halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more (e.g., one, two or three groups) independently selected from: $C_1$-$C_4$ alkyl; halogen; —CF$_3$; —CN; —OH; —O($C_1$-$C_4$ alkyl); $C_1$-$C_4$ alkyl substituted with one or more —OH groups; —NH$_2$; —NH($C_1$-$C_4$ alkyl); or —N($C_1$-$C_4$ alkyl)($C_1$-$C_4$ alkyl). More preferably, $R^3$ is selected from hydrogen, —F, —Cl, —I, $C_1$-$C_4$ haloalkyl (e.g., —CF$_3$), $C_1$-$C_4$ haloalkoxy (e.g., —OCF$_3$), —CN, $C_1$-$C_4$ alkyl, $C_2$-$C_4$ alkenyl, cycloalkyl, heterocycloalkyl, —OH, —O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, —CO—($C_1$-$C_4$ alkylene)-heterocycloalkyl, —CO—NH$_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH—($C_1$-$C_4$ alkylene)-cycloalkyl, —CO—N($C_1$-$C_4$ alkyl)-($C_1$-$C_4$ alkylene)-cycloalkyl, —CO—NH-heterocycloalkyl, —CO—N($C_1$-$C_4$ alkyl)-heterocycloalkyl, —CO—NH—($C_1$-$C_4$ alkylene)-heterocycloalkyl, —CO—N($C_1$-$C_4$ alkyl)-($C_1$-$C_4$ alkylene)-heterocycloalkyl, —NH—CO-cycloalkyl, —N($C_1$-$C_4$ alkyl)-CO-cycloalkyl, —NH—CO—($C_1$-$C_4$ alkylene)-cycloalkyl, —N($C_1$-$C_4$ alkyl)-CO—($C_1$-$C_4$ alkylene)-cycloalkyl, —NH—CO-heterocycloalkyl, —N($C_1$-$C_4$ alkyl)-CO-heterocycloalkyl, —NH—CO—($C_1$-$C_4$ alkylene)-heterocycloalkyl, —N($C_1$-$C_4$ alkyl)-CO—($C_1$-$C_4$ alkylene)-heterocycloalkyl, or —COOH, wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups (e.g., one, two or three groups) independently selected from: $C_1$-$C_4$ alkyl; halogen; —CF$_3$; —CN; —OH; —O($C_1$-$C_4$ alkyl); $C_1$-$C_4$ alkyl substituted with one or more —OH groups; —NH$_2$; —NH($C_1$-$C_4$ alkyl); or —N($C_1$-$C_4$ alkyl)($C_1$-$C_4$ alkyl). Even more preferably, $R^3$ is selected from hydrogen, —F, —Cl, —I, $C_1$-$C_4$ haloalkyl, $C_1$-$C_4$ haloalkoxy, —CN, $C_1$-$C_4$ alkyl, cycloalkyl, heterocycloalkyl, —OH, —O($C_1$-$C_4$ alkyl), —O-cycloalkyl, —O-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —CO-cycloalkyl, —CO-heterocycloalkyl, —CO—NH$_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH-heterocycloalkyl, —CO—N($C_1$-$C_4$ alkyl)-heterocycloalkyl, —NH—CO-cycloalkyl, —N($C_1$-$C_4$ alkyl)-CO-cycloalkyl, —NH—CO-heterocycloalkyl, or —N($C_1$-$C_4$ alkyl)-CO-heterocycloalkyl, wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups (e.g., one, two or three groups) independently selected from: $C_1$-$C_4$ alkyl; halogen; —CF$_3$; —CN; —OH; —O($C_1$-$C_4$ alkyl); $C_1$-$C_4$ alkyl substituted with one or more —OH groups; —NH$_2$; —NH($C_1$-$C_4$ alkyl); or —N($C_1$-$C_4$ alkyl)($C_1$-$C_4$ alkyl). Even more preferably, $R^3$ is selected from hydrogen, —F, —Cl, $C_1$-$C_4$ haloalkyl, $C_1$-$C_4$ haloalkoxy, —CN, $C_1$-$C_4$ alkyl, cycloalkyl, heterocycloalkyl, —OH, —O($C_1$-$C_4$ alkyl), —O-cycloalkyl, —O-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —CO-cycloalkyl, —CO-heterocycloalkyl, —CO—NH$_2$, —CO—NH($C_1$-$C_4$ alkyl), or —CO—N($C_1$-$C_4$ alkyl)($C_1$-$C_4$ alkyl), wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups (e.g., one, two or three groups) independently selected from: $C_1$-$C_4$ alkyl; halogen; —CF$_3$; —CN; —OH; —O($C_1$-$C_4$ alkyl); $C_1$-$C_4$ alkyl substituted with one or more —OH groups; —NH$_2$; —NH($C_1$-$C_4$ alkyl); or —N($C_1$-$C_4$ alkyl)($C_1$-$C_4$ alkyl). Even more preferably, $R^3$ is selected from hydrogen, —F, —Cl, $C_1$-$C_4$ haloalkyl (e.g., —CF$_3$), —CN, heterocycloalkyl (e.g., azetidinyl, pyrrolidinyl, piperidinyl, piperazinyl, or morpholinyl), —O($C_1$-$C_4$ alkyl), —NH($C_1$-$C_4$ alkyl), or —CO—N($C_1$-$C_4$ alkyl)($C_1$-$C_4$ alkyl), wherein said heterocycloalkyl is optionally substituted with one or more groups (e.g., one or two groups) independently selected from: $C_1$-$C_4$ alkyl; halogen; —CF$_3$; —CN; —OH; —O($C_1$-$C_4$ alkyl); $C_1$-$C_4$ alkyl substituted with one or more —OH groups (e.g., —(CH$_2$)$_{1-4}$-OH); —NH$_2$; —NH($C_1$-$C_4$ alkyl); or —N($C_1$-$C_4$ alkyl)($C_1$-$C_4$ alkyl). Yet even more preferably, $R^3$ is selected from hydrogen, —F, —Cl, —CF$_3$, —CN, 3-hydroxyazetidin-1-yl, 4-hydroxypiperidin-1-yl, morpholin-4-yl, —OCH$_3$, —NHCH$_3$, —CO—N(CH$_3$)$_2$, or —CO—N(CH$_2$CH$_3$)$_2$. Most preferably, $R^3$ is hydrogen.

It is particularly preferred that the compound of formula (I) according to the first, second or third aspect of the invention is selected from:

2-(2-chloro-pyridin-4-yl)-4-methyl-4H-pyrazolo[1,5-a]qui-nazolin-5-one;
4-methyl 2-(2-methyl-pyridin-4-yl)-4H-pyrazolo[1,5-a]qui-nazolin-5-one;
2-(2-ethyl-pyridin-4-yl)-4-methyl-4H-pyrazolo[1,5-a]qui-nazolin-5-one;
2-(2-propyl-pyridin-4-yl)-4-methyl-4H-pyrazolo[1,5-a]qui-nazolin-5-one;
2-(2-cyclopropyl-pyridin-4-yl)-4-methyl-4H-pyrazolo[1,5-a]quinazolin-5-one;
2-(2-cyclobutyl-pyridin-4-yl)-4-methyl-4H-pyrazolo[1,5-a]quinazolin-5-one;
2-(2-cyclopentyl-pyridin-4-yl)-4-methyl-4H-pyrazolo[1,5-a]quinazolin-5-one;
2-(2-cyclohexyl-pyridin-4-yl)-4-methyl-4H-pyrazolo[1,5-a]quinazolin-5-one;
4-methyl-2-(2-vinyl-pyridin-4-yl)-4H-pyrazolo[1,5-a]qui-nazolin-5-one;
2-(2-isopropenyl-pyridin-4-yl)-4-methyl-4H-pyrazolo[1,5-a]quinazolin-5-one;
2-(2-isopropyl-pyridin-4-yl)-4-methyl-4H-pyrazolo[1,5-a]quinazolin-5-one;
4-(4-methyl-5-oxo-4,5-dihydro-pyrazolo[1,5-a]quinazolin-2-yl)-pyridine-2-carbonitrile;
2-(2-fluoro-pyridin-4-yl)-4-methyl-4H-pyrazolo[1,5-a]qui-nazolin-5-one;
2-(2-methoxy-pyridin-4-yl)-4-methyl-4H-pyrazolo[1,5-a]quinazolin-5-one;
2-(2-ethoxy-pyridin-4-yl)-4-methyl-4H-pyrazolo[1,5-a]qui-nazolin-5-one;
2-(2-isopropoxy-pyridin-4-yl)-4-methyl-4H-pyrazolo[1,5-a]quinazolin-5-one;
2-(2-cyclobutoxy-pyridin-4-yl)-4-methyl-4H-pyrazolo[1,5-a]quinazolin-5-one;
4-methyl-2-[2-(oxetan-3-yloxy)-pyridin-4-yl]-4H-pyrazolo[1,5-a]quinazolin-5-one;
2-(2-cyclopropylmethoxy-pyridin-4-yl)-4-methyl-4H-pyra-zolo[1,5-a]quinazolin-5-one;
2-[2-(2-methoxy-ethoxy)-pyridin-4-yl]-4-methyl-4H-pyra-zolo[1,5-a]quinazolin-5-one;
4-methyl-2-[2-(2,2,2-trifluoro-ethoxy)-pyridin-4-yl]-4H-pyrazolo[1,5-a]quinazolin-5-one;
4-methyl-2-[2-(2,2-difluoro-ethoxy)-pyridin-4-yl]-4H-pyra-zolo[1,5-a]quinazolin-5-one;
2-[2-(2,2-difluoro-propoxy)-pyridin-4-yl]-4-methyl-4H-pyrazolo[1,5-a]quinazolin-5-one;
4-methyl-2-[2-(2,2,3,3,3-pentafluoro-propoxy)-pyridin-4-yl]-4H-pyrazolo[1,5-a]quinazolin-5-one;
4-methyl-2-[2-(2,2,2-trifluoro-1-trifluoromethyl-ethoxy)-pyridin-4-yl]-4H-pyrazolo[1,5-a]quinazolin-5-one;
4-methyl-2-(2-trifluoromethyl-pyridin-4-yl)-4H-pyrazolo[1,5-a]quinazolin-5-one;
4-methyl($D_3$)-2-(2-trifluoromethyl-pyridin-4-yl)-4H-pyra-zolo[1,5-a]quinazolin-5-one;
4-ethyl-2-(2-trifluoromethyl-pyridin-4-yl)-4H-pyrazolo[1,5-a]quinazolin-5-one;
4-(2,2-difluoro-ethyl)-2-(2-trifluoromethyl-pyridin-4-yl)-4H-pyrazolo[1,5-a]quinazolin-5-one;
4-(2-methoxy-ethyl)-2-(2-trifluoromethyl-pyridin-4-yl)-4H-pyrazolo[1,5-a]quinazolin-5-one;
4-methyl-2-(2-difluoromethyl-pyridin-4-yl)-4H-pyrazolo[1,5-a]quinazolin-5-one;
2-[2-(1,1-difluoro-ethyl)-pyridin-4-yl]-4-methyl-4H-pyra-zolo[1,5-a]quinazolin-5-one;
2-[2-(1,1-difluoro-ethyl)-pyridin-4-yl]-4-methyl(D$_3$)-4H-pyrazolo[1,5-a]quinazolin-5-one;
7-methyl-2-(2-trifluoromethyl-pyridin-4-yl)-4H-pyrazolo[1,5-a]quinazolin-5-one;
7-chloro-2-(2-trifluoromethyl-pyridin-4-yl)-4H-pyrazolo[1,5-a]quinazolin-5-one;
7-methoxy-2-(2-trifluoromethyl-pyridin-4-yl)-4H-pyrazolo[1,5-a]quinazolin-5-one;
7-trifluoromethyl-2-(2-trifluoromethyl-pyridin-4-yl)-4H-pyrazolo[1,5-a]quinazolin-5-one;
7-fluoro-2-(2-trifluoromethyl-pyridin-4-yl)-4H-pyrazolo[1,5-a]quinazolin-5-one;
7-bromo-2-(2-trifluoromethyl-pyridin-4-yl)-4H-pyrazolo[1,5-a]quinazolin-5-one;
4-methyl-7-methylamino-2-(2-trifluoromethyl-pyridin-4-yl)-4H-pyrazolo[1,5-a]quinazolin-5-one;
4-methyl-7-methyl(D3)amino-2-(2-trifluoromethyl-pyridin-4-yl)-4H-pyrazolo[1,5-a]quinazolin-5-one;
N-[4-methyl-5-oxo-2-(2-trifluoromethyl-pyridin-4-yl)-4,5-dihydro-pyrazolo[1,5-a]quinazolin-7-yl]-acetamide;
7-amino-4-methyl-2-(2-trifluoromethyl-pyridin-4-yl)-4H-pyrazolo[1,5-a]quinazolin-5-one;
7-dimethylamino-4-methyl-2-(2-trifluoromethyl-pyridin-4-yl)-4H-pyrazolo[1,5-a]quinazolin-5-one;
7-ethylamino-4-methyl-2-(2-trifluoromethyl-pyridin-4-yl)-4H-pyrazolo[1,5-a]quinazolin-5-one;
7-cyclobutylamino-4-methyl-2-(2-trifluoromethyl-pyridin-4-yl)-4H-pyrazolo[1,5-a]quinazolin-5-one;
4-methyl-7-morpholin-4-yl-2-(2-trifluoromethyl-pyridin-4-yl)-4H-pyrazolo[1,5-a]quinazolin-5-one;
7-hydroxy-4-methyl-2-(2-trifluoromethyl-pyridin-4-yl)-4H-pyrazolo[1,5-a]quinazolin-5-one;
7-ethoxy-4-methyl-2-(2-trifluoromethyl-pyridin-4-yl)-4H-pyrazolo[1,5-a]quinazolin-5-one;
7-(2-methoxy-ethoxy)-4-methyl-2-(2-trifluoromethyl-pyri-din-4-yl)-4H-pyrazolo[1,5-a]quinazolin-5-one;
4-methyl-7-(2-morpholin-4-yl-ethoxy)-2-(2-trifluorom-ethyl-pyridin-4-yl)-4H-pyrazolo[1,5-a]quinazolin-5-one;
4-methyl-7-trifluoromethoxy-2-(2-trifluoromethyl-pyridin-4-yl)-4H-pyrazolo[1,5-a]quinazolin-5-one;
7-methanesulfonyl-4-methyl-2-(2-trifluoromethyl-pyridin-4-yl)-4H-pyrazolo[1,5-a]quinazolin-5-one;
8-methoxy-4-methyl-2-(2-trifluoromethyl-pyridin-4-yl)-4H-pyrazolo[1,5-a]quinazolin-5-one;
8-fluoro-4-methyl-2-(2-trifluoromethyl-pyridin-4-yl)-4H-pyrazolo[1,5-a]quinazolin-5-one;
8-chloro-4-methyl-2-(2-trifluoromethyl-pyridin-4-yl)-4H-pyrazolo[1,5-a]quinazolin-5-one;
4-methyl-8-trifluoromethyl-2-(2-trifluoromethyl-pyridin-4-yl)-4H-pyrazolo[1,5-a]quinazolin-5-one;
8-bromo-4-methyl-2-(2-trifluoromethyl-pyridin-4-yl)-4H-pyrazolo[1,5-a]quinazolin-5-one;
4-methyl-8-morpholin-4-yl-2-(2-trifluoromethyl-pyridin-4-yl)-4H-pyrazolo[1,5-a]quinazolin-5-one;
4-methyl-8-pyrrolidin-1-yl-2-(2-trifluoromethyl-pyridin-4-yl)-4H-pyrazolo[1,5-a]quinazolin-5-one;
4-methyl-8-methylamino-2-(2-trifluoromethyl-pyridin-4-yl)-4H-pyrazolo[1,5-a]quinazolin-5-one;
8-(4-methoxy-piperidin-1-yl)-4-methyl-2-(2-trifluorom-ethyl-pyridin-4-yl)-4H-pyrazolo[1,5-a]quinazolin-5-one;
8-(4-hydroxy-piperidin-1-yl)-4-methyl-2-(2-trifluorom-ethyl-pyridin-4-yl)-4H-pyrazolo[1,5-a]quinazolin-5-one;
8-dimethylamino-4-methyl-2-(2-trifluoromethyl-pyridin-4-yl)-4H-pyrazolo[1,5-a]quinazolin-5-one;
4-methyl-8-(4-methyl-piperazin-1-yl)-2-(2-trifluoromethyl-pyridin-4-yl)-4H-pyrazolo[1,5-a]quinazolin-5-one;
4-methyl-8-piperazin-1-yl-2-(2-trifluoromethyl-pyridin-4-yl)-4H-pyrazolo[1,5-a]quinazolin-5-one;

8-(4-hydroxymethyl-piperidin-1-yl)-4-methyl-2-(2-trifluoromethyl-pyridin-4-yl)-4H-pyrazolo[1,5-a]quinazoin-5-one;
8-(3-hydroxy-azetidin-1-yl)-4-methyl-2-(2-trifluoromethyl-pyridin-4-yl)-4H-pyrazolo[1,5-a]quinazolin-5-one;
8-(3-hydroxymethyl-azetidin-1-yl)-4-methyl-2-(2-trifluoromethyl-pyridin-4-yl)-4H-pyrazolo[1,5-a]quinazolin-5-one;
8-(3-hydroxy-pyrrolidin-1-yl)-4-methyl-2-(2-trifluoromethyl-pyridin-4-yl)-4H-pyrazolo[1,5-a]quinazolin-5-one;
8-(4-hydroxy-4-methyl-piperidin-1-yl)-4-methyl-2-(2-trifluoromethyl-pyridin-4-yl)-4H-pyrazolo[1,5-a]quinazolin-5-one;
4,8-dimethyl-2-(2-trifluoromethyl-pyridin-4-yl)-4H-pyrazolo[1,5-a]quinazolin-5-one;
8-cyclopropyl-4-methyl-2-(2-trifluoromethyl-pyridin-4-yl)-4H-pyrazolo[1,5-a]quinazolin-5-one;
8-cyclopentyl-4-methyl-2-(2-trifluoromethyl-pyridin-4-yl)-4H-pyrazolo[1,5-a]quinazolin-5-one;
4-methyl-5-oxo-2-(2-trifluoromethyl-pyridin-4-yl)-4,5-dihydro-pyrazolo[1,5-a]quinazoline-8-carbonitrile;
4-methyl-5-oxo-2-(2-trifluoromethyl-pyridin-4-yl)-4,5-dihydro-pyrazolo[1,5-a]quinazoline-8-carboxylic acid;
4-methyl-5-oxo-2-(2-trifluoromethyl-pyridin-4-yl)-4,5-dihydro-pyrazolo[1,5-a]quinazoline-8-carboxylic acid amide;
4-methyl-5-oxo-2-(2-trifluoromethyl-pyridin-4-yl)-4,5-dihydro-pyrazolo[1,5-a]quinazoline-8-carboxylic acid methylamide;
4-methyl-5-oxo-2-(2-trifluoromethyl-pyridin-4-yl)-4,5-dihydro-pyrazolo[1,5-a]quinazoline-8-carboxylic acid dimethylamide;
4-methyl-5-oxo-2-(2-trifluoromethyl-pyridin-4-yl)-4,5-dihydro-pyrazolo[1,5-a]quinazoline-8-carboxylic acid diethylamide;
4-methyl-8-(morpholine-4-carbonyl)-2-(2-trifluoromethyl-pyridin-4-yl)-4H-pyrazolo[1,5-a]quinazolin-5-one;
4-methyl-8-(pyrrolidine-1-carbonyl)-2-(2-trifluoromethyl-pyridin-4-yl)-4H-pyrazolo[1,5-a]quinazolin-5-one;
8-(2-hydroxy-ethoxy)-4-methyl-2-(2-trifluoromethyl-pyridin-4-yl)-4H-pyrazolo[1,5-a]quinazolin-5-one;
4-methyl-6-trifluoromethyl-2-(2-trifluoromethyl-pyridin-4-yl)-4H-pyrazolo[1,5-a]quinazolin-5-one;
6-fluoro-4-methyl-2-(2-trifluoromethyl-pyridin-4-yl)-4H-pyrazolo[1,5-a]quinazolin-5-one;
9-methoxy-4-methyl-2-(2-trifluoromethyl-pyridin-4-yl)-4H-pyrazolo[1,5-a]quinazolin-5-one;
7,8-dimethoxy-4-methyl-2-(2-trifluoromethyl-pyridin-4-yl)-4H-pyrazolo[1,5-a]quinazolin-5-one;
7,8-difluoro-4-methyl-2-(2-trifluoromethyl-pyridin-4-yl)-4H-pyrazolo[1,5-a]quinazolin-5-one;
8-fluoro-7-methoxy-4-methyl-2-(2-trifluoromethyl-pyridin-4-yl)-4H-pyrazolo[1,5-a]quinazolin-5-one;
8-(4-hydroxy-piperidin-1-yl)-7-methoxy-4-methyl-2-(2-trifluoromethyl-pyridin-4-yl)-4H-pyrazolo[1,5-a]quinazolin-5-one;
8-dimethylamino-7-fluoro-4-methyl-2-(2-trifluoromethyl-pyridin-4-yl)-4H-pyrazolo[1,5-a]quinazolin-5-one;
7-bromo-8-fluoro-4-methyl-2-(2-trifluoromethyl-pyridin-4-yl)-4H-pyrazolo[1,5-a]quinazolin-5-one;
7-bromo-8-methoxy-4-methyl-2-(2-trifluoromethyl-pyridin-4-yl)-4H-pyrazolo[1,5-a]quinazolin-5-one;
8-methoxy-4-methyl-7-methylamino-2-(2-trifluoromethyl-pyridin-4-yl)-4H-pyrazolo[1,5-a]quinazolin-5-one;
7-chloro-2-(2-chloro-pyridin-4-yl)-4-methyl-4H-pyrazolo[1,5-a]quinazolin-5-one;
7-chloro-2-(2-chloro-pyridin-4-yl)-4-methyl-4H-pyrazolo[1,5-a]quinazolin-5-one;
7-chloro-2-(2-Fluoro-pyridin-4-yl)-4-methyl-4H-pyrazolo[1,5-a]quinazolin-5-one;
7-chloro-4-methyl-2-[2-(2,2,2-trifluoro-ethoxy)-pyridin-4-yl]-4H-pyrazolo[1,5-a]quinazolin-5-one;
2-(2-chloro-pyridin-4-yl)-7-methoxy-4-methyl-4H-pyrazolo[1,5-a]quinazolin-5-one;
2-(2-cyclopropyl-pyridin-4-yl)-7-methoxy-4-methyl-4H-pyrazolo[1,5-a]quinazolin-5-one;
2-(2-fluoro-pyridin-4-yl)-7-methoxy-4-methyl-4H-pyrazolo[1,5-a]quinazolin-5-one;
7-methoxy-4-methyl-2-[2-(2,2,2-trifluoro-ethoxy)-pyridin-4-yl]-4H-pyrazolo[1,5-a]quinazolin-5-one;
4-methyl-2-(1-methyl-1H-pyrazol-4-yl)-4H-pyrazolo[1,5-a]quinazolin-5-one;
4-methyl-2-pyridin-4-yl-4H-pyrazolo[1,5-a]quinazolin-5-one;
2-(2-chloro-6-methyl-pyridin-4-yl)-4-methyl-4H-pyrazolo[1,5-a]quinazolin-5-one;
2-(2-cyclopropyl-6-methyl-pyridin-4-yl)-4-methyl-4H-pyrazolo[1,5-a]quinazolin-5-one;
2-(3-fluoro-pyridin-4-yl)-4-methyl-4H-pyrazolo[1,5-a]quinazolin-5-one;
2-(3-chloro-pyridin-4-yl)-4-methyl-4H-pyrazolo[1,5-a]quinazolin-5-one;
4-methyl-2-(3-methyl-pyridin-4-yl)-4H-pyrazolo[1,5-a]quinazolin-5-one;
8-(3-Hydroxy-azetidine-1-carbonyl)-4-methyl-2-(2-trifluoromethyl-pyridin-4-yl)-4H-pyrazolo[1,5-a]quinazolin-5-one;
8-(3-Hydroxy-propoxy)-4-methyl-2-(2-trifluoromethyl-pyridin-4-yl)-4H-pyrazolo[1,5-a]quinazolin-5-one;
2-(2-Cyclopropyl-pyridin-4-yl)-8-fluoro-4-methyl-4H-pyrazolo[1,5-a]quinazolin-5-one;
2-(2-Cyclopropyl-pyridin-4-yl)-8-(4-hydroxy-piperidin-1-yl)-4-methyl-4H-pyrazolo[1,5-a]quinazolin-5-one;
2-(2-Difluoromethyl-pyridin-4-yl)-8-fluoro-4-methyl-4H-pyrazolo[1,5-a]quinazolin-5-one;
2-(2-Difluoromethyl-pyridin-4-yl)-8-(4-hydroxy-piperidin-1-yl)-4-methyl-4H-pyrazolo[1,5-a]quinazolin-5-one;
2-(2-Cyclobutyl-pyridin-4-yl)-8-fluoro-4-methyl-4H-pyrazolo[1,5-a]quinazolin-5-one;
2-(2-Chloro-pyridin-4-yl)-8-fluoro-4-methyl-4H-pyrazolo[1,5-a]quinazolin-5-one;
2-(2-Chloro-pyridin-4-yl)-8-(4-hydroxy-piperidin-1-yl)-4-methyl-4H-pyrazolo[1,5-a]quinazolin-5-one;
7-Fluoro-8-(3-hydroxy-azetidin-1-yl)-4-methyl-2-(2-trifluoromethyl-pyridin-4-yl)-4H-pyrazolo[1,5-a]quinazolin-5-one;
7-Fluoro-4-methyl-8-(oxetan-3-yloxy)-2-(2-trifluoromethyl-pyridin-4-yl)-4H-pyrazolo[1,5-a]quinazolin-5-one;
3-[7-Fluoro-4-methyl-5-oxo-2-(2-trifluoromethyl-pyridin-4-yl)-4,5-dihydro-pyrazolo[1,5-a]quinazolin-8-ylamino]-propionitrile;
7-Fluoro-8-(2-hydroxymethyl-pyrrolidin-1-yl)-4-methyl-2-(2-trifluoromethyl-pyridin-4-yl)-4H-pyrazolo[1,5-a]quinazolin-5-one;
7-Fluoro-8-(7-hydroxymethyl-1-aza-spiro[3.5]non-1-yl)-4-methyl-2-(2-trifluoromethyl-pyridin-4-yl)-4H-pyrazolo[1,5-a]quinazolin-5-one;
8-(3-Hydroxy-piperidin-1-yl)-4-methyl-2-(2-trifluoromethyl-pyridin-4-yl)-4H-pyrazolo[1,5-a]quinazolin-5-one;
8-(2,6-Dimethyl-morpholin-4-yl)-4-methyl-2-(2-trifluoromethyl-pyridin-4-yl)-4H-pyrazolo[1,5-a]quinazolin-5-one;

8-(2-Hydroxy-2-methyl-propylamino)-4-methyl-2-(2-trifluoromethyl-pyridin-4-yl)-4H-pyrazolo[1,5-a]quinazolin-5-one; and pharmaceutically acceptable salts, solvates and prodrugs of any one of the aforementioned compounds.

In the following, where reference is made to the compounds of the general formula (I), this is intended to refer to the compounds of formula (I) according to the first, second and/or third aspect of the invention.

Compounds of the general formula (I) may exist in the form of different isomers, in particular stereoisomers (including geometric isomers (or cis-trans isomers), enantiomers and diastereomers) or tautomers. All such isomers of the compounds according to the invention are contemplated as being part of the present invention, either in admixture or in pure or substantially pure form. As for stereoisomers, the invention embraces mixtures (such as racemic forms) and the isolated optical isomers of the compounds according to the invention. The racemic forms can be resolved by physical methods, such as, e.g., fractional crystallization, separation or crystallization of diastereomeric derivatives or separation by chiral column chromatography.

The scope of the invention also embraces compounds of the general formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^2$H; also referred to as "D"). Accordingly, the invention also embraces compounds of formula (I) which are enriched in deuterium. Naturally occurring hydrogen is an isotopic mixture comprising about 99.98 mol-% hydrogen-1 ($^1$H) and about 0.0156 mol-% deuterium ($^2$H or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water ($D_2O$). Further suitable deuteration techniques are described in: Atzrodt J et al., *Bioorg Med Chem*, 20(18), 5658-5667, 2012; William J S et al., *Journal of Labelled Compounds and Radiopharmaceuticals*, 53(11-12), 635-644, 2010; Modvig A et al., *J Org Chem*, 79, 5861-5868, 2014. The content of deuterium can be determined, e.g., using mass spectrometry or NMR spectroscopy. Unless specifically indicated otherwise, it is preferred that the compound of formula (I) is not enriched in deuterium. Accordingly, the presence of naturally occurring hydrogen atoms or $^1$H hydrogen atoms in the compounds of formula (I) is preferred. The present invention also embraces compounds of formula (I), in which one or more atoms are replaced by a positron-emitting isotope of the corresponding atom, such as, e.g., $^{18}$F, $^{11}$C, $^{13}$N, $^{15}$O, $^{76}$Br, $^{77}$Br, $^{120}$I and/or $^{124}$I. Such compounds can be used as tracers or imaging probes in positron emission tomography (PET). The invention thus includes (i) compounds of formula (I), in which one or more fluorine atoms (or, e.g., all fluorine atoms) are replaced by $^{18}$F atoms, (ii) compounds of formula (I), in which one or more carbon atoms (or, e.g., all carbon atoms) are replaced by $^{11}$C atoms, (iii) compounds of formula (I), in which one or more nitrogen atoms (or, e.g., all nitrogen atoms) are replaced by $^{13}$N atoms, (iv) compounds of formula (I), in which one or more oxygen atoms (or, e.g., all oxygen atoms) are replaced by $^{15}$O atoms, (v) compounds of formula (I), in which one or more bromine atoms (or, e.g., all bromine atoms) are replaced by $^{76}$Br atoms, (vi) compounds of formula (I), in which one or more bromine atoms (or, e.g., all bromine atoms) are replaced by $^{77}$Br atoms, (vii) compounds of formula (I), in which one or more iodine atoms (or, e.g., all iodine atoms) are replaced by $^{120}$I atoms, and (viii) compounds of formula (I), in which one or more iodine atoms (or, e.g., all iodine atoms) are replaced by $^{124}$I atoms. In general, it is preferred that none of the atoms in the compounds of formula (I) are replaced by specific isotopes.

The scope of the invention embraces all pharmaceutically acceptable salt forms of the compounds of the general formula (I) which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention embraces solid forms of the compounds of the general formula (I) in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

Pharmaceutically acceptable prodrugs of compounds of the general formula (I) are derivatives which have chemically or metabolically cleavable groups and become, by solvolysis or under physiological conditions, the compounds of formula (I) which are pharmaceutically active in vivo. Prodrugs of compounds of formula (I) may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound of the general formula (I) has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester or N,N-diethylglycolamidoester. When a compound of formula (I) has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)—C$_3$H$_7$, —OC(=O)-(tert-butyl), —OC(=O)—C$_{15}$H$_{31}$, —OC(=O)—CH$_2$CH$_2$COONa, —O(C=O)—CH(NH$_2$)CH$_3$ or —OC(=O)—CH$_2$—N(CH$_3$)$_2$. When a compound of formula (I) has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

The compounds of general formula (I) or pharmaceutically acceptable salts, solvates or prodrugs thereof, may be administered as compounds per se or may be formulated as medicaments. Within the scope of the present invention are pharmaceutical compositions comprising as an active ingredient one or more compounds of the general formula (I), or pharmaceutically acceptable salts, solvates or prodrugs thereof. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions may also comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds of the general formula (I) or pharmaceutically acceptable salts, solvates or prodrugs thereof, or the above described pharmaceutical compositions, may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e. g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (U.S. Pat. No. 3,773,919), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(–)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; Japanese Pat. Appl. 83-118008; U.S. Pat. Nos. 4,485,045 and 4,544,545; and EP0102324.

Alternatively, said compounds or pharmaceutical compositions can be administered in the form of a suppository or pessary, or may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of the general formula (I) for administration to a human (of approximately 70 kg body weight) may be 0.05 to 2000 mg, preferably 0.1 mg to 1000 mg, of the active ingredient per unit dose. The unit dose may be administered, for example, 1 to 4 times per day. The unit dose may also be administered 1 to 7 times per week, e.g., with not more than one administration per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The subject or patient, such as the subject in need of treatment or prophylaxis, may be an animal (e.g., a non-human animal), a vertebrate animal, a mammal (e.g., a non-human mammal), a rodent (e.g., a guinea pig, a hamster, a rat, a mouse), a murine (e.g., a mouse), a canine (e.g., a dog), a feline (e.g., a cat), an equine (e.g., a horse), a primate, a simian (e.g., a monkey or ape), a monkey (e.g., a marmoset, a baboon), an ape (e.g., a gorilla, chimpanzee, orangutan, gibbon), or a human. In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal. More preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig). Most preferably, the subject/patient is a human.

The term "treatment" of a condition, disorder or disease as used herein is well known in the art. "Treatment" of a condition, disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e. diagnose a disorder or disease).

The treatment of a condition, disorder or disease may, for example, lead to a halt in the progression of the condition, disorder or disease (e.g. no deterioration of symptoms) or a delay in the progression of the disorder or disease (in case the halt in progression is of a transient nature only). Treatment may also lead to a partial response (e.g. amelioration of symptoms) or complete response (e.g. disappearance of symptoms) of the subject/patient suffering from the condition, disorder or disease. Amelioration of a condition, disorder or disease may, for example, lead to a halt in the progression of the disorder or disease or a delay in the progresssion of the disorder or disease. Such a partial or complete response may be followed by a relapse. It is to be understood that a subject/patient may experience a broad range of responses to a treatment (e.g. the exemplary responses as described herein above).

Treatment of a condition, disorder or disease may, inter alia, comprise curative treatment (preferably leading to a complete response and eventually to healing of the disorder or disease) and palliative treatment (including symptomatic relief).

Also the term "prophylaxis" or "prevention" of a condition, disorder or disease as used herein is well known in the art. For example, a patient/subject suspected of being prone to suffer from a condition, disorder or disease as defined herein may, in particular, benefit from a prophylaxis of the disorder or disease. Said subject/patient may have a susceptibility or predisposition for a condition, disorder or disease, including but not limited to hereditary predisposition. Such a predisposition can be determined by standard assays, using, for example, genetic markers or phenotypic indicators. It is to be understood that a condition, disorder or disease to be prevented in accordance with the present invention has not been diagnosed or cannot be diagnosed in said patient/subject (for example, said patient/subject does not show any clinical or pathological symptoms). Thus, the term "prophylaxis" comprises the use of compounds of the present invention before any clinical and/or pathological symptoms are diagnosed or determined or can be diagnosed or determined by the attending physician. The terms "prophylaxis" and "prevention" are used herein interchangeably.

In the method for identifying an agent that binds to group II metabotropic glutamate receptor (mGluR2) described herein above, the test agent may, for example, be selected from nucleic acids, DNA, RNA, PNA, oligonucleotides, aptamers (Gold, Ann. Rev. Biochem. 64 (1995), 763-797)), aptazymes, RNAzymes, ribozymes (see e.g., EP-B1 0 291 533, EP-A1 0 321 201, EP-B1 0 360 257), antisense DNA, antisense oligonucleotides, antisense RNA, siRNA, RNAi, shRNA, amino acids, peptides, polypeptides, proteins, glycoproteins, lipoproteins, nucleoproteins, antibodies (Harlow and Lane "Antibodies, A Laboratory Manual", CSH Press, Cold Spring Harbor, 1988), monocloncal antibodies, polyclonal antibodies, immunoglobulins, affibodies (Hansson, Immunotechnology 4 (1999), 237-252; Henning, Hum Gene Ther. 13 (2000), 1427-1439), immunoreactive fragments, immunoreactive derivatives, antigens, epitopes, haptens, cell-surface molecules, cofactors, ligands, small organic molecules, lectins or derivatives thereof, lectin fragments, trinectins (Phylos Inc., Lexington, Mass., USA; Xu, Chem. Biol. 9 (2002), 933), anticalins (EP-B-1 1 017 814), hormones, peptide and protein hormones, non-peptide hormones, steroids, interleukins, interferons, cytokines, neurotransmitters, toxins, enzymes, polysaccharides, carbohydrates, lipids, lipopolysaccharides, vitamins, crown ethers, cyclodextrins, cryptands, calixarenes, aldehydes, thiols, amines, drugs, drugs of abuse, therapeutic agents, medicaments, pharmaceuticals, substrates, fragments, portions, components or products of microorganisms, metabolites of or antibodies to any of the above substances and the like.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in the general formula (I).

As used herein, "alkyl" represents a straight or branched chain saturated acyclic hydrocarbon residue (i.e., a group consisting of carbon atoms and hydrogen atoms) which does not comprise any carbon-to-carbon double bonds or carbon-to-carbon triple bonds. As exemplary groups, methyl, ethyl, propyl and butyl are mentioned.

As used herein, "alkenyl" represents a straight or branched chain unsaturated acyclic hydrocarbon residue comprising one or more than one (such as two or three) carbon-to-carbon double bond(s) which does not comprise any carbon-to-carbon triple bonds.

As used herein, "alkylene" represents a straight or branched chain alkanediyl group which does not comprise any carbon-to-carbon double bonds or carbon-to-carbon triple bonds.

As used herein, "aryl" represents an aromatic hydrocarbon ring group, including monocyclic aromatic rings as well as fused ring systems containing at least one aromatic ring (e.g., ring systems composed of two or three fused rings, wherein at least one of these fused rings is aromatic). "Aryl" may, for example, refer to phenyl or naphthyl. Unless defined otherwise, an "aryl" preferably has 6 to 10 ring members, and most preferably refers to phenyl.

As used herein, "heteroaryl" represents an aromatic ring group, including monocyclic aromatic rings as well as fused ring systems containing at least one aromatic ring (e.g., ring systems composed of two or three fused rings, wherein at least one of these fused rings is aromatic), wherein said aromatic ring group comprises one or more (such as, e.g., one, two, three, or four) ring heteroatoms independently selected from O, S, or N, wherein one or more S ring atoms (if present) and/or one or more N ring atoms (if present) may optionally be oxidized. "Heteroaryl" may, for example, refer to thienyl (thiophenyl), benzo[b]thienyl, naphtho[2,3-b]thienyl, thianthrenyl, furyl (furanyl), isobenzofuranyl, chromenyl, xanthenyl, phenoxathiinyl, pyrrolyl (including, without limitation, 2H-pyrrolyl), imidazolyl, pyrazolyl, pyridyl (pyridinyl; including, without limitation, 2-pyridyl, 3-pyridyl, and 4-pyridyl), pyrazinyl, pyrimidinyl, pyridazinyl, indolizinyl, isoindolyl, indolyl (including, without limitation, 3H-indolyl), indazolyl, purinyl, isoquinolyl, quinolyl, phthalazinyl, naphthyridinyl, quinoxalinyl, cinnolinyl, pteridinyl, carbazolyl, beta-carbolinyl, phenanthridinyl, acridinyl, perimidinyl, phenanthrolinyl (including, without limitation, [1,10]phenanthrolinyl, [1,7]phenanthrolinyl, and [4,7]phenanthrolinyl), phenazinyl, thiazolyl, isothiazolyl, phenothiazinyl, oxazolyl, isoxazolyl, furazanyl, phenoxazinyl, pyrazolo[1,5-a]pyrimidinyl (including, without limitation, pyrazolo[1,5-a]pyrimidin-3-yl), 1,2-benzoisoxazol-3-yl, benzimidazolyl, 1H-tetrazolyl, or 2H-tetrazolyl. Unless defined otherwise, a "heteroaryl" preferably refers to a 5 to 14 membered monocyclic ring or fused ring system comprising one or more (e.g., one, two, three or four) ring heteroatoms independently selected from O, S or N, wherein one or more S ring atoms (if present) and/or one or more N ring atoms (if present) may optionally be oxidized; and more preferably refers to a 5 or 6 membered monocyclic ring comprising one or more (e.g., one, two or three) ring heteroatoms independently selected from O, S or N, wherein one or more S ring atoms (if present) and/or one or more N ring atoms (if present) may optionally be oxidized.

As used herein, "cycloalkyl" represents a saturated hydrocarbon ring, including monocyclic rings as well as bridged ring, spiro ring and/or fused ring systems (which may be composed, e.g., of two or three rings, such as ring systems composed of two or three fused rings). "Cycloalkyl" may, for example, refer to cyclopropyl, cyclobutyl, cyclopentyl, cyclohexyl, or cycloheptyl. Unless defined otherwise, a "cycloalkyl" preferably has 3 to 11 ring members, and more preferably has 3 to 7 ring members.

As used herein, "heterocycloalkyl" represents a saturated ring group, including monocyclic rings as well as bridged ring, spiro ring and/or fused ring systems (which may be composed, e.g., of two or three rings, such as ring systems composed of two or three fused rings), wherein said ring group contains one or more (such as, e.g., one, two, three, or four) ring heteroatoms independently selected from O, S, or N, wherein one or more S ring atoms (if present) and/or one or more N ring atoms (if present) may optionally be oxidized. "Heterocycloalkyl" may, for example, refer to oxetanyl, tetrahydrofuranyl, piperidinyl, piperazinyl, aziridinyl, azetidinyl, pyrrolidinyl, imidazolidinyl, morpholinyl, pyrazolidinyl, tetrahydrothienyl, octahydroquinolinyl, octahydroisoquinolinyl, oxazolidinyl, isoxazolidinyl, azepanyl, diazepanyl, oxazepanyl or 2-oxa-5-aza-bicyclo[2.2.1]hept-5-yl. Unless defined otherwise, a "heterocycloalkyl" preferably refers to a 3 to 11 membered saturated ring group, which is a monocyclic ring or a fused ring system, containing one or more (e.g., one, two, or three) ring heteroatoms independently selected from O, S, or N.

As used herein, "cycloalkenyl" represents an unsaturated alicyclic (non-aromatic) hydrocarbon ring, including monocyclic rings as well as bridged ring, spiro ring and/or fused ring systems (which may be composed, e.g., of two or three rings, such as ring systems composed of two or three fused rings), wherein said hydrocarbon ring comprises at least one carbon-to-carbon double bond and does not comprise any carbon-to-carbon triple bond. Non-limiting examples of cycloalkenyl groups are cyclopropenyl, cyclobutenyl, cyclopentenyl, cyclohexenyl or cyclohexadienyl. Unless defined otherwise, a "cycloalkenyl" preferably has 3 to 11 ring members, and more preferably has 3 to 7 ring members.

As used herein, "heterocycloalkenyl" represents an unsaturated alicyclic (non-aromatic) ring group, including monocyclic rings as well as bridged ring, spiro ring and/or fused ring systems (which may be composed, e.g., of two or three rings, such as ring systems composed of two or three fused rings), wherein said ring group contains one or more (such as, e.g., one, two, three, or four) ring heteroatoms independently selected from O, S, or N, wherein one or more S ring atoms (if present) and/or one or more N ring atoms (if present) may optionally be oxidized, and further wherein said ring group comprises at least one double bond between adjacent ring atoms and does not comprise any triple bond between adjacent ring atoms. "Heterocycloalkenyl" may, for example, refer to 1,2,3,6-tetrahydropyridinyl. Unless defined otherwise, a "heterocycloalkenyl" preferably refers to a 3 to 11 membered unsaturated alicyclic ring group, which is a monocyclic ring or a fused ring system, containing one or more (e.g., one, two, or three) ring heteroatoms independently selected from O, S, or N, wherein said ring group comprises at least one double bond between adjacent ring atoms and does not comprise any triple bond between adjacent ring atoms.

As used herein, "halogen" represents fluoro, chloro, bromo, or iodo.

As used herein, "haloalkyl" represents an alkyl group substituted with one or more (preferably 1 to 6, more preferably 1 to 3) halogen atoms. It will be understood that the maximum number of halogen atoms is limited by the number of available attachment sites and, thus, depends on the number of carbon atoms comprised in the alkyl moiety of the haloalkyl group. "Haloalkyl" may, for example, refer to $-CF_3$, $-CHF_2$, or $-CF_2-CH_3$.

As used herein, "haloalkoxy" represents an $-O$-alkyl group substituted with one or more (preferably 1 to 6, more preferably 1 to 3) halogen atoms. It will be understood that the maximum number of halogen atoms is limited by the number of available attachment sites and, thus, depends on the number of carbon atoms comprised in the $-O$-alkyl moiety of the haloalkoxy group. "Haloalkoxy" may, for example, refer to $-OCF_3$, $-O-CH_2-CF_3$, $-O-CH_2-CHF_2$, $-O-CH_2-CF_2-CH_3$, $-O-CH_2-CF_2-CF_3$, or $-O-CH(CF_3)_2$.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in the context of this description. Generally, these groups may carry one or more than one, such as e.g. one, two, three or four substituents. It will be understood that the maximum number of substituents is limited by the number of attachment sites available on the substituted moiety. Unless defined otherwise in the specific context, these groups carry preferably not more than two substituents and may, in particular, carry only one substituent. Moreover, unless specifically defined otherwise, it is preferred that the optional substituents are absent.

For a person skilled in the field of synthetic chemistry, various ways for the preparation of the compounds of general formula (I) will be readily apparent. For example, the compounds of the invention can be prepared in accordance with or in analogy to the synthetic routes described in detail in the examples section. In particular, the compounds of formula (I) can be synthesized in accordance with the methods described in the following schemes (the substituent groups and variables shown in schemes 1 and 2 have the same meanings as the corresponding groups and variables in general formula (I)).

Intermediates E can be obtained in one step in the presence of the hydrazines D and the β-ketonitriles B under acidic conditions (Vasquez T E et al., *Mot Divers*, 7(2-4), 161-4, 2003). A way to generate hydrazines D is to convert the amino group of C into a diazonium salt in the presence of sodium nitrite under aqueous acidic conditions and to reduce it, e.g., with tin chloride (II). β-ketonitriles B can be generated from an activated acid A such as an acid chloride or an ester in the presence of the acetonitrile anion formed, e.g., from acetonitrile and butyl lithium (see scheme 1).

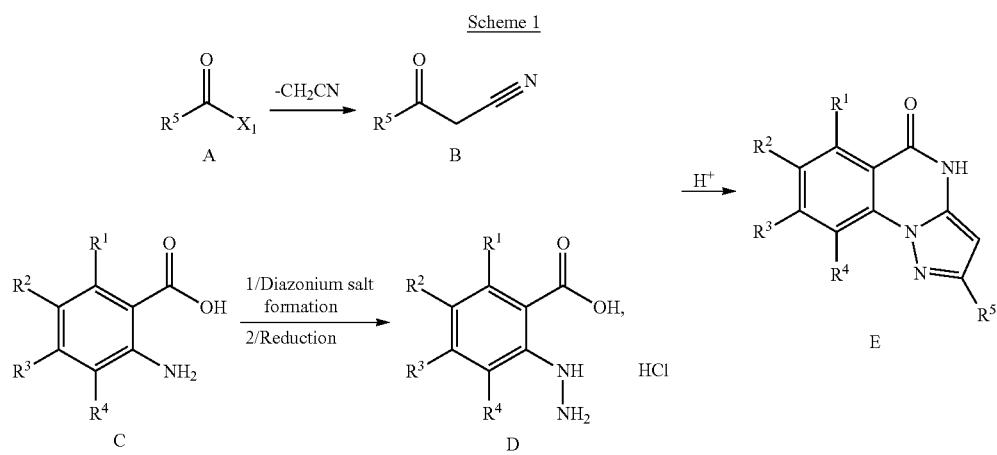

Scheme 1

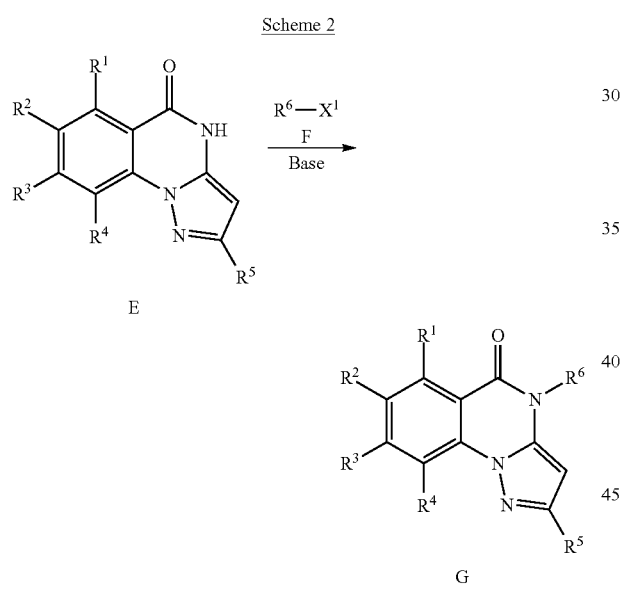

Scheme 2

Example G can be obtained from the pyrazolo[1,5-a] quinazolin-5-ones E in the presence of a base such as NaH, tBuOK or $K_2CO_3$ and the electrophiles F where $X^1$ is a halide or a pseudo halide (see scheme 2).

Example G can be further modified by methods well known in the art. For instance, on an example G containing a halide or a pseudo halide a cross coupling reaction involving a metallic species such as boronic derivatives, tin derivatives or zinc derivatives (and a catalytic amount of a transition metal like palladium or nickel) can be used to introduce groups such as an aryl, a heteroaryl, an alkene or an alkyne.

Also, on an example G containing a halide or a pseudo halide a nucleophile like an alcohol or an amine can be introduced. In some cases the nucleophilic displacement can be facilitated by a catalytic amount of a transition metal such palladium (David S. Surry and Stephen L. Buchwald, Chem Sci. 2011, 2(1), 27-50) or copper (Steven V. Ley and Andrew W. Thomas, Angew. Chem. Int. Ed., 2003, (42) 5400-5449; Yu Zhang et al., Organic letter, 2012, 14 (12), 3056-3059).

On an example G containing a hydroxyl group, an alkyl chain can be introduced with an electrophile such as a halo alkyl in the presence of a base such as NaH, tBuOK or $K_2CO_3$.

From an example G containing a carboxylic acid group, a nucleophile such as an amine can furnish an amide via activating agents (Christian A. G. N. Montalbetti and Virginie Falque, Tetrahedron, 61, (2005) 10827-10852).

The compounds of formula (I) having a pyrroloquinazolinone scaffold (i.e., where A in formula (I) is CH) can be obtained in 2 steps, as shown in scheme 3 below. The dicyanide H is prepared according to procedures well known in the art. This compound reacts with 2-amino benzoic acid derivatives C to give the cyanide derivatives J. Then, the cyanide moiety can be removed under acidic conditions or other conditions such as basic hydrolysis followed by thermal decarboxylation.

Scheme 3

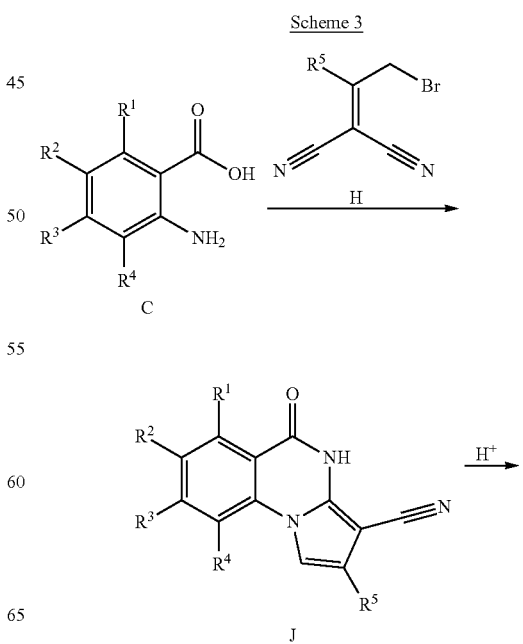

-continued

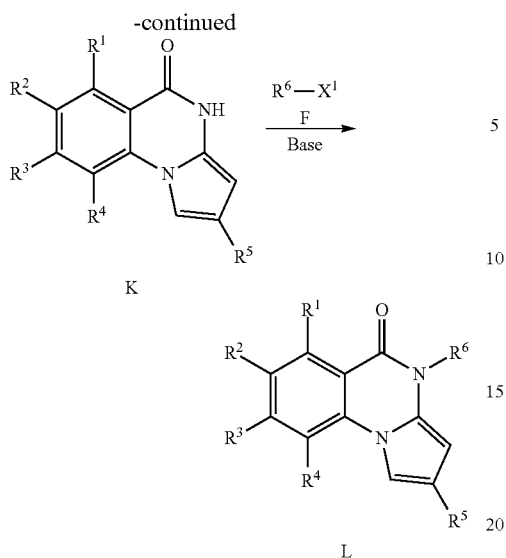

Like example G, example L can be obtained from the pyrroloquinazolinone K in the presence of a base such as NaH, tBuOK or K$_2$CO$_3$ and the electrophiles F where X$^1$ is a halide or a pseudo halide. Like example G, example L can be further modified by methods well known in the art.

The present invention particularly relates to the following items:

1. A compound of formula (I):

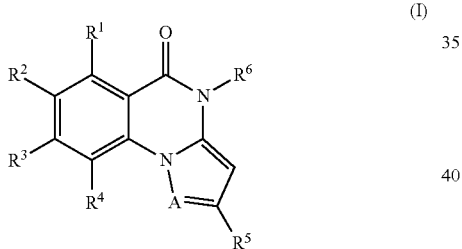

wherein:
A is N or —CH;
R$^1$, R$^2$ and R$^4$ are each independently selected from R$^7$, halogen, —CN, —OR$^7$, —NR$^7$R$^8$, —COOR$^7$, —SO$_3$H, —B(OH)$_2$, —CONR$^7$R$^8$, —COR$^7$, —SR$^7$, —SOR$^7$, —SO$_2$R$^7$, —SO$_2$NR$^7$R$^8$, —NR$^7$COR$^8$, —NR$^7$SO$_2$R$^8$, —OCOR$^7$, —NR$^7$C(O)NR$^8$R$^9$, —NR$^7$C(S)NR$^8$R$^9$, —NR$^7$COOR$^8$, aryl, or heteroaryl, wherein said aryl and said heteroaryl are each substituted with one or more groups independently selected from R$^7$, halogen, —CN, —OR$^7$, —NR$^7$R$^8$, —COOR$^7$, —SO$_3$H, —B(OH)$_2$, —CONR$^7$R$^8$, —COR$^7$, —SR$^7$, —SOR$^7$, —SO$_2$R$^7$, —SO$_2$NR$^7$R$^8$, —NR$^7$COR$^8$, —NR$^7$SO$_2$R$^8$, —OCOR$^7$, —NR$^7$C(O)NR$^8$R$^9$, —NR$^7$C(S)NR$^8$R$^9$, or —NR$^7$COOR$^8$;
R$^3$ is selected from hydrogen, halogen, —CN, —OR$^7$, —NR$^7$R$^8$, —COOR$^7$, —SO$_3$H, —B(OH)$_2$, —CONR$^7$R$^8$, —COR$^7$, —SR$^7$, —SOR$^7$, —SO$_2$R$^7$, —SO$_2$NR$^7$R$^8$, —NR$^7$COR$^8$, —NR$^7$SO$_2$R$^8$, —OCOR$^7$, —NR$^7$C(O)NR$^8$R$^9$, —NR$^7$C(S)NR$^8$R$^9$, —NR$^7$COOR$^8$, C$_1$-C$_4$ alkyl, C$_2$-C$_4$ alkenyl, cycloalkyl or heterocycloalkyl, wherein said C$_1$-C$_4$ alkyl and said C$_2$-C$_4$ alkenyl are each optionally substituted with one or more groups independently selected from halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl), and further wherein said cycloalkyl and said heterocycloalkyl are each optionally substituted with one or more groups independently selected from: C$_1$-C$_4$ alkyl; halogen; —CF$_3$; —CN; —OH; —O(C$_1$-C$_4$ alkyl); C$_1$-C$_4$ alkyl substituted with one or more —OH groups; —NH$_2$; —NH(C$_1$-C$_4$ alkyl); or —N(C$_1$-C$_4$ alkyl)(C$_1$-C$_4$ alkyl);
R$^5$ is heteroaryl which is optionally substituted with one or more groups independently selected from R$^7$, halogen, —CN, —NR$^7$R$^8$, —CONR$^7$R$^8$, —COR$^7$, —OR$^7$, —SR$^7$, —SOR$^7$, —SO$_2$R$^7$, —SO$_2$NR$^7$R$^8$, —NR$^7$COR$^8$, —NR$^7$SO$_2$R$^8$, —OCOR$^7$, or —COOR$^7$;
R$^6$ is selected from C$_1$-C$_4$ alkyl, cycloalkyl, or heterocycloalkyl, wherein said C$_1$-C$_4$ alkyl is optionally substituted with one or more groups independently selected from cycloalkyl, halogen, —CF$_3$, —CN, —OH or —O(C$_1$-C$_4$ alkyl), and further wherein, if R$^6$ is cycloalkyl or heterocycloalkyl, then said cycloalkyl and said heterocycloalkyl are each optionally substituted with one or more groups independently selected from C$_1$-C$_4$ alkyl, cycloalkyl, halogen, —CF$_3$, —CN, —OH or —O(C$_1$-C$_4$ alkyl); and
each R$^7$, R$^8$ and R$^9$ is independently selected from hydrogen, C$_1$-C$_4$ alkyl, C$_2$-C$_4$ alkenyl, cycloalkyl, cycloalkenyl, heterocycloalkyl, heterocycloalkenyl, aryl or heteroaryl, wherein said C$_1$-C$_4$ alkyl and said C$_2$-C$_4$ alkenyl are each optionally substituted with one or more groups independently selected from halogen, —CF$_3$, —CN, cycloalkyl, cycloalkenyl, heterocycloalkyl, heterocycloalkenyl, aryl, heteroaryl, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl), and further wherein, if R$^7$, R$^8$ or R$^9$ is cycloalkyl, cycloalkenyl, heterocycloalkyl, heterocycloalkenyl, aryl or heteroaryl, then said cycloalkyl, said cycloalkenyl, said heterocycloalkyl, said heterocycloalkenyl, said aryl and said heteroaryl are each optionally substituted with one or more groups independently selected from: C$_1$-C$_4$ alkyl; halogen; —CF$_3$; —CN; —OH; —O(C$_1$-C$_4$ alkyl); C$_1$-C$_4$ alkyl substituted with one or more —OH groups; —NH$_2$; —NH(C$_1$-C$_4$ alkyl); or —N(C$_1$-C$_4$ alkyl)(C$_1$-C$_4$ alkyl);
or a pharmaceutically acceptable salt, solvate or prodrug thereof
for use as a medicament.

2. A compound of formula (I):

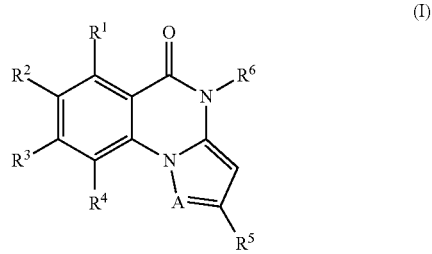

wherein:
A is N or —CH;
R¹, R² and R⁴ are each independently selected from R⁷, halogen, —CN, —OR⁷, —NR⁷R⁸, —COOR⁷, —SO₃H, —B(OH)₂, —CONR⁷R⁸, —COR⁷, —SR⁷, —SOR⁷, —SO₂R⁷, —SO₂NR⁷R⁸, —NR⁷COR⁸, —NR⁷SO₂R⁸, —OCOR⁷, —NR⁷C(O)NR⁸R⁹, —NR⁷C(S)NR⁸R⁹, —NR⁷COOR⁸, aryl, or heteroaryl, wherein said aryl and said heteroaryl are each substituted with one or more groups independently selected from R⁷, halogen, —CN, —OR⁷, —NR⁷R⁸, —COOR⁷, —SO₃H, —B(OH)₂, —CONR⁷R⁸, —COR⁷, —SR⁷, —SOR⁷, —SO₂R⁷, —SO₂NR⁷R⁸, —NR⁷COR⁸, —NR⁷SO₂R⁸, —OCOR⁷, —NR⁷C(O)NR⁸R⁹, —NR⁷C(S)NR⁸R⁹, or —NR⁷COOR⁸;
R³ is selected from hydrogen, halogen, —CN, —OR⁷, —NR⁷R⁸, —COOR⁷, —SO₃H, —B(OH)₂, —CONR⁷R⁸, —COR⁷, —SR⁷, —SOR⁷, —SO₂R⁷, —SO₂NR⁷R⁸, —NR⁷COR⁸, —NR⁷SO₂R⁸, —OCOR⁷, —NR⁷C(O)NR⁸R⁹, —NR⁷C(S)NR⁸R⁹, —NR⁷COOR⁸, $C_1$-$C_4$ alkyl, $C_2$-$C_4$ alkenyl, cycloalkyl or heterocycloalkyl, wherein said $C_1$-$C_4$ alkyl and said $C_2$-$C_4$ alkenyl are each optionally substituted with one or more groups independently selected from halogen, —CF₃, —CN, —OH, —O($C_1$-$C_4$ alkyl), —NH₂, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more groups independently selected from: $C_1$-$C_4$ alkyl; halogen; —CF₃; —CN; —OH; —O($C_1$-$C_4$ alkyl); $C_1$-$C_4$ alkyl substituted with one or more —OH groups; —NH₂; —NH($C_1$-$C_4$ alkyl); or —N($C_1$-$C_4$ alkyl)($C_1$-$C_4$ alkyl);
R⁵ is heteroaryl which is optionally substituted with one or more groups independently selected from R⁷, halogen, —CN, —NR⁷R⁸, —CONR⁷R⁸, —COR⁷, —OR⁷, —SR⁷, —SOR⁷, —SO₂R⁷, —SO₂NR⁷R⁸, —NR⁷COR⁸, —NR⁷SO₂R⁸, —OCOR⁷, or —COOR⁷;
R⁶ is selected from $C_1$-$C_4$ alkyl, cycloalkyl, or heterocycloalkyl, wherein said $C_1$-$C_4$ alkyl is optionally substituted with one or more groups independently selected from cycloalkyl, halogen, —CF₃, —CN, —OH or —O($C_1$-$C_4$ alkyl), and further wherein, if R⁶ is cycloalkyl or heterocycloalkyl, then said cycloalkyl and said heterocycloalkyl are each optionally substituted with one or more groups independently selected from $C_1$-$C_4$ alkyl, cycloalkyl, halogen, —CF₃, —CN, —OH or —O($C_1$-$C_4$ alkyl); and
each R⁷, R⁸ and R⁹ is independently selected from hydrogen, $C_1$-$C_4$ alkyl, $C_2$-$C_4$ alkenyl, cycloalkyl, cycloalkenyl, heterocycloalkyl, heterocycloalkenyl, aryl or heteroaryl, wherein said $C_1$-$C_4$ alkyl and said $C_2$-$C_4$ alkenyl are each optionally substituted with one or more groups independently selected from halogen, —CF₃, —CN, cycloalkyl, cycloalkenyl, heterocycloalkyl, heterocycloalkenyl, aryl, heteroaryl, —OH, —O($C_1$-$C_4$ alkyl), —NH₂, —NH($C_1$-$C_4$ alkyl) or —N($C_1$-$C_4$ alkyl)($C_1$-$C_4$ alkyl), and further wherein, if R⁷, R⁸ or R⁹ is cycloalkyl, cycloalkenyl, heterocycloalkyl, heterocycloalkenyl, aryl or heteroaryl, then said cycloalkyl, said cycloalkenyl, said heterocycloalkyl, said heterocycloalkenyl, said aryl and said heteroaryl are each optionally substituted with one or more groups independently selected from: $C_1$-$C_4$ alkyl; halogen; —CF₃; —CN; —OH; —O($C_1$-$C_4$ alkyl); $C_1$-$C_4$ alkyl substituted with one or more —OH groups; —NH₂; —NH($C_1$-$C_4$ alkyl); or —N($C_1$-$C_4$ alkyl)($C_1$-$C_4$ alkyl);
or a pharmaceutically acceptable salt, solvate or prodrug thereof;
with the proviso that the following compounds are excluded:
8-bromo-2-furan-2-yl-4-methyl-4H-pyrazolo[1,5-a]quinazolin-5-one;
8-bromo-2-(2,6-dimethyl-pyridin-4-yl)-4-methyl-4H-pyrazolo[1,5-a]quinazolin-5-one;
8-bromo-4-methyl-2-(1-methyl-1H-pyrazol-4-yl)-4H-pyrazolo[1,5-a]quinazolin-5-one;
8-bromo-4-methyl-2-(1-ethyl-1H-pyrazol-4-yl)-4H-pyrazolo[1,5-a]quinazolin-5-one;
8-bromo-2-(2-methyl-pyridin-4-yl)-4-methyl-4H-pyrazolo[1,5-a]quinazolin-5-one;
8-bromo-4-methyl-2-pyridin-3-yl-4H-pyrazolo[1,5-a]quinazolin-5-one; and
8-bromo-4-methyl-2-(2-trifluoromethyl-pyridin-4-yl)-4H-pyrazolo[1,5-a]quinazolin-5-one.
3. A compound of formula (I):

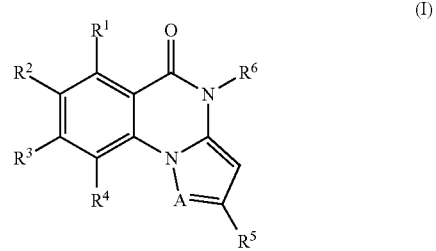

wherein:
A is N or —CH;
R¹, R² and R⁴ are each independently selected from R⁷, halogen, —CN, —OR⁷, —NR⁷R⁸, —COOR⁷, —SO₃H, —B(OH)₂, —CONR⁷R⁸, —COR⁷, —SR⁷, —SOR⁷, —SO₂R⁷, —SO₂NR⁷R⁸, —NR⁷COR⁸, —NR⁷SO₂R⁸, —OCOR⁷, —NR⁷C(O)NR⁸R⁹, —NR⁷C(S)NR⁸R⁹, —NR⁷COOR⁸, aryl, or heteroaryl, wherein said aryl and said heteroaryl are each substituted with one or more groups independently selected from R⁷, halogen, —CN, —OR⁷, —NR⁷R⁸, —COOR⁷, —SO₃H, —B(OH)₂, —CONR⁷R⁸, —COR⁷, —SR⁷, —SOR⁷, —SO₂R⁷, —SO₂NR⁷R⁸, —NR⁷COR⁸, —NR⁷SO₂R⁸, —OCOR⁷, —NR⁷C(O)NR⁸R⁹, —NR⁷C(S)NR⁸R⁹, or —NR⁷COOR⁸;
R³ is selected from hydrogen, —F, —Cl, —I, —CN, —OR⁷, —NR⁷R⁸, —COOR⁷, —SO₃H, —B(OH)₂, —CONR⁷R⁸, —COR⁷, —SR⁷, —SOR⁷, —SO₂R⁷, —SO₂NR⁷R⁸, —NR⁷COR⁸, —NR⁷SO₂R⁸, —OCOR⁷, —NR⁷C(O)NR⁸R⁹, —NR⁷C(S)NR⁸R⁹, —NR⁷COOR⁸, $C_1$-$C_4$ alkyl, $C_2$-$C_4$ alkenyl, cycloalkyl or heterocycloalkyl, wherein said $C_1$-$C_4$ alkyl and said $C_2$-$C_4$ alkenyl are each optionally substituted with one or more groups independently selected from halogen, —CF₃, —CN, —OH, —O($C_1$-$C_4$ alkyl), —NH₂, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more groups independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl);

$R^5$ is heteroaryl which is optionally substituted with one or more groups independently selected from $R^7$, halogen, —CN, —$NR^7R^8$, —$CONR^7R^8$, —$COR^7$, —$OR^7$, —$SR^7$, —$SOR^7$, —$SO_2R^7$, —$SO_2NR^7R^8$, —$NR^7COR^8$, —$NR^7SO_2R^8$, —$OCOR^7$, or —$COOR^7$;

$R^6$ is selected from $C_1$-$C_4$ alkyl, cycloalkyl, or heterocycloalkyl, wherein said $C_1$-$C_4$ alkyl is optionally substituted with one or more groups independently selected from cycloalkyl, halogen, —$CF_3$, —CN, —OH or —O($C_1$-$C_4$ alkyl), and further wherein, if $R^6$ is cycloalkyl or heterocycloalkyl, then said cycloalkyl and said heterocycloalkyl are each optionally substituted with one or more groups independently selected from $C_1$-$C_4$ alkyl, cycloalkyl, halogen, —$CF_3$, —CN, —OH or —O($C_1$-$C_4$ alkyl); and each $R^7$, $R^8$ and $R^9$ is independently selected from hydrogen, $C_1$-$C_4$ alkyl, $C_2$-$C_4$ alkenyl, cycloalkyl, cycloalkenyl, heterocycloalkyl, heterocycloalkenyl, aryl or heteroaryl, wherein said $C_1$-$C_4$ alkyl and said $C_2$-$C_4$ alkenyl are each optionally substituted with one or more groups independently selected from halogen, —$CF_3$, —CN, cycloalkyl, cycloalkenyl, heterocycloalkyl, heterocycloalkenyl, aryl, heteroaryl, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein, if $R^7$, $R^8$ or $R^9$ is cycloalkyl, cycloalkenyl, heterocycloalkyl, heterocycloalkenyl, aryl or heteroaryl, then said cycloalkyl, said cycloalkenyl, said heterocycloalkyl, said heterocycloalkenyl, said aryl and said heteroaryl are each optionally substituted with one or more groups independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl);

or a pharmaceutically acceptable salt, solvate or prodrug thereof.

4. The compound for use according to item 1 or the compound of item 2, wherein $R^3$ is selected from hydrogen, halogen, $C_1$-$C_4$ haloalkyl, $C_1$-$C_4$ haloalkoxy, —CN, $C_1$-$C_4$ alkyl, cycloalkyl, heterocycloalkyl, —OH, —O($C_1$-$C_4$ alkyl), —O-cycloalkyl, —O-heterocycloalkyl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —CO-cycloalkyl, —CO-heterocycloalkyl, —CO—$NH_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH-heterocycloalkyl, —CO—N($C_1$-$C_4$ alkyl)-heterocycloalkyl, —NH—CO-cycloalkyl, —N($C_1$-$C_4$ alkyl)-CO-cycloalkyl, —NH—CO-heterocycloalkyl, or —N($C_1$-$C_4$ alkyl)-CO-heterocycloalkyl, wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl).

5. The compound for use according to item 1 or 4 or the compound of item 2 or 4, wherein $R^3$ is selected from hydrogen, halogen, $C_1$-$C_4$ haloalkyl, —CN, heterocycloalkyl, —O($C_1$-$C_4$ alkyl), —NH($C_1$-$C_4$ alkyl), or —CO—N($C_1$-$C_4$ alkyl)($C_1$-$C_4$ alkyl), wherein said heterocycloalkyl is optionally substituted with one or more groups independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl).

6. The compound of item 3, wherein $R^3$ is selected from hydrogen, —F, —Cl, —I, $C_1$-$C_4$ haloalkyl, $C_1$-$C_4$ haloalkoxy, —CN, $C_1$-$C_4$ alkyl, cycloalkyl, heterocycloalkyl, —OH, —O($C_1$-$C_4$ alkyl), —O-cycloalkyl, —O-heterocycloalkyl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —CO-cycloalkyl, —CO-heterocycloalkyl, —CO—$NH_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH-heterocycloalkyl, —CO—N($C_1$-$C_4$ alkyl)-heterocycloalkyl, —NH—CO-cycloalkyl, —N($C_1$-$C_4$ alkyl)-CO-cycloalkyl, —NH—CO-heterocycloalkyl, or —N($C_1$-$C_4$ alkyl)-CO-heterocycloalkyl, wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl).

7. The compound of item 3 or 6, wherein $R^3$ is selected from hydrogen, —F, —Cl, $C_1$-$C_4$ haloalkyl, —CN, heterocycloalkyl, —O($C_1$-$C_4$ alkyl), —NH($C_1$-$C_4$ alkyl), or —CO—N($C_1$-$C_4$ alkyl)($C_1$-$C_4$ alkyl), wherein said heterocycloalkyl is optionally substituted with one or more groups independently selected from: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); or —N($C_1$-$C_4$ alkyl)($C_1$-$C_4$ alkyl).

8. The compound for use according to any one of items 1 or 4 to 7 or the compound of any one of items 2 to 7, wherein $R^1$, $R^2$ and $R^4$ are each independently selected from hydrogen, halogen, $C_1$-$C_4$ haloalkyl, $C_1$-$C_4$ haloalkoxy, —CN, $C_1$-$C_4$ alkyl, $C_2$-$C_4$ alkenyl, cycloalkyl, heterocycloalkyl, aryl, heteroaryl, —OH, —O($C_1$-$C_4$ alkyl), —O—($C_1$-$C_4$ alkylene)-OH, —O—($C_1$-$C_4$ alkylene)-O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —O-aryl, —O—($C_1$-$C_4$ alkylene)-aryl, —O-heteroaryl, —O—($C_1$-$C_4$ alkylene)-heteroaryl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —NH-aryl, —N($C_1$-$C_4$ alkyl)-aryl, —NH-heteroaryl, —N($C_1$-$C_4$ alkyl)-heteroaryl, —NH—($C_1$-$C_4$ alkylene)-aryl, —N($C_1$-$C_4$ alkyl)-($C_1$-$C_4$ alkylene)-aryl, —NH—($C_1$-$C_4$ alkylene)- heteroaryl, —N($C_1$-$C_4$ alkyl)-($C_1$-$C_4$ alkylene)-heteroaryl, —CO—($C_1$-$C_4$ alkyl), —CO-cycloalkyl, —CO-heterocycloalkyl, —CO—($C_1$-$C_4$ alkylene)-cycloalkyl, —CO—($C_1$-$C_4$ alkylene)-heterocycloalkyl, —CO-aryl, —CO-heteroaryl, —CO—($C_1$-$C_4$ alkylene)-aryl, —CO—($C_1$-$C_4$ alkylene)-heteroaryl, —CO—$NH_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH—($C_1$-$C_4$ alkylene)-cycloalkyl, —CO—N($C_1$-$C_4$ alkyl)-($C_1$-$C_4$ alkylene)-cycloalkyl, —CO—NH-heterocycloalkyl, —CO—N($C_1$-$C_4$ alkyl)-heterocycloalkyl, —CO—NH—($C_1$-$C_4$ alkylene)-heterocycloalkyl, —CO—N($C_1$-$C_4$ alkyl)-($C_1$-$C_4$ alkylene)-heterocycloalkyl, —CO—NH-aryl, —CO—N($C_1$-$C_4$ alkyl)-aryl, —CO—NH—($C_1$-$C_4$ alkylene)-aryl, —CO—N($C_1$-$C_4$ alkyl)-($C_1$-$C_4$ alkylene)-aryl, —CO—NH-heteroaryl, —CO—N($C_1$-$C_4$ alkyl)-heteroaryl, —CO—NH—($C_1$-$C_4$ alkylene)-heteroaryl, —CO—N($C_1$-$C_4$ alkyl)-($C_1$-$C_4$ alkylene)-heteroaryl, —NH—CHO, —N($C_1$-$C_4$ alkyl)-CHO, —NH—CO($C_1$-$C_4$ alkyl), —N($C_1$-$C_4$ alkyl)-CO($C_1$-$C_4$ alkyl), —NH—CO-cycloalkyl, —N($C_1$-$C_4$ alkyl)-CO-cycloalkyl, —NH—CO—($C_1$-$C_4$ alkylene)-cycloalkyl, —N($C_1$-$C_4$ alkyl)-CO—($C_1$-$C_4$ alkylene)-cycloalkyl, —NH—CO-heterocycloalkyl, —N($C_1$-$C_4$ alkyl)-CO-heterocycloalkyl, —NH—CO—($C_1$-$C_4$ alkylene)-heterocycloalkyl, —N($C_1$-$C_4$ alkyl)-CO—($C_1$-$C_4$ alkylene)-heterocycloalkyl, —NH—CO-aryl, —N($C_1$-$C_4$ alkyl)-CO-aryl, —NH—CO—($C_1$-$C_4$ alkylene)-aryl, —N($C_1$-$C_4$ alkyl)-CO—($C_1$-$C_4$ alkylene)-aryl, —NH—CO-heteroaryl, —N($C_1$-$C_4$ alkyl)-CO-heteroaryl, —NH—CO—($C_1$-$C_4$ alkylene)-heteroaryl, or —N($C_1$-$C_4$ alkyl)-CO—($C_1$-$C_4$ alkylene)-heteroaryl, wherein said aryl, said heteroaryl, the aryl moiety comprised in any of the aforementioned groups, and the heteroaryl moiety comprised in any of the aforementioned groups are each optionally substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl).

9. The compound for use according to any one of items 1 or 4 to 8 or the compound of any one of items 2 to 8, wherein $R^1$, $R^2$ and $R^4$ are each independently selected from hydrogen, halogen, $C_1$-$C_4$ haloalkyl, $C_1$-$C_4$ haloalkoxy, $C_1$-$C_4$ alkyl, —OH, —O($C_1$-$C_4$ alkyl), —NH($C_1$-$C_4$ alkyl), or —N($C_1$-$C_4$ alkyl)($C_1$-$C_4$ alkyl).

10. The compound for use according to any one of items 1 or 4 to 9 or the compound of any one of items 2 to 9, wherein $R^5$ is heteroaryl having 5 or 6 ring members and comprising one or more ring heteroatoms independently selected from O, S or N, wherein said heteroaryl having 5 or 6 ring members is optionally substituted with one or more groups independently selected from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, aryl, heteroaryl, —OH, —O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, or —CO—($C_1$-$C_4$ alkylene)-heterocycloalkyl, wherein said aryl, said heteroaryl, said cycloalkyl, said heterocycloalkyl, the cycloalkyl moiety comprised in any of the aforementioned groups, and the heterocycloalkyl moiety comprised in any of the aforementioned groups are each optionally substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl).

11. The compound for use according to any one of items 1 or 4 to 10 or the compound of any one of items 2 to 10, wherein $R^5$ is pyridinyl which is optionally substituted with one or more groups independently selected from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, aryl, heteroaryl, —OH, —O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, or —CO—($C_1$-$C_4$ alkylene)-heterocycloalkyl, wherein said aryl, said heteroaryl, said cycloalkyl, said heterocycloalkyl, the cycloalkyl moiety comprised in any of the aforementioned groups, and the heterocycloalkyl moiety comprised in any of the aforementioned groups are each optionally substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl).

12. The compound for use according to any one of items 1 or 4 to 11 or the compound of any one of items 2 to 11, wherein $R^5$ is pyridin-4-yl which is substituted with one substituent group at position 2 of said pyridin-4-yl or with two substituent groups at position 2 and 6 of said pyridin-4-yl, wherein said one or two substituent group(s) is/are selected independently from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, —O($C_1$-$C_4$ alkyl), —O-cycloalkyl, or —O-heterocycloalkyl.

13. The compound for use according to any one of items 1 or 4 to 12 or the compound of any one of items 2 to 12, wherein $R^5$ is pyridin-4-yl which is substituted with one substituent group at position 2 of said pyridin-4-yl, wherein said substituent group is selected from $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, —O($C_1$-$C_4$ alkyl), —O-cycloalkyl, or —O-heterocycloalkyl.

14. The compound for use according to any one of items 1 or 4 to 13 or the compound of any one of items 2 to 13, wherein $R^5$ is 2-trifluoromethyl-pyridin-4-yl.

15. The compound for use according to any one of items 1 or 4 to 14 or the compound of any one of items 2 to 14, wherein $R^6$ is $C_1$-$C_4$ alkyl which is optionally substituted with one or more groups independently selected from cycloalkyl, halogen, —$CF_3$, —CN, —OH or —O($C_1$-$C_4$ alkyl).

16. The compound for use according to any one of items 1 or 4 to 15 or the compound of any one of items 2 to 15, wherein $R^6$ is methyl.

17. The compound for use according to any one of items 1 or 4 to 16 or the compound of any one of items 2 to 16, wherein A is N.

18. The compound for use according to item 1 or the compound of item 2, wherein said compound is selected from:

2-(2-chloro-pyridin-4-yl)-4-methyl-4H-pyrazolo[1,5-a]quinazolin-5-one;
4-methyl 2-(2-methyl-pyridin-4-yl)-4H-pyrazolo[1,5-a]quinazolin-5-one;
2-(2-ethyl-pyridin-4-yl)-4-methyl-4H-pyrazolo[1,5-a]quinazolin-5-one;
2-(2-propyl-pyridin-4-yl)-4-methyl-4H-pyrazolo[1,5-a]quinazolin-5-one;
2-(2-cyclopropyl-pyridin-4-yl)-4-methyl-4H-pyrazolo[1,5-a]quinazolin-5-one;
2-(2-cyclobutyl-pyridin-4-yl)-4-methyl-4H-pyrazolo[1,5-a]quinazolin-5-one;
2-(2-cyclopentyl-pyridin-4-yl)-4-methyl-4H-pyrazolo[1,5-a]quinazolin-5-one;
2-(2-cyclohexyl-pyridin-4-yl)-4-methyl-4H-pyrazolo[1,5-a]quinazolin-5-one;
4-methyl-2-(2-vinyl-pyridin-4-yl)-4H-pyrazolo[1,5-a]quinazolin-5-one;
2-(2-isopropenyl-pyridin-4-yl)-4-methyl-4H-pyrazolo[1,5-a]quinazolin-5-one;
2-(2-isopropyl-pyridin-4-yl)-4-methyl-4H-pyrazolo[1,5-a]quinazolin-5-one;
4-(4-methyl-5-oxo-4,5-dihydro-pyrazolo[1,5-a]quinazolin-2-yl)-pyridine-2-carbonitrile;
2-(2-fluoro-pyridin-4-yl)-4-methyl-4H-pyrazolo[1,5-a]quinazolin-5-one;
2-(2-methoxy-pyridin-4-yl)-4-methyl-4H-pyrazolo[1,5-a]quinazolin-5-one;
2-(2-ethoxy-pyridin-4-yl)-4-methyl-4H-pyrazolo[1,5-a]quinazolin-5-one;
2-(2-isopropoxy-pyridin-4-yl)-4-methyl-4H-pyrazolo[1,5-a]quinazolin-5-one;
2-(2-cyclobutoxy-pyridin-4-yl)-4-methyl-4H-pyrazolo[1,5-a]quinazolin-5-one;
4-methyl-2-[2-(oxetan-3-yloxy)-pyridin-4-yl]-4H-pyrazolo[1,5-a]quinazolin-5-one;
2-(2-cyclopropylmethoxy-pyridin-4-yl)-4-methyl-4H-pyrazolo[1,5-a]quinazolin-5-one;
2-[2-(2-methoxy-ethoxy)-pyridin-4-yl]-4-methyl-4H-pyrazolo[1,5-a]quinazolin-5-one;
4-methyl-2-[2-(2,2,2-trifluoro-ethoxy)-pyridin-4-yl]-4H-pyrazolo[1,5-a]quinazolin-5-one;
4-methyl-2-[2-(2,2-difluoro-ethoxy)-pyridin-4-yl]-4H-pyrazolo[1,5-a]quinazolin-5-one;
2-[2-(2,2-difluoro-propoxy)-pyridin-4-yl]-4-methyl-4H-pyrazolo[1,5-a]quinazolin-5-one;
4-methyl-2-[2-(2,2,3,3,3-pentafluoro-propoxy)-pyridin-4-yl]-4H-pyrazolo[1,5-a]quinazolin-5-one;
4-methyl-2-[2-(2,2,2-trifluoro-1-trifluoromethyl-ethoxy)-pyridin-4-yl]-4H-pyrazolo[1,5-a]quinazolin-5-one;
4-methyl-2-(2-trifluoromethyl-pyridin-4-yl)-4H-pyrazolo[1,5-a]quinazolin-5-one;
4-methyl($D_3$)-2-(2-trifluoromethyl-pyridin-4-yl)-4H-pyrazolo[1,5-a]quinazolin-5-one;
4-ethyl-2-(2-trifluoromethyl-pyridin-4-yl)-4H-pyrazolo[1,5-a]quinazolin-5-one;
4-(2,2-difluoro-ethyl)-2-(2-trifluoromethyl-pyridin-4-yl)-4H-pyrazolo[1,5-a]quinazolin-5-one;
4-(2-methoxy-ethyl)-2-(2-trifluoromethyl-pyridin-4-yl)-4H-pyrazolo[1,5-a]quinazolin-5-one;
4-methyl-2-(2-difluoromethyl-pyridin-4-yl)-4H-pyrazolo[1,5-a]quinazolin-5-one;
2-[2-(1,1-difluoro-ethyl)-pyridin-4-yl]-4-methyl-4H-pyrazolo[1,5-a]quinazolin-5-one;
2-[2-(1,1-difluoro-ethyl)-pyridin-4-yl]-4-methyl($D_3$)-4H-pyrazolo[1,5-a]quinazolin-5-one;
7-methyl-2-(2-trifluoromethyl-pyridin-4-yl)-4H-pyrazolo[1,5-a]quinazolin-5-one;
7-chloro-2-(2-trifluoromethyl-pyridin-4-yl)-4H-pyrazolo[1,5-a]quinazolin-5-one;
7-methoxy-2-(2-trifluoromethyl-pyridin-4-yl)-4H-pyrazolo[1,5-a]quinazolin-5-one;
7-trifluoromethyl-2-(2-trifluoromethyl-pyridin-4-yl)-4H-pyrazolo[1,5-a]quinazolin-5-one;
7-fluoro-2-(2-trifluoromethyl-pyridin-4-yl)-4H-pyrazolo[1,5-a]quinazolin-5-one;
7-bromo-2-(2-trifluoromethyl-pyridin-4-yl)-4H-pyrazolo[1,5-a]quinazolin-5-one;
4-methyl-7-methylamino-2-(2-trifluoromethyl-pyridin-4-yl)-4H-pyrazolo[1,5-a]quinazolin-5-one;
4-methyl-7-methyl(D3)amino-2-(2-trifluoromethyl-pyridin-4-yl)-4H-pyrazolo[1,5-a]quinazolin-5-one;
N-[4-methyl-5-oxo-2-(2-trifluoromethyl-pyridin-4-yl)-4,5-dihydro-pyrazolo[1,5-a]quinazolin-7-yl]-acetamide;
7-amino-4-methyl-2-(2-trifluoromethyl-pyridin-4-yl)-4H-pyrazolo[1,5-a]quinazolin-5-one;
7-dimethylamino-4-methyl-2-(2-trifluoromethyl-pyridin-4-yl)-4H-pyrazolo[1,5-a]quinazolin-5-one;
7-ethylamino-4-methyl-2-(2-trifluoromethyl-pyridin-4-yl)-4H-pyrazolo[1,5-a]quinazolin-5-one;
7-cyclobutylamino-4-methyl-2-(2-trifluoromethyl-pyridin-4-yl)-4H-pyrazolo[1,5-a]quinazolin-5-one;
4-methyl-7-morpholin-4-yl-2-(2-trifluoromethyl-pyridin-4-yl)-4H-pyrazolo[1,5-a]quinazolin-5-one;
7-hydroxy-4-methyl-2-(2-trifluoromethyl-pyridin-4-yl)-4H-pyrazolo[1,5-a]quinazolin-5-one;
7-ethoxy-4-methyl-2-(2-trifluoromethyl-pyridin-4-yl)-4H-pyrazolo[1,5-a]quinazolin-5-one;
7-(2-methoxy-ethoxy)-4-methyl-2-(2-trifluoromethyl-pyridin-4-yl)-4H-pyrazolo[1,5-a]quinazolin-5-one;
4-methyl-7-(2-morpholin-4-yl-ethoxy)-2-(2-trifluoromethyl-pyridin-4-yl)-4H-pyrazolo[1,5-a]quinazolin-5-one;
4-methyl-7-trifluoromethoxy-2-(2-trifluoromethyl-pyridin-4-yl)-4H-pyrazolo[1,5-a]quinazolin-5-one;
7-methanesulfonyl-4-methyl-2-(2-trifluoromethyl-pyridin-4-yl)-4H-pyrazolo[1,5-a]quinazolin-5-one;
8-methoxy-4-methyl-2-(2-trifluoromethyl-pyridin-4-yl)-4H-pyrazolo[1,5-a]quinazolin-5-one;
8-fluoro-4-methyl-2-(2-trifluoromethyl-pyridin-4-yl)-4H-pyrazolo[1,5-a]quinazolin-5-one;
8-chloro-4-methyl-2-(2-trifluoromethyl-pyridin-4-yl)-4H-pyrazolo[1,5-a]quinazolin-5-one;
4-methyl-8-trifluoromethyl-2-(2-trifluoromethyl-pyridin-4-yl)-4H-pyrazolo[1,5-a]quinazolin-5-one;
8-bromo-4-methyl-2-(2-trifluoromethyl-pyridin-4-yl)-4H-pyrazolo[1,5-a]quinazolin-5-one;
4-methyl-8-morpholin-4-yl-2-(2-trifluoromethyl-pyridin-4-yl)-4H-pyrazolo[1,5-a]quinazolin-5-one;
4-methyl-8-pyrrolidin-1-yl-2-(2-trifluoromethyl-pyridin-4-yl)-4H-pyrazolo[1,5-a]quinazolin-5-one;
4-methyl-8-methylamino-2-(2-trifluoromethyl-pyridin-4-yl)-4H-pyrazolo[1,5-a]quinazolin-5-one;
8-(4-methoxy-piperidin-1-yl)-4-methyl-2-(2-trifluoromethyl-pyridin-4-yl)-4H-pyrazolo[1,5-a]quinazolin-5-one;
8-(4-hydroxy-piperidin-1-yl)-4-methyl-2-(2-trifluoromethyl-pyridin-4-yl)-4H-pyrazolo[1,5-a]quinazolin-5-one;
8-dimethylamino-4-methyl-2-(2-trifluoromethyl-pyridin-4-yl)-4H-pyrazolo[1,5-a]quinazolin-5-one;
4-methyl-8-(4-methyl-piperazin-1-yl)-2-(2-trifluoromethyl-pyridin-4-yl)-4H-pyrazolo[1,5-a]quinazolin-5-one;

4-methyl-8-piperazin-1-yl-2-(2-trifluoromethyl-pyridin-4-yl)-4H-pyrazolo[1,5-a]quinazolin-5-one;
8-(4-hydroxymethyl-piperidin-1-yl)-4-methyl-2-(2-trifluoromethyl-pyridin-4-yl)-4H-pyrazolo[1,5-a]quinazoin-5-one;
8-(3-hydroxy-azetidin-1-yl)-4-methyl-2-(2-trifluoromethyl-pyridin-4-yl)-4H-pyrazolo[1,5-a]quinazolin-5-one;
8-(3-hydroxymethyl-azetidin-1-yl)-4-methyl-2-(2-trifluoromethyl-pyridin-4-yl)-4H-pyrazolo[1,5-a]quinazolin-5-one;
8-(3-hydroxy-pyrrolidin-1-yl)-4-methyl-2-(2-trifluoromethyl-pyridin-4-yl)-4H-pyrazolo[1,5-a]quinazolin-5-one;
8-(4-hydroxy-4-methyl-piperidin-1-yl)-4-methyl-2-(2-trifluoromethyl-pyridin-4-yl)-4H-pyrazolo[1,5-a]quinazolin-5-one;
4,8-dimethyl-2-(2-trifluoromethyl-pyridin-4-yl)-4H-pyrazolo[1,5-a]quinazolin-5-one;
8-cyclopropyl-4-methyl-2-(2-trifluoromethyl-pyridin-4-yl)-4H-pyrazolo[1,5-a]quinazolin-5-one;
8-cyclopentyl-4-methyl-2-(2-trifluoromethyl-pyridin-4-yl)-4H-pyrazolo[1,5-a]quinazolin-5-one;
4-methyl-5-oxo-2-(2-trifluoromethyl-pyridin-4-yl)-4,5-dihydro-pyrazolo[1,5-a]quinazoline-8-carbonitrile;
4-methyl-5-oxo-2-(2-trifluoromethyl-pyridin-4-yl)-4,5-dihydro-pyrazolo[1,5-a]quinazoline-8-carboxylic acid;
4-methyl-5-oxo-2-(2-trifluoromethyl-pyridin-4-yl)-4,5-dihydro-pyrazolo[1,5-a]quinazoline-8-carboxylic acid amide;
4-methyl-5-oxo-2-(2-trifluoromethyl-pyridin-4-yl)-4,5-dihydro-pyrazolo[1,5-a]quinazoline-8-carboxylic acid methylamide;
4-methyl-5-oxo-2-(2-trifluoromethyl-pyridin-4-yl)-4,5-dihydro-pyrazolo[1,5-a]quinazoline-8-carboxylic acid dimethylamide;
4-methyl-5-oxo-2-(2-trifluoromethyl-pyridin-4-yl)-4,5-dihydro-pyrazolo[1,5-a]quinazoline-8-carboxylic acid diethylamide;
4-methyl-8-(morpholine-4-carbonyl)-2-(2-trifluoromethyl-pyridin-4-yl)-4H-pyrazolo[1,5-a]quinazolin-5-one;
4-methyl-8-(pyrrolidine-1-carbonyl)-2-(2-trifluoromethyl-pyridin-4-yl)-4H-pyrazolo[1,5-a]quinazolin-5-one;
8-(2-hydroxy-ethoxy)-4-methyl-2-(2-trifluoromethyl-pyridin-4-yl)-4H-pyrazolo[1,5-a]quinazolin-5-one;
4-methyl-6-trifluoromethyl-2-(2-trifluoromethyl-pyridin-4-yl)-4H-pyrazolo[1,5-a]quinazolin-5-one;
6-fluoro-4-methyl-2-(2-trifluoromethyl-pyridin-4-yl)-4H-pyrazolo[1,5-a]quinazolin-5-one;
9-methoxy-4-methyl-2-(2-trifluoromethyl-pyridin-4-yl)-4H-pyrazolo[1,5-a]quinazolin-5-one;
7,8-dimethoxy-4-methyl-2-(2-trifluoromethyl-pyridin-4-yl)-4H-pyrazolo[1,5-a]quinazolin-5-one;
7,8-difluoro-4-methyl-2-(2-trifluoromethyl-pyridin-4-yl)-4H-pyrazolo[1,5-a]quinazolin-5-one;
8-fluoro-7-methoxy-4-methyl-2-(2-trifluoromethyl-pyridin-4-yl)-4H-pyrazolo[1,5-a]quinazolin-5-one;
8-(4-hydroxy-piperidin-1-yl)-7-methoxy-4-methyl-2-(2-trifluoromethyl-pyridin-4-yl)-4H-pyrazolo[1,5-a]quinazolin-5-one;
8-dimethylamino-7-fluoro-4-methyl-2-(2-trifluoromethyl-pyridin-4-yl)-4H-pyrazolo[1,5-a]quinazolin-5-one;
7-bromo-8-fluoro-4-methyl-2-(2-trifluoromethyl-pyridin-4-yl)-4H-pyrazolo[1,5-a]quinazolin-5-one;
7-bromo-8-methoxy-4-methyl-2-(2-trifluoromethyl-pyridin-4-yl)-4H-pyrazolo[1,5-a]quinazolin-5-one;
8-methoxy-4-methyl-7-methylamino-2-(2-trifluoromethyl-pyridin-4-yl)-4H-pyrazolo[1,5-a]quinazolin-5-one;
7-chloro-2-(2-chloro-pyridin-4-yl)-4-methyl-4H-pyrazolo[1,5-a]quinazolin-5-one;
7-chloro-2-(2-chloro-pyridin-4-yl)-4-methyl-4H-pyrazolo[1,5-a]quinazolin-5-one;
7-chloro-2-(2-Fluoro-pyridin-4-yl)-4-methyl-4H-pyrazolo[1,5-a]quinazolin-5-one;
7-chloro-4-methyl-2-[2-(2,2,2-trifluoro-ethoxy)-pyridin-4-yl]-4H-pyrazolo[1,5-a]quinazolin-5-one;
2-(2-chloro-pyridin-4-yl)-7-methoxy-4-methyl-4H-pyrazolo[1,5-a]quinazolin-5-one;
2-(2-cyclopropyl-pyridin-4-yl)-7-methoxy-4-methyl-4H-pyrazolo[1,5-a]quinazolin-5-one;
2-(2-fluoro-pyridin-4-yl)-7-methoxy-4-methyl-4H-pyrazolo[1,5-a]quinazolin-5-one;
7-methoxy-4-methyl-2-[2-(2,2,2-trifluoro-ethoxy)-pyridin-4-yl]-4H-pyrazolo[1,5-a]quinazolin-5-one;
4-methyl-2-(1-methyl-1H-pyrazol-4-yl)-4H-pyrazolo[1,5-a]quinazolin-5-one;
4-methyl-2-pyridin-4-yl-4H-pyrazolo[1,5-a]quinazolin-5-one;
2-(2-chloro-6-methyl-pyridin-4-yl)-4-methyl-4H-pyrazolo[1,5-a]quinazolin-5-one;
2-(2-cyclopropyl-6-methyl-pyridin-4-yl)-4-methyl-4H-pyrazolo[1,5-a]quinazolin-5-one;
2-(3-fluoro-pyridin-4-yl)-4-methyl-4H-pyrazolo[1,5-a]quinazolin-5-one;
2-(3-chloro-pyridin-4-yl)-4-methyl-4H-pyrazolo[1,5-a]quinazolin-5-one;
4-methyl-2-(3-methyl-pyridin-4-yl)-4H-pyrazolo[1,5-a]quinazolin-5-one;
8-(3-Hydroxy-azetidine-1-carbonyl)-4-methyl-2-(2-trifluoromethyl-pyridin-4-yl)-4H-pyrazolo[1,5-a]quinazolin-5-one;
8-(3-Hydroxy-propoxy)-4-methyl-2-(2-trifluoromethyl-pyridin-4-yl)-4H-pyrazolo[1,5-a]quinazolin-5-one;
2-(2-Cyclopropyl-pyridin-4-yl)-8-fluoro-4-methyl-4H-pyrazolo[1,5-a]quinazolin-5-one;
2-(2-Cyclopropyl-pyridin-4-yl)-8-(4-hydroxy-piperidin-1-yl)-4-methyl-4H-pyrazolo[1,5-a]quinazolin-5-one;
2-(2-Difluoromethyl-pyridin-4-yl)-8-fluoro-4-methyl-4H-pyrazolo[1,5-a]quinazolin-5-one;
2-(2-Difluoromethyl-pyridin-4-yl)-8-(4-hydroxy-piperidin-1-yl)-4-methyl-4H-pyrazolo[1,5-a]quinazolin-5-one;
2-(2-Cyclobutyl-pyridin-4-yl)-8-fluoro-4-methyl-4H-pyrazolo[1,5-a]quinazolin-5-one;
2-(2-Chloro-pyridin-4-yl)-8-fluoro-4-methyl-4H-pyrazolo[1,5-a]quinazolin-5-one;
2-(2-Chloro-pyridin-4-yl)-8-(4-hydroxy-piperidin-1-yl)-4-methyl-4H-pyrazolo[1,5-a]quinazolin-5-one;
7-Fluoro-8-(3-hydroxy-azetidin-1-yl)-4-methyl-2-(2-trifluoromethyl-pyridin-4-yl)-4H-pyrazolo[1,5-a]quinazolin-5-one;
7-Fluoro-4-methyl-8-(oxetan-3-yloxy)-2-(2-trifluoromethyl-pyridin-4-yl)-4H-pyrazolo[1,5-a]quinazolin-5-one;
3-[7-Fluoro-4-methyl-5-oxo-2-(2-trifluoromethyl-pyridin-4-yl)-4,5-dihydro-pyrazolo[1,5-a]quinazolin-8-ylamino]-propionitrile;
7-Fluoro-8-(2-hydroxymethyl-pyrrolidin-1-yl)-4-methyl-2-(2-trifluoromethyl-pyridin-4-yl)-4H-pyrazolo[1,5-a]quinazolin-5-one;
7-Fluoro-8-(7-hydroxymethyl-1-aza-spiro[3.5]non-1-yl)-4-methyl-2-(2-trifluoromethyl-pyridin-4-yl)-4H-pyrazolo[1,5-a]quinazolin-5-one;
8-(3-Hydroxy-piperidin-1-yl)-4-methyl-2-(2-trifluoromethyl-pyridin-4-yl)-4H-pyrazolo[1,5-a]quinazolin-5-one;

8-(2,6-Dimethyl-morpholin-4-yl)-4-methyl-2-(2-trifluoromethyl-pyridin-4-yl)-4H-pyrazolo[1,5-a]quinazolin-5-one;

8-(2-Hydroxy-2-methyl-propylamino)-4-methyl-2-(2-trifluoromethyl-pyridin-4-yl)-4H-pyrazolo[1,5-a]quinazolin-5-one; and pharmaceutically acceptable salts, solvates and prodrugs thereof.

19. A pharmaceutical composition comprising a compound as defined in any one of items 1 to 18 or a pharmaceutically acceptable salt, solvate or prodrug thereof, and a pharmaceutically acceptable excipient.

20. A compound as defined in any one of items 1 to 18 or a pharmaceutically acceptable salt, solvate or prodrug thereof or the pharmaceutical composition of item 19 for use in the treatment and/or prophylaxis of conditions associated with altered glutamatergic signalling and/or functions, and/or conditions which can be affected by alteration of glutamate level or signalling.

21. Use of a compound as defined in any one of items 1 to 18 or a pharmaceutically acceptable salt, solvate or prodrug thereof for the preparation of a medicament for the treatment and/or prophylaxis of conditions associated with altered glutamatergic signalling and/or functions, and/or conditions which can be affected by alteration of glutamate level or signalling.

22. A method of treating and/or preventing a condition associated with altered glutamatergic signalling and/or functions, and/or a condition which can be affected by alteration of glutamate level or signalling, the method comprising the administration of a compound as defined in any one of items 1 to 18 or a pharmaceutically acceptable salt, solvate or prodrug thereof or the pharmaceutical composition of item 19 to a subject in need of such treatment or prevention.

23. The compound for use according to item 20 or the pharmaceutical composition for use according to item 20 or the use of item 21 or the method of item 22, wherein the condition to be treated or prevented is selected from: epilepsy; dementias; parkinsonism and movement disorders; motor neuron disease or amyotrophic lateral sclerosis; neurodegenerative and/or hereditary disorders of the nervous system; disorders of the peripheral nervous system; multiple sclerosis and other demyelinating diseases of the nervous system; infantile cerebral palsy; paralytic syndromes including hemiplegia and hemiparesis; cerebrovascular disorders; migraine; headache; myoneural disorders; disorders of the eye and visual pathways; intracranial trauma/injury and their sequels; trauma/injury to nerves and spinal cord and their sequels; poisoning and toxic effects of nonmedicinal substances; accidental poisoning by drugs, medicinal substances and biologicals acting on the central, peripheral and autonomic system; neurological and psychiatric adverse effects of drugs, medicinal and biological substances; disturbance of sphincter control and sexual function; mental disorders; delirium and cognitive disorders; substance related disorders; schizophrenia and psychotic disorders; mood disorders; anxiety disorders; eating disorders; sleep disorders and sleep/wake disorders; medication-induced movement disorders; endocrine and metabolic diseases; acute and chronic pain; nausea and vomiting; irritable bowel syndrome; cancers; or autism spectrum disorders.

24. The compound for use according to item 20 or 23 or the pharmaceutical composition for use according to item 20 or 23 or the use of item 21 or 23 or the method of item 22 or 23, wherein the condition to be treated or prevented is selected from: dementias; parkinsonism and movement disorders; acute or chronic pain; anxiety disorders; schizophrenia; mood disorders; endocrine or metabolic diseases; or cancers.

25. The compound for use according to item 24 or the pharmaceutical composition for use according to item 24 or the use of item 24 or the method of item 24, wherein said dementias are selected from: dementias of the Alzheimer's type (DAT); Alzheimer's disease; Pick's disease; vascular dementias; Lewy-body disease; dementias due to metabolic, toxic and deficiency diseases, including alcoholism, hypothyroidism, and vitamin B12 deficiency; AIDS-dementia complex; Creutzfeld-Jacob disease; or atypical subacute spongiform encephalopathy.

26. The compound for use according to item 24 or the pharmaceutical composition for use according to item 24 or the use of item 24 or the method of item 24, wherein said parkinsonism and movement disorders are selected from: Parkinson's disease; multiple system atrophy; progressive supranuclear palsy; corticobasal degeneration; hepatolenticular degeneration; chorea, including Huntington's disease and hemiballismus; athetosis; dystonias, including spasmodic torticollis, occupational movement disorder, and Gilles de la Tourette syndrome; tardive or drug induced dyskinesias; tremor; or myoclonus.

27. The compound for use according to item 24 or the pharmaceutical composition for use according to item 24 or the use of item 24 or the method of item 24, wherein said anxiety disorders are selected from: panic disorders, phobias, obsessive-compulsive disorders, stress disorders, or generalized anxiety disorders.

28. The compound for use according to item 24 or the pharmaceutical composition for use according to item 24 or the use of item 24 or the method of item 24, wherein said mood disorders are selected from depressive disorders or bipolar disorders.

29. The compound for use according to item 24 or the pharmaceutical composition for use according to item 24 or the use of item 24 or the method of item 24, wherein said endocrine or metabolic diseases are selected from diabetes, disorders of the endocrine glands, or hypoglycaemia.

30. The compound for use according to item 24 or the pharmaceutical composition for use according to item 24 or the use of item 24 or the method of item 24, wherein said cancers are selected from gliomas, colorectal cancer, melanoma, or prostate cancer.

31. A compound as defined in any one of items 1 to 18 or a pharmaceutically acceptable salt, solvate or prodrug thereof or the pharmaceutical composition of item 19 for use in the treatment and/or prophylaxis of Alzheimer's disease.

32. Use of a compound as defined in any one of items 1 to 18 or a pharmaceutically acceptable salt, solvate or prodrug thereof for the preparation of a medicament for the treatment and/or prophylaxis of Alzheimer's disease.

33. A method of treating and/or preventing Alzheimer's disease, the method comprising the administration of a compound as defined in any one of items 1 to 18 or a pharmaceutically acceptable salt, solvate or prodrug thereof or the pharmaceutical composition of item 19 to a subject in need of such treatment or prevention.

34. The method of any one of items 22 to 30 or 33, wherein said subject is a human.

35. A method for identifying an agent that binds to metabotropic glutamate receptor 2 (mGluR2), comprising the following steps:
(a) contacting mGluR2 with the compound of any one of items 1 to 18, wherein said compound is radio-labeled or fluorescence-labeled, under conditions that permit binding of the compound to mGluR2, thereby generating bound, labeled compound;
(b) detecting a signal that corresponds to the amount of bound, labeled compound in the absence of test agent;
(c) contacting the bound, labeled compound with a test agent;
(d) detecting a signal that corresponds to the amount of bound labeled compound in the presence of test agent; and
(e) comparing the signal detected in step (d) to the signal detected in step (b) to determine whether the test agent binds to mGluR2.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

In this section, the term "compound" is used to refer to a synthesis intermediate while the term "example" refers to a compound of general formula (I) according to the present invention.

The compounds/examples described in this section are defined by their chemical formulae and their corresponding chemical names. In case of conflict between any chemical formula and the corresponding chemical name indicated herein, the present invention relates to both the compound/example defined by the chemical formula and the compound/example defined by the chemical name.

Experimental

Experimental Section

All reagents were commercial grade and used without further purification. Commercially available anhydrous solvents were used for reactions conducted under inert atmosphere. Microwave experiments were performed with a Biotage initiator. The microwave modulates the power in order to reach the selected temperature as fast as possible. The time of each experiment is the time at the selected temperature.

Column chromatography were performed using a Biotage isolera 4® autopurification system, with the Biotage® SNAP cartridge KP-SIL. Thin layer chromatography was carried out using pre-coated silica gel F-254plate.

Reaction were monitor and molecules were characterized using a waters equity system couple with SQD2 platform or water HPLC system couple with Waters micromass platform. The HPLC system could be used also in preparative mode.

HPLC System:

The HPLC system was a Waters platform with a 2767 sample manager, a 2525 pump, a photodiode array detector (190-400 nM). The column used was a XSelect $C_{18}$ 3.5 µM (4.6×50 mm) in analytical mode and a XSelect $C_{18}$ 5 µM (30×100 mm) in preparative mode. The mobile phase in both cases consisted in an appropriate gradient of A and B. A was water with 0.05% of TFA and B was MeOH with 0.05% of TFA. Flow rate was 1 mL per min in analytical mode and 25 mL min in preparative mode. All LCMS were performed at room temperature. HPLC is coupled with a Waters micromass platform. All mass spectra were full-scan experiments (mass range 100-800 amu). Mass spectra were obtained using electro spray ionization.

UPLC System:

The UPLC system was a Waters Aquity platform with a photodiode array detector (190-400 nM). The column used was a Acuity CSH $C_{18}$ 1.7 µM (2.1×30 mm) The mobile phase consisted in a gradient of A and B. A was water with 0.025% of TFA and B was Acetonitrile with 0.025% of TFA. Flow rate was 0.8 mL per min. All analysis were performed at 55° C. UPLC is coupled with a Waters SQD2 platform. All mass spectra were full-scan experiments (mass range 100-800 amu). Mass spectra were obtained using electro spray ionization.

$^1$H NMR spectra were recorded on a Bruker AMX-400 spectrometer. Proton chemical shifts are listed relative to residual $CDCl_3$ (7.24 ppm), DMSO (2.50 ppm) or $D_2O$ (4.78 ppm). Splitting patterns are designated as s (singlet), d (doublet), dd (double-doublet), t (triplet), tt (triplet-trplet), td (triplet-doublet), q (quartet), quint (quintuplet), sex (sextuplet), sept (septuplet), m (multiplet), b (broad), bs (broad singlet).

Melting Points are measured on a Barnstead Electrothermal 9100 and are not corrected.

Most compounds and examples, when it is possible, are triturated in $Et_2O$ or pentane before drying.

General Procedure I: Formation of
4H-Pyrazolo[1,5-a]quinazolin-5-one E from
Hydrazine D and Activated Acid a Via a
Keto-Nitrile B not Isolated (Cf. Scheme 1)

Method (i): Under anhydrous condition, to a solution of acetonitrile (2.5 equiv.) in DME (c=0.6 mol·L$^{-1}$) cooled at −78° C., BuLi (1.6N in hexane-2.5 equiv.) was added dropwise. The mixture was stirred for 1 hour at −78° C., then a solution of the acid derivative A (acid chloride or ester—1.0 equiv.) in DME (cf=0.15 mol·L$^{-1}$) was added dropwise. The reaction mixture was stirred at −78° C. for 1 hour and then was allowed to warm to room temperature and the next step was performed.

Acetic acid (same volume as DME) was added, DME was removed under reduced pressure and hydrazine D, HCl salt (1.0 equiv.) was introduced. The reaction mixture was heat under reflux for 2 hours. After cooling, the reaction mixture was concentrated and the residue was coevaporated twice with toluene before hydrolysis with saturated aqueous $NaHCO_3$ solution. The precipitate was collected, washed with water and dried under reduced pressure at 60° C. with $P_2O_5$ for 18 hours. Sometimes, DME was switched by THF.

Method (ii): Under anhydrous condition, to a solution of acetonitrile (2.5 equiv.) in DME (c=0.8 mol·L$^{-1}$) cooled at −78° C., BuLi (1.6N in hexane-2.5 equiv.) was added dropwise. The mixture was stirred for 1 hour at −78° C., then a solution of the acid derivative A (acid chloride or ester—1.0 equiv.) in DME (cf=0.15 mol·L$^{-1}$) was added dropwise.

The reaction mixture was stirred at −78° C. for 1 hour and then was allowed to warm to room temperature and the next step was performed.

Acetic acid (10.0 equiv.) was added and hydrazine D, HCl salt (1.0 equiv.) was introduced. The reaction mixture was warmed for 18 hours at 100° C. After cooling, the reaction mixture was concentrated and the residue was coevaporated twice with toluene before hydrolysis with saturated aqueous NaHCO$_3$ solution. The precipitate was collected, washed with water and dried under reduced pressure at 60° C. with P$_2$O$_5$ for 18 hours.

Method (iii): Under anhydrous condition, to a solution of acetonitrile (2.5 equiv.) in THF (c=0.8 mol·L$^{-1}$) cooled at −78° C., BuLi (1.6N in hexane-2.5 equiv.) was added dropwise. The mixture was stirred for 1 hour at −78° C., then a solution of the acid derivative A (acid chloride or ester—1.0 equiv.) in THF (cf=0.15 mol·L$^{-1}$) was added dropwise. The reaction mixture was stirred at −78° C. for 1 hour, then was allowed to warm to room temperature and hydrolysed with saturated aqueous NH$_4$Cl solution and extracted with DCM. The organic layer was washed with brine, dried over MgSO$_4$ or Na$_2$SO$_4$ and concentrated. The ketonitrile B was used in the next step without further purification and was supposed quantitative.

To a solution of ketonitrile B (1.0 equiv.) in acetic acid (c=0.15 mol·L$^{-1}$) hydrazine D, HCl salt was added (1.0 equiv.). The reaction mixture was heated for 2 Hours at 120° C. After cooling, the reaction mixture was concentrated and the residue was coevaporated twice with toluene before hydrolysis with saturated aqueous NaHCO$_3$ solution. The precipitate was collected, washed with water and dried under reduced pressure at 60° C. with P$_2$O$_5$ for 18 hours.

Method (iv): Under anhydrous condition, to a solution of acetonitrile (2.5 equiv.) in THF (c=0.6 mol·L$^{-1}$) cooled at −78° C., BuLi (1.6N in hexane-2.5 equiv.) was added dropwise. The mixture was stirred for 1 hour at −78° C., then a solution of the acid derivative A (acid chloride or ester—1.0 equiv.) in THF (cf=0.15 mol·L$^{-1}$) was added dropwise. The reaction mixture was stirred at −78° C. for 1 hour, and then acetic acid (same volume as THF) was added before the mixture was allowed to warm to room temperature.

THF was removed under reduced pressure and hydrazine D, HCl salt (1.0 equiv.) was introduced. The reaction mixture was heated for 2 hours at reflux. After cooling, the reaction mixture was hydrolysed with saturated aqueous NaHCO$_3$ solution. The precipitate was collected, washed with water and dried under reduced pressure at 60° C. with P$_2$O$_5$ for 18 hours.

Compound 1: 2-(2-Chloro-pyridin-4-yl)-4H-pyrazolo[1,5-a]quinazolin-5-one

Compound 1 was obtained according to general procedure I(i), starting from 2-Chloro-isonicotinic acid methyl ester in presence of 2-hydrazino-benzoic acid as a beige solid in 91% yield.

$^1$H-NMR (400 MHz, DMSO): 6.63 (s, 1H, Ar); 7.52-7.56 (m, 1H, Ar); 7.89-7.94 (m, 1H, Ar); 7.98 (dd, J 5.1 Hz, J 1.5 Hz, 1H, Ar); 8.06 (bs 1H, Ar); 8.18 (d, J 8.0 Hz, J 1.3 Hz, 1H, Ar); 8.21 (d, J 7.8 Hz, 1H, Ar); 8.50 (d, J 5.1 Hz, 1H, Ar). Signal for NH is not observed.

M/Z (M[$^{35}$Cl]+H)$^+$=297.1.

General Procedure II: Formation of N-substituted 4H-Pyrazolo[1,5-a]quinazolin-5-one G from 4H-Pyrazolo[1,5-a]quinazolin-5-one E in Presence of Electrophile F (cf. Scheme 2)

Method (i): Under anhydrous condition, to a solution of quinazolin-5-one E (1.0 equiv.) in DMF (c=0.2 molL$^{-1}$) cooled by an ice bath, NaH (60% in mineral oil, 1.7 equiv.) was added in 3 portions. The mixture was stirred for 15 minutes, then the electrophile F (2.5 equiv.) was added. The ice bath was removed, and the reaction was stirred at room temperature. When the reaction is completed, the mixture was hydrolysed with saturated aqueous NH$_4$Cl solution. The precipitate was collected, washed with water, Et$_2$O and was dried under reduced pressure at 60° C. with P$_2$O$_5$ for 18 hours.

Method (ii): Under anhydrous condition, to a solution of quinazolin-5-one E (1.0 equiv.) in DMF (c=0.2 molL$^{-1}$) cooled by an ice bath, tBuOK (1.7 equiv.) was added. The mixture was stirred for 5 minutes, then the electrophile F (2.5 equiv.) was added. The ice bath was removed, and the reaction was stirred at room temperature. When the reaction is completed, the mixture was hydrolysed with saturated aqueous NH$_4$Cl solution. The precipitate was collected, washed with water, dried under reduced pressure and purified if required.

Method (iii): Under anhydrous condition, to a solution of quinazolin-5-one E (1.0 equiv.) in DMA (c=0.2 molL$^{-1}$) cooled by an ice bath, NaH (in mineral oil 60%, 1.7 equiv.) was added in 3 portions. The mixture was stirred for 10 minutes, then the electrophile F (2.5 equiv.) was added. The ice bath was removed, and the reaction was stirred at room temperature. When the reaction is completed, the mixture was hydrolysed. The precipitate was collected, washed with water, a minimum amount of EtOH, Et$_2$O and was dried under reduced pressure at 60° C. with P$_2$O$_5$ for 18 hours.

Example 1: 2-(2-Chloro-pyridin-4-yl)-4-methyl-4H-pyrazolo[1,5-a]quinazolin-5-one

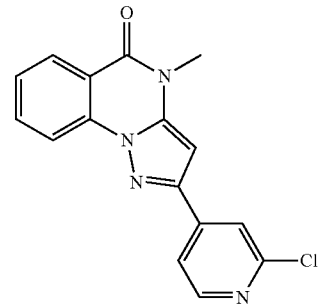 [SMILES: Cn1c(=O)c2ccccc2n2nc(-c3ccnc(Cl)c3)cc12]

Example 1 was obtained according to general procedure II(i), starting from compound 1 in presence of iodomethane. The reaction mixture was stirred at room temperature for 120 min. Example 1 was obtained as a beige solid in 70% yield.

$^1$H-NMR (400 MHz, DMSO): 3.55 (s, 3H, N—CH$_3$); 7.08 (s, 1H, Ar); 7.54-7.58 (m, 1H, Ar); 7.91-7.96 (m, 2H, Ar); 8.02 (bs, 1H, Ar); 8.19-8.27 (m, 2H, Ar); 8.52 (d, J 5.2 Hz, 1H, Ar).

M/Z (M[$^{35}$Cl]+H)$^+$=311.1.

General Procedure III: Negeshi Coupling: Cross-Coupling Reaction of a Halide and an Organozinc Derivative Under inert atmosphere, a mixture of halide, (1.0 equiv.), organozinc derivative (1.5-4.0 equiv.), PdCl$_2$(dppf)$_2$ (0.1 equiv.) and CuI (0.2 equiv.) in Dioxane (C=0.1 molL$^{-1}$) was heated for 1 hour at 80° C. After cooling, the reaction mixture was hydrolysed and extracted with EtOAc or DCM. The organic layers were combined, washed with brine, dried over MgSO$_4$, concentrated and purified to afford the product.

In some cases, the HCl salt was prepared.

General Procedure IV: Formation of HCl Salt

Method (i): To a solution of the free base in DCM, HCl in Et$_2$O (2N, 5 equiv.) was added. The resulting precipitate was collected, washed with Et$_2$O and dried at 50° C. under reduced pressure with P$_2$O$_5$.

Method (ii): To a solution or suspension of the free base in MeOH, HCl in MeOH (1.25N, 5 equiv.) was added. The mixture was vigorously stirred, then concentrated. The residue was taken in Et$_2$O. The resulting solid was collected, washed with Et$_2$O and dried at 50° C. under reduced pressure with P$_2$O$_5$.

Method (iii): The free base was suspended in MeOH and HCl in MeOH (1.25N, 5 equiv.) was added. The suspension was vigorously stirred, and then the solid was collected, washed with Et$_2$O and dried at 50° C. under reduced pressure with P$_2$O$_5$.

Example 2: 4-methyl 2-(2-methyl-pyridin-4-yl)-4H-pyrazolo[1,5-a]quinazolin-5-one

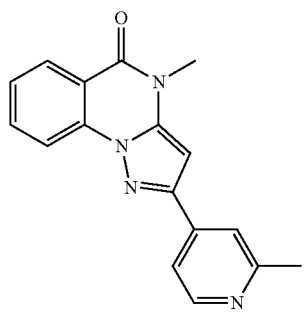 [SMILES: Cc1cc(-c2cc3n(C)c(=O)c4ccccc4n3n2)ccn1]

Example 2 was obtained according to general procedure III starting from example 1 in presence of dimethylzinc (in toluene 2M-1.5 equiv.). Purification by flash-chromatography (MeOH in DCM, 0 to 10%) afforded example 2 as a beige solid in 58% yield.

$^1$H-NMR (400 MHz, DMSO): 2.56 (s, 3H, CCH$_3$); 3.57 (s, 3H, NCH$_3$); 6.96 (s, 1H, Ar); 7.53-7.57 (m, 1H, Ar); 7.72-7.73 (m, 1H, Ar); 7.82 (bs, 1H, Ar); 7.91-7.96 (m, 1H, Ar); 8.19-8.22 (m, 2H, Ar); 8.55-8.56 (m, 1H, Ar).

M/Z (M+H)$^+$=291.2.

Example 3: 2-(2-Ethyl-pyridin-4-yl)-4-methyl-4H-pyrazolo[1,5-a]quinazolin-5-one, HCl Salt

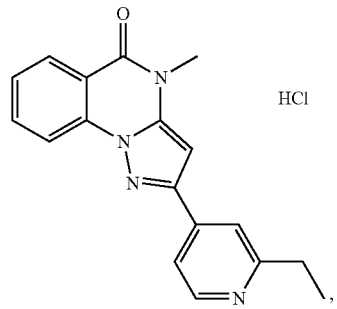 [SMILES: CCc1cc(-c2cc3n(C)c(=O)c4ccccc4n3n2)ccn1 ; Cl]

Example 3 was obtained according to general procedure III starting from example 1 in presence of diethylzinc (in toluene 1M-1.5 equiv.). Purification by flash-chromatography (EtOAc in cyclohexane, 40 to 70%) and salt formation according to procedure IV(i) afforded example 3 as a beige solid in 52% yield.

$^1$H-NMR (400 MHz, DMSO): 1.40 (t, 3H, J 7.6 Hz, CCH$_2$CH$_3$); 3.08 (Q, 2H, J 7.6 Hz, CCH$_2$CH$_3$); 3.58 (s, 3H, NCH$_3$); 7.25 (s, 1H, Ar); 7.58-7.63 (m, 1H, Ar); 7.95-7.99 (m, 1H, Ar); 8.21-8.30 (m, 3H, Ar); 8.37 (bs, 1H, Ar); 8.83 (d, J 6.1 Hz, 1H, Ar). Signal for HCl is not observed.

M/Z (M+H)$^+$=305.2.

MP: >250° C.

Example 4: 2-(2-propyl-pyridin-4-yl)-4-methyl-4H-pyrazolo[1,5-a]quinazolin-5-one, HCl Salt

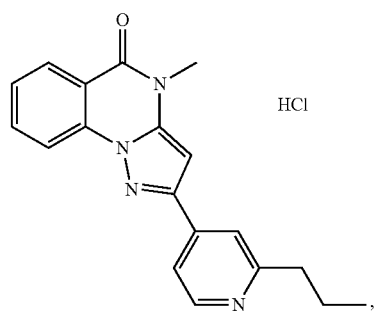 [SMILES: CCCc1cc(-c2cc3n(C)c(=O)c4ccccc4n3n2)ccn1 ; Cl]

Example 4 was obtained according to general procedure III starting from example 1 in presence of propylzinc bromide (in THF 0.5M-3.0 equiv.). Purification by flash-chromatography (MeOH in DCM, 0 to 10%) and salt formation according to procedure IV(ii) afforded example 4 as a white solid in 37% yield.

$^1$H-NMR (400 MHz, DMSO): 0.98 (t, 3H, J 7.5 Hz, CCH$_2$CH$_2$CH$_3$); 1.85 (sex, 2H, J 7.5 Hz, CCH$_2$CH$_2$CH$_3$); 3.03 (q, 2H, J 7.5 Hz, CCH$_2$CH$_2$CH$_3$); 3.58 (s, 3H, NCH$_3$); 7.24 (s, 1H, Ar); 7.59-7.63 (m, 1H, Ar); 7.95-7.99 (m, 1H, Ar); 8.22-8.28 (m, 3H, Ar); 8.36 (bs, 1H, Ar); 8.84 (d, J 6.1 Hz, 1H, Ar). Signal for HCl salt is not observed.

M/Z (M+H)$^+$=319.2.

MP: >250° C.

Example 5: 2-(2-Cyclopropyl-pyridin-4-yl)-4-methyl-4H-pyrazolo[1,5-a]quinazolin-5-one, HCl Salt

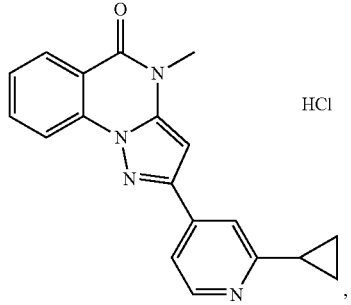 [SMILES: Cn1c(=O)c2ccccc2n2nc(-c3ccnc(C4CC4)c3)cc12 ; Cl]

Example 5 was obtained according to general procedure III starting from example 1 in presence of cyclopropylzinc bromide (in THF 0.5M-3.0 equiv.). Purification by flash-chromatography (EtOAct in cyclohexane, 50 to 80%) and salt formation according to procedure IV(i) afforded example 5 as a beige solid in 38% yield.

$^1$H-NMR (400 MHz, DMSO): 1.25-1.33 (m, 4H, 2CH$_2$); 2.42-2.47 (m, 1H, CCH); 3.57 (s, 3H, NCH$_3$); 7.22 (s, 1H, Ar); 7.57-7.61 (m, 1H, Ar); 7.93-7.99 (m, 2H, Ar); 8.10-8.11 (m, 1H, Ar); 8.20-8.25 (m, 2H, Ar); 8.67 (d, J 5.9 Hz, 1H, Ar). Signal for HCl salt is not observed.

M/Z (M+H)$^+$=317.3.

MP: 248-251° C.

Example 6: 2-(2-cyclobutyl-pyridin-4-yl)-4-methyl-4H-pyrazolo[1,5-a]quinazolin-5-one, HCl Salt

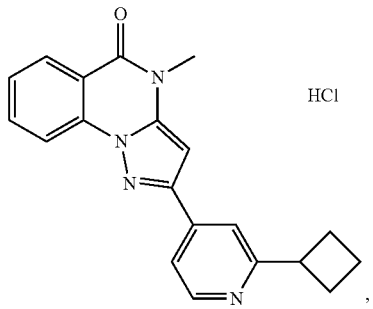 [SMILES: Cn1c(=O)c2ccccc2n2nc(-c3ccnc(C4CCC4)c3)cc12 ; Cl]

Example 6 was obtained according to general procedure III starting from example 1 in presence of cyclobutylzinc bromide (in THF 0.5M-3.0 equiv.). Purification by flash-chromatography (MeOH in DCM, 0 to 5%) and salt formation according to procedure IV(iii) afforded example 6 as a white solid in 8% yield.

$^1$H-NMR (400 MHz, DMSO): 1.90-1.99 (m, 1H, CH); 2.07-2.19 (m, 1H, CH); 2.43-2.48 (m, 4H, 2CH$_2$); 3.59 (s, 3H, NCH$_3$); 3.98 (quint, J 8.9 Hz, 1H, CH); 7.30 (s, 1H, Ar); 7.58-7.62 (m, 1H, Ar); 7.95-7.99 (m, 1H, Ar); 8.22-8.28 (m, 3H, Ar); 8.30 (bs, 1H, Ar); 8.79 (d, J 5.9 Hz, 1H, Ar). Signal for HCl salt is not observed.

M/Z (M+H)$^+$=331.0.

MP: 236-244° C.

Example 7: 2-(2-cyclopentyl-pyridin-4-yl)-4-methyl-4H-pyrazolo[1,5-a]quinazolin-5-one, HCl Salt

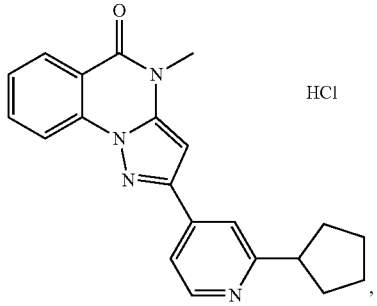 [SMILES: Cn1c(=O)c2ccccc2n2nc(-c3ccnc(C4CCCC4)c3)cc12 ; Cl]

Example 7 was obtained according to general procedure III starting from example 1 in presence of cyclopentylzinc bromide (in THF 0.5M-3.0 equiv.). Purification by flash-chromatography (MeOH in DCM, 0 to 10%) and salt formation according to procedure IV(iii) afforded example 7 as a white solid in 9% yield.

$^1$H-NMR (400 MHz, DMSO): 1.73-1.77 (m, 2H, 2CH); 1.86-192 (m, 4H, 4CH); 2.18-2.24 (m, 2H, 2CH); 3.44-3.53 (m, 1H, CH); 3.58 (s, 3H, NCH$_3$); 7.30 (s, 1H, Ar); 7.58-7.62 (m, 1H, Ar); 7.94-7.99 (m, 1H, Ar);); 8.23 (dd, J 8.0 Hz, J 1.3 Hz, 1H, A); 8.25-8.27 (m, 2H, Ar); 8.32 (bs, 1H, Ar); 8.80 (d, J 5.9 Hz, 1H, Ar). Signal for HCl salt is not observed.

M/Z (M+H)$^+$=345.2.

MP: >250° C.

Example 8: 2-(2-cyclohexyl-pyridin-4-yl)-4-methyl-4H-pyrazolo[1,5-a]quinazolin-5-one, HCl Salt

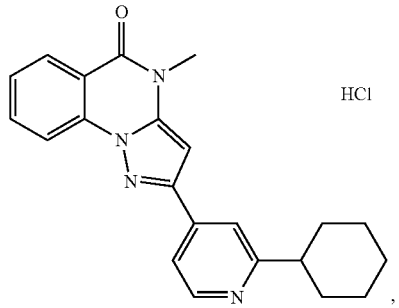 [SMILES: Cn1c(=O)c2ccccc2n2nc(-c3ccnc(C4CCCCC4)c3)cc12 ; Cl]

Example 8 was obtained according to general procedure III starting from example 1 in presence of cyclohexylzinc bromide (in THF 0.5M-3.0 equiv.). Purification by flash-chromatography (MeOH in DCM, 0 to 10%) and salt formation according to procedure IV(ii) afforded example 8 as a white solid in 25% yield.

$^1$H-NMR (400 MHz, DMSO): 1.27-1.48 (m, 3H, 3CH); 1.66-1.79 (m, 3H, 3CH); 1.87-1.90 (m, 2H, 2CH); 1.99-2.02 (m, 2H, 2CH); 3.03-3.10 (m, 1H, CH); 3.59 (s, 3H, NCH$_3$); 7.30 (s, 1H, Ar); 7.59-7.62 (m, 1H, Ar); 7.95-7.99 (m, 1H, Ar);); 8.23 (dd, J 8.0 Hz, J 1.1 Hz, 1H, A); 8.26-8.28 (m, 2H, Ar); 8.31 (bs, 1H, Ar); 8.81 (d, J 5.9 Hz, 1H, Ar). Signal for HCl salt is not observed.

M/Z (M+H)$^+$=359.3.

MP: >250° C.

Example 9: 4-Methyl-2-(2-vinyl-pyridin-4-yl)-4H-pyrazolo[1,5-a]quinazolin-5-one

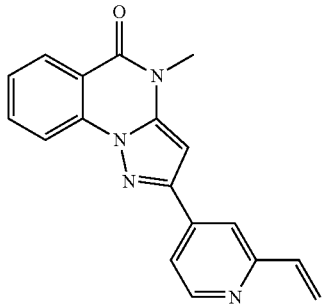 [SMILES: C=Cc1cc(-c2cc3n(C)c(=O)c4ccccc4n3n2)ccn1]

Under inert atmosphere, example 1 (1.0 equiv.), potassium vinyltrifluoroborate (2.0 equiv.), PdOAc$_2$ (0.1 equiv.), Ruphos (0.2 equiv.) and Cs$_2$CO$_3$ (3.0 equiv.) in a mixture of dioxanne/water (90/10) (C=0.1 molL$^{-1}$) was submitted to microwave irradiation (130° C., 20 min, P<70 W). To the uncompleted reaction, PdCl$_2$(dppf)$_2$ (0.1 equiv.) and potassium vinyltrifluoroborate (2.0 equiv.), were added and the mixture was submitted to microwave irradiation (130° C., 20 min, P<70 W) for a second time. After cooling, the reaction mixture was hydrolysed and then extracted with EtOAc. The organic layers were combined, washed with brine, dried over MgSO$_4$, concentrated and purified by flash-chromatography (EtOAc in cyclohexane, 0 to 50%). Example 9 was obtained as a brown solid in 63% yield.

$^1$H-NMR (400 MHz, DMSO): 3.58 (s, 3H, NCH$_3$); 5.56 (dd, J 10.8 Hz, J 1.6 Hz, 1H, CH); 6.36 (dd, J 17.4 Hz, J 1.6 Hz, 1H, CH); 6.92 (dd, J 17.4 Hz, J 10.8 Hz, 1H, CH); 7.02 (s, 1H, Ar); 7.53-7.57 (m, 1H, Ar); 7.82 (dd, J 5.1 Hz, J 1.6 Hz, 1H, Ar); 7.92-7.96 (m, 1H, Ar); 8.04 (bs, 1H, Ar); 8.21-8.23 (m, 2H, Ar); 8.66 (d, J 5.1 Hz, 1H, Ar).

M/Z (M+H)$^+$=303.2.

General Procedure V: Suzuki Coupling: Cross-Coupling Reaction of a Halide and Boronic Acid Derivatives Under inert atmosphere, a mixture of halide (1.0 equiv.), boronic acid derivative (1.5-equiv.), PdCl$_2$(dppf)$_2$ (0.1 equiv.) and aqueous Na$_2$CO$_3$ (1.2 M-3.0 equiv.) in DMF (C=0.15 molL$^{-1}$) was heated for 3 hours at 100° C. After cooling, the reaction mixture was hydrolysed. The precipitate was collected, washed with water, Et$_2$O, dried under reduced pressure and purified to afford the product.

Example 10: 2-(2-Isopropenyl-pyridin-4-yl)-4-methyl-4H-pyrazolo[1,5-a]quinazolin-5-one

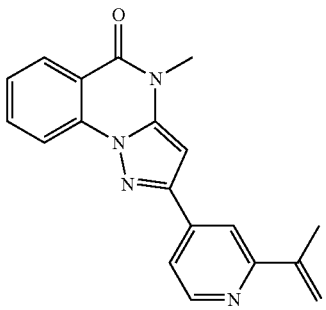 [SMILES: C=C(C)c1cc(-c2cc3n(C)c(=O)c4ccccc4n3n2)ccn1]

Example 10 was obtained according to general procedure V starting from example 1 in presence of Isopropenylboronic acid pinacol ester. Purification by flash-chromatography (MeOH in DCM, 0 to 5%) afforded example 10 as a beige solid in 68% yield.

$^1$H-NMR (400 MHz, DMSO): 2.23 (s, 3H, CCH$_3$); 3.58 (s, 3H, NCH$_3$); 5.40 (m, 1H, CH); 6.04 (m, 1H, CH); 7.08 (s, 1H, Ar); 7.53-7.57 (m, 1H, Ar); 7.84 (dd, J 5.1 Hz, J 1.4 Hz, 1H, Ar); 7.91-7.95 (m, 1H, Ar); 8.13 (bs, 1H, Ar); 8.20-8.24 (m, 2H, Ar); 8.67 (d, J 5.1 Hz, 1H, Ar).

M/Z (M+H)$^+$=317.2.

Example 11: 2-(2-Isopropyl-pyridin-4-yl)-4-methyl-4H-pyrazolo[1,5-a]quinazolin-5-one, HCl Salt

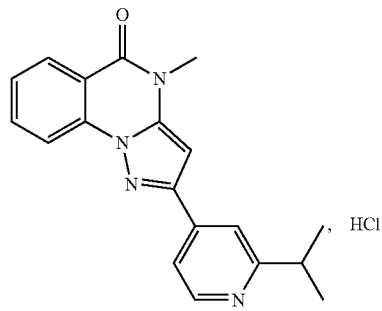 [SMILES: CC(C)c1cc(-c2cc3n(C)c(=O)c4ccccc4n3n2)ccn1 ; Cl]

To a solution of example 10 (1.0 equiv.) in MeOH (C=0.05 molL$^{-1}$), Pd/C (10% w/w) was added. The reaction mixture was purged with hydrogen and stirred for 48 hours at 60° C. under 4 bars hydrogen pressure. Catalyst was filtered off on celite and washed with MeOH. Filtrate was concentrated and purified by flash-chromatography (MeOH in DCM, 0 to 5%). Salt formation according to procedure IV(iii) afforded example 11 as a white solid in 11% yield.

$^1$H-NMR (400 MHz, DMSO): 1.44 (d, 6H, J 7.0 Hz, CH(CH$_3$)$_2$); 3.44 (sept, 1H, J 7.0 Hz, CH(CH$_3$)$_2$); 3.58 (s, 3H, NCH$_3$); 7.31 (s, 1H, Ar); 7.58-7.62 (m, 1H, Ar); 7.95-7.99 (m, 1H, Ar); 8.23 (dd, J 8.0 Hz, J 1.4 Hz, 1H, Ar); 8.25-8.30 (m, 2H, Ar); 8.36 (bs, 1H, Ar); 8.82 (d, J 6.1 Hz, 1H, Ar). Signal for HCl salt is not observed.

M/Z (M+H)$^+$=319.0.

MP: >250° C.

General Procedure VI: CN Introduction Starting from a Halide or a Pseudo Halide Under inert atmosphere, a mixture of halide, (1.0 equiv.), zinc cyanide (1.6-equiv.) and Pd(PPh$_3$)$_4$ (0.1 equiv.) in DMF (C=0.2 molL$^{-1}$) was submitted to microwave irradiation (130° C., 10 min, P<70 W). After cooling, the reaction mixture was hydrolysed with a saturated aqueous K$_2$CO$_3$ solution. The precipitate was collected, washed with water, dried under reduced pressure and purified to afford the product.

Example 12: 4-(4-Methyl-5-oxo-4,5-dihydro-pyrazolo[1,5-a]quinazolin-2-yl)-pyridine-2-carbonitrile

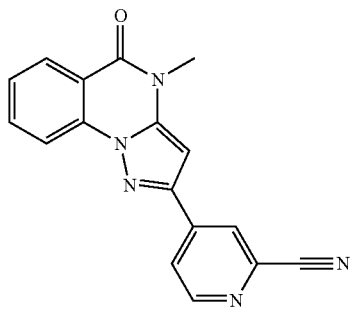 [SMILES: Cn1c(=O)c2ccccc2n2nc(-c3ccnc(C#N)c3)cc12]

Example 12 was obtained according to general procedure VI starting from example 1. Purification by flash-chromatography (MeOH in DCM, 0 to 10%) afforded example 12 as a white solid in 94% yield.

$^1$H-NMR (400 MHz, DMSO): 3.59 (s, 3H, NCH$_3$); 7.02 (s, 1H, Ar); 7.55-7.59 (m, 1H, Ar); 7.92-7.96 (m, 1H, Ar); 8.21-8.25 (m, 3H, Ar); 8.48 (bs, 1H, Ar); 8.85 (d, J 5.1 Hz, 1H, Ar).

M/Z (M+H)$^+$=302.2.

MP: >250° C.

Compound 2: 2-(2-Fluoro-pyridin-4-yl)-4H-pyrazolo[1,5-a]quinazolin-5-one

Compound 2 was obtained according to general procedure I(ii), starting from 2-fluoro-isonicotinic acid methyl ester in presence of 2-hydrazino-benzoic acid as a brown solid in 83% yield.

$^1$H-NMR (400 MHz, DMSO): 6.64 (s, 1H, Ar); 7.53-7.57 (m, 1H, Ar); 7.71 (bs 1H, Ar); 7.91-7.96 (m, 2H, Ar); 8.16-8.21 (m, 2H, Ar); 8.33 (d, J 5.2 Hz, 1H, Ar); 12.42 (bs, 1H, NH).

M/Z (M+H)$^+$=281.3.

Example 13: 2-(2-Fluoro-pyridin-4-yl)-4-methyl-4H-pyrazolo[1,5-a]quinazolin-5-one

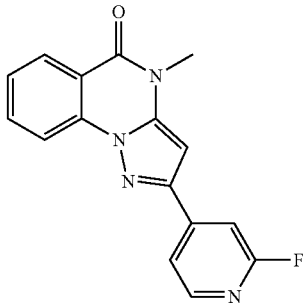 [SMILES: Cn1c(=O)c2ccccc2n2nc(-c3ccnc(F)c3)cc12]

Example 13 was obtained according to general procedure II(i), starting from compound 2 in presence of iodomethane. The reaction mixture was stirred at room temperature for 120 min. Example 13 was obtained as a brown solid in 78% yield.

$^1$H-NMR (400 MHz, DMSO): 3.57 (s, 3H, NCH$_3$); 7.08 (s, 1H, Ar); 7.56-7.60 (m, 1H, Ar); 7.70 (bs 1H, Ar); 7.92-7.97 (m, 2H, Ar); 8.22-8.24 (m, 2H, Ar); 8.37 (d, J 5.2 Hz, 1H, Ar).

M/Z (M+H)$^+$=295.2.

Example 14: 2-(2-Methoxy-pyridin-4-yl)-4-methyl-4H-pyrazolo[1,5-a]quinazolin-5-one

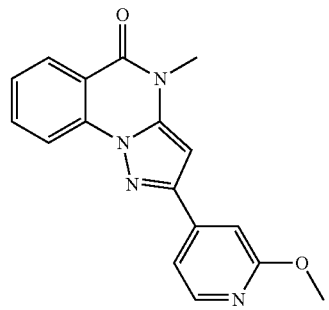 [SMILES: COc1cc(-c2cc3n(C)c(=O)c4ccccc4n3n2)ccn1]

To a solution of example 13 (1.0 equiv.) in MeOH (C=0.10 molL$^{-1}$) sodium methoxyde (2.0 equiv.) was introduced. The reaction mixture was submitted twice to microwave irradiation (150° C., 5 min.). Sodium methoxyde (2.0 equiv.) was added and the reaction mixture was submitted to microwave irradiation (150° C., 5 min.). After cooling, the precipitate was collected, washed with water and Et$_2$O and was dried under reduced pressure to afford example 14 as a white solid in 66% yield.

$^1$H-NMR (400 MHz, DMSO): 3.56 (s, 3H, NCH$_3$); 3.92 (s, 3H, OCH$_3$); 6.98 (s, 1H, Ar); 7.34 (bs, 1H, Ar); 7.53-7.57 (m, 2H, Ar); 7.91-7.95 (m, 1H, Ar); 8.19-8.22 (m, 2H, Ar); 8.28 (d, J 5.3 Hz, 1H, Ar).

M/Z (M+H)$^+$=307.2.

MP: >250° C.

Example 15: 2-(2-ethoxy-pyridin-4-yl)-4-methyl-4H-pyrazolo[1,5-a]quinazolin-5-one

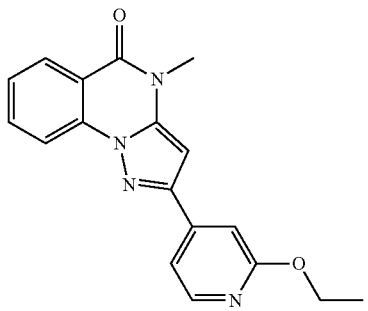 [SMILES: CCOc1cc(-c2cc3n(C)c(=O)c4ccccc4n3n2)ccn1]

To a suspension of example 13 (1.0 equiv.) in EtOH (C=0.10 molL$^{-1}$) sodium ethoxyde (5.0 equiv.) was introduced. The reaction mixture was submitted twice to microwave irradiation (150° C., 15 min.). Sodium ethoxyde (2.0 equiv.) was added four times and after each addition the reaction mixture was submitted to microwave irradiation (150° C., 15 min.). After cooling, the precipitate was collected, washed with saturated aqueous NH$_4$Cl solution, water and Et$_2$O and was dried under reduced pressure to afford example 15 as a beige solid in 19% yield.

$^1$H-NMR (400 MHz, DMSO): 1.35 (t, 3H, J 7.0 Hz, OCH$_2$CH$_3$); 3.55 (s, 3H, NCH$_3$); 4.36 (q, 2H, J 7.0 Hz,

OCH₂CH₃); 6.98 (s, 1H, Ar); 7.32 (bs, 1H, Ar); 7.52-7.56 (m, 2H, Ar); 7.90-7.94 (m, 1H, Ar); 8.18-8.21 (m, 2H, Ar); 8.25 (d, J 5.3 Hz, 1H, Ar).

M/Z (M+H)⁺=321.0.

MP: 180-182° C.

General Procedure VII: Alcohol Introduction Via Nucleophilic Substitution

Method (i): Under inert atmosphere, to a suspension of quinazolinone (1.0 equiv.) in DMA (C=0.1 molL⁻¹), alcohol (2.5 equiv.) and NaH (2.0 equiv.) were added. The reaction mixture was submitted to microwave irradiation (150° C., 5 min.). After cooling, the reaction mixture was hydrolysed. The resulting precipitate was collected, washed with water, dried under reduced pressure and purified to afford the product.

Method (ii): Under inert atmosphere, to a suspension of quinazolinone (1.0 equiv.) in DMA (C=0.1 molL⁻¹), alcohol (2.5 equiv.) and NaH (2.0 equiv.) were added. The reaction mixture was heated for 3 hours at 100° C. After cooling, the reaction mixture was hydrolysed. The resulting precipitate was collected, washed with water, dried under reduced pressure and purified to afford the product.

Method (iii): Under inert atmosphere, to a solution of quinazolinone (1.0 equiv.) and alcohol (10.0 equiv.) in THF (C=0.2 molL⁻¹), tBUOK (1.2 equiv.) was added. The reaction mixture was stirred for 17 hours at room temperature and then was hydrolysed. The resulting precipitate was collected, washed with water, dried under reduced pressure and purified to afford the product.

Example 16: 2-(2-Isopropoxy-pyridin-4-yl)-4-methyl-4H-pyrazolo[1,5-a]quinazolin-5-one

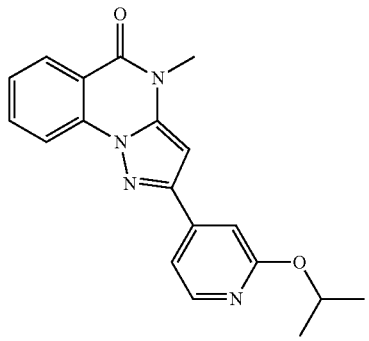 [SMILES: CC(C)Oc1cc(-c2cc3n(C)c(=O)c4ccccc4n3n2)ccn1]

Example 16 was obtained according to general procedure VII(i) starting from example 13 in presence of isopropanol. Purification by flash-chromatography (MeOH in DCM, 0 to 5%) afforded example 16 as a white solid in 13% yield.

¹H-NMR (400 MHz, DMSO): 1.33 (d, 6H, J 6.2 Hz, OCH(CH₃)₂); 3.55 (s, 3H, NCH₃); 5.30 (Sept, 1H, J 6.2 Hz, OCH(CH₃)₂); 6.98 (s, 1H, Ar); 7.28 (bs, 1H, Ar); 7.49-7.56 (m, 2H, Ar); 7.90-7.94 (m, 1H, Ar); 8.18-8.21 (m, 2H, Ar); 8.24 (d, J 5.2 Hz, 1H, Ar).

M/Z (M+H)⁺=335.2.

MP: 173-176° C.

Example 17: 2-(2-Cyclobutoxy-pyridin-4-yl)-4-methyl-4H-pyrazolo[1,5-a]quinazolin-5-one

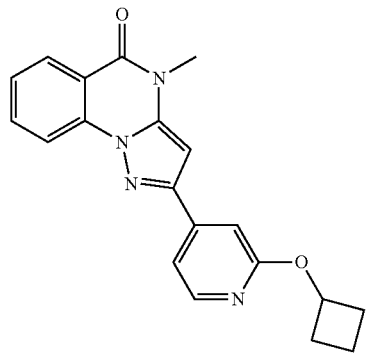 [SMILES: Cn1c(=O)c2ccccc2n2nc(-c3ccnc(OC4CCC4)c3)cc12]

Example 17 was obtained according to general procedure VII(i) starting from example 13 in presence of cyclobutanol. Purification by flash-chromatography (MeOH in DCM, 0 to 5%) afforded example 17 as a white solid in 24% yield.

¹H-NMR (400 MHz, DMSO): 1.63-1.72 (m, 1H, CH); 1.72-1.85 (m, 1H, CH); 2.04-2.14 (m, 2H, 2CH); 2.40-2.47 (m, 2H, 2CH); 3.56 (s, 3H, NCH₃); 5.20 (quint, J 7.4 Hz, 1H, CH); 7.00 (s, 1H, Ar); 7.31 (bs, 1H, Ar); 7.52-7.57 (m, 2H, Ar); 7.91-7.96 (m, 1H, Ar); 8.19-8.24 (m, 3H, Ar).

M/Z (M+H)⁺=347.2.

MP: 218-222° C.

Example 18: 4-Methyl-2-[2-(oxetan-3-yloxy)-pyridin-4-yl]-4H-pyrazolo[1,5-a]quinazolin-5-one

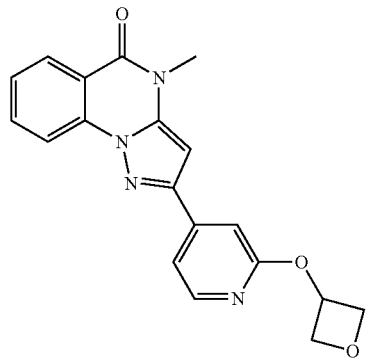 [SMILES: Cn1c(=O)c2ccccc2n2nc(-c3ccnc(OC4COC4)c3)cc12]

Example 18 was obtained according to general procedure VII(i) starting from example 13 in presence of 3-hydroxyoxetane. Purification by flash-chromatography (MeOH in DCM, 0 to 5%) afforded example 18 as a white solid in 20% yield.

¹H-NMR (400 MHz, DMSO): 3.56 (s, 3H, NCH₃); 4.61 (dd, J 7.0 Hz, J 5.7 Hz, 2H, OCH(CHaHb)2O); 4.90-4.94 (m, 2H, OCH(CHaHb)2O); 5.62 (quint, J 5.7 Hz, 1H, OCH(CHaHb)2O); 7.01 (s, 1H, Ar); 7.43 (bs, 1H, Ar); 7.53-7.60 (m, 2H, Ar); 7.91-7.95 (m, 1H, Ar); 8.19-8.22 (m, 3H, Ar).

M/Z (M+H)⁺=349.2.

MP: 219-223° C.

Example 19: 2-(2-Cyclopropylmethoxy-pyridin-4-yl)-4-methyl-4H-pyrazolo[1,5-a]quinazolin-5-one

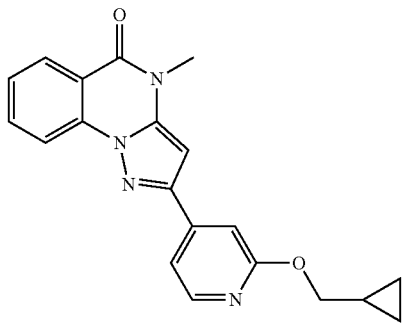 [SMILES: Cn1c(=O)c2ccccc2n2nc(-c3ccnc(OCC4CC4)c3)cc12]

Example 19 was obtained according to general procedure VII(ii) starting from example 13 in presence of cyclopropanemethanol. Trituration in Et$_2$O afforded example 19 as a white solid in 71% yield.

$^1$H-NMR (400 MHz, DMSO): 0.33-0.37 (m, 2H, 2CH); 0.55-0.60 (m, 2H, 2CH); 1.23-1.31 (m, 1H, CH); 3.55 (s, 3H, NCH$_3$); 4.15 (d, J 7.1 Hz, 2H, OCH$_2$); 6.99 (s, 1H, Ar); 7.36 (bs, 1H, Ar); 7.52-7.56 (m, 2H, Ar); 7.90-7.95 (m, 1H, Ar); 8.18-8.21 (m, 2H, Ar); 8.23 (d, J 5.3 Hz, 1H, Ar).

M/Z (M+H)$^+$=347.0.

MP: 185-189° C.

Example 20: 2-[2-(2-Methoxy-ethoxy)-pyridin-4-yl]-4-methyl-4H-pyrazolo[1,5-a]quinazolin-5-one

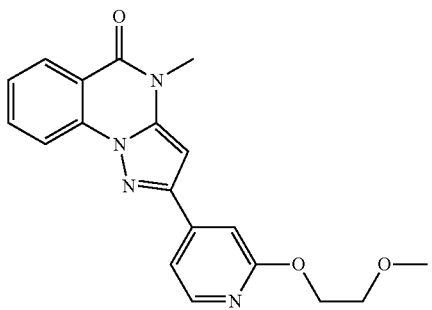 [SMILES: COCCOc1cc(-c2cc3n(C)c(=O)c4ccccc4n3n2)ccn1]

Example 20 was obtained according to general procedure VII(i) starting from example 13 in presence of 2-methoxyethanol. Purification by flash-chromatography (MeOH in DCM, 0 to 5%) afforded example 20 as a white solid in 40% yield.

$^1$H-NMR (400 MHz, DMSO): 3.33 (s, 3H, OCH$_3$); 3.55 (s, 3H, NCH$_3$); 3.66-3.71 (m, 2H, OCH$_2$); 4.42-4.44 (m, 2H, OCH$_2$); 6.99 (s, 1H, Ar); 7.36 (bs, 1H, Ar); 7.52-7.56 (m, 2H, Ar); 7.90-7.94 (m, 1H, Ar); 8.18-8.21 (m, 2H, Ar); 8.25 (d, J 5.3 Hz, 1H, Ar).

M/Z (M+H)$^+$=351.2

MP: 169-173° C.

Example 21: 4-Methyl-2-[2-(2,2,2-trifluoro-ethoxy)-pyridin-4-yl]-4H-pyrazolo[1,5-a]quinazolin-5-one

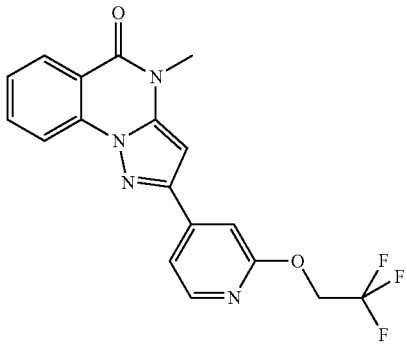 [SMILES: Cn1c(=O)c2ccccc2n2nc(-c3ccnc(OCC(F)(F)F)c3)cc12]

Example 21 was obtained according to general procedure VII(i) starting from example 13 in presence of 2,2,2-trifluoroethanol. Trituration in Et$_2$O afforded example 21 as a white solid in 75% yield.

$^1$H-NMR (400 MHz, DMSO): 3.55 (s, 3H, NCH$_3$); 5.05 (q, J 9.0 Hz, 2H, OCH$_2$CF$_3$); 7.05 (s, 1H, Ar); 7.52-7.57 (m, 2H, Ar); 7.69 (d, J 5.3 Hz, 1H, Ar); 7.91-7.95 (m, 1H, Ar); 8.20-8.22 (m, 2H, Ar); 8.31 (d, J 5.3 Hz, 1H, Ar).

M/Z (M+H)$^+$=375.2

MP: 219-223° C.

Example 22: 4-Methyl-2-[2-(2,2-difluoro-ethoxy)-pyridin-4-yl]-4H-pyrazolo[1,5-a]quinazolin-5-one

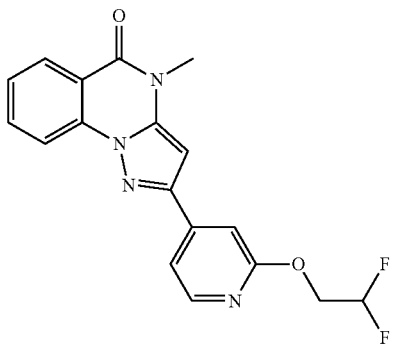 [SMILES: Cn1c(=O)c2ccccc2n2nc(-c3ccnc(OCC(F)F)c3)cc12]

Example 22 was obtained according to general procedure VII(ii) starting from example 13 in presence of 2,2-difluoroethanol. Trituration in Et$_2$O afforded example 22 as a white solid in 84% yield.

$^1$H-NMR (400 MHz, DMSO): 3.55 (s, 3H, NCH$_3$); 4.63 (td, J 15.1 Hz, J 3.6 Hz, 2H, OCH$_2$CHF$_2$); 6.43 (tt, J 54.8 Hz, J 3.6 Hz, 1H, OCH$_2$CHF$_2$); 7.02 (s, 1H, Ar); 7.45 (bs, 1H, Ar); 7.52-7.57 (m, 1H, Ar); 7.63 (dd, J 5.3 Hz, J 1.2 Hz, 1H, Ar); 7.90-7.94 (m, 1H, Ar); 8.19-8.21 (m, 2H, Ar); 8.28 (d, J 5.3 Hz, 1H, Ar).

M/Z (M+H)$^+$=357.1

MP: 209-213° C.

Example 23: 2-[2-(2,2-Difluoro-propoxy)-pyridin-4-yl]-4-methyl-4H-pyrazolo[1,5-a]quinazolin-5-one

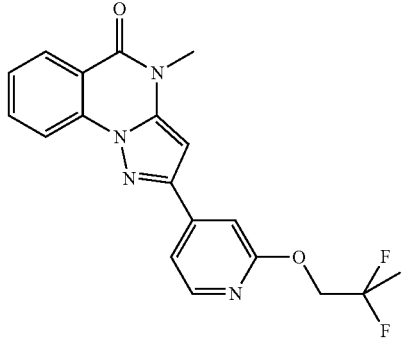 [SMILES: Cn1c(=O)c2ccccc2n2nc(-c3ccnc(OCC(C)(F)F)c3)cc12]

Example 23 was obtained according to general procedure VII(ii) starting from example 13 in presence of 2,2-difluoropropan-2-ol. Trituration in Et$_2$O afforded example 23 as a white solid in 86% yield.

$^1$H-NMR (400 MHz, DMSO): 1.77 (t, J 19.2 Hz, 3H, OCH$_2$CF$_2$CH$_3$); 3.55 (s, 3H, NCH$_3$); 4.62 (t, J 13.1 Hz, 2H, OCH$_2$CF$_2$CH$_3$); 7.03 (s, 1H, Ar); 7.46 (bs, 1H, Ar); 7.52-7.57 (m, 1H, Ar); 7.63 (dd, J 5.3 Hz, J 1.3 Hz, 1H, Ar); 7.90-7.94 (m, 1H, Ar); 8.19-8.21 (m, 2H, Ar); 8.28 (d, J 5.3 Hz, 1H, Ar).

M/Z (M+H)$^+$=371.1
MP: 189-191° C.

Example 24: 4-Methyl-2-[2-(2,2,3,3,3-pentafluoro-propoxy)-pyridin-4-yl]-4H-pyrazolo[1,5-a]quinazolin-5-one

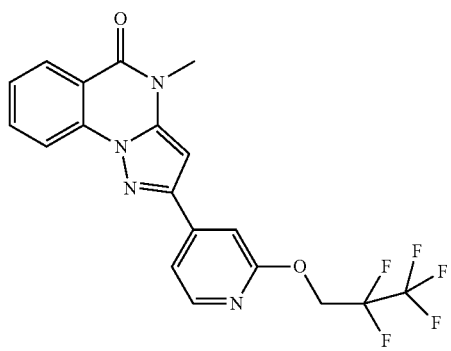 [SMILES: Cn1c(=O)c2ccccc2n2nc(-c3ccnc(OCC(F)(F)C(F)(F)F)c3)cc12]

Example 24 was obtained according to general procedure VII(ii) starting from example 13 in presence of 2,2,3,3,-pentafluoropropanol. In order to complete the reaction, 2,2,3,3,-pentafluoropropanol (2.5 equiv.) and NaH (2.0 equiv.) were introduced a second time, then the mixture was warmed for 3 hours at 100° C. Trituration in Et$_2$O afforded example 24 as a white solid in 55% yield.

$^1$H-NMR (400 MHz, DMSO): 3.55 (s, 3H, NCH$_3$); 5.15 (t, J 13.8 Hz, 2H, OCH$_2$CF$_2$CF$_3$); 7.07 (s, 1H, Ar); 7.50 (bs, 1H, Ar); 7.53-7.57 (m, 1H, Ar); 7.70 (d, J 5.3 Hz, 1H, Ar); 7.90-7.95 (m, 1H, Ar); 8.20-8.22 (m, 2H, Ar); 8.32 (d, J 5.3 Hz, 1H, Ar).

M/Z (M+H)$^+$=425.1
MP: 150-155° C.

Example 25: 4-Methyl-2-[2-(2,2,2-trifluoro-1-trifluoromethyl-ethoxy)-pyridin-4-yl]-4H-pyrazolo[1,5-a]quinazolin-5-one

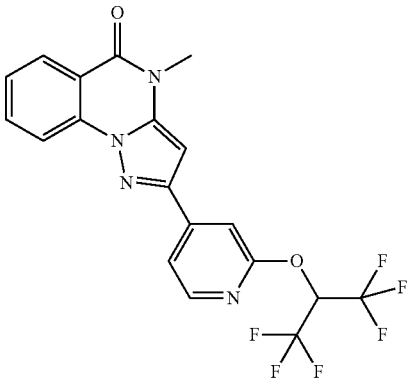 [SMILES: Cn1c(=O)c2ccccc2n2nc(-c3ccnc(OC(C(F)(F)F)C(F)(F)F)c3)cc12]

To a suspension of example 13 (1.0 equiv.) in 1,1,1,3,3,3-hexafluoro-2-propanol (C=0.07 molL$^{-1}$), potassium tert-butoxyde (10.0 equiv.) was introduced. The reaction mixture was submitted to microwave irradiation (150° C., 60 min.). After cooling, the reaction mixture was hydrolysed with saturated aqueous NH$_4$Cl solution and then extracted with DCM. The organic layers were combined, washed with brine, dried over MgSO$_4$, concentrated and purified by flash-chromatography (MeOH in DCM, 0 to 5%). Example 25 was obtained as a white solid in 19% yield.

$^1$H-NMR (400 MHz, DMSO): 3.55 (s, 3H, NCH$_3$); 7.10 (s, 1H, Ar); 7.21 (sept, 1H, J 6.5 Hz, CH(CF$_3$)$_2$); 7.54-7.58 (m, 1H, Ar); 7.67 (bs, 1H, Ar); 7.67 (dd, J 5.3 Hz, J 1.4 Hz, 1H, Ar); 7.91-7.95 (m, 1H, Ar); 8.20-8.23 (m, 2H, Ar); 8.38 (d, J 5.3 Hz, 1H, Ar).

M/Z (M+H)$^+$=443.2
MP: 188-194° C.

Compound 3: 2-(2-Trifluoromethyl-pyridin-4-yl)-4H-pyrazolo[1,5-a]quinazolin-5-one Compound 3 was obtained according to general procedure I(iii), starting from 2-trifluoromethyl-isonicotinic acid ethyl ester in presence of 2-hydrazino-benzoic acid as a beige solid in 86% yield.

$^1$H-NMR (400 MHz, DMSO): 6.76 (s, 1H, Ar); 7.54-7.58 (m, 1H, Ar); 7.91-7.96 (m, 1H, Ar); 8.18 (dd, J 7.9 Hz, J 1.2 Hz, 1H, Ar); 8.23-8.28 (m, 2H, Ar); 8.40 (bs, 1H, Ar); 8.85 (d, J 5.0 Hz, 1H, Ar); 12.39 (bs, 1H, NH).

M/Z (M+H)$^+$=331.2.

Example 26: 4-Methyl-2-(2-trifluoromethyl-pyridin-4-yl)-4H-pyrazolo[1,5-a]quinazolin-5-one

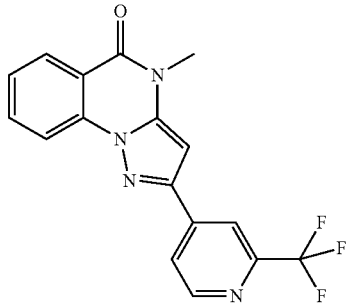 [SMILES: Cn1c(=O)c2ccccc2n2nc(-c3ccnc(C(F)(F)F)c3)cc12]

Example 26 was obtained according to general procedure II(i), starting from compound 3 in presence of iodomethane.

The reaction mixture was stirred at room temperature for 120 min. Example 26 was obtained as a white solid in 86% yield.

¹H-NMR (400 MHz, DMSO): 3.57 (s, 3H, NCH₃); 7.18 (s, 1H, Ar); 7.54-7.58 (m, 1H, Ar); 7.91-7.96 (m, 1H, Ar); 8.19-8.24 (m, 3H, Ar); 8.37 (bs, 1H, Ar); 8.88 (d, J 5.1 Hz, 1H, Ar).

M/Z (M+H)⁺=345.2.
MP: 232-244° C.

Example 27: 4-Methyl(D₃)-2-(2-trifluoromethyl-pyridin-4-yl)-4H-pyrazolo[1,5-a]quinazolin-5-one

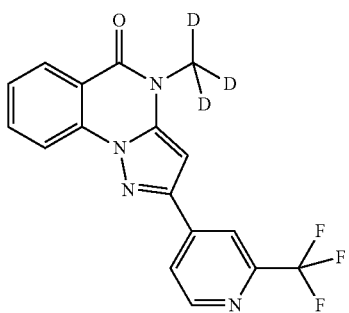 [SMILES: [2H]C([2H])([2H])n1c(=O)c2ccccc2n2nc(-c3ccnc(C(F)(F)F)c3)cc12]

Example 27 was obtained according to general procedure II(ii), starting from compound 3 in presence of deuterated iodomethane (CD₃I). The reaction mixture was stirred at room temperature for 60 min. Trituration in Et₂O afforded example 27 as a gray solid in 63% yield.

¹H-NMR (400 MHz, DMSO): 7.16 (s, 1H, Ar); 7.53-7.58 (m, 1H, Ar); 7.90-7.96 (m, 1H, Ar); 8.18-8.23 (m, 3H, Ar); 8.36 (bs, 1H, Ar); 8.88 (d, J 5.1 Hz, 1H, Ar).

M/Z (M+H)⁺=348.1.
MP: 232-237° C.

Example 28: 4-Ethyl-2-(2-trifluoromethyl-pyridin-4-yl)-4H-pyrazolo[1,5-a]quinazolin-5-one

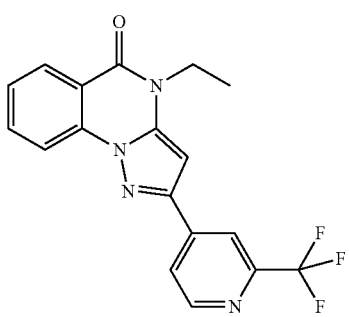 [SMILES: CCn1c(=O)c2ccccc2n2nc(-c3ccnc(C(F)(F)F)c3)cc12]

Example 28 was obtained according to general procedure II(ii), starting from compound 3 in presence of iodoethane. The reaction mixture was stirred at room temperature for 30 min. Purification by preparative HPLC afforded example 28 as a white solid in 18% yield.

¹H-NMR (400 MHz, DMSO): 1.34 (t, 3H, J 7.1 Hz, NCH₂CH₃); 4.13 (q, 2H, J 7.1 Hz, NCH₂CH₃); 7.27 (s, 1H, Ar); 7.55-7.59 (m, 1H, Ar); 7.92-7.96 (m, 1H, Ar); 8.20-8.26 (m, 3H, Ar); 8.39 (bs, 1H, Ar); 8.88 (d, J 5.1 Hz, 1H, Ar).

M/Z (M+H)⁺=359.0.
MP: 214-220° C.

Example 29: 4-(2,2-Difluoro-ethyl)-2-(2-trifluoromethyl-pyridin-4-yl)-4H-pyrazolo[1,5-a]quinazolin-5-one

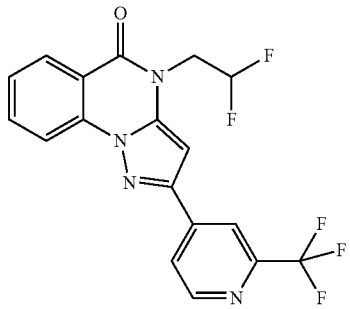 [SMILES: O=c1c2ccccc2n2nc(-c3ccnc(C(F)(F)F)c3)cc2n1CC(F)F]

Example 29 was obtained according to general procedure II(ii), starting from compound 3 in presence of 1,1-difluoro-2-iodoethane. The reaction mixture was stirred at room temperature overnight, then at 70° C. for 2 hours. Purification by preparative HPLC afforded example 29 as a white solid in 19% yield.

¹H-NMR (400 MHz, DMSO): 4.55 (td, J 14.5 Hz, J 3.8 Hz, 2H, NCH₂CHF₂); 6.47 (tt, J 55.1 Hz, J 3.8 Hz, 1H, NCH₂CHF₂); 7.35 (s, 1H, Ar); 7.58-7.62 (m, 1H, Ar); 7.96-8.00 (m, 1H, Ar); 8.22-8.28 (m, 3H, Ar); 8.36 (bs, 1H, Ar); 8.90 (d, J 5.0 Hz, 1H, Ar).

M/Z (M+H)⁺=395.4.
MP: 223-230° C.

Example 30: 4-(2-Methoxy-ethyl)-2-(2-trifluoromethyl-pyridin-4-yl)-4H-pyrazolo[1,5-a]quinazolin-5-one

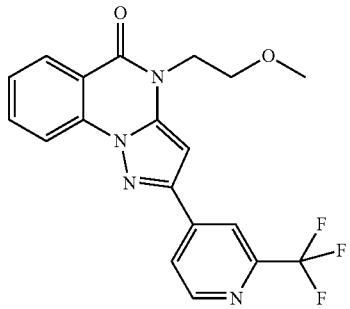 [SMILES: COCCn1c(=O)c2ccccc2n2nc(-c3ccnc(C(F)(F)F)c3)cc12]

Example 30 was obtained according to general procedure II(ii), starting from compound 3 in presence of 2-bromoethylmethyl ether. The reaction mixture was stirred for 17 hours at room. Purification by preparative HPLC afforded example 30 as a white solid in 30% yield.

¹H-NMR (400 MHz, DMSO): 3.28 (s, 3H, OCH₃); 3.74 (t, J 5.9 Hz, 2H, OCH₂CH₂N); 4.29 (t, J 5.9 Hz, 2H, OCH₂CH₂N); 7.25 (s, 1H, Ar); 7.56-7.60 (m, 1H, Ar); 7.93-7.97 (m, 1H, Ar); 8.20-8.26 (m, 3H, Ar); 8.39 (bs, 1H, Ar); 8.88 (d, J 5.0 Hz, 1H, Ar).

M/Z (M+H)⁺=389.1.
MP: 165-174° C.

General Procedure VIII: Formation of Ester a Via Innate Carbon-Hydrogen Functionalization Under inert atmosphere, a mixture of ethyl isocotinate (1.0 equiv.) and sulfinate (2.0 equiv.) was suspended in a mixture of DCM:water (8:2-C=0.14 mol·L$^{-1}$). TFA (1.0 equiv.), then tertbutylhydroperoxide (3.0 equiv.) were added and the mixture was vigorously stirred. When the starting material is consumed, the mixture was hydrolysed with a saturated aqueous NaHCO$_3$ solution and extracted with DCM. The organic layer was washed with brine, dried over MgSO$_4$ or Na$_2$SO$_4$ and concentrated. Compounds were used in the next steps without further purification.

Compound 4: 2-Difluoromethyl-isonicotinic Acid Ethyl Ester

Compound 4 was obtained according to general procedure VIII using bis {[(difluoromethyl)sulfonyl]oxy}zinc (DFMS). The reaction mixture was stirred for 4 hours at room temperature. Compound 4 was isolated as a yellow oil in a quantitative yield. To facilitate the extraction step, EDTA (8% w/w) was added to the NaHCO$_3$ solution.

$^1$H-NMR (400 MHz, DMSO): 1.35 (t, 3H, J 7.1 Hz, OCH$_2$CH$_3$); 4.39 (q, 2H, J 7.1 Hz, OCH$_2$CH$_3$); 7.09 (t, J 54.7 Hz, 1H, CHF$_2$); 8.02 (d, J 5.0 Hz, 1H, Ar); 8.06 (s, 1H, Ar); 8.92 (d, J 5.0 Hz, 1H, Ar).
M/Z (M+H)$^+$=202.0.

Compound 5: 2-(2-difluoromethyl-pyridin-4-yl)-4H-pyrazolo[1,5-a]quinazolin-5-one Compound 5 was obtained according to general procedure I(ii), starting from compound 4 in presence of 2-hydrazino-benzoic acid as a brown solid in 64% yield.

$^1$H-NMR (400 MHz, DMSO): 6.68 (s, 1H, Ar); 7.03 (t, J 54.8 Hz, 1H, CHF$_2$); 7.54-7.58 (m, 1H, Ar); 7.92-7.96 (m, 1H, Ar); 8.12-8.13 (m, 1H, Ar); 8.18 (dd, J 8.0 Hz, J 1.2 Hz, 1H, Ar); 8.20-8.24 (m, 2H, Ar); 8.77 (d, J 5.2 Hz, 1H, Ar); 12.46 (bs, 1H, NH).
M/Z (M+H)$^+$=313.2.

Example 31: 4-Methyl-2-(2-difluoromethyl-pyridin-4-yl)-4H-pyrazolo[1,5-a]quinazolin-5-one

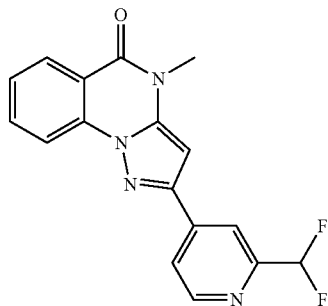 [SMILES: Cn1c(=O)c2ccccc2n2nc(-c3ccnc(C(F)F)c3)cc12]

Example 31 was obtained according to general procedure II(ii), starting from compound 5 in presence of iodomethane. The reaction mixture was stirred for 16 hours at room temperature. Purification by flash-chromatography (MeOH in DCM, 0 to 10%) afforded example 31 as a white solid in 26% yield.

$^1$H-NMR (400 MHz, DMSO): 3.57 (s, 3H, NCH$_3$); 7.04 (t, J 55.0 Hz, 1H, CHF$_2$); 7.12 (s, 1H, Ar); 7.54-7.58 (m, 1H, Ar); 7.91-7.96 (m, 1H, Ar); 8.10-8.12 (m, 1H, Ar); 8.20-8.24 (m, 3H, Ar); 8.80 (d, J 5.0 Hz, 1H, Ar).
M/Z (M+H)$^+$=327.2.
MP: 192-196° C.

Compound 6: 2-(1,1-Difluoro-ethyl)-isonicotinic Acid Ethyl Ester

Compound 6 was obtained according to general procedure VIII using sodium 1,1-difluoromethanesulfinate. The reaction mixture was stirred for 20 hours at room temperature. Compound 6 was isolated as a yellow oil in quantitative yield. To ensure a full conversion, sodium 1,1-difluoromethanesulfinate (2.0 equiv.) and tertbutyl hydroperoxide (3.0 equiv.) were added a second time after 18 hours.

$^1$H-NMR (400 MHz, DMSO): 1.35 (t, 3H, J 7.1 Hz, OCH$_2$CH$_3$); 2.03 (t, J 19.2 Hz, 1H, CF$_2$CH$_3$); 4.39 (q, 2H, J 7.1 Hz, OCH$_2$CH$_3$); 7.99-8.01 (m, 1H, Ar); 8.03-8.04 (m, 1H, Ar); 8.90 (d, J 5.0 Hz, 1H, Ar).
M/Z (M+H)$^+$=216.4.

Compound 7: 2-[2-(1,1-Difluoro-ethyl)-pyridin-4-yl]-4H-pyrazolo[1,5-a]quinazolin-5-one Compound 7 was obtained according to general procedure I(ii), starting from compound 6 in presence of 2-hydrazino-benzoic acid as a brown solid in 61% yield.

$^1$H-NMR (400 MHz, DMSO): 2.06 (t, J 19.1 Hz, 1H, CF$_2$CH$_3$); 6.68 (s, 1H, Ar); 7.54-7.58 (m, 1H, Ar); 7.91-7.96 (m, 1H, Ar); 8.08-8.10 (m, 1H, Ar); 8.18 (dd, J 8.0 Hz, J 1.3 Hz, 1H, Ar); 8.23-8.24 (m, 2H, Ar); 8.75 (d, J 5.2 Hz, 1H, Ar); 12.46 (bs, 1H, NH).
M/Z (M+H)$^+$=327.2.

Example 32: 2-[2-(1,1-Difluoro-ethyl)-pyridin-4-yl]-4-methyl-4H-pyrazolo[1,5-a]quinazolin-5-one

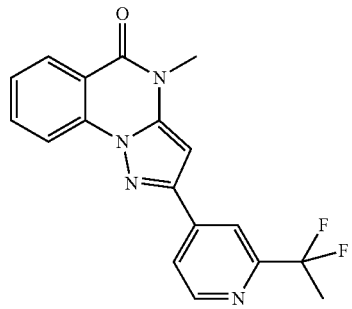 [SMILES: Cn1c(=O)c2ccccc2n2nc(-c3ccnc(C(C)(F)F)c3)cc12]

Example 32 was obtained according to general procedure II(i), starting from compound 7 in presence of iodomethane. The reaction mixture was stirred for 2 hours at room temperature. Example 32 was obtained without further purification as a beige solid in 55% yield.

$^1$H-NMR (400 MHz, DMSO): 2.07 (t, J 19.1 Hz, 1H, CF$_2$CH$_3$); 3.57 (s, 3H, NCH$_3$); 7.13 (s, 1H, Ar); 7.54-7.58 (m, 1H, Ar); 7.91-7.95 (m, 1H, Ar); 8.07-8.08 (m, 1H, Ar); 8.20-8.24 (m, 3H, Ar); 8.78 (d, J 5.0 Hz, 1H, Ar).
M/Z (M+H)$^+$=341.2.
MP: 196-207° C.

Example 33: 2-[2-(1,1-Difluoro-ethyl)-pyridin-4-yl]-4-methyl(D₃)-4H-pyrazolo[1,5-a]quinazolin-5-one

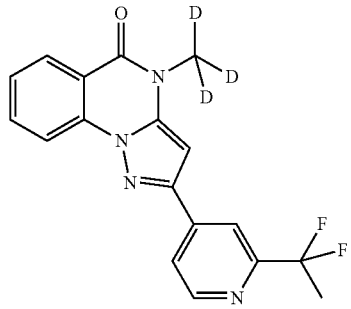 [SMILES: [2H]C([2H])([2H])n1c(=O)c2ccccc2n2nc(-c3ccnc(C(C)(F)F)c3)cc12]

Example 33 was obtained according to general procedure II(i), starting from compound 7 in presence of iodomethane D₃. The reaction mixture was stirred for 2 hours at room temperature. Example 33 was obtained without further purification as a beige solid in 52% yield.

¹H-NMR (400 MHz, DMSO): 2.07 (t, J 19.1 Hz, 1H, CF₂CH₃); 7.13 (s, 1H, Ar); 7.54-7.58 (m, 1H, Ar); 7.91-7.95 (m, 1H, Ar); 8.07-8.09 (m, 1H, Ar); 8.20-8.24 (m, 3H, Ar); 8.78 (d, J 5.2 Hz, 1H, Ar).
M/Z (M+H)⁺=344.2.
MP: 198-205° C.

General Procedure IX: Formation of Hydrazine D from the Corresponding Amino Derivative C (Cf. Scheme 1)

To a suspension of amino acid A (1.0 equiv.) in concentrated aqueous HCl solution (0.15 mol·L⁻¹) cooled by an ice bath, a cold solution of NaNO₂ (1.2 equiv.) in water (c=2.8 mol·L⁻¹) was added dropwise. The reaction mixture turned yellow with a suspension. After 1 hour, under vigorous stirring, a cold solution of SnCl₂ (3.1 equiv.) in concentrated aqueous HCl solution (c=2.8 mol·L⁻¹) was added dropwise. A suspension was obtained. The reaction mixture was filtered off 2 hours later. The solid was washed with a minimum of a cold aqueous HCl solution (1N) before being dried under reduced pressure at 80° C. with P₂O₅ for 18 hours.

Compound 8: 2-hydrazino-5-methyl-benzoic Acid, HCl

Compound 8 was obtained according to general procedure IX, starting from 2-amino-5-methyl-benzoic acid, as a beige solid in 90% yield.

¹H-NMR (400 MHz, DMSO): 2.26 (s, 3H, CH₃); 7.06 (d, J 8.5 Hz, 1H, Ar); 7.41 (dd, J 8.5 Hz, 2.2 Hz, 1H, Ar); 7.72 (d, J 2.2 Hz, 1H, Ar); 8.93 (bs, 1H, NH); 10.50 (bs, 3H, NH₃).
M/Z (M+H)⁺=167.1.

Compound 9: 7-Methyl-2-(2-trifluoromethyl-pyridin-4-yl)-4H-pyrazolo[1,5-a]quinazolin-5-one Compound 9 was obtained according to general procedure I(iii), starting from 2-trifluoromethyl-isonicotinic acid ethyl ester in presence of hydrazine 8 as a brown solid in 30% yield.

¹H-NMR (400 MHz, DMSO): 2.45 (s, 3H, CH₃); 6.61 (s, 1H, Ar); 7.66-7.68 (m, 1H, Ar); 7.95 (bs, 1H, Ar); 8.08-8.10 (m, 1H, Ar); 8.22 (bs, 1H, Ar); 8.35 (bs, 1H, Ar); 8.82 (bs, 1H, Ar). Signal for NH is not observed.
M/Z (M+H)⁺=345.2.

Example 34: 7-Methyl-2-(2-trifluoromethyl-pyridin-4-yl)-4H-pyrazolo[1,5-a]quinazolin-5-one

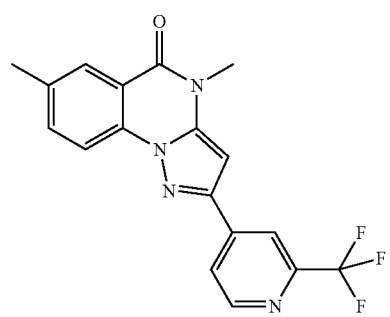 [SMILES: Cc1ccc2c(c1)c(=O)n(C)c1cc(-c3ccnc(C(F)(F)F)c3)nn21]

Example 34 was obtained according to general procedure II(i), starting from compound 9 in presence of iodomethane. The reaction mixture was stirred for 2 hours at room temperature. Example 34 was obtained without further purification as a beige solid in 55% yield.

¹H-NMR (400 MHz, DMSO): 3.59 (s, 3H, NCH₃); 7.14 (s, 1H, Ar); 7.73-7.75 (m, 1H, Ar); 7.99 (m, 1H, Ar); 8.10-8.12 (m, 1H, Ar); 8.21-8.22 (m, 1H, Ar); 8.35 (bs, 1H, Ar); 8.86-8.87 (m, 1H, Ar). Signal for CH₃ is not observed.
M/Z (M+H)⁺=359.1.
MP: 215-218° C.

Compound 10: 5-Chloro-2-hydrazino-benzoic Acid, HCl

Compound 10 was obtained according to general procedure IX, starting from 2-amino-5-chlorobenzoic acid, as a beige solid in 88% yield.

¹H-NMR (400 MHz, DMSO): 7.07 (d, J 8.9 Hz, 1H, Ar); 7.57 (dd, J 8.9 Hz, 2.5 Hz, 1H, Ar); 7.75 (d, J 2.5 Hz, 1H, Ar); 9.08 (bs, 1H, NH); 10.73 (bs, 3H, NH₃).

Compound 11: 7-Chloro-2-(2-trifluoromethyl-pyridin-4-yl)-4H-pyrazolo[1,5-a]quinazolin-5-one Compound 11 was obtained according to general procedure I(iii), starting from 2-trifluoromethyl-isonicotinic acid ethyl ester in presence of hydrazine 10 as a brown solid in 31% yield.

¹H-NMR (400 MHz, DMSO): 6.65 (s, 1H, Ar); 7.88 (dd, J 8.8 Hz, J 2.4 Hz, 1H, Ar); 8.07 (d, J 2.4 Hz, 1H, Ar); 8.20 (d, J 8.8 Hz, 1H, Ar); 8.23-8.24 (m, 1H, Ar); 8.37 (bs, 1H, Ar); 8.83 (d, J 4.9 Hz, 1H, Ar). Signal for NH is not observed.
M/Z (M[³⁵Cl]+H)⁺=365.0.

Example 35: 7-Chloro-2-(2-trifluoromethyl-pyridin-4-yl)-4H-pyrazolo[1,5-a]quinazolin-5-one

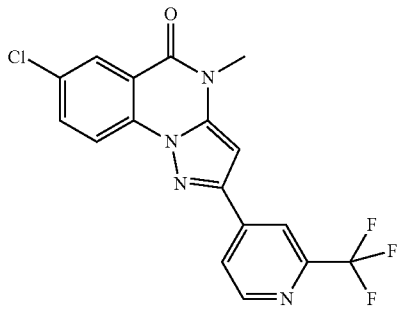 [SMILES: Cn1c(=O)c2cc(Cl)ccc2n2nc(-c3ccnc(C(F)(F)F)c3)cc12]

Example 35 was obtained according to general procedure II(i), starting from compound 11 in presence of iodomethane. The reaction mixture was stirred for 2 hours at room temperature. Example 35 was obtained without further purification as a white solid in 68% yield.

$^1$H-NMR (400 MHz, DMSO): 3.56 (s, 3H, NCH$_3$); 7.20 (s, 1H, Ar); 7.96 (dd, J 8.7 Hz, J 2.4 Hz, 1H, Ar); 8.10 (d, J 2.4 Hz, 1H, Ar); 8.22-8.24 (m, 2H, Ar); 8.36 (bs, 1H, Ar); 8.88 (d, J 5.0 Hz, 1H, Ar).

M/Z (M[$^{35}$Cl]+H)$^+$=379.4.

MP: 231-236° C.

Compound 12: 2-hydrazino-5-methoxy-benzoic Acid, HCl

Compound 12 was obtained according to general procedure IX, starting from 2-amino-5-methoxybenzoic acid, as a beige solid in quantitative yield.

$^1$H-NMR (400 MHz, DMSO): 3.75 (s, 3H, OCH$_3$); 7.15 (d, J 8.9 Hz, 1H, Ar); 7.25 (dd, J 8.9 Hz, 2.8 Hz, 1H, Ar); 7.42 (d, J 2.8 Hz, 1H, Ar); 8.84 (bs, 1H, NH); 10.17 (bs, 3H, NH$_3$).

M/Z (M+H)$^+$=183.1.

Compound 13: 7-Methoxy-2-(2-trifluoromethyl-pyridin-4-yl)-4H-pyrazolo[1,5-a]quinazolin-5-one Compound 13 was obtained according to general procedure I(iii), starting from 2-trifluoromethyl-isonicotinic acid ethyl ester in presence of hydrazine 12 as a brown solid in 37% yield.

$^1$H-NMR (400 MHz, DMSO): 3.86 (s, 3H, OCH$_3$); 6.44 (s, 1H, Ar); 7.33-7.35 (m, 1H, Ar); 7.57 (bs, 1H, Ar); 8.06-8.08 (m, 1H, Ar); 8.16 (bs, 1H, Ar); 8.30 (bs, 1H, Ar); 8.77 (bs, 1H, Ar). Signal for NH is not observed.

M/Z (M+H)$^+$=361.0.

Example 36: 7-Methoxy-2-(2-trifluoromethyl-pyridin-4-yl)-4H-pyrazolo[1,5-a]quinazolin-5-one

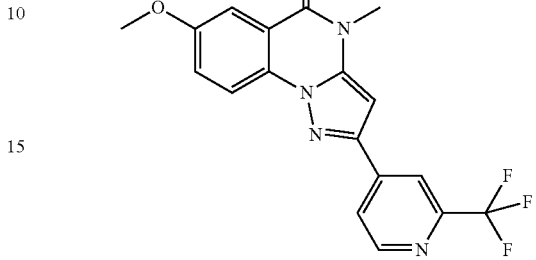

Example 36 was obtained according to general procedure II(i), starting from compound 13 in presence of iodomethane. The reaction mixture was stirred for 2 hours at room temperature. Example 36 was obtained without further purification as a beige solid in 48% yield.

$^1$H-NMR (400 MHz, DMSO): 3.59 (s, 3H, NCH$_3$); 3.91 (s, 3H, OCH$_3$); 7.20 (s, 1H, Ar); 7.55 (dd, J 9.0 Hz, J 2.8 Hz, 1H, Ar); 7.63 (d, J 2.8 Hz, 1H, Ar); 8.21 (d, J 9.0 Hz, 1H, Ar); 8.24-8.26 (m, 1H, Ar); 8.38 (bs, 1H, Ar); 8.88 (d, J 5.0 Hz, 1H, Ar).

M/Z (M+H)$^+$=375.1.

MP: 201-205° C.

Compound 14: 2-hydrazino-5-trifluoromethyl-benzoic Acid, HCl

Compound 14 was obtained according to general procedure IX, starting from 2-amino-5-trifluoromethylbenzoic acid, as a beige solid in 64% yield.

$^1$H-NMR (400 MHz, DMSO): 7.27 (d, J 8.9 Hz, 1H, Ar); 7.89 (dd, J 8.9 Hz, 2.1 Hz, 1H, Ar); 8.10 (d, J 2.1 Hz, 1H, Ar); 9.38 (bs, 1H, NH); 10.58 (bs, 3H, NH$_3$).

M/Z (M+H)$^+$=221.2.

Compound 15: 7-Trifluoromethyl-2-(2-trifluoromethyl-pyridin-4-yl)-4H-pyrazolo[1,5-a]quinazolin-5-one Compound 15 was obtained according to general procedure I(iii), starting from 2-trifluoromethyl-isonicotinic acid ethyl ester in presence of hydrazine 14 as a brown solid in 40% yield.

$^1$H-NMR (400 MHz, DMSO): 6.68 (s, 1H, Ar); 8.17 (dd, J 8.6 Hz, J 1.5 Hz, 1H, Ar); 8.26 (d, J 5.0 Hz, 1H, Ar); 8.35-8.37 (m, 2H, Ar); 8.39 (bs, 1H, Ar); 8.84 (d, J 5.0 Hz, 1H, Ar). Signal for NH is not observed.

M/Z (M+H)$^+$=399.1.

Example 37: 7-Trifluoromethyl-2-(2-trifluoromethyl-pyridin-4-yl)-4H-pyrazolo[1,5-a]quinazolin-5-one

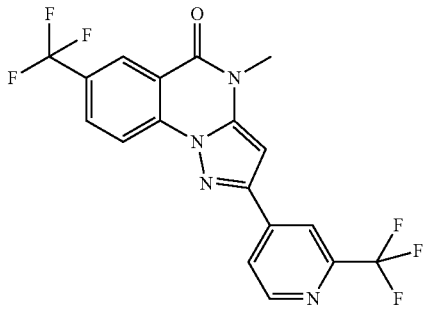 [SMILES: Cn1c(=O)c2cc(C(F)(F)F)ccc2n2nc(-c3ccnc(C(F)(F)F)c3)cc12]

Example 37 was obtained according to general procedure II(i), starting from compound 15 in presence of iodomethane. The reaction mixture was stirred for 2 hours at room temperature. Example 37 was obtained without further purification as a brown solid in 33% yield.

$^1$H-NMR (400 MHz, DMSO): 3.58 (s, 3H, NCH$_3$); 7.25 (s, 1H, Ar); 8.24-8.27 (m, 2H, Ar); 8.39-8.41 (m, 3H, Ar); 8.88 (d, J 4.9 Hz, 1H, Ar).

M/Z (M+H)$^+$=413.2.

MP: 205-210° C.

Compound 16: 5-fluoro-2-hydrazino-5-trifluoromethyl-benzoic Acid, HCl

Compound 16 was obtained according to general procedure IX, starting from 2-amino-5-fluoromethylbenzoic acid, as a beige solid in 46% yield.

M/Z (M+H)$^+$=171.8.

Compound 17: 7-fluoro-2-(2-trifluoromethyl-pyridin-4-yl)-4H-pyrazolo[1,5-a]quinazolin-5-one Compound 17 was obtained according to general procedure I(iv), starting from 2-trifluoromethyl-isonicotinic acid ethyl ester in presence of hydrazine 16 as a brown solid in 54% yield.

$^1$H-NMR (400 MHz, DMSO): 6.78 (s, 1H, Ar); 7.80-7.89 (m, 2H, Ar); 8.26-8.31 (m, 2H, Ar); 8.40 (bs, 1H, Ar); 8.85 (d, J 4.9 Hz, 1H, Ar); 12.64 (bs, 1H, NH).

M/Z (M+H)$^+$=349.0.

Example 38: 7-fluoro-2-(2-trifluoromethyl-pyridin-4-yl)-4H-pyrazolo[1,5-a]quinazolin-5-one

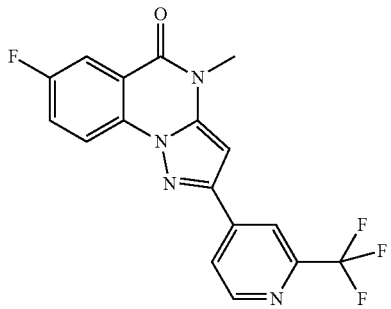 [SMILES: Cn1c(=O)c2cc(F)ccc2n2nc(-c3ccnc(C(F)(F)F)c3)cc12]

Example 38 was obtained according to general procedure II(iii), starting from compound 17 in presence of iodomethane. The reaction mixture was stirred for 3 hours at room temperature. Example 38 was obtained without further purification as a beige solid in 84% yield.

$^1$H-NMR (400 MHz, DMSO): 3.57 (s, 3H, NCH$_3$); 7.20 (s, 1H, Ar); 7.82 (td, J 9.0 Hz, J 2.9 Hz, 1H, Ar); 7.90 (dd, J 8.7 Hz, J 2.9 Hz, 1H, Ar); 8.23-8.24 (m, 1H, Ar); 8.28 (dd, J 9.0 Hz, J 4.6 Hz, 1H, Ar); 8.37 (bs, 1H, Ar); 8.88 (d, J 5.1 Hz, 1H, Ar).

M/Z (M+H)$^+$=363.0.

MP: >250° C.

Compound 18: 5-Bromo-2-hydrazino-benzoic Acid, HCl

Compound 18 was obtained according to general procedure IX, starting from 2-amino-5-bromo-benzoic acid, as a beige solid in a quantitative yield.

$^1$H-NMR (400 MHz, DMSO): 7.10 (d, J 8.9 Hz, 1H, Ar); 7.78 (dd, J 8.9 Hz, 2.5 Hz, 1H, Ar); 7.97 (d, J 2.5 Hz, 1H, Ar); 9.08 (bs, 1H, NH); 10.64 (bs, 3H, NH$_3$).

M/Z (M[$^{79}$Br]-18+H)$^+$=213.

Compound 19: 7-Bromo-2-(2-trifluoromethyl-pyridin-4-yl)-4H-pyrazolo[1,5-a]quinazolin-5-one Compound 19 was obtained according to general procedure I(i), starting from 2-trifluoromethyl-isonicotinic acid ethyl ester in presence of hydrazine 8 as a brown solid in 24% yield.

$^1$H-NMR (400 MHz, DMSO): 6.77 (s, 1H, Ar); 8.08 (dd, J 8.7 Hz, J 2.3 Hz, 1H, Ar); 8.16 (d, J 8.7 Hz, 1H, Ar); 8.21 (d, J 2.3 Hz, 1H, Ar); 8.24-8.26 (m, 1H, Ar); 8.39 (bs, 1H, Ar); 8.85 (d, J 5.1 Hz, 1H, Ar); 12.62 (bs, 1H, NH).

M/Z (M[$^{79}$Br]+H)$^+$=409.2.

Example 39: 7-Bromo-2-(2-trifluoromethyl-pyridin-4-yl)-4H-pyrazolo[1,5-a]quinazolin-5-one

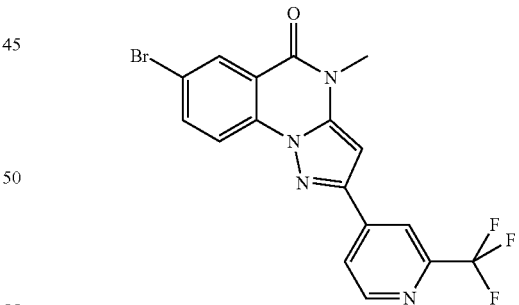

Example 39 was obtained according to general procedure II(i), starting from compound 19 in presence of iodomethane. The reaction mixture was stirred for 2 hours at room temperature. Example 39 was obtained without further purification as a brown solid in 85% yield.

$^1$H-NMR (400 MHz, DMSO): 3.56 (s, 3H, N—CH$_3$); 7.20 (s, 1H, Ar); 8.09 (dd, J 8.8 Hz, J 2.3 Hz, 1H, Ar); 8.17 (d, J 8.8 Hz, 1H, Ar); 8.23-8.25 (m, 2H, Ar); 8.37 (bs, 1H, Ar); 8.89 (d, J 5.1 Hz, 1H, Ar).

M/Z (M[$^{79}$Br]+H)$^+$=423.1.

MP: 223-235° C.

General Procedure X: Amine Introduction Via Buchwald, Ullmann or Nucleophilic Substitution Method (i): Under inert atmosphere, a mixture of halide (1.0 equiv.), amine (2.4 equiv.), tBuOK (1.6 equiv.; 2.4 more equivalent are added when the amine is an HCl salt) and BrettPhos precatalyst (0.1 equiv.) were suspended in DMA (C=0.1 molL$^{-1}$). The mixture was warmed overnight at 80° C. After cooling, the reaction mixture was hydrolysed with saturated aqueous NH$_4$Cl solution. The solid was collected, washed with water, dried under reduced pressure and purified to afford the product.

Method (ii): Under inert atmosphere, a mixture of halide (1.0 equiv.), amine (2.4 equiv.), a solution of LiHMDS in THF (1.0 N; 1.2 equiv.) and BrettPhos precatalyst (0.1 equiv.) were suspended in DME (C=0.1 molL$^{-1}$) and stirred for 2 hours at room temperature. The reaction mixture was hydrolysed with a saturated aqueous NH$_4$Cl solution and then extracted with EtOAc. The organic layers were combined, washed with brine, dried over MgSO$_4$, concentrated and purified to afford the product.

Method (iii): Under inert atmosphere, in a seal tube, a mixture of halide (1.0 equiv.), amine (1.2 equiv.), a solution of LiHMDS in THF (1.0 N; 2.4 equiv.) and BrettPhos precatalyst (0.1 equiv.) were suspended in DME (C=0.1 molL$^{-1}$) and warmed for 2 hours at 60° C. The reaction mixture was hydrolysed with a saturated aqueous NH$_4$Cl solution. The solid was collected, washed with water, dried under reduced pressure and purified to afford the product.

Method (iv): Under inert atmosphere, in a seal tube, a mixture of halide (1.0 equiv.), amine (1.5 equiv.), K$_3$PO$_4$ (4.0 equiv.), CuI (0.1 equiv.) and DMPAO (0.2 equiv.) in DMSO (C=0.1 molL$^{-1}$) was heated for 17 hours at 100° C. The reaction mixture was hydrolysed with a saturated aqueous NH$_4$Cl solution. The solid was collected, washed with water, dried under reduced pressure and purified to afford the product.

Method (v): Under inert atmosphere, in a seal tube, a mixture of halide (1.0 equiv.), amine (1.5 equiv.), tBuOK (3.0 equiv.) palladium acetate (0.1 equiv.) and BINAP (0.2 equiv.) were suspended in toluene (C=0.06 molL$^{-1}$) and heated for 2 hours at 120° C. The reaction mixture was hydrolysed with a saturated aqueous NH$_4$Cl solution. The solid was collected, washed with water, dried under reduced pressure and purified to afford the product.

Method (vi): Under inert atmosphere, in a seal tube, a mixture of halide (1.0 equiv.), amine (5.0 equiv.), K$_2$CO$_3$ (5.0 equiv.) in DMA (C=0.1 molL$^{-1}$) was heated for 1 hour at 90° C. The reaction mixture was hydrolysed with a saturated aqueous NH$_4$Cl solution. The solid was collected, washed with water, dried under reduced pressure and purified to afford the product.

Example 40: 4-Methyl-7-methylamino-2-(2-trifluoromethyl-pyridin-4-yl)-4H-pyrazolo[1,5-a]quinazolin-5-one

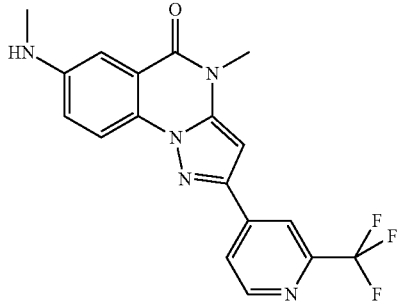 [SMILES: Cn1c(=O)c2cc(Br)ccc2n2nc(-c3ccnc(C(F)(F)F)c3)cc12]

Example 40 was obtained according to general procedure X(i) starting from example 39 in presence of methylamine hydrochloride. Purification by flash-chromatography (MeOH in DCM, 0 to 1%) afforded example 40 as a yellow solid in 34% yield.

$^1$H-NMR (400 MHz, DMSO): 2.77 (d, J 5.0 Hz, 3H, NHCH$_3$); 3.55 (s, 3H, NCH$_3$); 6.30 (q, J 5.0 Hz, 1H, NHCH$_3$); 7.09 (s, 1H, Ar); 7.14-7.17 (m, 2H, Ar); 8.00-8.02 (m, 1H, Ar); 8.18-8.20 (m, 1H, Ar); 8.32 (bs, 1H, Ar); 8.84 (d, J 5.1 Hz, 1H, Ar).

M/Z (M+H)$^+$=373.7.

MP: >250° C.

Example 41: 4-Methyl-7-methyl(D3)amino-2-(2-trifluoromethyl-pyridin-4-yl)-4H-pyrazolo[1,5-a]quinazolin-5-one

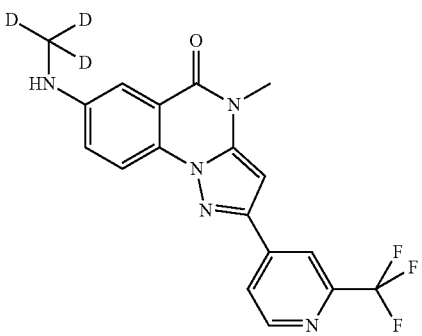 [SMILES: [2H]C([2H])([2H])Nc1ccc2c(c1)c(=O)n(C)c1cc(-c3ccnc(C(F)(F)F)c3)nn21]

Example 41 was obtained according to general procedure X(i) starting from example 39 in presence of methylamine (D3) hydrochloride. Purification by flash-chromatography (MeOH in DCM, 0 to 5%) afforded example 41 as a beige solid in 30% yield.

$^1$H-NMR (400 MHz, DMSO): 3.55 (s, 3H, NCH$_3$); 6.26 (bs, 1H, NH); 7.09 (s, 1H, Ar); 7.14-7.17 (m, 2H, Ar); 7.99-8.02 (m, 1H, Ar); 8.18-8.29 (m, 1H, Ar); 8.32 (bs, 1H, Ar); 8.84 (d, J 5.1 Hz, 1H, Ar).

M/Z (M+H)$^+$=377.0.

MP: >250° C.

Example 42: N-[4-Methyl-5-oxo-2-(2-trifluoromethyl-pyridin-4-yl)-4,5-dihydro-pyrazolo[1,5-a]quinazolin-7-yl]-acetamide

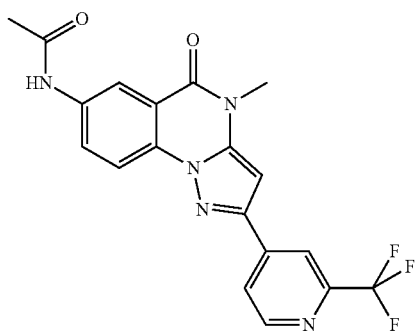 [SMILES: CC(=O)Nc1ccc2c(c1)c(=O)n(C)c1cc(-c3ccnc(C(F)(F)F)c3)nn21]

Under inert atmosphere, a mixture of bromide 39, (60.0 mg, 1.0 equiv.), acetamide (8.8 mg, 1.05 equiv.), Cs$_2$CO$_3$ (93.4 mg, 2.0 equiv.), Pd$_2$dba$_3$ (7.3 mg, 0.1 equiv.) and XantPhos (16.4 mg, 0.2 equiv.) were suspended in DMA (2.8 mL, C=0.05 molL$^{-1}$). The mixture was heated for 2 hours at 110° C. After cooling, the reaction mixture was hydrolysed with a saturated aqueous NH$_4$Cl solution. The solid was collected, washed with water, dried under reduced pressure and purified by flash-chromatography (MeOH in DCM, 0 to 3%) to afford example 42 as a beige solid in 63% yield.

$^1$H-NMR (400 MHz, DMSO): 2.09 (s, 3H, COCH$_3$); 3.56 (s, 3H, NCH$_3$); 7.15 (s, 1H, Ar); 8.09 (dd, J 9.0 Hz, J 2.4 Hz, 1H, Ar); 8.16 (d, J 9.0 Hz, 1H, Ar); 8.20-8.22 (m, 1H, Ar); 8.35 (bs, 1H, Ar); 8.47 (d, J 2.4 Hz, 1H, Ar); 8.87 (d, J 5.1 Hz, 1H, Ar); 10.32 (s, 1H, NH).

M/Z (M+H)$^+$=402.0.

MP: >250° C.

Example 43: 7-Amino-4-methyl-2-(2-trifluoromethyl-pyridin-4-yl)-4H-pyrazolo[1,5-a]quinazolin-5-one

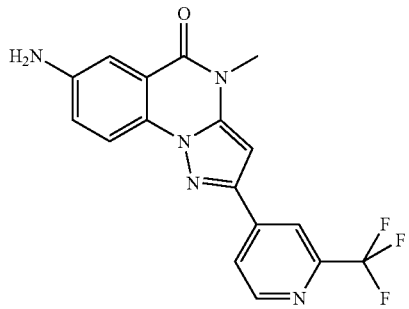 [SMILES: Cn1c(=O)c2cc(N)ccc2n2nc(-c3ccnc(C(F)(F)F)c3)cc12]

In a seal tube, a suspension of amide 42 (23.2 mg, 1.0 equiv.) in HCl MeOH solution (1.25 N; 1.2 mL, C=0.05 molL$^{-1}$) was heated for 18 hours at 80° C. The reaction mixture was concentrated. The resulting residue was suspended in Et$_2$O. Solid was collected, washed with Et$_2$O and dried under reduced pressure to afford example 43 as a brown solid in 71% yield.

$^1$H-NMR (400 MHz, DMSO): 3.56 (s, 3H, NCH$_3$); 7.15 (s, 1H, Ar); 7.41 (dd, J 8.8 Hz, J 2.5 Hz, 1H, Ar); 7.64 (d, J 2.5 Hz, 1H, Ar); 8.10 (d, J 8.8 Hz, 1H, Ar); 8.20-8.22 (m, 1H, Ar); 8.35 (bs, 1H, Ar); 8.86 (d, J 5.2 Hz, 1H, Ar). Signal for NH$_2$ is not observed.

M/Z (M+H)$^+$=360.1.

MP: 245-250° C.

Example 44: 7-Dimethylamino-4-methyl-2-(2-trifluoromethyl-pyridin-4-yl)-4H-pyrazolo[1,5-a]quinazolin-5-one

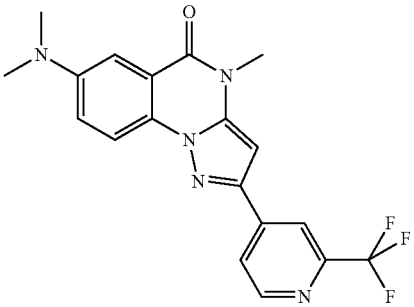 [SMILES: CN(C)c1ccc2c(c1)c(=O)n(C)c1cc(-c3ccnc(C(F)(F)F)c3)nn21]

Example 44 was obtained according to general procedure X(i) starting from example 39 in presence of dimethylamine (2 N in THF). After hydrolysis, example 44 was extracted with EtOAc. Organic layers were washed with brine, dried over MgSO$_4$. Purification by flash-chromatography (MeOH in DCM, 0 to 10%) afforded example 44 as a yellow solid in 7% yield.

$^1$H-NMR (400 MHz, DMSO): 3.04 (s, 6H, N(CH$_3$)$_2$); 3.60 (s, 3H, NCH$_3$); 7.01 (s, 1H, Ar); 7.36-7.39 (m, 2H, Ar); 8.10 (d, J 8.6 Hz, 1H, Ar); 8.17-8.19 (m, 1H, Ar); 8.31 (bs, 1H, Ar); 8.84 (d, J 5.1 Hz, 1H, Ar).

M/Z (M+H)$^+$=387.5.

MP: >250° C.

Example 45: 7-Ethylamino-4-methyl-2-(2-trifluoromethyl-pyridin-4-yl)-4H-pyrazolo[1,5-a]quinazolin-5-one

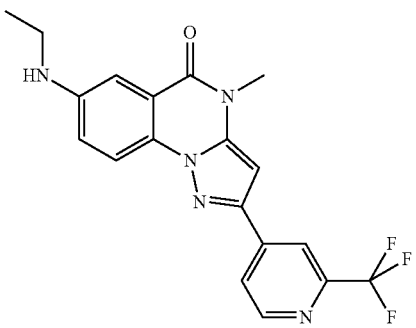 [SMILES: CCNc1ccc2c(c1)c(=O)n(C)c1cc(-c3ccnc(C(F)(F)F)c3)nn21]

Example 45 was obtained according to general procedure X(i) starting from example 39 in presence of ethylamine hydrochloride. Ethylamine HCl (0.2 equiv.), tBuOK (0.2 equiv.) and BrettPhos precatalyst (0.1 iquiv.) were added and the reaction mixture was heated for two more hours at 80° C. Purification by flash-chromatography (EtOAc in CyHex, 0 to 50%) afforded example 45 as a beige solid in 26% yield.

$^1$H-NMR (400 MHz, DMSO): 1.21 (t, J 7.1 Hz, 3H, NHCH$_2$CH$_3$); 3.09-3.15 (m, 2H, NHCH$_2$CH$_3$); 3.55 (s, 3H, NCH$_3$); 6.21 (t, J 5.2 Hz, 1H, NHCH$_2$CH$_3$); 7.09 (s, 1H, Ar); 7.16-7.20 (m, 2H, Ar); 8.00 (d, J 8.7 Hz, 1H, Ar); 8.18-8.19 (m, 1H, Ar); 8.32 (bs, 1H, Ar); 8.84 (d, J 5.0 Hz, 1H, Ar).

M/Z (M+H)$^+$=388.0.

MP: 239-242° C.

Example 46: 7-Cyclobutylamino-4-methyl-2-(2-trifluoromethyl-pyridin-4-yl)-4H-pyrazolo[1,5-a]quinazolin-5-one

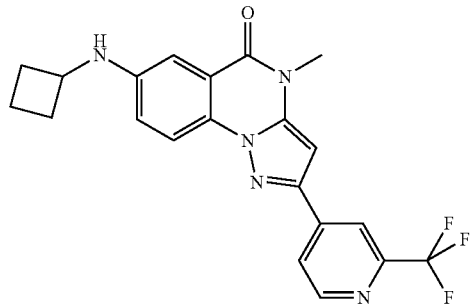 [SMILES: Cn1c(=O)c2cc(NC3CCC3)ccc2n2nc(-c3ccnc(C(F)(F)F)c3)cc12]

Example 46 was obtained according to general procedure X(i) starting from example 39 in presence of cyclobutylamine. Purification by preparative HPLC afforded example 46 as a beige solid in 16% yield.

$^1$H-NMR (400 MHz, DMSO): 1.73-1.92 (m, 4H, CH$_2$+ 2CHaHb); 2.35-2.40 (m, 2H, 2CHaHb); 3.55 (s, 3H, NCH$_3$); 3.92 (sex, J 7.1 Hz, 1H, NHCH(CH$_2$)$_2$); 6.55 (d, J 7.1 Hz, 1H, NHCH(CH$_2$)$_2$); 7.10 (s, 1H, Ar); 7.13 (dd, J 8.8 Hz, J 2.5 Hz, 1H, Ar); 7.16 (d, J 2.5 Hz, 1H, Ar); 8.00 (d, J 8.8 Hz, 1H, Ar); 8.18-8.20 (m, 1H, Ar); 8.33 (bs, 1H, Ar); 8.84 (d, J 5.0 Hz, 1H, Ar).

M/Z (M+H)$^+$=414.2.

MP: 220-225° C.

Example 47: 4-Methyl-7-morpholin-4-yl-2-(2-trifluoromethyl-pyridin-4-yl)-4H-pyrazolo[1,5-a]quinazolin-5-one

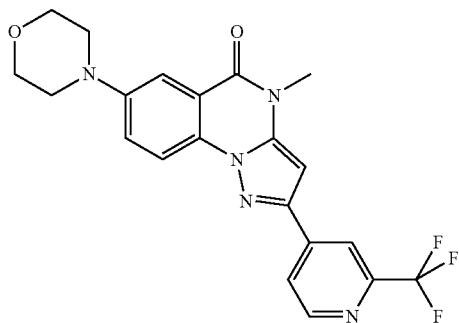 [SMILES: Cn1c(=O)c2cc(N3CCOCC3)ccc2n2nc(-c3ccnc(C(F)(F)F)c3)cc12]

Example 47 was obtained according to general procedure X(ii) starting from example 39 in presence of morpholine. Purification by flash-chromatography (MeOH in DCM, 0 to 1%) afforded example 47 as a grey solid in 21% yield.

$^1$H-NMR (400 MHz, DMSO): 3.22-3.25 (m, 4H, 2 CH$_2$); 3.57 (s, 3H, NCH$_3$); 3.75-3.80 (m, 4H, 2 CH$_2$); 7.14 (s, 1H, Ar); 7.55 (d, J 2.8 Hz, 1H, Ar); 7.62 (dd, J 9.1 Hz, J 2.8 Hz, 1H, Ar); 8.11 (d, J 9.1 Hz, 1H, Ar); 8.21-8.22 (m, 1H, Ar); 8.35 (bs, 1H, Ar); 8.86 (d, J 5.1 Hz, 1H, Ar).

M/Z (M+H)$^+$=430.3.

MP: 149-163° C.

Example 48: 7-Hydroxy-4-methyl-2-(2-trifluoromethyl-pyridin-4-yl)-4H-pyrazolo[1,5-a]quinazolin-5-one

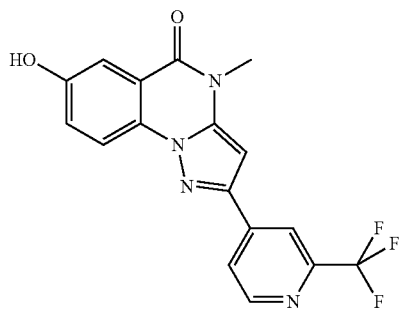 [SMILES: Cn1c(=O)c2cc(O)ccc2n2nc(-c3ccnc(C(F)(F)F)c3)cc12]

Under inert atmosphere, in a seal tube, to a well degased mixture of bromide 39 (100.0 mg, 1.0 equiv.), Pd$_2$dba$_3$ (12.2 mg, 0.1 equiv.) and tBuXPhos (10.2 mg, 0.1 equiv.) in dioxane (0.5 mL, C=0.5 molL$^{-1}$), a well degased solution of KOH (79.5 mg, 6.0 equiv.) in water (0.5 mL, C=2.8 molL$^{-1}$) was added dropwise and was heated for 16 hours at 100° C. After cooling, the reaction mixture was hydrolysed with a saturated aqueous NH$_4$Cl solution and then extracted with EtOAc. The organic layers were combined, washed with brine, dried over MgSO$_4$, concentrated and purified by flash-chromatography (MeOH in DCM, 0 to 5%) to afford example 48 as a white solid in 35% yield.

$^1$H-NMR (400 MHz, DMSO): 3.55 (s, 3H, NCH$_3$); 7.13 (s, 1H, Ar); 7.35 (dd, J 8.8 Hz, J 2.6 Hz, 1H, Ar); 7.52 (d, J 2.6 Hz, 1H, Ar); 8.09 (d, J 8.8 Hz, 1H, Ar); 8.19-8.21 (m, 1H, Ar); 8.34 (bs, 1H, Ar); 8.86 (d, J 4.9 Hz, 1H, Ar); 10.17 (s, 1H, OH).

M/Z (M+H)$^+$=361.5.

MP: >250° C.

General Procedure XI: Hydroxy Group Alkylation

Under inert atmosphere, to a suspension of hydroxyl quinazolinone (1.0 equiv.) in DMF (C=0.1 molL$^{-1}$), tBuOK (1.5 equiv.) was added. After 15 minutes, electrophile (1.2 equiv.) was introduced and the reaction mixture was heated for 18 hours at 80° C. After cooling, the reaction mixture was hydrolysed. The resulting precipitate was collected, washed with water, dried under reduced pressure and purified to afford the product.

Example 49: 7-Ethoxy-4-methyl-2-(2-trifluoromethyl-pyridin-4-yl)-4H-pyrazolo[1,5-a]quinazolin-5-one

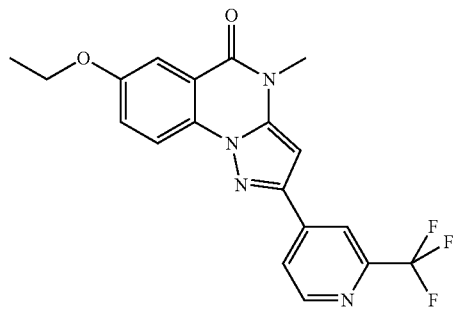 [SMILES: CCOc1ccc2c(c1)c(=O)n(C)c1cc(-c3ccnc(C(F)(F)F)c3)nn21]

Example 49 was obtained according to general procedure XI starting from example 48 in presence of iodoethane. Iodoethane (1.2 equiv.) and tBuOK (1.5 equiv.) were added and the reaction mixture was heated for 48 hours at 80° C. Purification by flash-chromatography (MeOH in DCM, 0 to 5%) afforded example 49 as a yellow solid in 27% yield.

$^1$H-NMR (400 MHz, DMSO): 1.37 (t, J 7.0 Hz, 3H, OCH$_2$CH$_3$); 3.55 (s, 3H, NCH$_3$); 4.13 (q, J 7.0 Hz, 2H, OCH$_2$CH$_3$); 7.11 (s, 1H, Ar); 7.47 (dd, J 9.0 Hz, J 2.8 Hz, 1H, Ar); 7.53 (d, J 2.8 Hz, 1H, Ar); 8.11 (d, J 9.0 Hz, 1H, Ar); 8.17-8.19 (m, 1H, Ar); 8.31 (bs, 1H, Ar); 8.85 (d, J 5.1 Hz, 1H, Ar).

M/Z (M+H)$^+$=389.1.

MP: 152-158° C.

Example 50: 7-(2-Methoxy-ethoxy)-4-methyl-2-(2-trifluoromethyl-pyridin-4-yl)-4H-pyrazolo[1,5-a]quinazolin-5-one

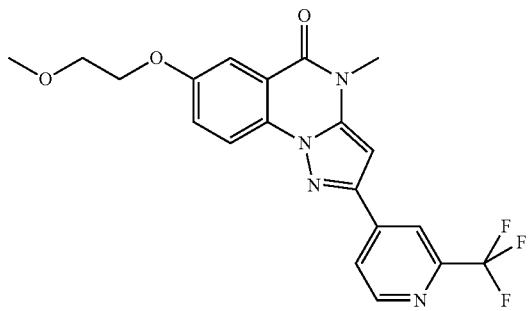 [SMILES: COCCOc1ccc2c(c1)c(=O)n(C)c1cc(-c3ccnc(C(F)(F)F)c3)nn21]

Example 50 was obtained according to general procedure XI starting from example 48 in presence of 2-bromoethylmerthyl ether. 2-bromoethylmerthyl ether (1.2 equiv.) and tBuOK (1.5 equiv.) were added and the reaction mixture was heated for 48 hours at 80° C. Purification by flash-chromatography (MeOH in DCM, 0 to 5%) afforded example 50 as a white solid in 34% yield.

$^1$H-NMR (400 MHz, DMSO): 3.34 (s, 3H, OCH$_3$); 3.56 (s, 3H, NCH$_3$); 3.70-3.72 (m, 2H, OCH$_2$); 4.22-4.24 (m, 2H, OCH$_2$); 7.14 (s, 1H, Ar); 7.53 (dd, J 9.0 Hz, J 2.8 Hz, 1H, Ar); 7.59 (d, J 2.8 Hz, 1H, Ar); 8.15 (d, J 9.0 Hz, 1H, Ar); 8.20-8.21 (m, 1H, Ar); 8.34 (bs, 1H, Ar); 8.86 (d, J 5.0 Hz, 1H, Ar).

M/Z (M+H)$^+$=419.2.

MP: 182-189° C.

Example 51: 4-Methyl-7-(2-morpholin-4-yl-ethoxy)-2-(2-trifluoromethyl-pyridin-4-yl)-4H-pyrazolo[1,5-a]quinazolin-5-one, HCl Salt

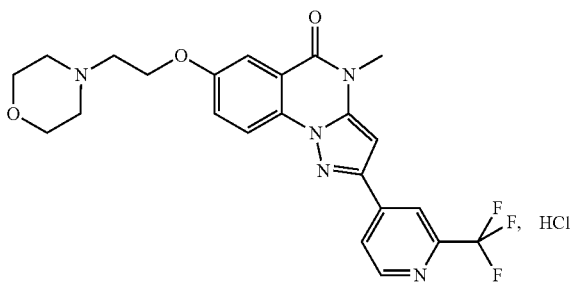 [SMILES: Cn1c(=O)c2cc(OCCN3CCOCC3)ccc2n2nc(-c3ccnc(C(F)(F)F)c3)cc12 ; Cl]

Example 51 was obtained according to general procedure VII(i) starting from example 38 in presence of 4-hydroxy-ethylmorpholine. Salt formation according to procedure IV(iii) afforded example 51 as a beige solid in 34% yield.

$^1$H-NMR (400 MHz, DMSO): 3.25-3.29 (m, 4H, 2NCH$_2$); 3.50-3.54 (m, 2H, NCH$_2$); 3.62 (s, 3H, NCH$_3$); 3.88-3.90 (m, 4H, 2 OCH$_2$); 4.54-4.56 (m, 2H, OCH$_2$); 7.09 (s, 1H, Ar); 7.62 (dd, J 8.9 Hz, J 2.5 Hz, 1H, Ar); 7.77 (d, J 2.5 Hz, 1H, Ar); 8.21-8.22 (m, 1H, Ar); 8.25 (d, J 8.9 Hz, 1H, Ar); 8.35 (bs, 1H, Ar); 8.87 (d, J 4.9 Hz, 1H, Ar).

M/Z (M+H)$^+$=474.1.

MP: >250° C.

Compound 20: 2-Hydrazino-5-trifluoromethoxy-benzoic Acid, HCl

Compound 20 was obtained according to general procedure IX, starting from 2-Amino-5-trifluoromethoxylbenzoic acid, as a white solid in 59% yield.

$^1$H-NMR (400 MHz, DMSO): 7.22 (d, J 9.1 Hz, 1H, Ar); 7.66 (dd, J 9.1 Hz, 2.4 Hz, 1H, Ar); 7.77 (d, J 2.4 Hz, 1H, Ar); 9.12 (bs, 1H, NH); 10.62 (bs, 3H, NH$_3$).

Compound 21: 7-Trifluoromethoxy-2-(2-trifluoromethyl-pyridin-4-yl)-4H-pyrazolo[1,5-a]quinazolin-5-one Compound 21 was obtained according to general procedure I(i), starting from 2-trifluoromethyl-isonicotinic acid ethyl ester in presence of hydrazine 20 as a brown solid in 61% yield.

$^1$H-NMR (400 MHz, DMSO): 6.82 (s, 1H, Ar); 7.94-7.97 (m, 1H, Ar); 8.02-8.03 (m, 1H, Ar); 8.27-8.30 (m, 1H, Ar); 8.35-8.37 (m, 1H, Ar); 8.42 (bs, 1H, Ar); 8.85-8.87 (m, 1H, Ar); 12.69 (bs, 1H, NH).

M/Z (M+H)$^+$=415.2.

Example 52: 4-Methyl-7-trifluoromethoxy-2-(2-trifluoromethyl-pyridin-4-yl)-4H-pyrazolo[1,5-a]quinazolin-5-one

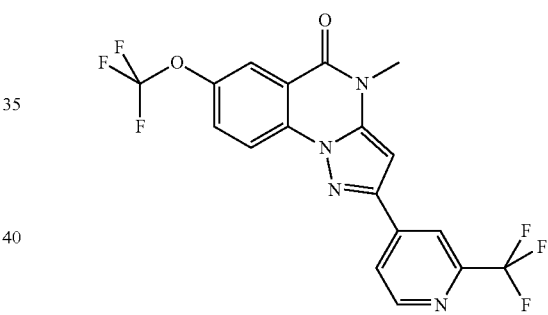

Example 52 was obtained according to general procedure II(iii), starting from compound 21 in presence of iodomethane. The reaction mixture was stirred for 2 hours at room temperature. Example 52 was obtained without further purification as a white solid in 55% yield.

$^1$H-NMR (400 MHz, DMSO): 3.57 (s, 3H, NCH$_3$); 7.22 (s, 1H, Ar); 7.95 (dd, J 9.0 Hz, 1.7 Hz, 1H, Ar); 8.05 (d, 1.7 Hz, 1H, Ar); 8.23-8.25 (m, 1H, Ar); 8.34 (d, 9.0 Hz, 1H, Ar); 8.38 (bs, 1H, Ar); 8.89 (d, 4.9 Hz, 1H, Ar).

M/Z (M+H)$^+$=429.2.

MP: 240-245° C.

Compound 22: 2-Hydrazino-5-methanesulfonyl-benzoic Acid, HCl

Compound 22 was obtained according to general procedure IX, starting from 2-amino-5-methylsulfonylbenzoic acid, as a white solid in 51% yield.

$^1$H-NMR (400 MHz, DMSO): 3.19 (s, 3H, SO$_2$CH$_3$); 7.26 (d, J 8.9 Hz, 1H, Ar); 8.03 (dd, J 8.9 Hz, 2.3 Hz, 1H, Ar); 8.32 (d, J 2.3 Hz, 1H, Ar); 9.55 (bs, 1H, NH); 10.62 (bs, 3H, NH$_3$).

Compound 23: 7-Methanesulfonyl-2-(2-trifluoromethyl-pyridin-4-yl)-4H-pyrazolo[1,5-a]quinazolin-5-one Compound 23 was obtained according to general procedure I(iv), starting from 2-trifluoromethyl-isonicotinic acid ethyl ester in presence of hydrazine 22 as a brown solid in 40% yield.

$^1$H-NMR (400 MHz, DMSO): 3.35 (s, 3H, SO$_2$CH$_3$); 6.85 (s, 1H, Ar); 8.31-8.32 (m, 1H, Ar); 8.40-8.46 (m, 3H, Ar); 8.62 (bs, 1H, Ar); 8.88 (d, 4.9 Hz, 1H, Ar); 12.76 (bs, 1H, NH).

M/Z (M+H)$^+$=409.0.

Example 53: 7-Methanesulfonyl-4-methyl-2-(2-trifluoromethyl-pyridin-4-yl)-4H-pyrazolo[1,5-a]quinazolin-5-one

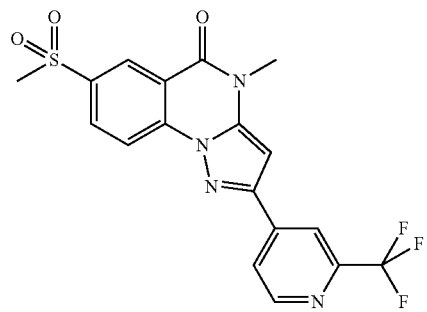 [SMILES: Cn1c(=O)c2cc(S(C)(=O)=O)ccc2n2nc(-c3ccnc(C(F)(F)F)c3)cc12]

Example 53 was obtained according to general procedure II(iii), starting from compound 23 in presence of iodomethane. The reaction mixture was stirred for 3 hours at room temperature. Example 53 was obtained without further purification as a white solid in 54% yield.

$^1$H-NMR (400 MHz, DMSO): 3.36 (s, 3H, SO$_2$CH$_3$); 3.60 (s, 3H, NCH$_3$); 7.28 (s, 1H, Ar); 8.27-8.28 (m, 1H, Ar); 8.41-8.46 (m, 3H, Ar); 8.65 (d, J 1.6 Hz, 1H, Ar); 8.92 (d, 5.1 Hz, 1H, Ar).

M/Z (M+H)$^+$=423.1.
MP: >250° C.

Compound 24: 2-Hydrazino-4-methoxy-benzoic Acid, HCl

Compound 24 was obtained according to general procedure IX, starting from 2-amino-4-methoxybenzoic acid, as a white solid in 96% yield.

$^1$H-NMR (400 MHz, DMSO): 3.81 (s, 3H, OCH$_3$); 6.50 (dd, J 8.8 Hz, 2.4 Hz, 1H, Ar); 6.71 (d, J 2.4 Hz, 1H, Ar); 7.82 (d, J 8.8 Hz, 1H, Ar); 9.09 (bs, 1H, NH); 10.03 (bs, 3H, NH$_3$).

M/Z (M+H)$^+$=183.1.

Compound 25: 8-Methoxy-2-(2-trifluoromethyl-pyridin-4-yl)-4H-pyrazolo[1,5-a]quinazolin-5-one Compound 25 was obtained according to general procedure I(iv), starting from 2-trifluoromethyl-isonicotinic acid ethyl ester in presence of hydrazine 24 as a pale brown solid in 76% yield.

$^1$H-NMR (400 MHz, DMSO): 4.01 (s, 3H, OCH$_3$); 6.75 (s, 1H, Ar); 7.12 (dd, J 8.9 Hz, 2.4 Hz, 1H, Ar); 7.65 (d, J 2.4 Hz, 1H, Ar); 8.09 (d, J 8.9 Hz, 1H, Ar); 8.28-8.30 (m, 1H, Ar); 8.43 (bs, 1H, Ar); 8.85 (d, J 5.1 Hz, 1H, Ar); 12.34 (bs, 1H, NH).

M/Z (M+H)$^+$=361.1.

Example 54: 8-Methoxy-4-methyl-2-(2-trifluoromethyl-pyridin-4-yl)-4H-pyrazolo[1,5-a]quinazolin-5-one

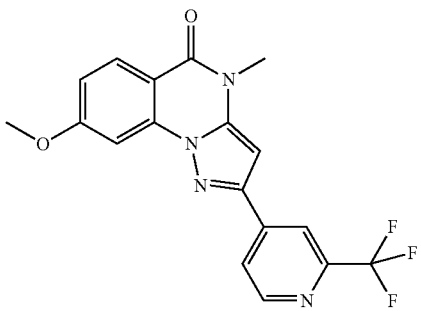 [SMILES: COc1ccc2c(=O)n(C)c3cc(-c4ccnc(C(F)(F)F)c4)nn3c2c1]

Example 54 was obtained according to general procedure II(iii), starting from compound 25 in presence of iodomethane. The reaction mixture was stirred for 3 hours at room temperature. Example 54 was obtained without further purification as a beige solid in 68% yield.

$^1$H-NMR (400 MHz, DMSO): 3.55 (s, 3H, NCH$_3$); 4.00 (s, 3H, OCH$_3$); 7.12 (dd, J 8.8 Hz, J 2.5 Hz, 1H, Ar); 7.17 (s, 1H, Ar); 7.64 (d, J 2.5 Hz, 1H, Ar); 8.12 (d, J 8.8 Hz, 1H, Ar); 8.26-8.28 (m, 1H, Ar); 8.40 (bs, 1H, Ar); 8.89 (d, J 5.0 Hz, 1H, Ar).

M/Z (M+H)$^+$=375.1.
MP: >250° C.

Compound 26: 4-Fluoro-2-hydrazino-benzoic Acid, HCl

Compound 26 was obtained according to general procedure IX, starting from 2-amino-4-fluorobenzoic acid, as a white solid in 71% yield.

$^1$H-NMR (400 MHz, DMSO): 6.69-6.73 (m, 1H, Ar); 6.93 (dd, J 11.9 Hz, J 2.5 Hz, 1H, Ar);

7.93 (dd, J 8.9 Hz, J 6.8 Hz, 1H, Ar); 9.14 (bs, 4H, NHNH$_3$).

M/Z (M+H)$^+$=171.2.

Compound 27: 8-Fluoro-2-(2-trifluoromethyl-pyridin-4-yl)-4H-pyrazolo[1,5-a]quinazolin-5-one Compound 27 was obtained according to general procedure I(iv), starting from 2-trifluoromethyl-isonicotinic acid ethyl ester in presence of hydrazine 26 as a pale brown solid in 53% yield.

$^1$H-NMR (400 MHz, DMSO): 6.77 (s, 1H, Ar); 7.40 (td, J 8.8 Hz, J 2.5 Hz, 1H, Ar); 7.99 (dd, J 9.5 Hz, J 2.5 Hz, 1H, Ar); 8.23 (dd, J 8.8 Hz, J 5.9 Hz, 1H, Ar); 8.27-8.29 (m, 1H, Ar); 8.43 (bs, 1H, Ar); 8.86 (d, J 5.0 Hz, 1H, Ar); 12.53 (bs, 1H, NH).

M/Z (M+H)$^+$=349.1.

Example 55: 8-Fluoro-4-methyl-2-(2-trifluoromethyl-pyridin-4-yl)-4H-pyrazolo[1,5-a]quinazolin-5-one

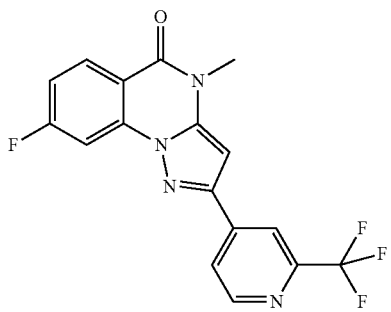 [SMILES: Cn1c(=O)c2ccc(F)cc2n2nc(-c3ccnc(C(F)(F)F)c3)cc12]

Example 55 was obtained according to general procedure II(iii), starting from compound 27 in presence of iodomethane. The reaction mixture was stirred for 3 hours at room temperature. Example 55 was obtained without further purification as a beige solid in 70% yield.

$^1$H-NMR (400 MHz, DMSO): 3.56 (s, 3H, NCH$_3$); 7.20 (s, 1H, Ar); 7.41 (td, J 8.8 Hz, J 2.5 Hz, 1H, Ar); 8.00 (dd, J 9.3 Hz, J 2.5 Hz, 1H, Ar); 8.25-8.28 (m, 2H, Ar); 8.41 (bs, 1H, Ar); 8.90 (d, J 5.0 Hz, 1H, Ar).

M/Z (M+H)$^+$=363.1.

MP: >250° C.

Compound 28: 4-Chloro-2-hydrazino-benzoic Acid, HCl

Compound 28 was obtained according to general procedure IX, starting from 2-amino-4-chlorobenzoic acid, as a white solid in 38% yield.

$^1$H-NMR (400 MHz, DMSO): 7.00 (dd, J 8.6 Hz, 2.0 Hz, 1H, Ar); 7.23 (d, J 2.0 Hz, 1H, Ar); 7.88 (d, J 8.6 Hz, 1H, Ar); 9.16 (bs, 1H, NH); 10.74 (bs, 3H, NH$_3$).

Compound 29: 8-Chloro-2-(2-trifluoromethyl-pyridin-4-yl)-4H-pyrazolo[1,5-a]quinazolin-5-one Compound 29 was obtained according to general procedure I(iv), starting from 2-trifluoromethyl-isonicotinic acid ethyl ester in presence of hydrazine 28 as a pale brown solid in 57% yield.

$^1$H-NMR (400 MHz, DMSO): 6.78 (s, 1H, Ar); 7.60 (dd, J 8.5 Hz, 2.0 Hz, 1H, Ar); 8.16 (d, J 8.5 Hz, 1H, Ar); 8.25 (d, J 2.0 Hz, 1H, Ar); 8.29-8.31 (m, 1H, Ar); 8.44 (bs, 1H, Ar); 8.86 (d, J 5.0 Hz, 1H, Ar); 12.57 (bs, 1H, NH).

M/Z (M[$^{35}$Cl]+H)$^+$=365.0.

Example 56: 8-Chloro-4-methyl-2-(2-trifluoromethyl-pyridin-4-yl)-4H-pyrazolo[1,5-a]quinazolin-5-one

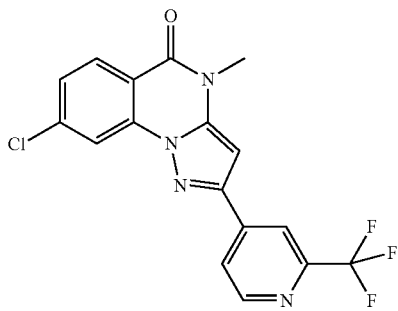 [SMILES: Cn1c(=O)c2ccc(Cl)cc2n2nc(-c3ccnc(C(F)(F)F)c3)cc12]

Example 56 was obtained according to general procedure II(iii), starting from compound 29 in presence of iodomethane. The reaction mixture was stirred for 3 hours at room temperature. Example 56 was obtained without further purification as a beige solid in 77% yield.

$^1$H-NMR (400 MHz, DMSO): 3.55 (s, 3H, NCH$_3$); 7.19 (s, 1H, Ar); 7.59 (dd, J 8.6 Hz, 2.0 Hz, 1H, Ar); 8.18 (d, J 8.6 Hz, 1H, Ar); 8.23 (d, J 2.0 Hz, 1H, Ar); 8.25-8.27 (m, 1H, Ar); 8.40 (bs, 1H, Ar); 8.89 (d, J 5.1 Hz, 1H, Ar).

M/Z (M[$^{35}$Cl]+H)$^+$=379.1.

MP: 220-225° C.

Compound 30: 2-Hydrazino-4-trifluoromethyl-benzoic Acid, HCl

Compound 30 was obtained according to general procedure IX, starting from 2-amino-4-trifluoromethylbenzoic acid, as a beige solid in 62% yield.

$^1$H-NMR (400 MHz, DMSO): 7.26 (d, J 8.7 Hz, 1H, Ar); 7.92 (dd, J 8.7 Hz, 2.0 Hz, 1H, Ar); 8.11 (d, J 2.0 Hz, 1H, Ar); 9.42 (bs, 1H, NH); 10.74 (bs, 3H, NH$_3$).

M/Z (M+H)$^+$=221.2.

Compound 31: 8-Trifluoromethyl-2-(2-trifluoromethyl-pyridin-4-yl)-4H-pyrazolo[1,5-a]quinazolin-5-one Compound 31 was obtained according to general procedure I(iii), starting from 2-trifluoromethyl-isonicotinic acid ethyl ester in presence of hydrazine 30 as a brown solid in 50% yield.

$^1$H-NMR (400 MHz, DMSO): 6.68 (s, 1H, Ar); 8.17 (dd, J 8.7 Hz, 1.9 Hz, 1H, Ar); 8.25-8.26 (m, 1H, Ar); 8.34-8.39 (m, 3H, Ar); 8.84 (d, J 5.1 Hz, 1H, Ar). Signal for NH is not observed.

M/Z (M+H)$^+$=399.1.

Example 57: 4-Methyl-8-trifluoromethyl-2-(2-trifluoromethyl-pyridin-4-yl)-4H-pyrazolo[1,5-a]quinazolin-5-one

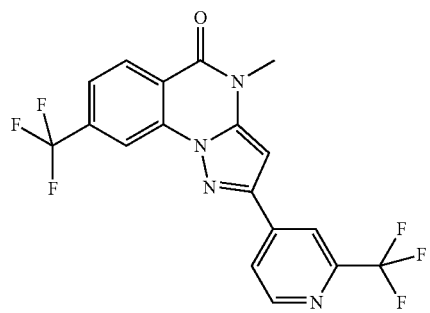 [SMILES: Cn1c(=O)c2ccc(C(F)(F)F)cc2n2nc(-c3ccnc(C(F)(F)F)c3)cc12]

Example 57 was obtained according to general procedure II(i), starting from compound 31 in presence of iodomethane. The reaction mixture was stirred for 2 hours at room temperature. Example 57 was obtained without further purification as a brown solid in 33% yield.

$^1$H-NMR (400 MHz, DMSO): 3.57 (s, 3H, NCH$_3$); 7.23 (s, 1H, Ar); 8.24-8.26 (m, 2H, Ar); 8.37-8.39 (m, 3H, Ar); 8.90 (d, J 4.9 Hz, 1H, Ar).

M/Z (M+H)$^+$=413.2.

Compound 32: 4-Bromo-2-hydrazino-benzoic Acid, HCl

Compound 32 was obtained according to general procedure I, starting from 2-amino-4-bromo-benzoic acid, as a white solid in a quantitative yield.

¹H-NMR (400 MHz, DMSO): 7.14 (dd, J 8.5 Hz, 1.9 Hz, 1H, Ar); 7.37 (d, J 1.9 Hz, 1H, Ar); 7.81 (d, J 8.5 Hz, 1H, Ar); 9.15 (bs, 1H, NH); 10.63 (bs, 3H, NH$_3$).

M/Z (M[$^{79}$Br]-18+H)$^+$=213.

Compound 33: 8-Bromo-2-(2-trifluoromethyl-pyridin-4-yl)-4H-pyrazolo[1,5-a]quinazolin-5-one Compound 33 was obtained according to general procedure I(i), starting from 2-trifluoromethyl-isonicotinic acid ethyl ester in presence of hydrazine 32 as a brown solid in 69% yield.

¹H-NMR (400 MHz, DMSO): 6.60 (s, 1H, Ar); 7.64 (dd, J 8.5 Hz, 1.9 Hz, 1H, Ar); 8.03 (d, J 8.5 Hz, 1H, Ar); 8.23-8.25 (m, 1H, Ar); 8.31 (d, 1.9 Hz, 1H, Ar); 8.38 (bs, 1H, Ar); 8.82 (d, J 5.0 Hz, 1H, Ar). Signal for NH is not observed.

M/Z (M[$^{79}$Br]+H)$^+$=409.0.

Example 58: 8-Bromo-4-methyl-2-(2-trifluoromethyl-pyridin-4-yl)-4H-pyrazolo[1,5-a]quinazolin-5-one

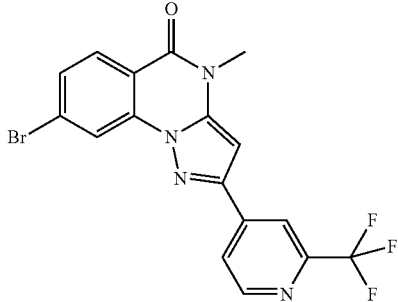

Example 58 was obtained according to general procedure II(ii), starting from compound 33 in presence of iodomethane. The reaction mixture was stirred for 1 hour at room temperature. Example 58 was obtained without further purification as a beige solid in 84% yield.

¹H-NMR (400 MHz, DMSO): 3.53 (s, 3H, NCH$_3$); 7.16 (s, 1H, Ar); 7.71 (dd, J 8.5 Hz, 1.9 Hz, 1H, Ar); 8.07 (d, J 8.5 Hz, 1H, Ar); 8.23-8.25 (m, 1H, Ar); 8.34 (d, 1.9 Hz, 1H, Ar); 8.34 (bs, 1H, Ar); 8.87 (d, J 5.1 Hz, 1H, Ar).

M/Z (M[$^{79}$Br]+H)$^+$=423.2.

Example 59: 4-Methyl-8-morpholin-4-yl-2-(2-trifluoromethyl-pyridin-4-yl)-4H-pyrazolo[1,5-a]quinazolin-5-one

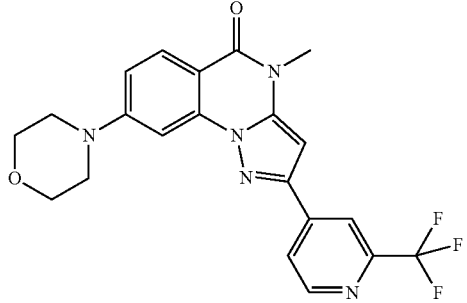 [SMILES: Cn1c(=O)c2ccc(N3CCOCC3)cc2n2nc(-c3ccnc(C(F)(F)F)c3)cc12]

Example 59 was obtained according to general procedure X(v) starting from example 58 in presence of morpholine. Purification by flash-chromatography (MeOH in DCM, 0 to 2%) afforded example 59 as a beige solid in 44% yield.

¹H-NMR (400 MHz, DMSO at 80° C.): 3.46-3.48 (m, 4H, 2 CH$_2$); 3.56 (s, 3H, NCH$_3$); 3.80-3.84 (m, 4H, 2 CH$_2$); 7.00 (s, 1H, Ar); 7.13 (dd, J 9.0 Hz, 2.3 Hz, 1H, Ar); 7.52 (d, 2.3 Hz, 1H, Ar); 8.03 (d, J 9.0 Hz, 1H, Ar); 8.23-8.25 (m, 1H, Ar); 8.35 (bs, 1H, Ar); 8.86 (d, J 5.1 Hz, 1H, Ar).

M/Z (M+H)$^+$=430.3.

MP: >250° C.

Example 60: 4-Methyl-8-pyrrolidin-1-yl-2-(2-trifluoromethyl-pyridin-4-yl)-4H-pyrazolo[1,5-a]quinazolin-5-one

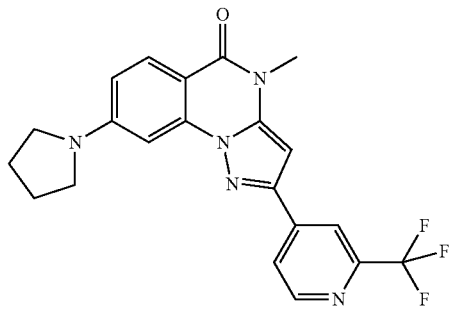

Example 60 was obtained according to general procedure X(iii) starting from example 58 in presence of pyrolidine. The reaction was heated for 1 hour. Purification by flash-chromatography (MeOH in DCM, 0 to 5%) afforded example 60 as a beige solid in 25% yield.

¹H-NMR (400 MHz, CDCl$_3$): 2.08-2.12 (m, 4H, 2 CH$_2$); 3.48-3.52 (m, 4H, 2 CH$_2$); 3.60 (s, 3H, NCH$_3$); 6.28 (s, 1H, Ar); 6.63 (dd, J 9.0 Hz, 2.4 Hz, 1H, Ar); 7.14 (d, 2.4 Hz, 1H, Ar); 7.95-7.97 (m, 1H, Ar); 8.11 (d, J 9.0 Hz, 1H, Ar); 8.22 (bs, 1H, Ar); 8.77 (d, J 5.1 Hz, 1H, Ar).

M/Z (M+H)$^+$=414.2.

MP: >250° C.

Example 61: 4-Methyl-8-methylamino-2-(2-trifluoromethyl-pyridin-4-yl)-4H-pyrazolo[1,5-a]quinazolin-5-one

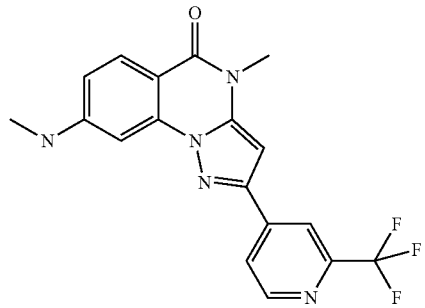 [SMILES: CNc1ccc2c(=O)n(C)c3cc(-c4ccnc(C(F)(F)F)c4)nn3c2c1]

Example 61 was obtained according to general procedure X(iii) starting from example 58 in presence of methyl amine HCl. The reaction was performed with 3.0 equiv of LiHMDS. The reaction mixture was heated for 4 hours, then methylamine HCl (1.2 equiv.), LiHMDS (1N in THF; 3.0 equiv.) and BrettPhos precatalyst (0.1 equiv.) were added. The reaction mixture was further heated for one hour at 60° C. Purification by flash-chromatography (MeOH in DCM, 0 to 3%) afforded example 61 as a beige solid in 44% yield.

$^1$H-NMR (400 MHz, DMSO): 2.86 (d, J 4.9 Hz, 3H, NHCH$_3$); 3.50 (s, 3H, NCH$_3$); 6.72 (dd, J 8.8 Hz, 2.2 Hz, 1H, Ar); 7.06 (s, 1H, Ar); 7.08-7.12 (m, 2H, Ar+NHCH$_3$); 7.87 (d, J 8.8 Hz, 1H, Ar); 8.22-8.24 (m, 1H, Ar); 8.35 (bs, 1H, Ar); 8.87 (d, J 5.2 Hz, 1H, Ar).

M/Z (M+H)$^+$=374.0.
MP: >250° C.

Example 62: 8-(4-Methoxy-piperidin-1-yl)-4-methyl-2-(2-trifluoromethyl-pyridin-4-yl)-4H-pyrazolo[1,5-a]quinazolin-5-one

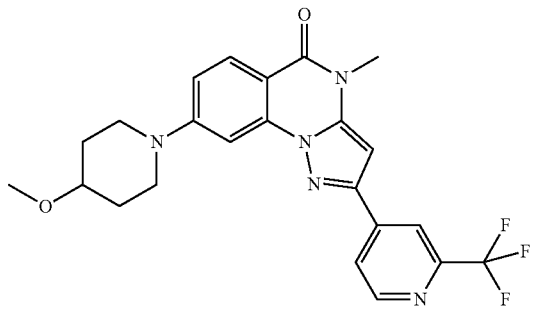 [SMILES: COC1CCN(c2ccc3c(=O)n(C)c4cc(-c5ccnc(C(F)(F)F)c5)nn4c3c2)CC1]

Example 62 was obtained according to general procedure X(iii) starting from example 58 in presence of 4-methoxypiperidine HCl. The reaction was performed with 3.0 equiv of LiHMDS. The reaction mixture was heated for 2 hours, then 4-methoxypiperidine HCl (1.2 equiv.), LiHMDS (1N in THF; 3.0 equiv.) and BrettPhos precatalyst (0.1 equiv.) were added. The reaction mixture was further heated for one hour at 60° C. Purification by flash-chromatography (MeOH in DCM, 0 to 3%) afforded example 62 as a beige solid in 48% yield.

$^1$H-NMR (400 MHz, DMSO): 1.51-1.59 (m, 2H, 2 CH$_a$H$_b$); 1.95-1.99 (m, 2H, 2CH$_a$H$_b$); 3.23-3.30 (m, 5H, OCH$_3$+2NCH$_a$H$_b$); 3.45-3.51 (m, 4H, NCH$_3$+OCH); 3.45-3.51 (m, 2H, 2 NCH$_a$H$_b$); 7.08 (s, 1H, Ar); 7.11 (dd, J 9.0 Hz, 2.4 Hz, 1H, Ar); 7.45 (d, 2.4 Hz, 1H, Ar); 7.93 (d, J 9.0 Hz, 1H, Ar); 8.25-8.27 (m, 1H, Ar); 8.37 (bs, 1H, Ar); 8.86 (d, J 5.1 Hz, 1H, Ar).

M/Z (M+H)$^+$=458.2.
MP: >250° C.

Example 63: 8-(4-Hydroxy-piperidin-1-yl)-4-methyl-2-(2-trifluoromethyl-pyridin-4-yl)-4H-pyrazolo[1,5-a]quinazolin-5-one

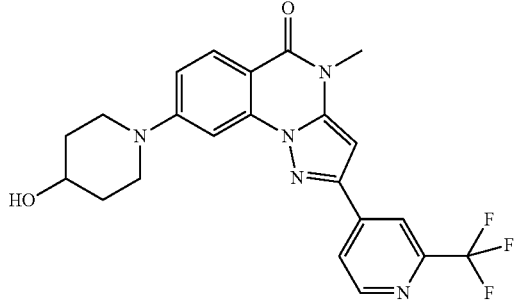 [SMILES: Cn1c(=O)c2ccc(N3CCC(O)CC3)cc2n2nc(-c3ccnc(C(F)(F)F)c3)cc12]

Example 63 was obtained according to general procedure X(iii) starting from example 58 in presence of 4-hydroxypiperidine. Purification by flash-chromatography (MeOH in DCM, 0 to 5%) afforded example 63 as a beige solid in 20% yield.

$^1$H-NMR (400 MHz, DMSO): 1.43-1.52 (m, 2H, 2 CH$_a$H$_b$); 1.85-1.89 (m, 2H, 2 CH$_a$H$_b$); 3.16-3.24 (m, 2H, 2NCH$_a$H$_b$); 3.51 (s, 3H, NCH$_3$); 3.73-3.80 (m, 1H, OCH); 3.82-3.87 (m, 2H, 2 NCH$_a$H$_b$); 4.77 (d, 4.2 Hz, 1H, OH); 7.09 (s, 1H, Ar); 7.11 (dd, J 9.1 Hz, 2.4 Hz, 1H, Ar); 7.45 (d, 2.4 Hz, 1H, Ar); 7.93 (d, J 9.1 Hz, 1H, Ar); 8.26-8.28 (m, 1H, Ar); 8.38 (bs, 1H, Ar); 8.86 (d, J 5.1 Hz, 1H, Ar).

M/Z (M+H)$^+$=444.1.
MP: 112-117° C.

Example 64: 8-Dimethylamino-4-methyl-2-(2-trifluoromethyl-pyridin-4-yl)-4H-pyrazolo[1,5-a]quinazolin-5-one

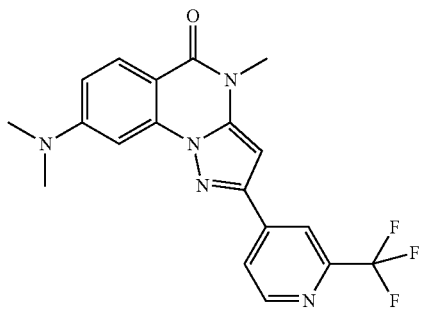 [SMILES: CN(C)c1ccc2c(=O)n(C)c3cc(-c4ccnc(C(F)(F)F)c4)nn3c2c1]

Example 64 was obtained according to general procedure X(iii) starting from example 58 in presence of dimethyl amine HCl. The reaction was performed with 3.0 equiv of LiHMDS. Purification by flash-chromatography (MeOH in DCM, 0 to 3%) afforded example 64 as a beige solid in 43% yield.

$^1$H-NMR (400 MHz, CDCl$_3$): 3.18 (s, 6H, N(CH$_3$)$_2$); 3.60 (s, 3H, NCH$_3$); 6.28 (s, 1H, Ar); 6.76 (dd, J 9.0 Hz, 2.5 Hz, 1H, Ar); 7.29 (d, 2.5 Hz, 1H, Ar); 7.96-7.98 (m, 1H, Ar); 8.12 (d, J 9.0 Hz, 1H, Ar); 8.22 (bs, 1H, Ar); 8.77 (d, J 5.1 Hz, 1H, Ar).

M/Z (M+H)$^+$=388.0.
MP: >250° C.

Example 65: 4-Methyl-8-(4-methyl-piperazin-1-yl)-2-(2-trifluoromethyl-pyridin-4-yl)-4H-pyrazolo[1,5-a]quinazolin-5-one, HCl Salt

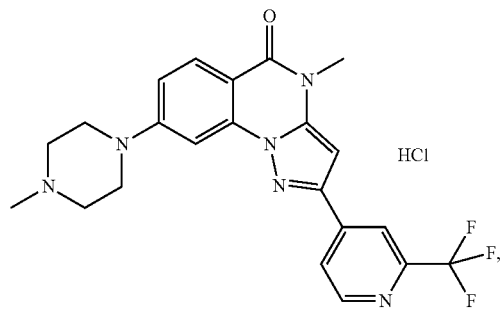 [SMILES: CN1CCN(c2ccc3c(=O)n(C)c4cc(-c5ccnc(C(F)(F)F)c5)nn4c3c2)CC1 ; Cl]

Example 65 was obtained according to general procedure X(iii) starting from example 58 in presence of N-methyl-piperazine. Purification by flash-chromatography (MeOH in DCM, 0 to 5%) and salt formation according to procedure IV(ii) afforded example 65 as a brown solid in 35% yield.

$^1$H-NMR (400 MHz, DMSO): 2.85 (s, 3H, NCH$_3$); 3.13-3.24 (m, 2H, 2NCH$_a$H$_b$); 3.36-3.42 (m, 2H, 2NCH$_a$H$_b$); 3.54-3.58 (m, 5H, NCH$_3$+2NCH$_a$H$_b$); 4.23-4.26 (m, 2H, 2NCH$_a$H$_b$); 7.15 (s, 1H, Ar); 7.21 (dd, J 9.0 Hz, 2.4 Hz, 1H, Ar); 7.78 (d, 2.4 Hz, 1H, Ar); 8.03 (d, J 9.0 Hz, 1H, Ar); 8.27-8.29 (m, 1H, Ar); 8.41 (bs, 1H, Ar); 8.89 (d, J 5.1 Hz, 1H, Ar); 10.76 (bs, 1H, NH).

M/Z (M+H)$^+$=443.1.

MP: >250° C.

Example 66: 4-Methyl-8-piperazin-1-yl-2-(2-trifluoromethyl-pyridin-4-yl)-4H-pyrazolo[1,5-a]quinazolin-5-one, HCl Salt

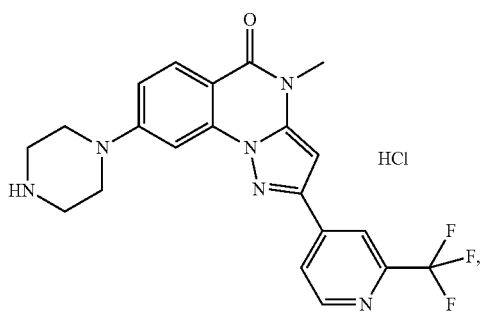 [SMILES: Cn1c(=O)c2ccc(N3CCNCC3)cc2n2nc(-c3ccnc(C(F)(F)F)c3)cc12 ; Cl]

Example 66 was obtained according to general procedure X(ii) starting from example 58 in presence of piperazine (5.0 equiv.). The reaction was performed with 3.0 equiv of LiHMDS and THF was used as solvent. After hydrolysis, the resulting solid was collected, washed with water, dried over MgSO$_4$ and purified by flash-chromatography (MeOH in DCM, 0 to 20%). Salt formation according to procedure IV(iii) afforded example 66 as a beige solid in 21% yield.

$^1$H-NMR (400 MHz, DMSO/D20): 3.25-3.29 (m, 4H, 2NCH$_2$); 3.46 (m, 3H, NCH$_3$); 3.65-3.69 (m, 4H, 2NCH$_2$); 6.90 (s, 1H, Ar); 7.12 (dd, J 9.0 Hz, 1.9 Hz, 1H, Ar); 7.47 (d, 1.9 Hz, 1H, Ar); 7.96 (d, J 9.0 Hz, 1H, Ar); 8.14-8.16 (m, 1H, Ar); 8.29 (bs, 1H, Ar); 8.88 (d, J 4.9 Hz, 1H, Ar).

M/Z (M+H)$^+$=429.1.

MP: >250° C.

Example 67: 8-(4-Hydroxymethyl-piperidin-1-yl)-4-methyl-2-(2-trifluoromethyl-pyridin-4-yl)-4H-pyrazolo[1,5-a]quinazoin-5-one

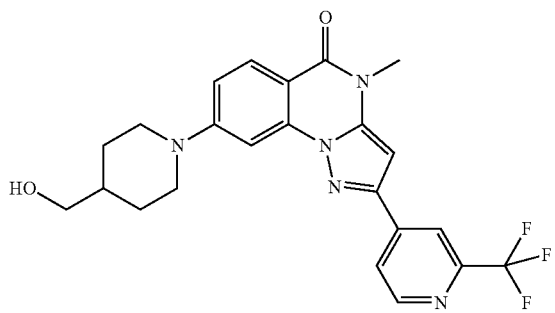 [SMILES: Cn1c(=O)c2ccc(N3CCC(CO)CC3)cc2n2nc(-c3ccnc(C(F)(F)F)c3)cc12]

Example 67 was obtained according to general procedure X(iii) starting from example 58 in presence of 4-piperidinemethanol. The reaction mixture was heated for 2 hours, then 4-piperidinemethanol (1.2 equiv.), LiHMDS (1N in THF; 2.4 equiv.) and BrettPhos precatalyst (0.1 equiv.) were added. The reaction mixture was further heated for 17 hours at 60° C. Purification by flash-chromatography (MeOH in DCM, 0 to 5%) afforded example 67 as a beige solid in 28% yield.

$^1$H-NMR (400 MHz, DMSO): 1.18-1.28 (m, 2H, 2 CH$_a$H$_b$); 1.64-1.72 (m, 1H, CH); 1.78-1.82 (m, 2H, 2 CH$_a$H$_b$); 2.93-3.00 (m, 2H, 2NCH$_a$H$_b$); 3.27-3.31 (m, 2H, 2NCH$_a$H$_b$); 3.50 (s, 3H, NCH$_3$); 4.05-4.08 (m, 2H, CH$_2$OH); 4.50-4.52 (m, 1H, CH$_2$OH); 7.07 (s, 1H, Ar); 7.10 (dd, J 9.1 Hz, 2.4 Hz, 1H, Ar); 7.42 (d, 2.4 Hz, 1H, Ar); 7.92 (d, J 9.1 Hz, 1H, Ar); 8.25-8.27 (m, 1H, Ar); 8.36 (bs, 1H, Ar); 8.86 (d, J 5.1 Hz, 1H, Ar).

M/Z (M+H)$^+$=458.2.

MP: 205-210° C.

Example 68: 8-(3-Hydroxy-azetidin-1-yl)-4-methyl-2-(2-trifluoromethyl-pyridin-4-yl)-4H-pyrazolo[1,5-a]quinazolin-5-one

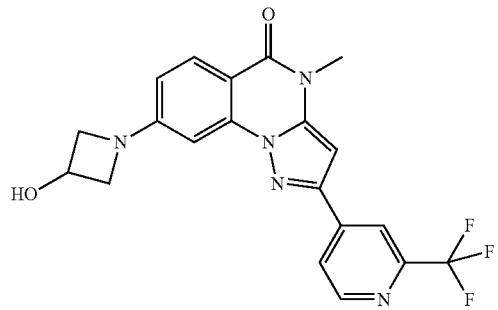 [SMILES: Cn1c(=O)c2ccc(N3CC(O)C3)cc2n2nc(-c3ccnc(C(F)(F)F)c3)cc12]

Example 68 was obtained according to general procedure X(iv) starting from example 58 in presence of 4-hydroxyazetidine. Purification by flash-chromatography (MeOH in DCM, 0 to 5%) afforded example 68 as a beige solid in 51% yield.

$^1$H-NMR (400 MHz, DMSO): 3.51 (s, 3H, NCH$_3$); 3.81 (dd, J 8.7 Hz, 4.4 Hz, 2H, 2NCH$_a$H$_b$); 4.29-4.33 (m, 2H, 2NCH$_a$H$_b$); 4.63-4.70 (m, 1H, CHOH); 5.82 (d, 6.2 Hz, 1H, CHOH); 6.55 (dd, J 8.8 Hz, 2.3 Hz, 1H, Ar); 6.91 (d, 2.3 Hz, 1H, Ar); 7.10 (s, 1H, Ar); 7.95 (d, J 8.8 Hz, 1H, Ar); 8.25-8.26 (m, 1H, Ar); 8.36 (bs, 1H, Ar); 8.87 (d, J 5.1 Hz, 1H, Ar).

M/Z (M+H)$^+$=416.0.

MP: >250° C.

Example 69: 8-(3-Hydroxymethyl-azetidin-1-yl)-4-methyl-2-(2-trifluoromethyl-pyridin-4-yl)-4H-pyrazolo[1,5-a]quinazolin-5-one

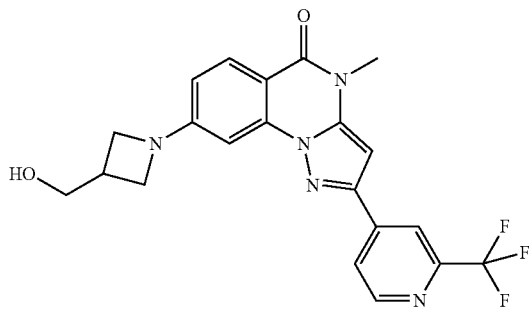 [SMILES: Cn1c(=O)c2ccc(N3CC(CO)C3)cc2n2nc(-c3ccnc(C(F)(F)F)c3)cc12]

Example 69 was obtained according to general procedure X(iv) starting from example 58 in presence of 4-azetidin-3-ylmethanol HCl. Purification by flash-chromatography (MeOH in DCM, 0 to 5%) afforded example 69 as a beige solid in 38% yield.

$^1$H-NMR (400 MHz, DMSO): 2.84-2.93 (m, 1H, CH); 3.51 (s, 3H, NCH$_3$); 3.62 (t, J 5.4 Hz, 2H, 2CHCH$_2$OH); 3.82 (dd, J 8.1 Hz, J 5.4 Hz, 2H, 2NCH$_a$H$_b$); 4.10 (t, J 8.1 Hz, 2H, 2NCH$_a$H$_b$); 4.84 (t, 5.4 Hz, 1H, CH$_2$OH); 6.53 (dd, J 8.7 Hz, 2.2 Hz, 1H, Ar); 6.89 (d, 2.2 Hz, 1H, Ar); 7.08 (s, 1H, Ar); 7.94 (d, J 8.7 Hz, 1H, Ar); 8.24-8.25 (m, 1H, Ar); 8.36 (bs, 1H, Ar); 8.87 (d, J 5.1 Hz, 1H, Ar).

M/Z (M+H)$^+$=430.1.
MP: >250° C.

Example 70: 8-(3-Hydroxy-pyrrolidin-1-yl)-4-methyl-2-(2-trifluoromethyl-pyridin-4-yl)-4H-pyrazolo[1,5-a]quinazolin-5-one

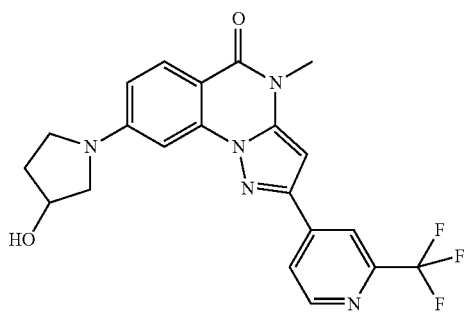 [SMILES: Cn1c(=O)c2ccc(N3CCC(O)C3)cc2n2nc(-c3ccnc(C(F)(F)F)c3)cc12]

Example 70 was obtained according to general procedure X(iii) starting from example 58 in presence of 3-pyrolidinol. The reaction mixture was heated for 2 hours, then 3-pyrolidinol (1.2 equiv.), LiHMDS (1N in THF; 2.4 equiv.) and BrettPhos precatalyst (0.1 equiv.) were added. The reaction mixture was further heated for 17 hours at 60° C. Purification by flash-chromatography (MeOH in DCM, 0 to 5%) afforded example 70 as a beige solid in 47% yield.

$^1$H-NMR (400 MHz, DMSO): 1.95-2.01 (m, 1H, CH$_a$H$_b$); 2.06-2.15 (m, 1H, CH$_a$H$_b$); 3.28-3.30 (m, 1H, NCH); 3.50-3.54 (m, 5H, 2NCH+NCH$_3$); 3.58 (dd, J 10.7 Hz, 4.5 Hz, 1H, NCH$_a$H$_b$); 4.47 (m, 1H, CHOH); 5.07 (d, 3.7 Hz, 1H, CHOH); 6.72 (dd, J 8.9 Hz, 2.3 Hz, 1H, Ar); 7.04 (d, 2.3 Hz, 1H, Ar); 7.07 (s, 1H, Ar); 7.94 (d, J 8.9 Hz, 1H, Ar); 8.24-8.26 (m, 1H, Ar); 8.36 (bs, 1H, Ar); 8.86 (d, J 5.0 Hz, 1H, Ar).

M/Z (M+H)$^+$=430.2.
MP: >250° C.

Example 71: 8-(4-Hydroxy-4-methyl-piperidin-1-yl)-4-methyl-2-(2-trifluoromethyl-pyridin-4-yl)-4H-pyrazolo[1,5-a]quinazolin-5-one

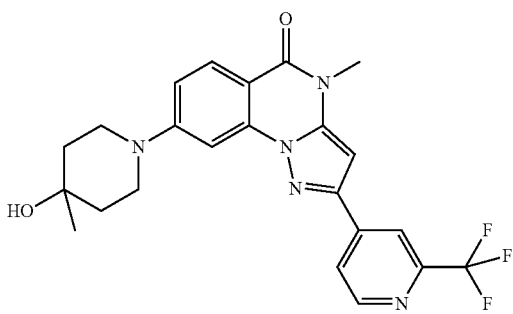 [SMILES: Cn1c(=O)c2ccc(N3CCC(C)(O)CC3)cc2n2nc(-c3ccnc(C(F)(F)F)c3)cc12]

Example 71 was obtained according to general procedure X(iv) starting from example 58 in presence of 4-methylpiperidin-4-ol. The reaction mixture was heated for 17 hours, then 4-methylpiperidin-4-ol (0.8 equiv.), K$_3$PO$_4$ (2.0 equiv.), CuI (0.05 equiv.) and DMPAO (0.1 equiv.) were added. The reaction mixture was further heated for 24 hours at 100° C. Purification by flash-chromatography (MeOH in DCM, 0 to 5%) afforded example 71 as a beige solid in 22% yield.

$^1$H-NMR (400 MHz, DMSO): 1.18 (s, 3H, CCH$_3$); 1.53-1.64 (m, 4H, 2 CH$_2$); 3.37-3.43 (m, 2H, 2 NCH$_a$H$_b$); 3.51 (s, 3H, NCH$_3$); 3.68-3.73 (m, 2H, 2NCH$_a$H$_b$); 4.44 (s, 1H, OH); 7.09 (s, 1H, Ar); 7.11 (dd, J 9.1 Hz, 2.4 Hz, 1H, Ar); 7.45 (d, 2.4 Hz, 1H, Ar); 7.93 (d, J 9.1 Hz, 1H, Ar); 8.26-8.28 (m, 1H, Ar); 8.38 (bs, 1H, Ar); 8.86 (d, J 5.1 Hz, 1H, Ar).

M/Z (M+H)$^+$=458.2.
MP: >250° C.

Example 72: 4,8-Dimethyl-2-(2-trifluoromethyl-pyridin-4-yl)-4H-pyrazolo[1,5-a]quinazolin-5-one

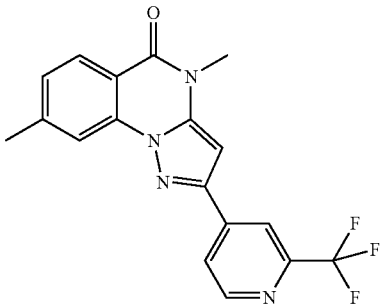 [SMILES: Cc1ccc2c(=O)n(C)c3cc(-c4ccnc(C(F)(F)F)c4)nn3c2c1]

Example 72 was obtained according to general procedure III starting from example 58 in presence of a solution of dimethylzinc in toluene (2M-4.0 equiv.). The reaction was performed without CuI and was heated for 17 hours at 90° C. Purification by flash-chromatography (MeOH in DCM, 0 to 5%) and trituration of the resulting solid by EtOH and then Et$_2$O afforded example 72 as an orange solid in 24% yield.

¹H-NMR (400 MHz, DMSO): 2.54 (s, 3H, CH₃); 3.55 (s, 3H, NCH₃); 7.15 (s, 1H, Ar); 7.36-7.39 (m, 1H, Ar); 8.05 (bs, 1H, Ar); 8.08 (d, J 8.2 Hz, 1H, Ar); 8.23-8.25 (m, 1H, Ar); 8.37 (bs, 1H, Ar); 8.88 (d, J 5.1 Hz, 1H, Ar).
M/Z (M+H)⁺=359.0.
MP: >250° C.

Example 73: 8-Cyclopropyl-4-methyl-2-(2-trifluoromethyl-pyridin-4-yl)-4H-pyrazolo[1,5-a]quinazolin-5-one

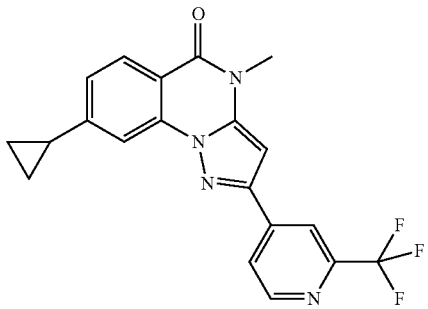 [SMILES: Cn1c(=O)c2ccc(C3CC3)cc2n2nc(-c3ccnc(C(F)(F)F)c3)cc12]

Example 73 was obtained according to general procedure III starting from example 58 in presence of a solution of cyclopropylzinc bromide in THF (0.5N-3.0 equiv.). Purification by flash-chromatography (MeOH in DCM, 0 to 5%) afforded example 73 as a beige solid in 26% yield.
¹H-NMR (400 MHz, DMSO): 0.90-0.93 (m, 2H, 2CH$_a$H$_b$); 1.13-1.18 (m, 2H, 2CH$_a$H$_b$); 2.20-2.27 (m, 1H, CH); 3.55 (s, 3H, NCH₃); 7.15 (s, 1H, Ar); 7.22 (dd, J 8.3 Hz, J 1.6 Hz, 1H, Ar); 7.93 (d, J 1.6 Hz, 1H, Ar); 8.06 (d, J 8.3 Hz, 1H, Ar); 8.25-8.27 (m, 1H, Ar); 8.38 (bs, 1H, Ar); 8.88 (d, J 5.1 Hz, 1H, Ar).
M/Z (M+H)⁺=385.2.
MP: >250° C.

Example 74: 8-Cyclopentyl-4-methyl-2-(2-trifluoromethyl-pyridin-4-yl)-4H-pyrazolo[1,5-a]quinazolin-5-one

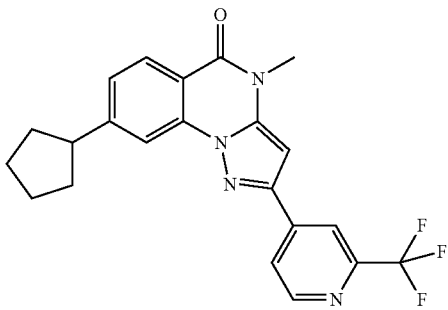 [SMILES: Cn1c(=O)c2ccc(C3CCCC3)cc2n2nc(-c3ccnc(C(F)(F)F)c3)cc12]

Example 74 was obtained according to general procedure III starting from example 58 in presence of a solution of cyclopentylzinc bromide in THF (0.5N-2.2 equiv.). Purification by flash-chromatography (EtOAc in cyHex, 0 to 50%) afforded example 74 as a beige solid in 22% yield.
¹H-NMR (400 MHz, DMSO at 80° C.): 1.67-1.77 (m, 4H, 2CH₂); 1.84-1.88 (m, 2H, 2CH$_a$H$_b$); 2.13-2.19 (m, 2H, 2CH$_a$H$_b$); 3.25-3.30 (m, 1H, CH); 3.59 (s, 3H, NCH₃); 7.06 (s, 1H, Ar); 7.47 (dd, J 8.2 Hz, J 1.4 Hz, 1H, Ar); 8.10 (d, J 1.4 Hz, 1H, Ar); 8.14 (d, J 8.2 Hz, 1H, Ar); 8.23-8.25 (m, 1H, Ar); 8.35 (bs, 1H, Ar); 8.87 (d, J 5.0 Hz, 1H, Ar).
M/Z (M+H)⁺=413.4.
MP: 246-250° C.

Example 75: 4-Methyl-5-oxo-2-(2-trifluoromethyl-pyridin-4-yl)-4,5-dihydro-pyrazolo[1,5-a]quinazoline-8-carbonitrile

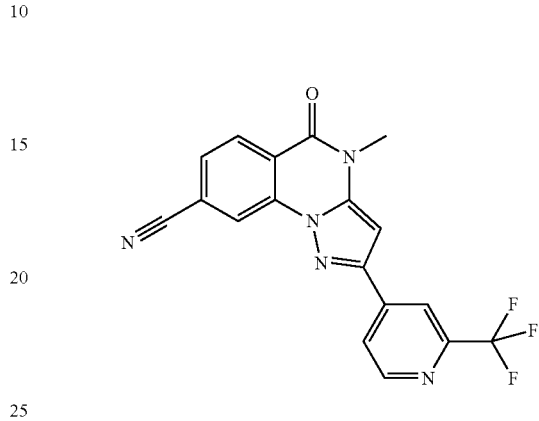

Example 75 was obtained according to general procedure VI starting from example 58. The reaction was heated for 17 hours at 100° C. Purification by flash-chromatography (MeOH in DCM, 0 to 2%) afforded example 75 as a beige solid in 22% yield.
¹H-NMR (400 MHz, DMSO): 3.55 (s, 3H, NCH₃); 7.20 (s, 1H, Ar); 7.93 (dd, J 8.1 Hz, 1.4 Hz, 1H, Ar); 8.23-8.25 (m, 1H, Ar); 8.29 (d, J 8.1 Hz, 1H, Ar); 8.40 (bs, 1H, Ar); 8.65 (d, J 1.4 Hz, 1H, Ar); 8.89 (d, J 5.0 Hz, 1H, Ar).
M/Z (M+H)⁺=370.2.
MP: >250° C.

Example 76: 4-Methyl-5-oxo-2-(2-trifluoromethyl-pyridin-4-yl)-4,5-dihydro-pyrazolo[1,5-a]quinazoline-8-carboxylic Acid

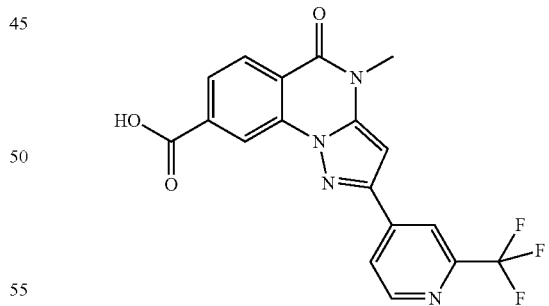

To a solution of example 75 (287 mg, 1.0 equiv.) in DMSO (4 mL, C=0.2 molL⁻¹), a solution of aqueous NaOH (1N, 4 mL, 5.1 equiv.) was added and the mixture was heated for 17 hours at 90° C. After cooling, the reaction mixture was hydrolyzed with an aqueous HCl solution (1N). The solid was collected, washed with water and dried under reduced pressure at 50° C. with P₂O₅. Trituration in Et₂O afforded example 76 as a yellow solid in 69% yield.
¹H-NMR (400 MHz, DMSO): 3.59 (s, 3H, NCH₃); 7.24 (s, 1H, Ar); 8.04 (dd, J 8.1 Hz, 1.4 Hz, 1H, Ar); 8.28-8.31

(m, 2H, Ar); 8.40 (bs, 1H, Ar); 8.69 (d, J 1.4 Hz, 1H, Ar); 8.89 (d, J 5.0 Hz, 1H, Ar). Signal for COOH is not observed.
M/Z (M+H)$^+$=389.1.
MP: >250° C.

General Procedure XII: Amide Formation Via Acid Activation

Method (i): Under inert atmosphere, to a solution of acid (1.0 equiv.) in DMF (C=0.1 molL$^{-1}$), BOP (1.1 equiv.), diisopropylamine (1.1 equiv.), and amine (1.1 equiv.) were added. The resulting mixture was stirred for 1 hour at room temperature. The reaction mixture was hydrolysed with a saturated aqueous NH$_4$Cl solution. The solid was collected, washed with water, dried under reduced pressure and purified to afford the amide.

Example 77: 4-Methyl-5-oxo-2-(2-trifluoromethyl-pyridin-4-yl)-4,5-dihydro-pyrazolo[1,5-a]quinazoline-8-carboxylic Acid Amide

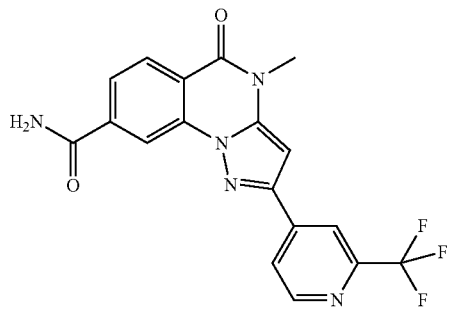 [SMILES: Cn1c(=O)c2ccc(C(N)=O)cc2n2nc(-c3ccnc(C(F)(F)F)c3)cc12]

Example 77 was obtained according to general procedure XII(i) starting from example 58 with ammoniac as nucleophile (0.5 N in Dioxane). The reaction mixture was stirred for 3 hours at room temperature. Trituration in EtOH, DCM and then Et$_2$O afforded example 77 as a beige solid in 23% yield.
$^1$H-NMR (400 MHz, DMSO): 3.58 (s, 3H, NCH$_3$); 7.21 (s, 1H, Ar); 7.77 (bs, 1H, CONH$_a$H$_b$); 8.00 (dd, J 8.2 Hz, 1.2 Hz, 1H, Ar); 8.25-8.29 (m, 2H, Ar); 8.40-8.42 (m, 2H, 1Ar+CONH$_a$H$_b$); 8.68 (d, J 1.2 Hz, 1H, Ar); 8.89 (d, J 5.1 Hz, 1H, Ar).
M/Z (M+H)$^+$=388.0.
MP: >250° C.

Example 78: 4-Methyl-5-oxo-2-(2-trifluoromethyl-pyridin-4-yl)-4,5-dihydro-pyrazolo[1,5-a]quinazoline-8-carboxylic Acid Methylamide

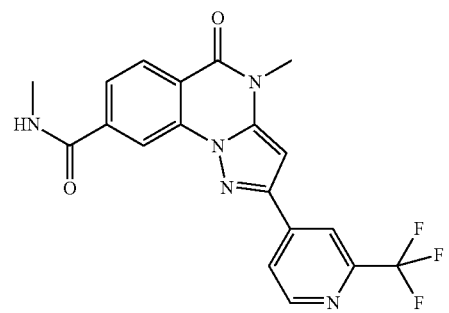 [SMILES: CNC(=O)c1ccc2c(=O)n(C)c3cc(-c4ccnc(C(F)(F)F)c4)nn3c2c1]

Example 78 was obtained according to general procedure XII(i) starting from example 58 with methylamine HCl as nucleophile (2.2 equiv. of iPr$_2$NEt was added instead of 1.1 equiv.). Trituration in EtOH then Et$_2$O afforded example 78 as a white solid in 33% yield.
$^1$H-NMR (400 MHz, DMSO): 2.86 (d, J 4.6 Hz, 3H, CONHCH$_3$); 3.57 (s, 3H, NCH$_3$); 7.20 (s, 1H, Ar); 7.94 (dd, J 8.3 Hz, 1.6 Hz, 1H, Ar); 8.24-8.26 (m, 2H, Ar); 8.39 (bs, 1H, Ar); 8.60 (d, 1.6 Hz, 1H, Ar); 8.88-8.90 (m, 2H, 1Ar+CONHCH$_3$).
M/Z (M+H)$^+$=402.5.
MP: >250° C.

Example 79: 4-Methyl-5-oxo-2-(2-trifluoromethyl-pyridin-4-yl)-4,5-dihydro-pyrazolo[1,5-a]quinazoline-8-carboxylic Acid Dimethylamide

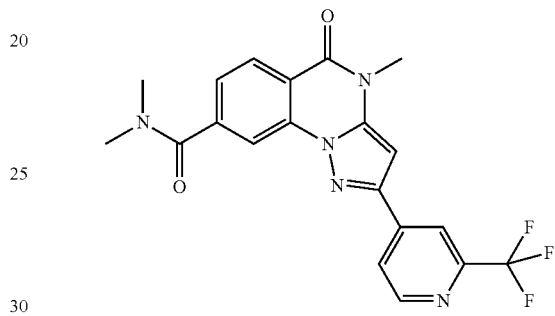

Example 79 was obtained according to general procedure XII(i) starting from example 58 with dimethylamine HCl as nucleophile (3.0 equiv. of iPr$_2$NEt was added instead of 1.1 equiv.). The reaction mixture was stirred for 17 hours at room temperature. Trituration in EtOH then Et$_2$O afforded example 79 as a beige solid in 3% yield.
$^1$H-NMR (400 MHz, DMSO): 2.94 (s, 3H, CON(CH$_3$)(CH$_3$)); 3.06 (s, 3H, CON(CH$_3$)(CH$_3$)); 3.58 (s, 3H, NCH$_3$); 7.22 (s, 1H, Ar); 7.54-7.55 (m, 1H, Ar); 8.20-8.28 (m, 3H, Ar); 8.41 (bs, 1H, Ar); 8.88-8.89 (m, 1H, 1Ar).
M/Z (M+H)$^+$=415.9.

Example 80: 4-Methyl-5-oxo-2-(2-trifluoromethyl-pyridin-4-yl)-4,5-dihydro-pyrazolo[1,5-a]quinazoline-8-carboxylic Acid Diethylamide

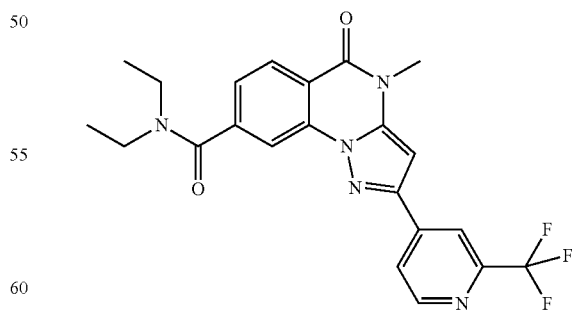

Example 80 was obtained according to general procedure XII(i) starting from example 58 with diethylamine as nucleophile. Purification by flash-chromatography (MeOH in DCM, 0 to 5%) afforded example 80 as a white solid in 40% yield.

¹H-NMR (400 MHz, DMSO): 1.06-1.23 (m, 6H, CON(CH₂CH₃)(CH₂CH₃)); 3.19-3.25 (m, 2H, CON(CH₂CH₃)(CH₂CH₃)); 3.48-3.54 (m, 2H, CON(CH₂CH₃)(CH₂CH₃)); 3.58 (s, 3H, NCH₃); 7.22 (s, 1H, Ar); 7.50-7.53 (m, 1H, Ar); 8.14 (bs, 1H, Ar); 8.25 (d, J 8.2 Hz, 1H, Ar); 8.27-8.28 (m, 1H, Ar); 8.41 (bs, 1H, Ar); 8.88 (d, J 4.9 Hz, 1H, 1Ar).

M/Z (M+H)⁺=444.3.

MP: 240-245° C.

Example 81: 4-Methyl-8-(morpholine-4-carbonyl)-2-(2-trifluoromethyl-pyridin-4-yl)-4H-pyrazolo[1,5-a]quinazolin-5-one

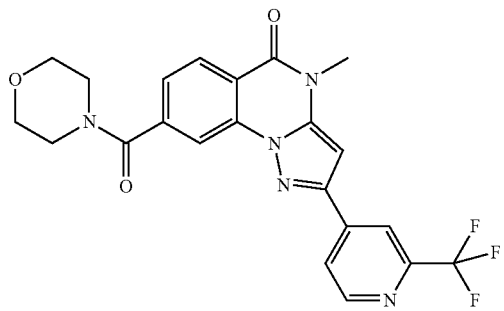 [SMILES: Cn1c(=O)c2ccc(C(=O)N3CCOCC3)cc2n2nc(-c3ccnc(C(F)(F)F)c3)cc12]

Example 81 was obtained according to general procedure XII(i) starting from example 58 with morpholine as nucleophile. Trituration in DCM then Et₂O afforded example 81 as a white solid in 34% yield.

¹H-NMR (400 MHz, DMSO): 3.52-3.58 (m, 4H, 2 CH₂); 3.62 (s, 3H, NCH₃); 3.64-3.69 (m, 4H, 2 CH₂); 7.11 (s, 1H, Ar); 7.55 (d, J 8.0 Hz, 1H, Ar); 8.23-8.29 (m, 3H, Ar); 8.37 (bs, 1H, Ar); 8.88 (d, J 4.7 Hz, 1H, Ar).

M/Z (M+H)⁺=458.3.

MP: >250° C.

Example 82: 4-Methyl-8-(pyrrolidine-1-carbonyl)-2-(2-trifluoromethyl-pyridin-4-yl)-4H-pyrazolo[1,5-a]quinazolin-5-one

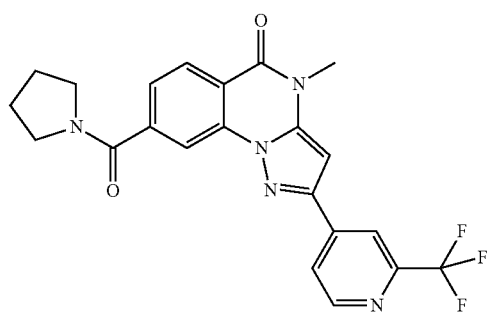 [SMILES: Cn1c(=O)c2ccc(C(=O)N3CCCC3)cc2n2nc(-c3ccnc(C(F)(F)F)c3)cc12]

Example 82 was obtained according to general procedure XII(i) starting from example 58 with pyrolidine as nucleophile. Trituration in EtOH then Et₂O afforded example 82 as a beige solid in 56% yield.

¹H-NMR (400 MHz, DMSO): 1.82-1.96 (m, 4H, 2 CH₂); 3.40 (t, J 6.4 Hz, 2H, 2NCH$_a$H$_b$); 3.54 (t, J 6.8 Hz, 2H, 2NCH$_a$H$_b$); 3.58 (s, 3H, NCH₃); 7.21 (s, 1H, Ar); 7.64 (dd, J 8.2 Hz, 1.5 Hz, 1H, Ar); 8.24 (d, 8.2 Hz, 1H, Ar); 8.26-8.27 (m, 2H, Ar); 8.40 (bs, 1H, Ar); 8.88 (d, J 5.1 Hz, 1H, Ar).

M/Z (M+H)⁺=442.0.

MP: >250° C.

Example 83: 8-(2-Hydroxy-ethoxy)-4-methyl-2-(2-trifluoromethyl-pyridin-4-yl)-4H-pyrazolo[1,5-a]quinazolin-5-one

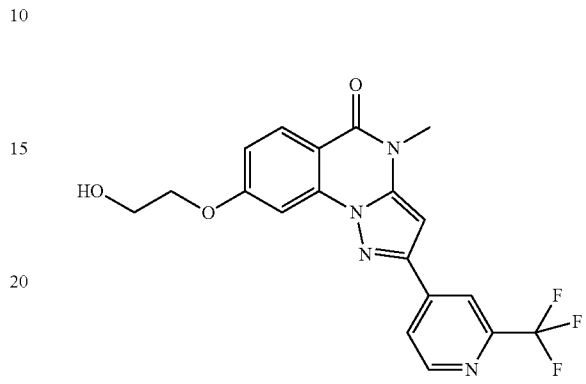

Example 83 was obtained according to general procedure VII(iii) starting from example 55 in presence of ethylene glycol. The reaction mixture was heated for 3 hours at 60° C., then tBuOK (1.2 equiv.) were added and the mixture was heated for additional 17 hours at 60° C. Trituration in DCM and Et₂O afforded example 83 as a beige solid in 47% yield.

¹H-NMR (400 MHz, DMSO): 3.53 (s, 3H, NCH₃); 3.79-3.82 (m, 2H, OCH₂CH₂OH); 4.23 (t, J 4.9 Hz, 2H, OCH₂CH₂OH); 4.97 (t, J 5.4 Hz, 1H, OCH₂CH₂OH); 7.11 (dd, J 8.8 Hz, J 2.4 Hz, 1H, Ar); 7.13 (s, 1H, Ar); 7.61 (d, J 2.4 Hz, 1H, Ar); 8.09 (d, J 8.8 Hz, 1H, Ar); 8.24-8.26 (m, 1H, Ar); 8.37 (bs, 1H, Ar); 8.87 (d, J 5.0 Hz, 1H, Ar).

M/Z (M+H)⁺=405.1.

MP: 128-134° C.

Compound 34:
2-Hydrazino-6-trifluoromethyl-benzoic Acid, HCl

Compound 34 was obtained according to general procedure IX, starting from 2-amino-6-trifluoromethylbenzoic acid, as a white solid in 35% yield.

¹H-NMR (400 MHz, DMSO): 7.33-7.43 (m, 2H, Ar); 7.60-7.67 (m, 1H, Ar); 8.06 (bs, 1H, NH); 10.32 (bs, 3H, NH₃).

M/Z (M-18+H)⁺=203.0.

Compound 35: 6-Trifluoromethyl-2-(2-trifluoromethyl-pyridin-4-yl)-4H-pyrazolo[1,5-a]quinazolin-5-one Compound 35 was obtained according to general procedure I(iii), starting from 2-trifluoromethyl-isonicotinic acid ethyl ester in presence of hydrazine 34 as a brown solid in 25% yield.

¹H-NMR (400 MHz, DMSO): 6.34 (s, 1H, Ar); 7.78 (d, J 7.4 Hz, 1H, Ar); 7.82-7.86 (m, 1H, Ar); 8.17-8.19 (m, 1H, Ar); 8.32 (bs, 1H, Ar); 8.50 (d, J 8.1 Hz, 1H, Ar); 8.79 (d, J 5.1 Hz, 1H, Ar).

M/Z (M+H)⁺=399.1.

Example 84: 4-Methyl-6-trifluoromethyl-2-(2-trifluoromethyl-pyridin-4-yl)-4H-pyrazolo[1,5-a]quinazolin-5-one

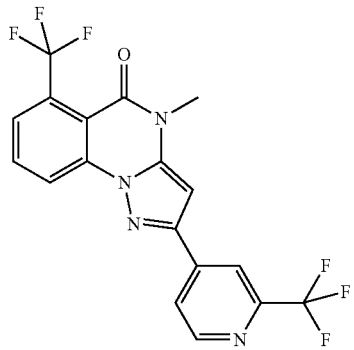 [SMILES: Cn1c(=O)c2c(C(F)(F)F)cccc2n2nc(-c3ccnc(C(F)(F)F)c3)cc12]

Example 84 was obtained according to general procedure II(i), starting from compound 35 in presence of iodomethane. The reaction mixture was stirred for 2 hours at room temperature. Example 84 was obtained without further purification as a grey solid in 19% yield.

$^1$H-NMR (400 MHz, DMSO): 3.53 (s, 3H, NCH$_3$); 7.20 (s, 1H, Ar); 7.99-8.01 (m, 1H, Ar); 8.06-8.11 (m, 1H, Ar); 8.27-8.28 (m, 1H, Ar); 8.41 (bs, 1H, Ar); 8.66-8.68 (m, 1H, Ar); 8.91-8.92 (m, 1H, Ar).

M/Z (M+H)$^+$=413.1.

Compound 36: 6-Fluoro-2-hydrazino-benzoic Acid, HCl

Compound 36 was obtained according to general procedure IX, starting from 2-amino-6-fluoromethylbenzoic acid, as a beige solid in 48% yield.

$^1$H-NMR (400 MHz, DMSO): 6.65 (dd, J 106 Hz, J 8.4 Hz, 1H, Ar); 6.9 (d, J 8.5 Hz, 1H, Ar); 7.51-7.57 (m, 1H, Ar); 8.70 (bs, 1H, NH); 10.28 (bs, 3H, NH$_3$).

M/Z (M+H)$^+$=171.8.

Compound 37: 6-Fluoro-2-(2-trifluoromethyl-pyridin-4-yl)-4H-pyrazolo[1,5-a]quinazolin-5-one Compound 37 was obtained according to general procedure I(iv), starting from 2-trifluoromethyl-isonicotinic acid ethyl ester in presence of hydrazine 36 as a pale brown solid in 53% yield.

$^1$H-NMR (400 MHz, DMSO): 6.72 (s, 1H, Ar); 7.32 (dd, J 11.2 Hz, J 8.5 Hz, 1H, Ar); 7.88-7.94 (m, 1H, Ar); 8.08 (d, J 8.2 Hz, 1H, Ar); 8.25-8.27 (m, 1H, Ar); 8.40 (bs, 1H, Ar); 8.85 (d, J 4.8 Hz, 1H, Ar). Signal for NH is not observed.

M/Z (M+H)$^+$=349.1.

Example 85: 6-Fluoro-4-methyl-2-(2-trifluoromethyl-pyridin-4-yl)-4H-pyrazolo[1,5-a]quinazolin-5-one

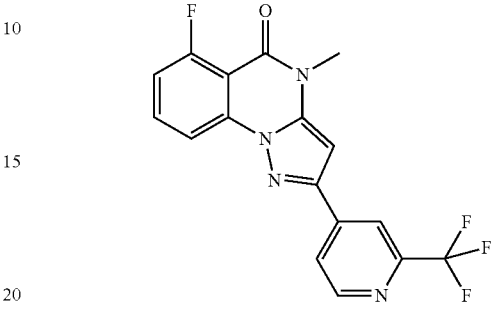

Example 85 was obtained according to general procedure II(iii), starting from compound 37 in presence of iodomethane. The reaction mixture was stirred for 3 hours at room temperature. Example 85 was obtained without further purification as a brown solid in 69% yield.

$^1$H-NMR (400 MHz, DMSO): 3.53 (s, 3H, NCH$_3$); 7.19 (s, 1H, Ar); 7.36 (dd, J 11.0 Hz, J 8.2 Hz, 1H, Ar); 7.91-7.96 (m, 1H, Ar); 8.11 (d, J 8.3 Hz, 1H, Ar); 8.25-8.27 (m, 1H, Ar); 8.40 (bs, 1H, Ar); 8.90 (d, J 5.1 Hz, 1H, Ar).

M/Z (M+H)$^+$=363.1.

MP: >250° C.

Compound 38: 2-Hydrazino-3-methoxy-benzoic Acid, HCl

Compound 38 was obtained according to general procedure IX, starting from 2-amino-3-methoxylbenzoic acid, as a white solid in 19% yield.

$^1$H-NMR (400 MHz, DMSO): 3.89 (s, 3H, OCH$_3$); 7.18 (t, J 8.1 Hz, 1H, Ar); 7.34 (dd, J 8.1 Hz, 1.3 Hz, 1H, Ar); 7.55 (dd, J 8.1 Hz, J 1.3 Hz, 1H, Ar); 9.04 (bs, 1H, NH); 9.75 (bs, 3H, NH$_3$).

Compound 39: 9-Methoxy-2-(2-trifluoromethyl-pyridin-4-yl)-4H-pyrazolo[1,5-a]quinazolin-5-one Compound 39 was obtained according to general procedure I(iv), starting from 2-trifluoromethyl-isonicotinic acid ethyl ester in presence of hydrazine 38 as a brown solid in 24% yield.

$^1$H-NMR (400 MHz, DMSO): 3.92 (s, 3H, OCH$_3$); 6.32 (s, 1H, Ar); 7.26 (t, J 7.8 Hz, 1H, Ar); 7.33 (dd, J 7.8 Hz, J 1.5 Hz, 1H, Ar); 7.74 (dd, J 7.8 Hz, J 1.5 Hz, 1H, Ar); 8.10-8.11 (m, 1H, Ar); 8.24 (bs, 1H, Ar); 8.71 (d, J 5.2 Hz, 1H, Ar). Signal for NH is not observed.

M/Z (M+H)$^+$=361.1.

Example 86: 9-Methoxy-4-methyl-2-(2-trifluoromethyl-pyridin-4-yl)-4H-pyrazolo[1,5-a]quinazolin-5-one

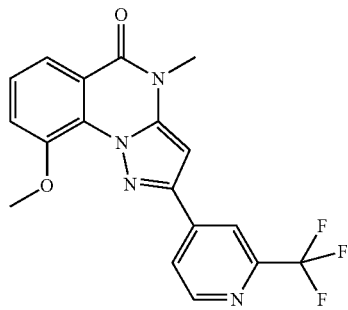 [SMILES: COc1cccc2c(=O)n(C)c3cc(-c4ccnc(C(F)(F)F)c4)nn3c12]

Example 86 was obtained according to general procedure II(iii), starting from compound 39 in presence of iodomethane. The reaction mixture was stirred for 3 hours at room temperature. The solid was further washed with DCM, DCM/MeOH, EtOH and Et2O to obtained example 86 as a white solid in 14% yield.

$^1$H-NMR (400 MHz, DMSO): 3.61 (s, 3H, NCH$_3$); 4.06 (s, 3H, OCH$_3$); 7.07 (s, 1H, Ar); 7.52 (t, J 8.0 Hz, 1H, Ar); 7.64 (d, J 8.0 Hz, 1H, Ar); 7.92 (d, J 8.0 Hz, 1H, Ar); 8.22-8.24 (m, 1H, Ar); 8.34 (bs, 1H, Ar); 8.86 (d, J 5.1 Hz, 1H, Ar).

M/Z (M+H)$^+$=374.9.

MP: >250° C.

Compound 40: 2-Hydrazino-4,5-dimethoxy-benzoic Acid, HCl

Compound 40 was obtained according to general procedure IX, starting from 2-amino-4,5-dimethoxybenzoic acid, as a beige solid in 92% yield.

$^1$H-NMR (400 MHz, DMSO): 3.73 (s, 3H, OCH$_3$); 3.85 (s, 3H, OCH$_3$); 7.00 (s, 1H, Ar); 7.36 (s, 1H, Ar); 9.00 (bs, 1H, NH); 10.24 (bs, 3H, NH$_3$).

Compound 41: 7, 8-Dimethoxy-2-(2-trifluoromethyl-pyridin-4-yl)-4H-pyrazolo[1,5-a]quinazolin-5-one Compound 41 was obtained according to general procedure I(iv), starting from 2-trifluoromethyl-isonicotinic acid ethyl ester in presence of hydrazine 40 as a brown solid in 57% yield.

$^1$H-NMR (400 MHz, DMSO): 3.90 (s, 3H, OCH$_3$); 4.04 (s, 3H, OCH$_3$); 6.74 (s, 1H, Ar); 7.44 (s, 1H, Ar); 7.68 (s, 1H, Ar) 8.27-8.28 (m, 1H, Ar); 8.41 (bs, 1H, Ar); 8.84 (d, J 5.2 Hz, 1H, Ar); 12.39 (bs, 1H, NH).

Example 87: 7,8-Dimethoxy-4-methyl-2-(2-trifluoromethyl-pyridin-4-yl)-4H-pyrazolo[1,5-a]quinazolin-5-one

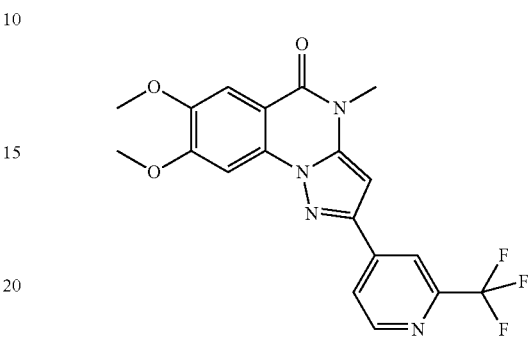

Example 87 was obtained according to general procedure II(iii), starting from compound 41 in presence of iodomethane. The reaction mixture was stirred for 3 hours at room temperature. Example 87 was obtained without further purification as a beige solid in 63% yield.

$^1$H-NMR (400 MHz, DMSO): 3.60 (s, 3H, NCH$_3$); 3.92 (s, 3H, OCH$_3$); 4.06 (s, 3H, OCH$_3$); 7.05 (s, 1H, Ar); 7.62 (s, 1H, Ar); 7.72 (s, 1H, Ar); 8.24-8.25 (m, 1H, Ar); 8.36 (bs, 1H, Ar); 8.86 (d, J 5.2 Hz, 1H, Ar).

M/Z (M+H)$^+$=405.0.

MP: >250° C.

Compound 42: 4,5-Difluoro-2-hydrazino-benzoic Acid, HCl

Compound 42 was obtained according to general procedure IX, starting from 2-amino-4,5-dimethoxybenzoic acid, as a beige solid in 67% yield.

$^1$H-NMR (400 MHz, DMSO): 7.28 (dd, J 13.0 Hz, J 6.7 Hz, 1H, Ar); 7.87 (dd, J 11.2 Hz, J 9.6 Hz, 1H, Ar); 9.12 (bs, 1H, NH); 10.64 (bs, 3H, NH$_3$).

Compound 43: 7, 8-Difluoro-2-(2-trifluoromethyl-pyridin-4-yl)-4H-pyrazolo[1,5-a]quinazolin-5-one Compound 43 was obtained according to general procedure I(iv), starting from 2-trifluoromethyl-isonicotinic acid ethyl ester in presence of hydrazine 42 as a brown solid in 48% yield.

$^1$H-NMR (400 MHz, DMSO): 6.80 (s, 1H, Ar); 8.15 (dd, J 10.2 Hz, J 8.2 Hz, 1H, Ar); 8.26-8.31 (m, 2H, Ar); 8.44 (bs, 1H, Ar); 8.86 (d, J 5.1 Hz, 1H, Ar); 12.67 (bs, 1H, NH).

M/Z (M+H)$^+$=366.9.

Example 88: 7,8-Difluoro-4-methyl-2-(2-trifluoromethyl-pyridin-4-yl)-4H-pyrazolo[1,5-a]quinazolin-5-one

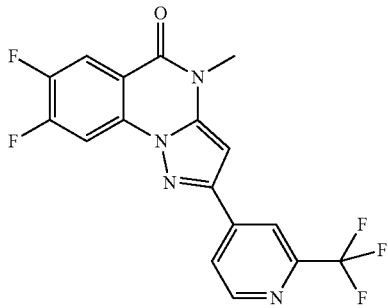 [SMILES: Cn1c(=O)c2cc(F)c(F)cc2n2nc(-c3ccnc(C(F)(F)F)c3)cc12]

Example 88 was obtained according to general procedure II(iii), starting from compound 43 in presence of iodomethane. The reaction mixture was stirred for 3 hours at room temperature. Example 88 was obtained without further purification as a white solid in 13% yield.

$^1$H-NMR (400 MHz, DMSO): 3.56 (s, 3H, NCH$_3$); 7.20 (s, 1H, Ar); 8.15 (dd, J 10.2 Hz, J 8.2 Hz, 1H, Ar); 8.23-8.30 (m, 2H, Ar); 8.39 (bs, 1H, Ar); 8.89 (d, J 5.1 Hz, 1H, Ar).

M/Z (M+H)$^+$=380.9.

MP: >206-212° C.

Compound 44: 4-Fluoro-2-hydrazino-5-methoxy-benzoic Acid, HCl

Compound 44 was obtained according to general procedure IX, starting from 2-amino-4-fluoro-5-methoxybenzoic acid, as a white solid in 78% yield.

$^1$H-NMR (400 MHz, DMSO): 3.82 (s, 3H, OCH$_3$); 7.16 (d, J 13.5 Hz, 1H, Ar); 7.58 (d, J 9.5 Hz, 1H, Ar); 9.13 (bs, 1H, NH); 10.55 (bs, 3H, NH$_3$).

Compound 45: 8-Fluoro-7-methoxy-2-(2-trifluoromethyl-pyridin-4-yl)-4H-pyrazolo[1,5-a]quinazolin-5-one Compound 45 was obtained according to general procedure I(iv), starting from 2-trifluoromethyl-isonicotinic acid ethyl ester in presence of hydrazine 43 as a brown solid in 49% yield.

$^1$H-NMR (400 MHz, DMSO): 3.98 (s, 3H, OCH$_3$); 6.75 (s, 1H, Ar); 7.76 (d, J 8.7 Hz, 1H, Ar); 8.06 (d, J 11.2 Hz, 1H, Ar); 8.24-8.26 (m, 1H, Ar); 8.40 (bs, 1H, Ar); 8.84 (d, J 5.1 Hz, 1H, Ar); 12.55 (bs, 1H, NH).

M/Z (M+H)$^+$=379.0.

Example 89: 8-Fluoro-7-methoxy-4-methyl-2-(2-trifluoromethyl-pyridin-4-yl)-4H-pyrazolo[1,5-a]quinazolin-5-one

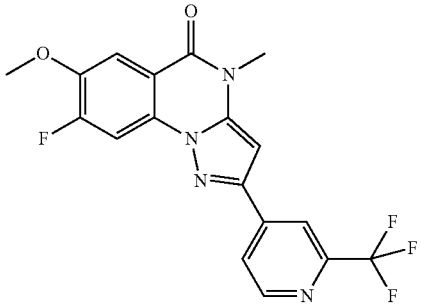 [SMILES: COc1cc2c(=O)n(C)c3cc(-c4ccnc(C(F)(F)F)c4)nn3c2cc1F]

Example 89 was obtained according to general procedure II(iii), starting from compound 45 in presence of iodomethane. The reaction mixture was stirred for 3 hours at room temperature. Example 89 was obtained without further purification as a brown solid in 79% yield.

$^1$H-NMR (400 MHz, DMSO): 3.56 (s, 3H, NCH$_3$); 3.98 (s, 3H, OCH$_3$); 7.16 (s, 1H, Ar); 7.76 (d, J 8.6 Hz, 1H, Ar); 8.05 (d, J 11.1 Hz, 1H, Ar) 8.21-8.22 (m, 1H, Ar); 8.37 (bs, 1H, Ar); 8.87 (d, J 5.1 Hz, 1H, Ar).

M/Z (M+H)$^+$=393.0.

MP: 220-230° C.

Example 90: 8-(4-Hydroxy-piperidin-1-yl)-7-methoxy-4-methyl-2-(2-trifluoromethyl-pyridin-4-yl)-4H-pyrazolo[1,5-a]quinazolin-5-one

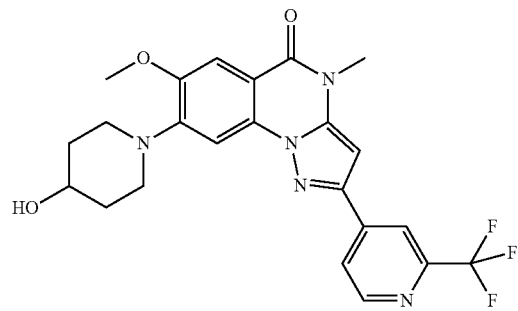 [SMILES: COc1cc2c(=O)n(C)c3cc(-c4ccnc(C(F)(F)F)c4)nn3c2cc1N1CCC(O)CC1]

Example 90 was obtained according to general procedure X(vi) starting from example 89 in presence of 4-hydroxypiperidine. Trituration in DCM afforded example 90 as a white solid in 80% yield.

$^1$H-NMR (400 MHz, DMSO): 1.54-1.62 (m, 2H, 2 CH$_a$H$_b$); 1.89-1.93 (m, 2H, 2 CH$_a$H$_b$); 2.93-2.99 (m, 2H, 2NCH$_a$H$_b$); 3.54-3.56 (s, 5H, 2NCH$_a$H$_b$+NCH$_3$); 3.67-3.73 (m, 1H, OCH); 3.92 (s, 3H, OCH$_3$); 7.14 (s, 1H, Ar); 7.50 (s, 1H, Ar); 7.57 (s, 1H, Ar) 8.25-8.26 (m, 1H, Ar); 8.36 (bs, 1H, Ar); 8.86 (d, J 5.0 Hz, 1H, Ar). Signal for OH is not observed.

M/Z (M+H)$^+$=474.1.

MP: >250° C.

Compound 46: 8-Dimethylamino-7-fluoro-2-(2-trifluoromethyl-pyridin-4-yl)-4H-pyrazolo[1,5-a]quinazolin-5-one Compound 46 was obtained according to general procedure X(vi) starting from compound 43 in presence of dimethylamine (2 N in THF). The reaction mixture was heated for 1 hour, then dimethylamine (2 N in THF, 1.6 equiv.) was added again. The reaction mixture was further heated for 17 Hrs at 90° C., then dimethylamine (2 N in THF, 1.6 equiv.) was added a last time. The reaction mixture was further heated for 24 hours at 90° C. Compound 46 was isolate without further purification.

M/Z (M+H)$^+$=392.0.

Example 91: 8-Dimethylamino-7-fluoro-4-methyl-2-(2-trifluoromethyl-pyridin-4-yl)-4H-pyrazolo[1,5-a]quinazolin-5-one

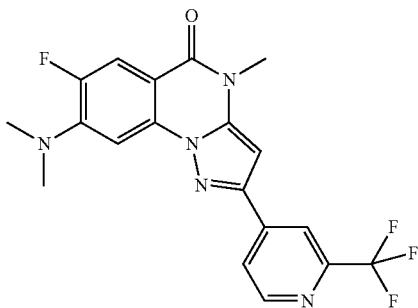 [SMILES: CN(C)c1cc2c(cc1F)c(=O)n(C)c1cc(-c3ccnc(C(F)(F)F)c3)nn21]

Example 91 was obtained according to general procedure II(iii), starting from compound 46 in presence of iodomethane. The reaction mixture was stirred for 3 hours at room temperature. Example 91 was obtained without further purification as a white solid in 64% yield.

$^1$H-NMR (400 MHz, DMSO): 3.14 (s, 6H, N(CH$_3$)$_2$); 3.57 (s, 3H, NCH$_3$); 7.04 (s, 1H, Ar); 7.48 (d, J 8.0 Hz, 1H, Ar); 7.73 (d, J 14.3 Hz, 1H, Ar); 8.23-8.25 (m, 1H, Ar); 8.34 (bs, 1H, Ar); 8.87 (d, J 5.2 Hz, 1H, Ar).

M/Z (M+H)$^+$=406.0.

MP: >250° C.

Compound 47:
5-Bromo-4-fluoro-2-hydrazino-benzoic Acid, HCl

Compound 47 was obtained according to general procedure IX, starting from 2-amino-5-bromo-4-fluorobenzoic acid, as a white solid in 85% yield.

$^1$H-NMR (400 MHz, DMSO): 7.15 (d, J 11.5 Hz, 1H, Ar); 8.08 (d, J 8.0 Hz, 1H, Ar); 9.20 (bs, 1H, NH); 10.58 (bs, 3H, NH$_3$).

Compound 48: 7-Bromo-8-fluoro-2-(2-trifluoromethyl-pyridin-4-yl)-4H-pyrazolo[1,5-a]quinazolin-5-one Compound 48 was obtained according to general procedure I(iv), starting from 2-trifluoromethyl-isonicotinic acid ethyl ester in presence of hydrazine 47 as a reddish solid in 52% yield.

M/Z (M[$^{79}$Br]+H)$^+$=427.0.

Example 92: 7-Bromo-8-fluoro-4-methyl-2-(2-trifluoromethyl-pyridin-4-yl)-4H-pyrazolo[1,5-a]quinazolin-5-one

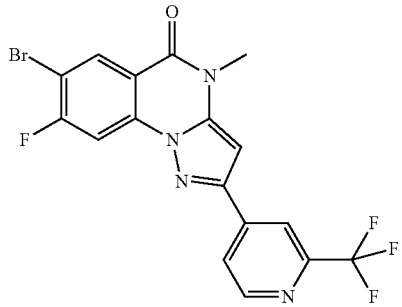

Example 92 was obtained according to general procedure II(iii), starting from compound 48 in presence of iodomethane. The reaction mixture was stirred for 3 hours at room temperature. Example 92 was obtained without further purification as a brown solid in 97% yield.

$^1$H-NMR (400 MHz, DMSO): 3.55 (s, 3H, NCH$_3$); 7.21 (s, 1H, Ar); 8.16 (d, J 9.0 Hz, 1H, Ar); 8.23-8.25 (m, 1H, Ar); 8.38-8.40 m, 2H, Ar); 8.90 (d, J 5.1 Hz, 1H, Ar).

M/Z (M[$^{79}$Br]+H)$^+$=441.0.

MP: 230-235° C.

Example 93: 7-Bromo-8-methoxy-4-methyl-2-(2-trifluoromethyl-pyridin-4-yl)-4H-pyrazolo[1,5-a]quinazolin-5-one

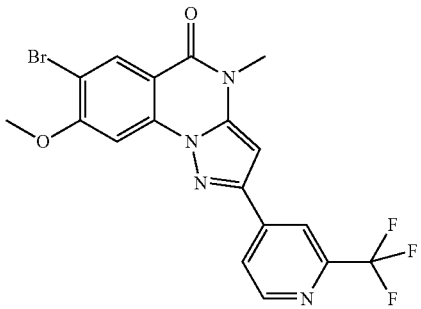 [SMILES: COc1cc2c(cc1Br)c(=O)n(C)c1cc(-c3ccnc(C(F)(F)F)c3)nn21]

Example 93 was obtained according to general procedure VII(iii) starting from example 92 in presence of methanol. Trituration in Et$_2$O afforded example 93 as a beige solid in 78% yield.

$^1$H-NMR (400 MHz, DMSO): 3.55 (s, 3H, NCH$_3$); 4.13 (s, 3H, OCH$_3$); 7.20 (s, 1H, Ar); 7.72 (s, 1H, Ar); 8.26 (s, 1H, Ar); 8.27-8.29 (m, 1H, Ar); 8.40 (bs, 1H, Ar); 8.89 (d, J 5.1 Hz, 1H, Ar).

M/Z (M[$^{79}$Br]+H)$^+$=453.0.

MP: >250° C.

Example 94: 8-Methoxy-4-methyl-7-methylamino-2-(2-trifluoromethyl-pyridin-4-yl)-4H-pyrazolo[1,5-a]quinazolin-5-one

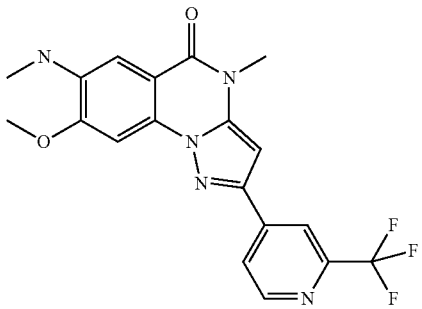 [SMILES: CNc1cc2c(=O)n(C)c3cc(-c4ccnc(C(F)(F)F)c4)nn3c2cc1OC]

Example 94 was obtained according to general procedure X(iii) starting from example 93 in presence of methylamine HCl. DMA was used as solvent and the reaction was heated for 1 hour at 60° C. After hydrolysis with a saturated aqueous NH$_4$Cl solution, example 95 was extracted with EtOAc. The organic layers were combined, washed with brine and dried over MgSO$_4$. Purification by preparative HPLC afforded example 94 as a yellow solid in 11% yield.

$^1$H-NMR (400 MHz, DMSO/D$_2$O): 2.80 (s, 3H, NHCH$_3$); 3.55 (s, 3H, NCH$_3$); 4.06 (s, 3H, OCH$_3$); 5.66 (s, 3H, NHCH$_3$); 7.00 (s, 1H, Ar); 7.09 (s, 1H, Ar); 7.54 (s, 1H, Ar); 8.22-8.23 (m, 1H, Ar); 8.35 (bs, 1H, Ar); 8.85 (d, J 5.1 Hz, 1H, Ar).

M/Z (M+H+CH$_3$CN)$^+$=445.1.

MP: >250° C.

Compound 49: 7-Chloro-2-(2-chloro-pyridin-4-yl)-4H-pyrazolo[1,5-a]quinazolin-5-one Compound 49 was obtained according to general procedure I(i), starting from 2-chloro-isonicotinic methyl ester in presence of hydrazine 10 as a brown solid in 51% yield.

$^1$H-NMR (400 MHz, DMSO): 6.68 (s, 1H, Ar); 7.96-7.99 (m, 2H, Ar); 8.07 (bs, 1H, Ar); 8.09 (d, J 2.3 Hz, 1H, Ar); 8.22 (d, J 8.7 Hz, 1H, Ar); 8.50 (d, J 5.2 Hz, 1H, Ar); 12.55 (bs, 1H, NH).

M/Z (M[$^{35}$Cl]$_2$+H)$^+$=331.1.

Example 95: 7-Chloro-2-(2-chloro-pyridin-4-yl)-4-methyl-4H-pyrazolo[1,5-a]quinazolin-5-one

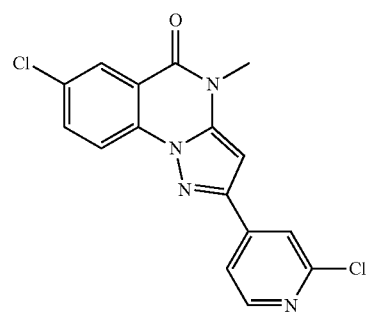 [SMILES: Cn1c(=O)c2cc(Cl)ccc2n2nc(-c3ccnc(Cl)c3)cc12]

Example 95 was obtained according to general procedure II(iii), starting from compound 49 in presence of iodomethane. The reaction mixture was stirred for 2 hours at room temperature. DMF was used instead of DMA. Example 95 was obtained without further purification as a beige solid in 82% yield.

$^1$H-NMR (400 MHz, DMSO): 3.55 (s, 3H, NCH$_3$); 7.11 (s, 1H, Ar); 7.94-7.98 (m, 2H, Ar); 8.02 (bs, 1H, Ar); 8.11 (d, J 2.3 Hz, 1H, Ar); 8.21 (d, J 8.9 Hz, 1H, Ar); 8.52 (d, J 5.1 Hz, 1H, Ar).

M/Z (M[$^{35}$Cl]$_2$+H)$^+$=345.1.

MP: >250° C.

Example 96: 7-Chloro-2-(2-chloro-pyridin-4-yl)-4-methyl-4H-pyrazolo[1,5-a]quinazolin-5-one, HCl Salt

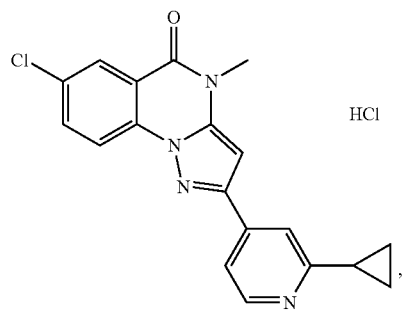 [SMILES: Cn1c(=O)c2cc(Cl)ccc2n2nc(-c3ccnc(C4CC4)c3)cc12 ; Cl]

Example 96 was obtained according to general procedure III starting from example 95 in presence of a solution of cyclopropylzinc bromide in THF (0.5M-3.0 equiv.). Purification by flash-chromatography (MeOH in DCM, 0 to 5%) and salt formation according to procedure IV(i) afforded example 96 as a beige solid in 51% yield.

$^1$H-NMR (400 MHz, DMSO): 1.17-1.23 (m, 4H, 2CH2); 2.28-2.35 (m, 1H, CCH); 3.51 (s, 3H, NCH$_3$); 7.15 (s, 1H, Ar); 7.91 (bs, 1H, Ar); 7.94 (dd, J 8.8 Hz, J 2.4 Hz, 1H, Ar); 7.98-7.99 (m, 1H, Ar); 8.08 (d, J 2.4 Hz, 1H, Ar); 8.19 (d, J 8.8 Hz, 1H, Ar); 8.60 (d, J 5.8 Hz, 1H, Ar). Signal for HCl salt is not observed.

M/Z (M[$^{35}$Cl]$_2$+H)$^+$=351.4.

MP: 245-250° C.

Compound 50: 7-Chloro-2-(2-Fluoro-pyridin-4-yl)-4H-pyrazolo[1,5-a]quinazolin-5-one Compound 50 was obtained according to general procedure I(ii), starting from 2-fluoro-isonicotinic methyl ester in presence of hydrazine 10 as a brown solid in 54% yield.

$^1$H-NMR (400 MHz, DMSO): 6.66 (s, 1H, Ar); 7.71 (bs, 1H, Ar); 7.92-7.93 (m, 1H, Ar); 7.98 (dd, J 8.7 Hz, J 2.5 Hz, 1H, Ar); 8.09 (d, J 2.5 Hz, 1H, Ar); 8.20 (d, J 8.7 Hz, 1H, Ar); 8.33 (d, J 5.2 Hz, 1H, Ar); 12.59 (bs, 1H, NH).

M/Z (M[$^{35}$Cl]+H)$^+$=315.4.

Example 97: 7-Chloro-2-(2-Fluoro-pyridin-4-yl)-4-methyl-4H-pyrazolo[1,5-a]quinazolin-5-one

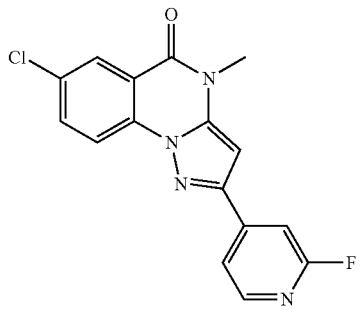 [SMILES: Cn1c(=O)c2cc(Cl)ccc2n2nc(-c3ccnc(F)c3)cc12]

Example 97 was obtained according to general procedure II(iii), starting from compound 50 in presence of iodomethane. The reaction mixture was stirred for 2 hours at room temperature. DMF was used instead of DMA. Example 97 was obtained without further purification as a white solid in 71% yield.

$^1$H-NMR (400 MHz, DMSO): 3.55 (s, 3H, NCH$_3$); 7.07 (s, 1H, Ar); 7.66 (bs, 1H, Ar); 7.88-7.90 (m, 1H, Ar); 7.97 (dd, J 8.8 Hz, J 2.4 Hz, 1H, Ar); 8.10 (d, J 2.4 Hz, 1H, Ar); 8.19 (d, J 8.8 Hz, 1H, Ar); 8.36 (d, J 5.2 Hz, 1H, Ar).
M/Z (M[$^{35}$Cl]+H)$^+$=329.2.
MP: >250° C.

Example 98: 7-Chloro-4-methyl-2-[2-(2,2,2-trifluoro-ethoxy)-pyridin-4-yl]-4H-pyrazolo[1,5-a]quinazolin-5-one

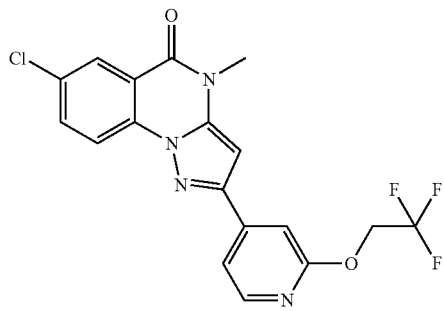 [SMILES: Cn1c(=O)c2cc(Cl)ccc2n2nc(-c3ccnc(OCC(F)(F)F)c3)cc12]

Example 98 was obtained according to general procedure VII(i) starting from example 97 in presence of 2,2,2-trifluoroethanol. The reaction was stirred for 5 hours at room temperature. Trituration in Et$_2$O afforded example 98 as a white solid in 87% yield.

$^1$H-NMR (400 MHz, DMSO): 3.54 (s, 3H, NCH$_3$); 5.05 (q, J 9.1 Hz, 2H, OCH$_2$CF$_3$); 7.06 (s, 1H, Ar); 7.50 (bs, 1H, Ar); 7.66-7.67 (m, 1H, Ar); 7.96 (dd, J 8.8 Hz, J 2.4 Hz, 1H, Ar); 8.10 (d, J 2.4 Hz, 1H, Ar); 8.19 (d, J 8.8 Hz, 1H, Ar); 8.31 (d, J 5.3 Hz, 1H, Ar).
M/Z (M[$^{35}$Cl]+H)$^+$=409.4
MP: 180-190° C.

Compound 51: 2-(2-Chloro-pyridin-4-yl)-7-methoxy-4H-pyrazolo[1,5-a]quinazolin-5-one Compound 51 was obtained according to general procedure I(i), starting from 2-chloro-isonicotinic methyl ester in presence of hydrazine 12 as a brown solid in 54% yield.

$^1$H-NMR (400 MHz, DMSO): 3.90 (s, 3H, OCH$_3$); 6.65 (s, 1H, Ar); 7.53 (d, J 9.0 Hz, J 2.9 Hz, 1H, Ar); 7.60 (d, J 2.9 Hz, 1H, Ar); 7.96 (d, J 5.2 Hz, J 1.4 Hz, 1H, Ar); 8.04 (bs, 1H, Ar); 8.16 (d, J 9.0 Hz, 1H, Ar); 8.48 (d, J 5.2 Hz, 1H, Ar); 12.45 (bs, 1H, NH).
M/Z (M[$^{35}$Cl]+H)$^+$=327.2.

Example 99: 2-(2-Chloro-pyridin-4-yl)-7-methoxy-4-methyl-4H-pyrazolo[1,5-a]quinazolin-5-one

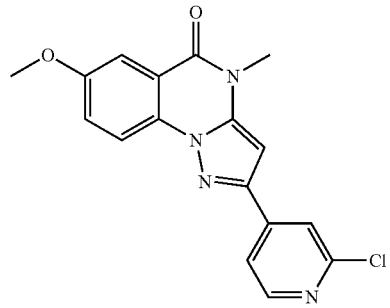 [SMILES: COc1ccc2c(c1)c(=O)n(C)c1cc(-c3ccnc(Cl)c3)nn21]

Example 99 was obtained according to general procedure II(iii), starting from compound 51 in presence of iodomethane. The reaction mixture was stirred for 2 hours at room temperature. DMF was used instead of DMA. Example 99 was obtained without further purification as a brown solid in 75% yield.

$^1$H-NMR (400 MHz, DMSO): 3.56 (s, 3H, NCH$_3$); 3.90 (s, 3H, OCH$_3$); 7.05 (s, 1H, Ar); 7.52 (d, J 9.0 Hz, J 2.9 Hz, 1H, Ar); 7.60 (d, J 2.9 Hz, 1H, Ar); 7.93 (d, J 5.2 Hz, J 1.4 Hz, 1H, Ar); 8.00 (bs, 1H, Ar); 8.15 (d, J 9.0 Hz, 1H, Ar); 8.51 (d, J 5.2 Hz, 1H, Ar).
M/Z (M[$^{35}$Cl]+H)$^+$=341.2.
MP: >250° C.

Example 100: 2-(2-Cyclopropyl-pyridin-4-yl)-7-methoxy-4-methyl-4H-pyrazolo[1,5-a]quinazolin-5-one, HCl Salt

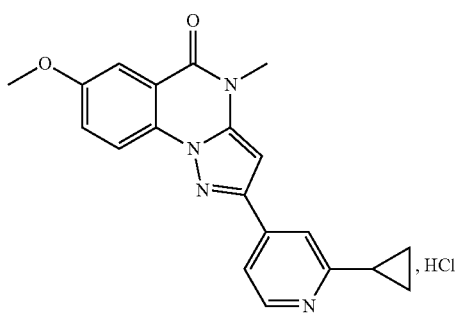

Example 100 was obtained according to general procedure III starting from example 99 in presence of a solution of cyclopropylzinc bromide in THF (0.5M-3.0 equiv.). Purification by flash-chromatography (MeOH in DCM, 0 to 5%) and salt formation according to procedure IV(i) afforded example 100 as an orange solid in 39% yield.

$^1$H-NMR (400 MHz, DMSO): 1.26-1.33 (m, 4H, 2CH$_2$); 2.38-2.45 (m, 1H, CCH); 3.57 (s, 3H, NCH$_3$); 3.90 (s, 3H, OCH$_3$); 7.19 (s, 1H, Ar); 7.54 (dd, J 9.0 Hz, J 2.8 Hz, 1H,

Ar); 7.60 (d, J 2.8 Hz, 1H, Ar); 7.96 (bs, H, Ar); 8.08-8.09 (m, 1H, Ar); 8.17 (d, J 9.0 Hz, 1H, Ar); 8.66 (d, J 5.9 Hz, 1H, Ar). Signal for HCl salt is not observed.
M/Z (M+H)$^+$=347.5.
MP: 230-240° C.

Compound 52: 2-(2-Fluoro-pyridin-4-yl)-7-methoxy-4H-pyrazolo[1,5-a]quinazolin-5-one Compound 52 was obtained according to general procedure I(ii), starting from 2-chloro-isonicotinic methyl ester in presence of hydrazine 12 as a greenish solid in 40% yield.
M/Z (M+H)$^+$=311.4.

Example 101: 2-(2-Fluoro-pyridin-4-yl)-7-methoxy-4-methyl-4H-pyrazolo[1,5-a]quinazolin-5-one

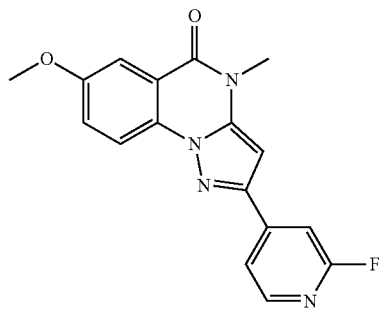 [SMILES: COc1ccc2c(c1)c(=O)n(C)c1cc(-c3ccnc(F)c3)nn21]

Example 101 was obtained according to general procedure II(iii), starting from compound 52 in presence of iodomethane. The reaction mixture was stirred for 2 hours at room temperature. DMF was used instead of DMA. Example 101 was obtained without further purification as a brown solid in 34% yield.
$^1$H-NMR (400 MHz, DMSO): 3.57 (s, 3H, NCH$_3$); 3.90 (s, 3H, OCH$_3$); 7.04 (s, 1H, Ar); 7.53-7.55 (m, 1H, Ar); 7.61-7.66 (m, 2H, Ar); 7.89 (bs, 1H, Ar); 814-8.16 (m, 1H, Ar); 8.34-8.35 (m, 1H, Ar).
M/Z (M+H)$^+$=325.2.
MP: 235-245° C.

Example 102: 7-Methoxy-4-methyl-2-[2-(2,2,2-trifluoro-ethoxy)-pyridin-4-yl]-4H-pyrazolo[1,5-a]quinazolin-5-one

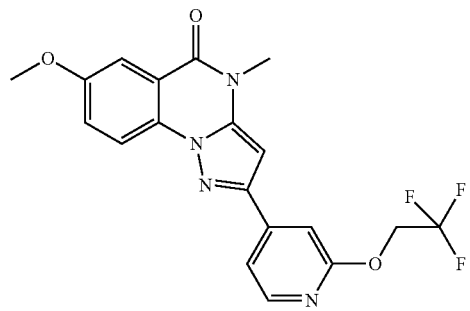 [SMILES: COc1ccc2c(c1)c(=O)n(C)c1cc(-c3ccnc(OCC(F)(F)F)c3)nn21]

Example 102 was obtained according to general procedure VII(i) starting from example 101 in presence of 2,2,2-trifluoroethanol. The reaction was stirred for 1 hour at 50° C. Trituration in EtOH and cyclohexane afforded example 102 as a beige solid in 60% yield.
$^1$H-NMR (400 MHz, DMSO): 3.56 (s, 3H, NCH$_3$); 3.90 (s, 3H, OCH$_3$); 5.04-5.06 (m, 2H, OCH$_2$CF$_3$); 7.03 (s, 1H, Ar); 7.50-7.54 (m, 2H, Ar); 7.61-7.67 (m, 2H, Ar); 8.14-8.16 (m, 1H, Ar); 8.30 (bs, 1H, Ar).
M/Z (M+H)$^+$=405.2
MP: 172-180° C.

Compound 53: 2-(1-Methyl-1H-pyrazol-4-yl)-4H-pyrazolo[1,5-a]quinazolin-5-one

Compound 53 was obtained according to general procedure I(i), starting 1-Methyl-1H-pyrazole-4-carboxylic acid methyl ester in presence of 2-hydrazino-benzoic acid as a brown solid in 55% yield.
$^1$H-NMR (400 MHz, DMSO): 3.89 (s, 3H, NCH$_3$); 6.10 (s, 1H, Ar); 7.43-7.47 (m, 1H, Ar); 7.84-7.89 (m, 2H, Ar); 8.04-8.06 (m, 1H, Ar); 8.11-8.14 (m, 1H, Ar); 8.19 (bs, 1H, Ar); 12.10 (bs, 1H, NH).
M/Z (M+H)$^+$=266.2.

Example 103: 4-Methyl-2-(1-methyl-1H-pyrazol-4-yl)-4H-pyrazolo[1,5-a]quinazolin-5-one

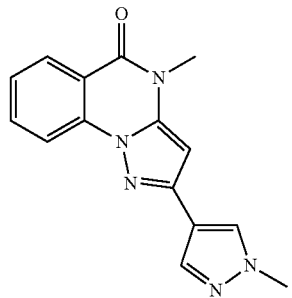 [SMILES: Cn1cc(-c2cc3n(C)c(=O)c4ccccc4n3n2)cn1]

Example 103 was obtained according to general procedure II(i), starting from compound 53 in presence of iodomethane. The reaction mixture was stirred at room temperature for 2 Hrs. Example 103 was obtained without further purification as a beige solid in 78% yield.
$^1$H-NMR (400 MHz, DMSO): 3.53 (s, 3H, NCH$_3$); 3.91 (s, 3H, NCH$_3$); 6.48 (s, 1H, Ar); 7.45-7.49 (m, 1H, Ar); 7.86-7.90 (m, 2H, Ar); 8.05-8.08 (m, 1H, Ar); 8.16-8.18 (m, 2H, Ar).
M/Z (M+H)$^+$=280.2.
MP: 195-199° C.

Example 104: 4-Methyl-2-pyridin-4-yl-4H-pyrazolo[1,5-a]quinazolin-5-one, HCl Salt

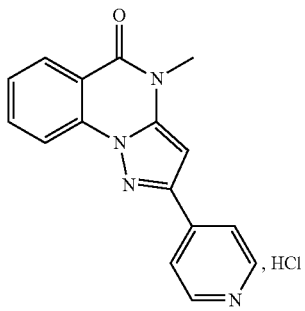

To a solution of example 1 (50.0 mg, 1.0 equiv.) in MeOH (1.6 mL, C=0.1 molL⁻¹), Pd/C (10% w/w, 17 mg) was added. The reaction mixture was sparged with hydrogen and hydrogen pressure was maintained for 18 hours through balloon. The reaction mixture was filtered off through a celite pad. The pad was washed with MeOH and the filtrate was concentrated. Purification by flash-chromatography (MeOH in DCM, 0 to 10%) and salt formation according to procedure IV(iii) afforded example 104 as a beige solid in 19% yield.

¹H-NMR (400 MHz, DMSO): 3.59 (s, 3H, NCH₃); 7.22 (s, 1H, Ar); 7.59-7.63 (m, 1H, Ar); 7.95-7.99 (m, 1H, Ar); 8.22-8.26 (m, 2H, Ar); 8.38-8.40 (m, 2H, Ar); 9.83 (d, J 6.3 Hz, 2H, Ar). Signal for HCl salt is not observed.

M/Z (M+H)⁺=277.2.

MP: >250° C.

Compound 54: 2-(2-Chloro-6-methyl-pyridin-4-yl)-4H-pyrazolo[1,5-a]quinazolin-5-one Compound 54 was obtained according to general procedure I(i), starting from 2-chloro-6-methylpyridine-4-carboxylic acid methyl ester in presence of 2-hydrazino-benzoic acid as a yellow solid in 87% yield.

¹H-NMR (400 MHz, DMSO): 2.52 (s, 3H, CH₃); 6.52 (s, 1H, Ar); 7.47-7.51 (m, 1H, Ar); 7.82-7.88 (m, 3H, Ar); 8.13-8.18 (m, 2H, Ar). Signal for NH is not observed.

M/Z (M[³⁵Cl]+H)⁺=311.1.

Example 105: 2-(2-Chloro-6-methyl-pyridin-4-yl)-4-methyl-4H-pyrazolo[1,5-a]quinazolin-5-one

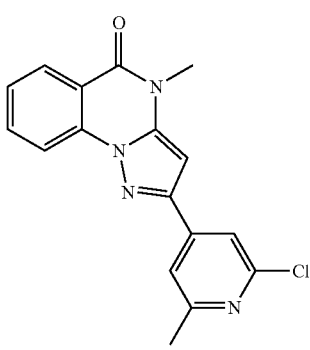 [SMILES: Cc1cc(-c2cc3n(C)c(=O)c4ccccc4n3n2)cc(Cl)n1]

Example 105 was obtained according to general procedure II(i), starting from compound 54 in presence of iodomethane. The reaction mixture was stirred for 2 hours at room temperature. Example 105 was obtained without further purification as a beige solid in 89% yield.

¹H-NMR (400 MHz, DMSO): 2.53 (s, 3H, CH₃); 3.54 (s, 3H, NCH₃); 7.02 (s, 1H, Ar); 7.53-7.57 (m, 1H, Ar); 7.80-7.81 (m, 2H, Ar); 7.90-7.94 (m, 1H, Ar); 8.18-8.20 (m, 2H, Ar).

M/Z (M[³⁵Cl]+H)⁺=325.2.

MP:236-242° C.

Example 106: 2-(2-Cyclopropyl-6-methyl-pyridin-4-yl)-4-methyl-4H-pyrazolo[1,5-a]quinazolin-5-one, HCl Salt

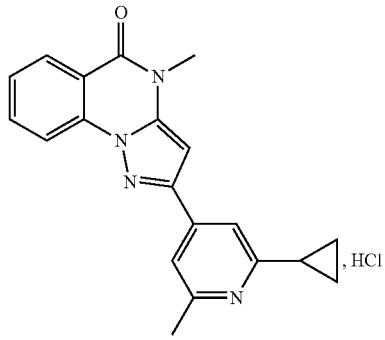

Example 106 was obtained according to general procedure III starting from example 105 in presence of a solution of cyclopropylzinc bromide in THF (0.5N-3.0 equiv.). After hydrolysis, the solid was collected, washed with water and MeOH. To the MeOH filtrate, aqueous HCl solution (1N) was added. The resulting precipitate was collected, washed with water, Et₂O and was dried under reduced pressure to afford example 106 as a white solid in 26% yield.

¹H-NMR (400 MHz, DMSO): 1.26-1.36 (m, 4H, 2CH2); 2.53-2.55 (m, 1H, CCH); 2.74 (s, 3H, CCH₃); 3.56 (s, 3H, NCH₃); 7.21 (s, 1H, Ar); 7.57-7.61 (m, 1H, Ar); 7.72 (bs, 1H, Ar); 7.93-7.98 (m, 1H, Ar); 8.6 (bs, 1H, Ar); 8.19-8.24 (m, 2H, Ar). Signal for HCl salt is not observed.

M/Z (M+H)⁺=331.3.

MP: >250° C.

Compound 55: 2-(3-Fluoro-pyridin-4-yl)-4H-pyrazolo[1,5-a]quinazolin-5-one

Compound 55 was obtained according to general procedure I(i), starting 3-fluoro-isonicotinic acid ethyl ester in presence of 2-hydrazino-benzoic acid as a brown solid in 33% yield. The reaction mixture was heated for 18 hours instead of 2 hours.

¹H-NMR (400 MHz, DMSO): 6.40 (d, J 3.5 Hz, 1H, Ar); 7.55-7.59 (m, 1H, Ar); 7.92-7.97 (m, 1H, Ar); 8.09 (dd, J 6.6 Hz, J 5.1 Hz, 1H, Ar); 8.17-8.22 (m, 2H, Ar); 8.53-8.54 (m, 1H, Ar); 8.71 (d, J 2.8 Hz, 1H, Ar); 12.36 (bs, 1H, NH).

M/Z (M+H)⁺=281.3.

Example 107: 2-(3-Fluoro-pyridin-4-yl)-4-methyl-4H-pyrazolo[1,5-a]quinazolin-5-one

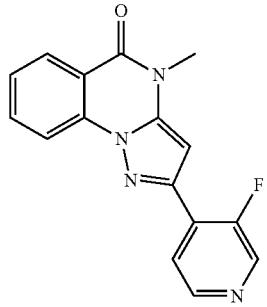 [SMILES: Cn1c(=O)c2ccccc2n2nc(-c3ccncc3F)cc12]

Example 107 was obtained according to general procedure II(ii), starting from compound 55 in presence of iodomethane. The reaction mixture was stirred for 1 hour at room temperature. Example 107 was obtained without further purification as a grey solid in 69% yield.

$^1$H-NMR (400 MHz, DMSO): 3.51 (s, 3H, NCH$_3$); 6.80 (d, J 3.0 Hz, 1H, Ar); 7.56-7.50 (m, 1H, Ar); 7.93-7.97 (m, 1H, Ar); 8.08-8.11 (m, 1H, Ar); 8.22-8.24 (m, 2H, Ar); 8.55-8.57 (m, 1H, Ar); 8.74 (d, J 2.8 Hz, 1H, Ar).

M/Z (M+H)$^+$=295.3.

MP: 244-247° C.

Compound 56: 2-(3-Chloro-pyridin-4-yl)-4H-pyrazolo[1,5-a]quinazolin-5-one

Compound 56 was obtained according to general procedure I(i), starting 2-chloro-isonicotinic acid ethyl ester in presence of 2-hydrazino-benzoic acid as a brown solid in 71% yield. The reaction mixture was heated for 18 hours instead of 2 hours.

$^1$H-NMR (400 MHz, DMSO): 6.58 (s, 1H, Ar); 7.55-7.59 (m, 1H, Ar); 7.92-7.96 (m, 1H, Ar); 8.02 (d, J 5.1 Hz, 1H, Ar); 8.18-8.21 (m, 2H, Ar); 8.63 (d, J 5.1 Hz, 1H, Ar); 8.78 (s, 1H, Ar); 12.41 (bs, 1H, NH).

M/Z (M[$^{35}$Cl]+H)$^+$=297.2.

Example 108: 2-(3-Chloro-pyridin-4-yl)-4-methyl-4H-pyrazolo[1,5-a]quinazolin-5-one

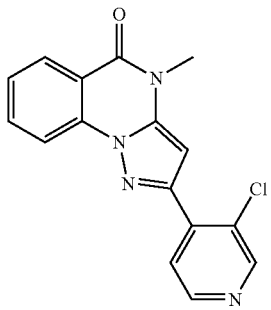 [SMILES: Cn1c(=O)c2ccccc2n2nc(-c3ccncc3Cl)cc12]

Example 108 was obtained according to general procedure II(ii), starting from compound 56 in presence of iodomethane. The reaction mixture was stirred for 1 hour at room temperature. Example 108 was obtained without further purification as a grey solid in 57% yield.

$^1$H-NMR (400 MHz, DMSO): 3.59 (s, 3H, NCH$_3$); 6.93 (s, 1H, Ar); 7.56-7.60 (m, 1H, Ar); 7.92-7.96 (m, 1H, Ar); 7.99 (d, J 5.1 Hz, 1H, Ar); 8.19-8.24 (m, 2H, Ar); 8.64 (d, J 5.1 Hz, 1H, Ar); 8.79 (s, 1H, Ar).

M/Z (M[$^{35}$Cl]+H)$^+$=311.1.

MP: 230-236° C.

Example 109: 4-Methyl-2-(3-methyl-pyridin-4-yl)-4H-pyrazolo[1,5-a]quinazolin-5-one

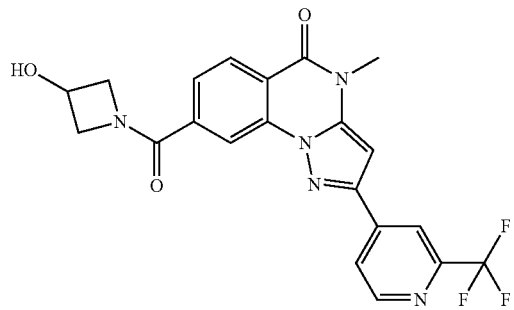 [SMILES: Cn1c(=O)c2ccc(C(=O)N3CC(O)C3)cc2n2nc(-c3ccnc(C(F)(F)F)c3)cc12]

Example 109 was obtained according to general procedure III starting from example 108 in presence of a solution of dimetylzinc in Toluene (2N-3.0 equiv.). After hydrolysis, the solid was collected. The solid was dissolved in a DMSO/MeOH mixture. Smopex resin was added and the suspension was stirred for 1 hour at room temperature. The resin was filtered off, washed with DMSO and MeOH. Water was added to the filtrate. The resulting solid was collected, washed with water, EtOH, and Et$_2$O and was dried under reduce pressure to afford example 109 as a beige solid in 27% yield.

$^1$H-NMR (400 MHz, DMSO at 80° C.): 2.64 (s, 3H, CCH$_3$); 3.60 (s, 3H, NCH$_3$); 6.70 (s, 1H, Ar); 7.52-7.56 (m, 1H, Ar); 7.71 (d, J 4.3 Hz, 1H, Ar); 7.92-7.94 (m, 1H, Ar); 8.18 (d, J 8.2 Hz, 1H, Ar); 8.23 (d, J 8.0 Hz, J 1.0 Hz, 1H, Ar); 8.52-8.61 (m, 2H, Ar).

M/Z (M+H)$^+$=291.3.

MP: 145-150° C.

Example 110: 8-(3-Hydroxy-azetidine-1-carbonyl)-4-methyl-2-(2-trifluoromethyl-pyridin-4-yl)-4H-pyrazolo[1,5-a]quinazolin-5-one Example 110 was obtained according to general procedure XII(i), starting from example 58 with 3-hydroxyazetidine hydrochloride as nucleophile (diisopropylamine was added in excess in order to release the free base). Purification by flash-chromatography (MeOH in DCM, 0 to 5%) afforded example 110 as a white solid in 40% yield.

$^1$H-NMR (400 MHz, DMSO): 3.57 (s, 3H, NCH$_3$); 3.85-3.88 (m, 1H, NCHaCHb); 4.09-4.12 (m, 1H, NCHaCHb); 4.33-4.35 (m, 1H, NCHaCHb); 4.50-4.56 (m, 2H, NCHaCHb+CH(OH)); 5.82 (bs, 1H, OH); 7.21 (s, 1H, Ar); 7.73 (dd, J 8.1 Hz, J 1.5 Hz, 1H, Ar); 8.23 (d, J 8.1 Hz, 1H,

Ar); 8.29 (dd, J 5.1 Hz, J 1.0 Hz, 1H, Ar); 8.36 (d, J 1.4 Hz, 1H, Ar); 8.39 (s, 1H, Ar); 8.89 (d, J 5.1 Hz, 1H Ar).

M/Z (M+H)⁺=444.1.

MP: >250° C.

Example 111: 8-(3-Hydroxy-propoxy)-4-methyl-2-(2-trifluoromethyl-pyridin-4-yl)-4H-pyrazolo[1,5-a]quinazolin-5-one

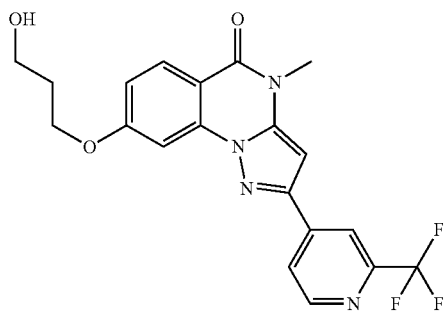 [SMILES: Cn1c(=O)c2ccc(OCCCO)cc2n2nc(-c3ccnc(C(F)(F)F)c3)cc12]

Example 111 was obtained according to general procedure VII(iii) starting from example 55 in presence of 1,3-propanediol. The reaction mixture was heated for 17 hours at 60° C. Purification by flash-chromatography (MeOH in DCM, 0 to 5%) afforded example 111 as a white solid in 66% yield.

¹H-NMR (400 MHz, DMSO): 1.97 (quint, J 6.2 Hz, 2H, HOCH₂CH₂CH₂O); 3.55 (s, 3H, NCH₃); 3.63 (q, J 5.4 Hz, 2H, HOCH₂CH₂CH₂O); 4.30 (t, J 6.3 Hz, 2H, HOCH₂CH₂CH₂O); 4.63 (t, J 5.1 Hz, 1H, HOCH₂); 7.14 (dd, J 8.8 Hz, J 2.4 Hz, 1H, Ar); 7.17 (s, 1H, Ar); 7.64 (d, J 2.3 Hz, 1H, Ar); 8.12 (d, J 8.8 Hz, 1H, Ar); 8.29 (dd, J 5.1 Hz, J 0.9 Hz, 1H, Ar); 8.40 (s, 1H, Ar); 8.90 (d, J 5.1 Hz, 1H, Ar).

M/Z (M+H)⁺=419.1.

MP: 223-226° C.

Compound 57: 2-(2-Cyclopropyl-pyridin-4-yl)-8-fluoro-4H-pyrazolo[1,5-a]quinazolin-5-one Compound 57 was obtained according to general procedure I(i), starting 2-Cyclopropyl-isonicotinic acid methyl ester in presence compound 26 as a brown solid in 55% yield.

1H-NMR (400 MHz, DMSO): 1.25-1.27 (m, 4H, 2CH₂); 2.36-2.42 (m, 1H, CCH); 6.81 (s, 1H, Ar); 7.42 (td, J 8.7 Hz, J 2.4 Hz, 1H, Ar); 7.99 (dd, J 9.4H, J 2.4 Hz, 1H, Ar); 8.02 (bs, 1H, Ar); 8.09-8.11 (m, 1H, Ar); 8.24 (dd, J 8.7 Hz, J 5.8 Hz, 1H, Ar); 8.64 (d, J 5.8 Hz, 1H, Ar); 12.60 (bs, 1H, NH).

M/Z (M+H)⁺=321.0.

Example 112: 2-(2-Cyclopropyl-pyridin-4-yl)-8-fluoro-4-methyl-4H-pyrazolo[1,5-a]quinazolin-5-one

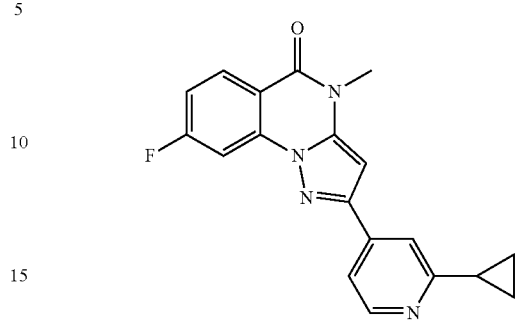

Example 112 was obtained according to general procedure II(iii), starting from compound 57 in presence of iodomethane. The reaction mixture was stirred at room temperature for 60 min. Example 112 was obtained as a beige solid in 70% yield.

¹H-NMR (400 MHz, DMSO): 1.01-1.04 (m, 4H, 2CH₂); 2.18-2.23 (m, 1H, CCH); 3.57 (s, 3H, NCH₃); 7.00 (s, 1H, Ar); 7.40 (td, J 8.7 Hz, J 2.3 Hz, 1H, Ar); 7.70 (d, J 5.1 Hz, 1H, Ar); 7.86 (bs, 1H, Ar); 7.93 (dd, J 9.2H, J 2.3 Hz, 1H, Ar); 8.27 (dd, J 8.7 Hz, J 5.9 Hz, 1H, Ar); 8.52 (d, J 5.1 Hz, 1H, Ar).

M/Z (M+H)⁺=335.1.

MP: 230-235° C.

Example 113: 2-(2-Cyclopropyl-pyridin-4-yl)-8-(4-hydroxy-piperidin-1-yl)-4-methyl-4H-pyrazolo[1,5-a]quinazolin-5-one

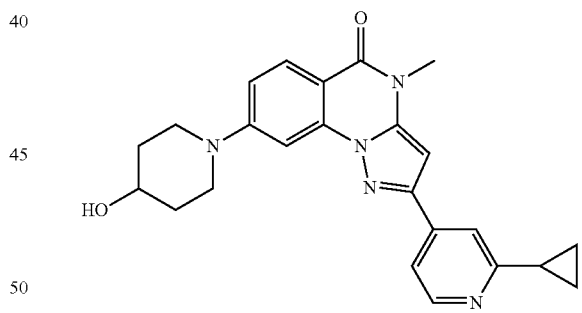

Example 113 was obtained according to general procedure X(vi) starting from example 112 in presence of 4-hydroxypiperidine. Example 113 was obtained as a beige solid in 75% yield.

¹H-NMR (400 MHz, DMSO): 0.99-1.01 (m, 4H, 2CH₂), 1.44-1.52 (m, 2H, 2CHaHb); 1.86-1.89 (m, 2H, 2CHaHb); 2.17-2.23 (m, 1H, CCH); 3.19-3.25 (m, 2H, 2NCHaHb); 3.51 (s, 3H, NCH₃); 3.74-3.79 (m, 1H, CH(OH)); 3.83-3.86 (m, 2H, 2NCHaHb); 4.77 (bs, 1H, OH); 6.88 (s, 1H, Ar); 7.16 (dd, J 9.1 Hz, J 2.2 Hz, 1H, Ar); 7.45 (d, J 2.2 Hz, 1H, Ar); 7.69-7.70 (m, 1H, Ar); 7.85 (bs, 1H, Ar); 7.95 (d, J 9.1 Hz, 1H); 8.49 (d, J 5.1 Hz, 1H, Ar).

M/Z (M+H)⁺=416.3.

MP: 221-233° C.

Compound 58: 2-(2-Difluoromethyl-pyridin-4-yl)-8-fluoro-4H-pyrazolo[1,5-a]quinazolin-5-one Compound 58 was obtained according to general procedure I(ii), starting from compound 4 in presence compound 26. After 17 hours at 100° C. with AcOH (10 equiv.) the reaction was not completed. DME was concentrated and AcOH (same volume as DME) was added. The reaction mixture was heated at 120° C. for 3 hours. After cooling, the reaction mixture was concentrated and the residue was coevaporated twice with toluene before hydrolysis with saturated aqueous NaHCO$_3$ solution. The precipitate was collected, washed with water, EtOH and dried under reduced pressure at 60° C. with P$_2$O$_5$ for 18 hours. Compound 58 was isolated as a brown solid in 45% yield.

1H-NMR (400 MHz, DMSO): 6.68 (s, 1H, Ar); 7.02 (t, J 54.9 Hz, 1H, CHF$_2$); 7.39 (td, J 8.7 Hz, J 2.5 Hz, 1H, Ar); 7.95 (dd, J 9.4H, J 2.5 Hz, 1H, Ar); 8.13 (d, J 5.1 Hz, 1H, Ar); 8.21-8.25 (m, 2H, Ar); 8.78 (d, J 5.1 Hz, 1H, Ar); 12.49 (bs, 1H, NH).
M/Z (M+H)$^+$=331.1.

Example 114: 2-(2-Difluoromethyl-pyridin-4-yl)-8-fluoro-4-methyl-4H-pyrazolo[1,5-a]quinazolin-5-one

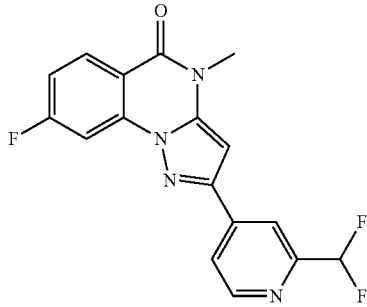 [SMILES: Cn1c(=O)c2ccc(F)cc2n2nc(-c3ccnc(C(F)F)c3)cc12]

Example 114 was obtained according to general procedure II(iii), starting from compound 58 in presence of iodomethane. The reaction mixture was stirred at room temperature for 90 min. Example 114 was obtained as a beige solid in 77% yield.

$^1$H-NMR (400 MHz, DMSO): 3.55 (s, 3H, NCH$_3$); 7.04 (t, J 54.9 Hz, 1H, CHF$_2$); 7.12 (s, 1H, Ar); 7.40 (td, J 8.7 Hz, J 2.4 Hz, 1H, Ar); 7.96 (dd, J 9.3H, J 2.4 Hz, 1H, Ar); 8.11 (d, J 4.8 Hz, 1H, Ar); 8.23-8.27 (m, 2H, Ar); 8.81 (d, J 4.8 Hz, 1H, Ar).
M/Z (M+H)$^+$=345.0.
MP: 220-226° C.

Example 115: 2-(2-Difluoromethyl-pyridin-4-yl)-8-(4-hydroxy-piperidin-1-yl)-4-methyl-4H-pyrazolo[1,5-a]quinazolin-5-one

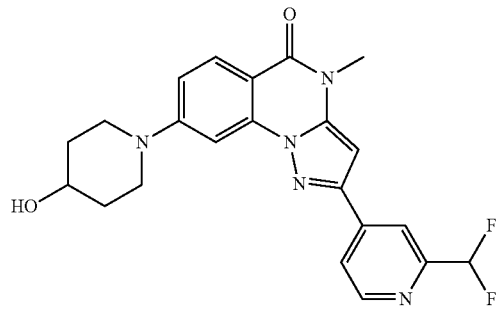 [SMILES: Cn1c(=O)c2ccc(N3CCC(O)CC3)cc2n2nc(-c3ccnc(C(F)F)c3)cc12]

Example 115 was obtained according to general procedure X(vi) starting from example 114 in presence of 4-hydroxypiperidine. Trituration in EtOH afforded example 115 as a beige solid in 74% yield.

$^1$H-NMR (400 MHz, DMSO): 1.45-1.52 (m, 2H, 2CHaHb); 1.87-1.89 (m, 2H, 2CHaHb); 3.19-3.25 (m, 2H, 2NCHaHb), 3.52 (s, 3H, NCH$_3$); 3.76-3.79 (m, 1H, CH(OH)); 3.83-3.86 (m, 2H, 2NCHaHb); 4.78 (d, J 3.8 Hz, 1H, OH); 6.90-7.17 (m, 3H, CHF$_2$+2Ar); 7.45 (s, 1H, Ar); 7.96 (d, J 9.0 Hz, 1H, Ar); 8.14 (d, J 4.5 Hz, 1H, Ar); 8.22 (bs, 1H, Ar); 8.79 (d, J 4.5 Hz, 1H, Ar).
M/Z (M+H)$^+$=426.2.
MP: >250° C.

Compound 59: 2-Cyclobutyl-isonicotinic Acid Methyl Ester

Compound 59 was obtained according to general procedure III starting from 2-Chloro-isonicotinic acid methyl ester in presence of cyclobutylzinc bromide (in THF 0.5M-3.0 equiv.). Purification by flash-chromatography (EtOAc in Cyclohexane, 0 to 80%) afforded compound 59 as yellow oil in 46% yield.

$^1$H-NMR (400 MHz, DMSO): 1.80-1.90 (m, 1H, CH); 1.96-2.08 (m, 1H, CH); 2.25-2.33 (m, 4H, 2CH$_2$); 3.76 (quint, J 8.6 Hz, 1H, CCH); 3.90 (s, 3H, OCH$_3$); 7.63-7.65 (m, 2H, Ar); 8.73 (d, J 4.9 Hz, 1H, Ar).
M/Z (M+H)$^+$=192.1.

Compound 60: 2-(2-Cyclobutyl-pyridin-4-yl)-8-fluoro-4H-pyrazolo[1,5-a]quinazolin-5-one Compound 60 was obtained according to general procedure I(i), starting compound 59 in presence compound 26 as a brown solid in 37% yield.

$^1$H-NMR (400 MHz, DMSO): 1.88-1.94 (m, 1H, CH); 2.00-2.16 (m, 1H, CH); 2.28-2.45 (m, 4H, 2CH$_2$); 3.86 (quint, J 8.7 Hz, 1H, CCH); 6.76 (s, 1H, Ar); 7.41 (td, J 8.6 Hz, J 2.3 Hz, 1H, Ar); 7.98 (dd, J 9.4H, J 2.3 Hz, 1H, Ar); 8.05-8.12 (m, 2H, Ar); 8.24 (dd, J 8.6 Hz, J 5.9 Hz, 1H, Ar); 8.70 (d, J 5.5 Hz, 1H, Ar); 12.56 (bs, 1H, NH).
M/Z (M+H)$^+$=335.2.

Example 116: 2-(2-Cyclobutyl-pyridin-4-yl)-8-fluoro-4-methyl-4H-pyrazolo[1,5-a]quinazolin-5-one

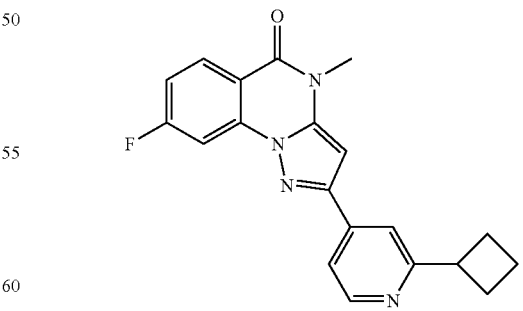

Example 116 was obtained according to general procedure II(iii), starting from compound 60 in presence of iodomethane. The reaction mixture was stirred at room temperature for 120 min. Example 116 was obtained as a brown solid in 44% yield.

¹H-NMR (400 MHz, DMSO): 1.85-1.96 (m, 1H, CH); 1.98-2.11 (m, 1H, CH); 2.32-2.39 (m, 4H, 2CH₂); 3.56 (s, 3H, NCH₃); 3.74 (quint, J 8.6 Hz, 1H, CCH); 7.02 (s, 1H, Ar); 7.39 (td, J 8.6 Hz, J 2.3 Hz, 1H, Ar); 7.75-7.80 (m, 2H, Ar); 7.93 (d, J 8.6 Hz, 1H, Ar); 8.26 (dd, J 8.6 Hz, J 6.1 Hz, 1H, Ar); 8.63 (d, J 4.7 Hz, 1H, Ar).
M/Z (M+H)⁺=349.0.
MP: 210-220° C.

Compound 61: 2-(2-Chloro-pyridin-4-yl)-8-fluoro-4H-pyrazolo[1,5-a]quinazolin-5-one Compound 61 was obtained according to general procedure I(i), starting from 2-chloro-isonicotinic methyl ester in presence of compound 26 as a brown solid in 44% yield.
¹H-NMR (400 MHz, DMSO): 6.66 (s, 1H, Ar); 7.39 (td, J 8.7 Hz, J 2.6 Hz, 1H, Ar); 7.95 (dd, J 9.5 Hz, J 2.6 Hz, 1H, Ar); 7.99 (dd, J 5.2 Hz, J 1.4 Hz, 1H, Ar); 8.09 (bs, 1H, Ar); 8.22 (dd, J 8.7 Hz, J 5.8 Hz, 1H, Ar); 8.50 (d, J 5.2 Hz, 1H Ar); 12.40 (bs, 1H, NH).
M/Z (M[³⁵Cl]+H)⁺=315.1.

Example 117: 2-(2-Chloro-pyridin-4-yl)-8-fluoro-4-methyl-4H-pyrazolo[1,5-a]quinazolin-5-one

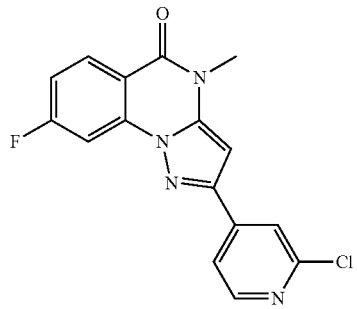 [SMILES: Cn1c(=O)c2ccc(F)cc2n2nc(-c3ccnc(Cl)c3)cc12]

Example 117 was obtained according to general procedure II(iii), starting from compound 61 in presence of iodomethane. The reaction mixture was stirred at room temperature for 60 min. Example 117 was obtained as a beige solid in 71% yield.
¹H-NMR (400 MHz, DMSO): 3.54 (s, 3H, NCH₃); 7.09 (s, 1H, Ar); 7.38-7.42 (m, 1H, Ar); 7.94-7.97 (m, 2H, Ar); 8.05 (s, 1H, Ar); 8.24-8.27 (m, 1H, Ar); 8.54 (d, J 5.1 Hz, 1H Ar).
M/Z (M[³⁵Cl]+H)⁺=329.1.
MP: >250° C.

Example 118: 2-(2-Chloro-pyridin-4-yl)-8-(4-hydroxy-piperidin-1-yl)-4-methyl-4H-pyrazolo[1,5-a]quinazolin-5-one

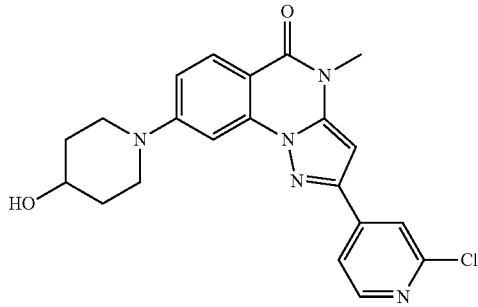 [SMILES: Cn1c(=O)c2ccc(N3CCC(O)CC3)cc2n2nc(-c3ccnc(Cl)c3)cc12]

Example 118 was obtained according to general procedure X(vi) starting from example 117 in presence of 4-hydroxypiperidine. Trituration in EtOH afforded example 118 as a beige solid in 86% yield.
¹H-NMR (400 MHz, DMSO): 1.48-1.56 (m, 2H, 2CHaHb); 1.91-2.00 (m, 2H, 2CHaHb); 3.23-3.36 (m, 2H, 2NCHaHb); 3.55 (s, 3H, NCH₃); 3.78-3.84 (m, 1H, CH(OH)); 3.88-3.92 (m, 2H, 2NCHaHb); 4.81 (bs, 1H, OH); 7.04 (s, 1H, Ar); 7.17 (dd, J 9.1 Hz, J 2.3 Hz, 1H, Ar); 7.50 (d, J 2.1 Hz, 1H, Ar); 7.97-8.03 (m, 2H, Ar); 8.10 (s, 1H, Ar); 8.56 (d, J 5.1 Hz, 1H, Ar).
M/Z (M[³⁵Cl]+H)⁺=410.1.
MP: >250° C.

Example 119: 7-Fluoro-8-(3-hydroxy-azetidin-1-yl)-4-methyl-2-(2-trifluoromethyl-pyridin-4-yl)-4H-pyrazolo[1,5-a]quinazolin-5-one

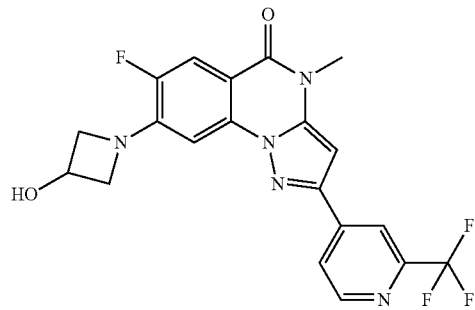 [SMILES: Cn1c(=O)c2cc(F)c(N3CC(O)C3)cc2n2nc(-c3ccnc(C(F)(F)F)c3)cc12]

Example 119 was obtained according to general procedure X(vi) starting from example 88 in presence of 3-hydroxyazetidine. Purification by flash-chromatography (MeOH in DCM, 0 to 7%) afforded example 119 as a white solid in 56% yield.
¹H-NMR (400 MHz, DMSO): 3.52 (s, 3H, NCH₃); 385-3.98 (m, 2H, 2NCHaCHb); 4.44-4.47 (m, 2H, 2NCHaCHb); 4.63-4.68 (m, 1H, CH(OH)); 5.83 (d, J 6.1 Hz, 1H, OH); 7.01 (d, J 7.8 Hz, 1H, Ar); 7.12 (s, 1H, Ar); 7.63 (d, J 12.6 Hz, 1H, Ar); 8 26 (d, J 4.8 Hz, 1H, Ar); 8.37 (s, 1H Ar); 8.89 (d, J 5.1 Hz, 1H, Ar).
M/Z (M+H)⁺=434.2.
MP: >250° C.

Example 120: 7-Fluoro-4-methyl-8-(oxetan-3-yloxy)-2-(2-trifluoromethyl-pyridin-4-yl)-4H-pyrazolo[1,5-a]quinazolin-5-one

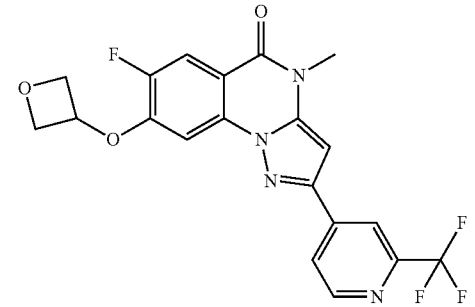 [SMILES: Cn1c(=O)c2cc(F)c(OC3COC3)cc2n2nc(-c3ccnc(C(F)(F)F)c3)cc12]

Example 120 was obtained according to general procedure VII(iii) starting from example 88 in presence of 3-hydroxyoxetane. The reaction mixture was stirred for 1 hour at room temperature. Purification by flash-chromatography (MeOH in DCM, 0 to 2%) afforded example 120 as a white solid in 35% yield.

$^1$H-NMR (400 MHz, DMSO): 3.61 (s, 3H, NCH$_3$); 4.75-4.78 (m, 2H, 2OCHaCHb); 5.13 (t, J 6.9 Hz, 2H, 2OCHaCHb); 5.77-5.83 (m, 1H, CH(O)); 7.25 (s, 1H, Ar); 7.52 (d, J 7.1 Hz, 1H, Ar); 8.03 (d, J 11.0 Hz, 1H, Ar); 8.37 (d, J 5.1 Hz, 1H, Ar); 8.46 (s, 1H, Ar); 8.92 (d, J 5.1 Hz, 1H, Ar).

M/Z (M+H)$^+$=435.1.
MP: >250° C.

Example 121: 3-[7-Fluoro-4-methyl-5-oxo-2-(2-trifluoromethyl-pyridin-4-yl)-4,5-dihydro-pyrazolo[1,5-a]quinazolin-8-ylamino]-propionitrile

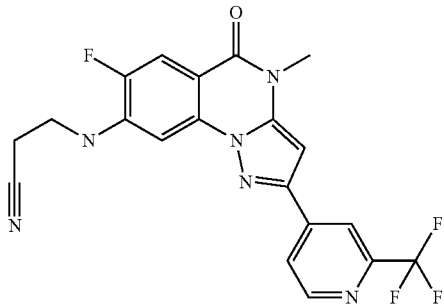 [SMILES: Cn1c(=O)c2cc(F)c(NCCC#N)cc2n2nc(-c3ccnc(C(F)(F)F)c3)cc12]

Example 121 was obtained according to general procedure X(vi) starting from example 88 in presence of 3-aminopropionitrile. Example 121 was isolated as a beige solid in 64% yield.

$^1$H-NMR (400 MHz, DMSO): 3.06 (t, J 6.4 Hz, 2H, NHCH$_2$CH$_2$CN); 3.62 (s, 3H, NCH$_3$); 3.71-3.76 (m, 2H, NHCH$_2$CH$_2$CN); 7.20 (s, 1H, Ar); 7.24-7.27 (m, 1H, NH); 7.47 (d, J 7.3 Hz, 1H, Ar); 7.81 (d, J 11.7 Hz, 1H, Ar); 8.35-8.36 (m, 1H, Ar); 8.47 (s, 1H, Ar); 8.80 (d, J 5.1 Hz, 1H, Ar).

M/Z (M+H)$^+$=431.1.
MP: >250° C.

Example 122: 7-Fluoro-8-(2-hydroxymethyl-pyrrolidin-1-yl)-4-methyl-2-(2-trifluoromethyl-pyridin-4-yl)-4H-pyrazolo[1,5-a]quinazolin-5-one

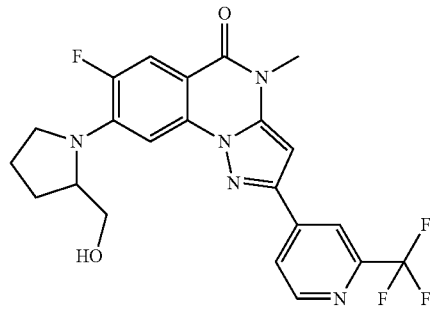 [SMILES: Cn1c(=O)c2cc(F)c(N3CCCC3CO)cc2n2nc(-c3ccnc(C(F)(F)F)c3)cc12]

Example 122 was obtained according to general procedure X(vi) starting from example 88 in presence of DL-prolinol. Example 122 was isolated as a brown solid in 64% yield.

$^1$H-NMR (400 MHz, DMSO): 1.91-1.92 (m, 4H, 2 CH$_2$); 3.39-3.59 (m, 6H, NCH$_3$+NCH$_2$+NCH); 3.66 (bs, 1H, HOCHaCHb); 4.22 (bs, 1H, HOCHaCHb); 4.91 (bs, 1H, OH); 7.11 (s, 1H, Ar); 7.28 (d, J 7.7 Hz, 1H, Ar); 7.67 (d, J 14.7 Hz, 1H, Ar); 8.24-8.25 (m, 1H, Ar); 8.35 (s, 1H, Ar); 8.88 (d, J 5.1 Hz, 1H, Ar).

M/Z (M+H)$^+$=462.2.
MP: >250° C.

Example 123: 7-Fluoro-8-(7-hydroxymethyl-1-azaspiro[3.5]non-1-yl)-4-methyl-2-(2-trifluoromethyl-pyridin-4-yl)-4H-pyrazolo[1,5-a]quinazolin-5-one

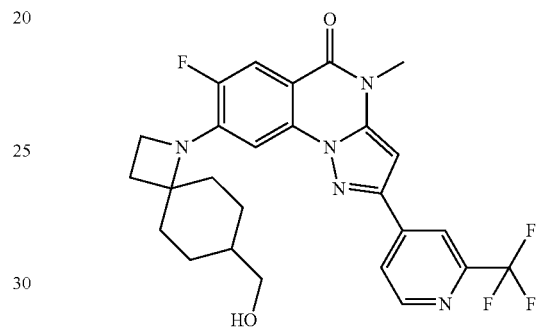

Example 123 was obtained according to general procedure X(vi) starting from example 88 in presence of (1-Azaspiro[3.5]non-7-yl)-methanol. Purification by TLC-preparative (MeOH in DCM, 4%) afforded example 123 as a beige solid in 32% yield.

$^1$H-NMR (400 MHz, DMSO): 0.98-1.04 (m, 2H, 2CHaHb); 1.34 (bs, 1H, CH); 1.73-1.75 (m, 2H, 2CHaHb); 1.91-2.01 (m, 4H, 2CH$_2$); 2.16-2.24 (m, 2H, CH$_2$); 3.10 (t, J 5.6 Hz, 2H, NCH$_2$); 3.51 (s, 3H, NCH$_3$); 4.03-4.11 (m, 2H, HOCH$_2$); 4.43 (t, J 5.3 Hz, 1H, OH); 7.08-7.12 (m, 2H, Ar); 7.69 (d, J 13.3 Hz, 1H, Ar); 8.24 (d, J 5.1 Hz, 1H, Ar); 8.34 (s, 1H, Ar); 8.88 (d, J 5.2 Hz, 1H, Ar).

M/Z (M+H)$^+$=516.2.
MP: >250° C.

Example 124: 8-(3-Hydroxy-piperidin-1-yl)-4-methyl-2-(2-trifluoromethyl-pyridin-4-yl)-4H-pyrazolo[1,5-a]quinazolin-5-one

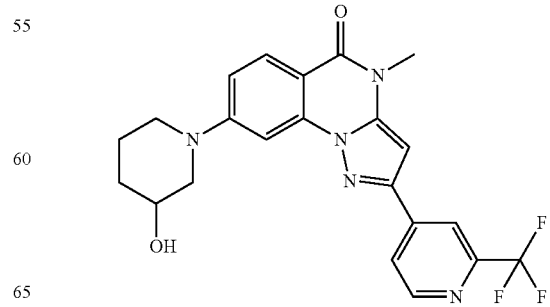

Under inert atmosphere, in a seal tube, a mixture of example 58 (1.0 equiv.), 3-hydroxypiperidine (1.2 equiv.), a solution of LiHMDS in THF (1.0 N; 3.0 equiv.) and RuPhos precatalyst (0.1 equiv.) were suspended in THF (C=0.1 molL$^{-1}$) and warmed for 17 hours at 65° C. The reaction mixture was hydrolysed with a saturated aqueous NH$_4$Cl solution. The solid was collected, washed with water, dried under reduced pressure. Purification by flash-chromatography (MeOH in DCM, 0 to 5%) afforded example 124 as a beige solid in 19% yield.

$^1$H-NMR (400 MHz, DMSO): 1.41-1.58 (m, 2H, CH$_2$); 1.81-1.94 (m, 2H, CH$_2$); 2.96-3.15 (m, 2H, NCHaHb+ NCHaHc); 3.51 (s, 3H, NCH$_3$); 3.59-3.66 (m, 1H, NCHaCHb); 3.76-3.79 (m, 1H, NCHaCHc); 3.84-3.88 (m, 1H, CH(OH)); 4.96 (d, J 4.2 Hz, 1H, OH); 7.07-7.10 (m, 2H, Ar); 7.43 (d, J 2.4 Hz, 1H, Ar); 7.95 (d, J 9.0 Hz, 1H, Ar); 8.28 (dd, J 5.1 Hz, J 1.0 Hz, 1H, Ar); 8.38 (s, 1H, Ar); 8.87 (d, J 5.1 Hz, 1H, Ar).

M/Z (M+H)$^+$=444.1.

MP: >250° C.

Example 125: 8-(2, 6-Dimethyl-morpholin-4-yl)-4-methyl-2-(2-trifluoromethyl-pyridin-4-yl)-4H-pyrazolo[1,5-a]quinazolin-5-one

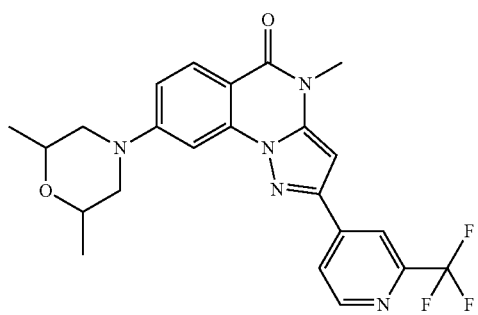 [SMILES: CC1CN(c2ccc3c(=O)n(C)c4cc(-c5ccnc(C(F)(F)F)c5)nn4c3c2)CC(C)O1]

Under inert atmosphere, in a seal tube, a mixture of example 58 (1.0 equiv.), 2,6-dimethylmorpholine (1.2 equiv.), a solution of LiHMDS in THF (1.0 N; 3.0 equiv.) and RuPhos precatalyst (0.1 equiv.) were suspended in THF (C=0.1 molL$^{-1}$) and warmed for 3 days at 65° C. The reaction mixture was hydrolysed with a saturated aqueous NH$_4$Cl solution. The solid was collected, washed with water, dried under reduced pressure. Purification by flash-chromatography (MeOH in DCM, 0 to 5%) afforded example 125 as a beige solid in 19% yield.

$^1$H-NMR (400 MHz, DMSO): 1.22 (d, J 6.2 Hz, 6H, 2CH3); 2.53-2.56 (m, 2H, 2NCHaCHb); 3.51 (s, 3H, NCH3); 3.68-3.75 (m, 2H, 2NCHaCHb); 3.92-3.94 (m, 2H, 2OCH); 7.10 (s, 1H, Ar); 7.16 (dd, J 9.1 Hz, J 2.4 Hz, 1H Ar); 7.46 (d, J 2.3 Hz, 1H, Ar); 7.97 (d, J 9.0 Hz, 1H, Ar); 8.27-8.28 (m, 1H, Ar); 8.38 (s, 1H, Ar); 8.88 (d, J 5.1 Hz, 1H, Ar).

M/Z (M+H)$^+$=458.1.

MP: >250° C.

Example 126: 8-(2-Hydroxy-2-methyl-propylamino)-4-methyl-2-(2-trifluoromethyl-pyridin-4-yl)-4H-pyrazolo[1,5-a]quinazolin-5-one

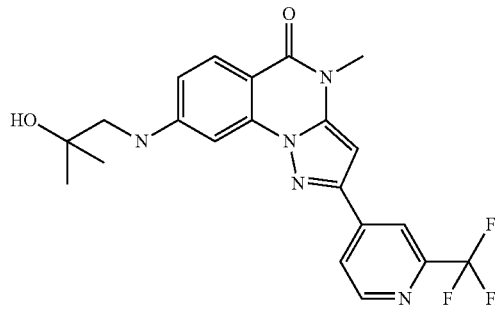 [SMILES: Cn1c(=O)c2ccc(NCC(C)(C)O)cc2n2nc(-c3ccnc(C(F)(F)F)c3)cc12]

Under inert atmosphere, in a seal tube, a mixture of example 58 (1.0 equiv.), 1-amino-2-methyl-2-propanol (1.2 equiv.), a solution of LiHMDS in THF (1.0 N; 3.0 equiv.) and BrettPhos precatalyst (0.1 equiv.) were suspended in THF (C=0.1 molL$^{-1}$) and warmed for 17 hours at 65° C. The reaction mixture was hydrolysed with a saturated aqueous NH$_4$Cl solution. The solid was collected, washed with water, dried under reduced pressure. Purification by flash-chromatography (MeOH in DCM, 0 to 5%) afforded example 126 as a white solid in 6% yield $^1$H-NMR (400 MHz, DMSO): 1.21 (s, 6H, 2CH$_3$); 3.16 (d, J 5.5 Hz, 2H, NCH$_2$); 3.51 (s, 3H, NCH$_3$); 4.58 (s, 1H, OH); 6.87-6.88 (m, 2H, NH+Ar); 7.07 (s, 1H, Ar); 7.29 (s, 1H, Ar); 7.86 (d, J 8.8 Hz, 1H, Ar); 8.24 (d, J 4.7 Hz, 1H, Ar); 8.36 (s, 1H, Ar); 8.88 (d, J 5.1 Hz, 1H, Ar).

M/Z (M+H)$^+$=432.0.

MP: >250° C.

Example 127: Human mGluR2 and mGluR3 Evaluation Using Ca$^{++}$ Functional Assay Examples of the present invention were tested successively for their agonist and negative allosteric modulator activities on human mGluR2 (hmGluR2) and mGluR3 (hmGluR3) transiently over-expressed in HEK-293 cells. Compounds exert agonist activity if, by themselves in absence of glutamate, they are able to activate hmGluR2 or hmGluR3; and they exert negative allosteric modulator activity if they decrease the action of glutamate (which is employed at its EC$_{80}$ concentration).

Cell Culture and Transfection

HEK-293 cells are maintained in Modified Eagle's Medium supplemented with 10% Foetal Calf Serum, 1% Penicillin/Streptomycin and 1% non-essential amino acids at 37° C./5% CO$_2$.

Cells are co-transfected by electroporation with four DNA plasmids encoding hmGluR2 or hmGluR3, a chimeric G protein allowing redirection of the activation signal to intracellular calcium pathway (Brabet I et al., *Neuropharmacology* 37(8), 1043-51, 1998), and two glutamate transporters minimizing receptor desensitization by endogenous glutamate. After transfection, cells are cultured for 24 h at 37° C./5% CO$_2$.

Calcium Assay IC$_{50}$ Determination

Receptor activity is detected by changes in intracellular calcium measured using the fluorescent Ca$^{2+}$ sensitive dye, Fluo4AM (Molecular Probes).

On the day of the assay, culture medium is aspirated and replaced during 3 hours by medium without serum supplemented with 1% Glutamax, 1% Penicillin/Streptomycin and 1% non-essential amino acids. Then, cells are washed with freshly prepared buffer B (HBSS 1×(PAA), Hepes 20 mM, MgSO$_4$-7H$_2$O 1 mM, Na$_2$CO$_3$ 3.3 mM, CaCl$_2$-2H$_2$O 1.3 mM, 0.1% BSA, Probenecid 2.5 mM) and loaded at 37° C. in 5% CO$_2$ for 1.5 hours with buffer B containing 1 µM Fluo4AM, 0.1 mg/mL Pluronic Acid, 7 µg/mL Glutamate Pyruvate Transaminase and 2 mM sodium pyruvate. Afterwards cells are washed twice with buffer B. Then cells are detached using StemPro Accutase (Fischer Scientific), resuspended in buffer B and seeded in 384 well plate at a density of 30,000 cells per well. Addition of compounds and intracellular Ca$^{2+}$ measurements (excitation 485 nm, emission 525 nm) are performed by the fluorescence microplate reader FLIPRTetra (Molecular Devices).

Agonist and negative allosteric modulator activities of compounds are consecutively evaluated on the same cell plate. Agonist activity is first tested during 10 minutes with the addition of compound alone on the cells. Then, cells are stimulated by an EC$_{80}$ glutamate concentration and fluorescence is recorded for additional 3 minutes. EC$_{80}$ glutamate concentration is the concentration giving 80% of the maximal glutamate response. Agonist or negative allosteric modulator activity(ies) are evaluated in comparison to basal signals evoked by buffer B or EC$_{80}$ glutamate alone, respectively.

For IC$_{50}$ determination, a dose-response test is performed using 20 concentrations (ranging over 6 logs) of each compound. Dose-response curves are fitted using the sigmoidal dose-response (variable slope) analysis in GraphPad Prism program (Graph Pad Inc) and IC$_{50}$ of negative allosteric modulator activity is calculated. Dose-response experiments are performed in duplicate, two times independently.

The compounds of the present invention were found to have no agonist activity on hmGluR2 and hmGluR3. On hmGluR2, the compounds of the present invention have preferably an IC$_{50}$ of 5 µM or less, more preferably 1 µM or less and the ratio [IC$_{50}$ hmGluR3]/[IC$_{50}$ hmGluR2] is higher than 3, more preferably is higher than 5.

The following list represents selected examples of the compounds of the present invention showing hmGluR2 negative allosteric modulator activity with an IC$_{50}$<1 µM and a ratio [IC$_{50}$ hmGluR3]/[IC$_{50}$ hmGluR2] higher than 3:
Examples: 1, 2, 3, 4, 5, 6, 9, 10, 11, 12, 14, 15, 16, 17, 19, 21, 22, 23, 24, 25, 26, 27, 28, 31, 32, 33, 34, 35, 36, 38, 39, 40, 41, 44, 45, 48, 49, 55, 56, 58, 61, 63, 64, 68, 70, 77, 78, 79, 80, 81, 82, 85, 87, 88, 89, 90, 91, 94, 95, 96, 98, 99, 100, 102, 105, 106, 108, 110, 113, 114, 115, 116, 117, 119, 120, 121, 122, and 125.

The invention claimed is:

1. A pharmaceutical composition, comprising a compound of formula (I):

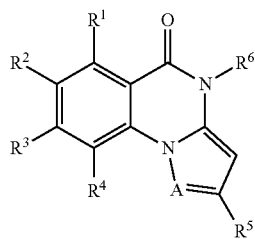

wherein:
A is N;
R$^1$, R$^2$ and R$^4$ are each independently selected from the group consisting of R$^{10}$, halogen, —CN, —NR$^7$R$^8$, —COOR$^7$, —SO$_3$H, —B(OH)$_2$, —CONR$^7$R$^8$, —COR$^7$, —SR$^7$, —SOR$^7$, —SO$_2$R$^7$, —SO$_2$NR$^7$R$^8$, —NR$^7$COR$^8$, —NR$^7$SO$_2$R$^8$, —OCOR$^7$, —NR$^7$C(O)NR$^8$R$^9$, —NR$^7$C(S)NR$^8$R$^9$, and —NR$^7$COOR$^8$;
R$^3$ is selected from the group consisting of hydrogen, halogen, —CN, —NR$^7$R$^8$, —COOR$^7$, —SO$_3$H, —B(OH)$_2$, —CONR$^7$R$^8$, —COR$^7$, —SOR$^7$, —SO$_2$R$^7$, —SO$_2$NR$^7$R$^8$, —NR$^7$COR$^8$, —NR$^7$SO$_2$R$^8$, —OCOR$^7$, —NR$^7$C(O)NR$^8$R$^9$, —NR$^7$C(S)NR$^8$R$^9$, —NR$^7$COOR$^8$, C$_1$-C$_4$ alkyl, C$_2$-C$_4$ alkenyl, cycloalkyl and heterocycloalkyl, wherein said C$_1$-C$_4$ alkyl and said C$_2$-C$_4$ alkenyl are each optionally substituted with one or more groups independently selected from the group consisting of halogen, —CF$_3$, —CN, —OH, —O(C$_1$-C$_4$ alkyl), —NH$_2$, —NH(C$_1$-C$_4$ alkyl) and —N(C$_1$-C$_4$ alkyl)(C$_1$-C$_4$ alkyl), and further wherein said cycloalkyl and said heterocycloalkyl are each optionally substituted with one or more groups independently selected from the group consisting of: C$_1$-C$_4$ alkyl; halogen; CF$_3$; —CN; —OH; —O(C$_1$-C$_4$ alkyl); C$_1$-C$_4$ alkyl substituted with one or more —OH groups; —NH$_2$; —NH(C$_1$-C$_4$ alkyl); and —N(C$_1$-C$_4$ alkyl)(C$_1$-C$_4$ alkyl);
R$^5$ is heteroaryl which is optionally substituted with one or more groups independently selected from the group consisting of R$^7$, halogen, —CN, —NR$^7$R$^8$, —CONR$^7$R$^8$, —COR$^7$, —SR$^7$, —SOR$^7$, —SO$_2$R$^7$, —SO$_2$NR$^7$R$^8$, —NR$^7$COR$^8$, —NR$^7$SO$_2$R$^8$, —OCOR$^7$, and —COOR$^7$;
R$^6$ is selected from the group consisting of C$_1$-C$_4$ alkyl, cycloalkyl, and heterocycloalkyl, wherein said C$_1$-C$_4$ alkyl is optionally substituted with one or more groups independently selected from the group consisting of cycloalkyl, halogen, —CF$_3$, —CN, —OH and —O(C$_1$-C$_4$ alkyl), and further wherein, if R$^6$ is cycloalkyl or heterocycloalkyl, then said cycloalkyl and said heterocycloalkyl are each optionally substituted with one or more groups independently selected from the group consisting of C$_1$-C$_4$ alkyl, cycloalkyl, halogen, —CF$_3$, —CN, —OH and —O(C$_1$-C$_4$ alkyl); and
each R$^7$, R$^8$ and R$^9$ is independently selected from the group consisting of hydrogen, C$_1$-C$_4$ alkyl, C$_2$-C$_4$ alkenyl, cycloalkyl, cycloalkenyl, heterocycloalkyl, heterocycloalkenyl, aryl and heteroaryl, wherein said C$_1$-C$_4$ alkyl and said C$_2$-C$_4$ alkenyl are each optionally substituted with one or more groups independently selected from the group consisting of halogen, —CF$_3$, —CN, cycloalkyl, cycloalkenyl, heterocycloalkyl, heterocycloalkenyl, aryl, heteroaryl, —OH, —O(C$_1$-C$_4$ alkyl), —NH$_2$, —NH(C$_1$-C$_4$ alkyl) and —N(C$_1$-C$_4$ alkyl)(C$_1$-C$_4$ alkyl), and further wherein, if R$^7$, R$^8$ or R$^9$ is cycloalkyl, cycloalkenyl, heterocycloalkyl, heterocycloalkenyl, aryl or heteroaryl, then said cycloalkyl, said cycloalkenyl, said heterocycloalkyl, said heterocycloalkenyl, said aryl and said heteroaryl are each optionally substituted with one or more groups independently selected from the group consisting of: C$_1$-C$_4$ alkyl; halogen; —CF$_3$; —CN; —OH; —O(C$_1$-C$_4$ alkyl); C$_1$-C$_4$ alkyl substituted with one or more —OH groups; —NH$_2$; —NH (C$_1$-C$_4$ alkyl); and —N(C$_1$-C$_4$ alkyl)(C$_1$-C$_4$ alkyl);

each $R^{10}$ is independently selected from the group consisting of hydrogen, $C_1$-$C_4$ alkyl, $C_2$-$C_4$ alkenyl, cycloalkyl, cycloalkenyl, heterocycloalkyl and heterocycloalkenyl, wherein said $C_1$-$C_4$ alkyl and said $C_2$-$C_4$ alkenyl are each optionally substituted with one or more groups independently selected from the group consisting of halogen, —$CF_3$, —CN, cycloalkyl, cycloalkenyl, heterocycloalkyl, heterocycloalkenyl, aryl, heteroaryl, —OH, —O($C_1$-$C_4$ alkyl), —$NH_2$, —NH($C_1$-$C_4$ alkyl) and —N($C_1$-$C_4$ alkyl)($C_1$-$C_4$ alkyl), and further wherein, if $R^{10}$ is cycloalkyl, cycloalkenyl, heterocycloalkyl or heterocycloalkenyl, then said cycloalkyl, said cycloalkenyl, said heterocycloalkyl and said heterocycloalkenyl are each optionally substituted with one or more groups independently selected from the group consisting of: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); and —N($C_1$-$C_4$ alkyl)($C_1$-$C_4$ alkyl);

or a pharmaceutically acceptable salt or solvate thereof, and a pharmaceutically acceptable excipient.

2. A compound of formula (I):

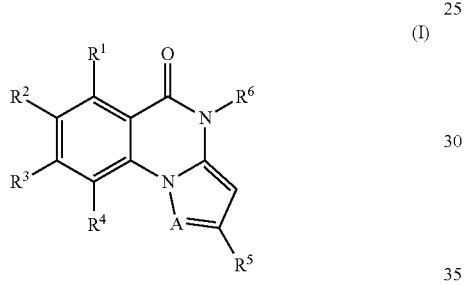

(I)

wherein:

A is N;

$R^1$, $R^2$ and $R^4$ are each independently selected from the group consisting of $R^{10}$, halogen, —CN, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, and —$NR^7COOR^8$;

$R^3$ is selected from the group consisting of hydrogen, —F, —Cl, —I, —CN, —$NR^7R^8$, —$COOR^7$, —$SO_3H$, —$B(OH)_2$, —$CONR^7R^8$, —$COR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, —$NR^7COOR^8$, $C_1$-$C_4$ alkyl, $C_2$-$C_4$ alkenyl, cycloalkyl and heterocycloalkyl, wherein said $C_1$-$C_4$ alkyl and said $C_2$-$C_4$ alkenyl are each optionally substituted with one or more groups independently selected from the group consisting of halogen, —$CF_3$, —CN, —OH, —O($C_1$-$C_4$ alkyl), —$NH_2$, —NH($C_1$-$C_4$ alkyl) and —N($C_1$-$C_4$ alkyl)($C_1$-$C_4$ alkyl), and further wherein said cycloalkyl and said heterocycloalkyl are each optionally substituted with one or more groups independently selected from the group consisting of: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); and —N($C_1$-$C_4$ alkyl)($C_1$-$C_4$ alkyl);

$R^5$ is heteroaryl which is optionally substituted with one or more groups independently selected from the group consisting of $R^7$, halogen, —CN, —$NR^7R^8$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, and —$COOR^7$;

$R^6$ is selected from the group consisting of $C_1$-$C_4$ alkyl, cycloalkyl, and heterocycloalkyl, wherein said $C_1$-$C_4$ alkyl is optionally substituted with one or more groups independently selected from the group consisting of cycloalkyl, halogen, —$CF_3$, —CN, —OH and —O($C_1$-$C_4$ alkyl), and further wherein, if $R^6$ is cycloalkyl or heterocycloalkyl, then said cycloalkyl and said heterocycloalkyl are each optionally substituted with one or more groups independently selected from the group consisting of $C_1$-$C_4$ alkyl, cycloalkyl, halogen, —$CF_3$, —CN, —OH and —O($C_1$-$C_4$ alkyl); and each $R^7$, $R^8$ and $R^9$ is independently selected from the group consisting of hydrogen, $C_1$-$C_4$ alkyl, $C_2$-$C_4$ alkenyl, cycloalkyl, cycloalkenyl, heterocycloalkyl, heterocycloalkenyl, aryl and heteroaryl, wherein said $C_1$-$C_4$ alkyl and said $C_2$-$C_4$ alkenyl are each optionally substituted with one or more groups independently selected from the group consisting of halogen, —$CF_3$, —CN, cycloalkyl, cycloalkenyl, heterocycloalkyl, heterocycloalkenyl, aryl, heteroaryl, —OH, —O($C_1$-$C_4$ alkyl), —$NH_2$, —NH($C_1$-$C_4$ alkyl) and —N($C_1$-$C_4$ alkyl)($C_1$-$C_4$ alkyl), and further wherein, if $R^7$, $R^8$ or $R^9$ is cycloalkyl, cycloalkenyl, heterocycloalkyl, heterocycloalkenyl, aryl or heteroaryl, then said cycloalkyl, said cycloalkenyl, said heterocycloalkyl, said heterocycloalkenyl, said aryl and said heteroaryl are each optionally substituted with one or more groups independently selected from the group consisting of: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); and —N($C_1$-$C_4$ alkyl)($C_1$-$C_4$ alkyl);

each $R^{10}$ is independently selected from the group consisting of hydrogen, $C_1$-$C_4$ alkyl, $C_2$-$C_4$ alkenyl, cycloalkyl, cycloalkenyl, heterocycloalkyl and heterocycloalkenyl, wherein said $C_1$-$C_4$ alkyl and said $C_2$-$C_4$ alkenyl are each optionally substituted with one or more groups independently selected from the group consisting of halogen, —$CF_3$, —CN, cycloalkyl, cycloalkenyl, heterocycloalkyl, heterocycloalkenyl, aryl, heteroaryl, —OH, —O($C_1$-$C_4$ alkyl), —$NH_2$, —NH($C_1$-$C_4$ alkyl) and —N($C_1$-$C_4$ alkyl)($C_1$-$C_4$ alkyl), and further wherein, if $R^{19}$ is cycloalkyl, cycloalkenyl, heterocycloalkyl or heterocycloalkenyl, then said cycloalkyl, said cycloalkenyl, said heterocycloalkyl and said heterocycloalkenyl are each optionally substituted with one or more groups independently selected from the group consisting of: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); and —N($C_1$-$C_4$ alkyl)($C_1$-$C_4$ alkyl);

or a pharmaceutically acceptable salt or solvate thereof;

wherein the heterocycloalkyl is a saturated ring group which may be a monocyclic ring or a bridged ring, spiro ring and/or fused ring system, wherein said ring group contains one or more ring heteroatoms, wherein said ring heteroatoms are independently selected from the group consisting of O, S and N, and wherein one or more S ring atoms, if present, and/or one or more N ring atoms, if present, may be oxidized.

3. The pharmaceutical composition of claim 1, wherein $R^3$ is selected from the group consisting of hydrogen, halogen, $C_1$-$C_4$ haloalkyl, $C_1$-$C_4$ haloalkoxy, —CN, $C_1$-$C_4$ alkyl, cycloalkyl, heterocycloalkyl, —OH, —O($C_1$-$C_4$ alkyl), —O-cycloalkyl, —O-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —CO-cycloalkyl, —CO-heterocycloalkyl, —CO—NH$_2$, —CO—NH($C_1$-$C_4$ alkyl), —CO—N($C_1$-$C_4$ alkyl)($C_1$-$C_4$ alkyl), —CO—NH-cycloalkyl, $C_4$ alkyl)-cycloalkyl, —CO—NH-heterocycloalkyl, —CO—N($C_1$-$C_4$ alkyl)-heterocycloalkyl, —NH—CO-cycloalkyl, —N($C_1$-$C_4$ alkyl)-CO-cycloalkyl, —NH—CO-heterocycloalkyl, and —N($C_1$-$C_4$ alkyl)-CO-heterocycloalkyl, wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups independently selected from the group consisting of: $C_1$-$C_4$ alkyl; halogen; —CF$_3$; —CN; —OH; —O($C_1$-$C_4$ alkyl); $C_1$-$C_4$ alkyl substituted with one or more —OH groups; —NH$_2$; —NH($C_1$-$C_4$ alkyl); and —N($C_1$-$C_4$ alkyl)($C_1$-$C_4$ alkyl).

4. The pharmaceutical composition of claim 1, wherein $R^1$, $R^2$ and $R^4$ are each independently selected from the group consisting of hydrogen, halogen, $C_1$-$C_4$ haloalkyl, $C_1$-$C_4$ haloalkoxy, —CN, $C_1$-$C_4$ alkyl, $C_2$-$C_4$ alkenyl, cycloalkyl, heterocycloalkyl, —OH, —O($C_1$-$C_4$ alkyl), —O—($C_1$-$C_4$ alkylene)-OH, —O—($C_1$-$C_4$ alkylene)-O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —O-aryl, —O—($C_1$-$C_4$ alkylene)-aryl, —O-heteroaryl, —O—($C_1$-$C_4$ alkylene)-heteroaryl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —NH-aryl, —N($C_1$-$C_4$ alkyl)-aryl, —NH-heteroaryl, $C_4$ alkyl)-heteroaryl, —NH—($C_1$-$C_4$ alkylene)-aryl, —N($C_1$-$C_4$ alkyl)-($C_1$-$C_4$ alkylene)-aryl, —NH—($C_1$-$C_4$ alkylene)-heteroaryl, —N($C_1$-$C_4$ alkyl)-($C_1$-$C_4$ alkylene)-heteroaryl, —CO—($C_1$-$C_4$ alkyl), —CO-cycloalkyl, —CO-heterocycloalkyl, —CO—($C_1$-$C_4$ alkylene)-cycloalkyl, —CO—($C_1$-$C_4$ alkylene)-heterocycloalkyl, —CO-aryl, —CO-heteroaryl, —CO—($C_1$-$C_4$ alkylene)-aryl, —CO—($C_1$-$C_4$ alkylene)-heteroaryl, —CO—NH$_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH—($C_1$-$C_4$ alkylene)-cycloalkyl, —CO—N($C_1$-$C_4$ alkyl)-($C_1$-$C_4$ alkylene)-cycloalkyl, —CO—NH-heterocycloalkyl, —CO—N($C_1$-$C_4$ alkyl)-heterocycloalkyl, —CO—NH—($C_1$-$C_4$ alkylene)-heterocycloalkyl, —CO—N($C_1$-$C_4$ alkyl)-($C_1$-$C_4$ alkylene)-heterocycloalkyl, —CO—NH-aryl, —CO—N($C_1$-$C_4$ alkyl)-aryl, —CO—NH—($C_1$-$C_4$ alkylene)-aryl, —CO—N($C_1$-$C_4$ alkyl)-($C_1$-$C_4$ alkylene)-aryl, —CO—NH-heteroaryl, —CO—N($C_1$-$C_4$ alkyl)-heteroaryl, —CO—NH—($C_1$-$C_4$ alkylene)-heteroaryl, —CO—N($C_1$-$C_4$ alkyl)-($C_1$-$C_4$ alkylene)-heteroaryl, —NH—CHO, —N($C_1$-$C_4$ alkyl)-CHO, —NH—CO($C_1$-$C_4$ alkyl), —N($C_1$-$C_4$ alkyl)-CO($C_1$-$C_4$ alkyl), —NH—CO-cycloalkyl, —N($C_1$-$C_4$ alkyl)-CO-cycloalkyl, —NH—CO—($C_1$-$C_4$ alkylene)-cycloalkyl, —N($C_1$-$C_4$ alkyl)-CO—($C_1$-$C_4$ alkylene)-cycloalkyl, —NH—CO-heterocycloalkyl, —N($C_1$-$C_4$ alkyl)-CO-heterocycloalkyl, —NH—CO—($C_1$-$C_4$ alkylene)-heterocycloalkyl, —N($C_1$-$C_4$ alkyl)-CO—($C_1$-$C_4$ alkylene)-heterocycloalkyl, —NH—CO-aryl, —N($C_1$-$C_4$ alkyl)-CO-aryl, —NH—CO—($C_1$-$C_4$ alkylene)-aryl, —N($C_1$-$C_4$ alkyl)-CO—($C_1$-$C_4$ alkylene)-aryl, —NH—CO-heteroaryl, —N($C_1$-$C_4$ alkyl)-CO-heteroaryl, —NH—CO—($C_1$-$C_4$ alkylene)-heteroaryl, and —N($C_1$-$C_4$ alkyl)-CO—($C_1$-$C_4$ alkylene)-heteroaryl, wherein the aryl moiety comprised in any of the aforementioned groups and the heteroaryl moiety comprised in any of the aforementioned groups are each optionally substituted with one or more groups independently selected from the group consisting of $C_1$-$C_4$ alkyl, halogen, —CF$_3$, —CN, —OH, —O($C_1$-$C_4$ alkyl), —NH$_2$, —NH($C_1$-$C_4$ alkyl) and —N($C_1$-$C_4$ alkyl)($C_1$-$C_4$ alkyl).

5. The pharmaceutical composition of claim 1, wherein $R^5$ is heteroaryl having 5 or 6 ring members and comprising one or more ring heteroatoms independently selected from the group consisting of O, S and N, wherein said heteroaryl having 5 or 6 ring members is optionally substituted with one or more groups independently selected from the group consisting of $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, aryl, heteroaryl, —OH, —O($C_1$-$C_4$ alkyl), —O-cycloalkyl, —O—($C_1$-$C_4$ alkylene)-cycloalkyl, —O-heterocycloalkyl, —O—($C_1$-$C_4$ alkylene)-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, and —CO—($C_1$-$C_4$ alkylene)-heterocycloalkyl, wherein said aryl, said heteroaryl, said cycloalkyl, said heterocycloalkyl, the cycloalkyl moiety comprised in any of the aforementioned groups, and the heterocycloalkyl moiety comprised in any of the aforementioned groups are each optionally substituted with one or more groups independently selected from the group consisting of $C_1$-$C_4$ alkyl, halogen, —CF$_3$, —CN, —OH, —O($C_1$-$C_4$ alkyl), —NH$_2$, —NH($C_1$-$C_4$ alkyl) and —N($C_1$-$C_4$ alkyl)($C_1$-$C_4$ alkyl).

6. The pharmaceutical composition of claim 1, wherein $R^5$ is pyridinyl which is optionally substituted with one or more groups independently selected from the group consisting of $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, aryl, heteroaryl, —OH, —O($C_1$-$C_4$ alkyl), —O-cycloalkyl, alkylene)-cycloalkyl, —O-heterocycloalkyl, —O—($C_1$-$C_4$ alkylene)-heterocycloalkyl, —NH$_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —NH—($C_1$-$C_4$ alkylene)-cycloalkyl, —N($C_1$-$C_4$ alkyl)-($C_1$-$C_4$ alkylene)-cycloalkyl, —NH—($C_1$-$C_4$ alkylene)-heterocycloalkyl, —N($C_1$-$C_4$ alkyl)-($C_1$-$C_4$ alkylene)-heterocycloalkyl, —CO—($C_1$-$C_4$ alkyl), —CO-cycloalkyl, —CO-heterocycloalkyl, —CO—($C_1$-$C_4$ alkylene)-cycloalkyl, and —CO—($C_1$-$C_4$ alkylene)-heterocycloalkyl, wherein said aryl, said heteroaryl, said cycloalkyl, said heterocycloalkyl, the cycloalkyl moiety comprised in any of the aforementioned groups, and the heterocycloalkyl moiety comprised in any of the aforementioned groups are each optionally substituted with one or more groups independently selected from the group consisting of $C_1$-$C_4$ alkyl, halogen, —CF$_3$, —CN, —OH, —O($C_1$-$C_4$ alkyl), —NH$_2$, —NH($C_1$-$C_4$ alkyl) and —N($C_1$-$C_4$ alkyl)($C_1$-$C_4$ alkyl).

7. The pharmaceutical composition of claim 1, wherein $R^5$ is pyridin-4-yl which is substituted with one substituent group at position 2 of said pyridin-4-yl or with two substituent groups at position 2 and 6 of said pyridin-4-yl, wherein said one or two substituent group(s) is/are selected independently from the group consisting of $C_1$-$C_4$ alkyl, $C_2$-$C_4$ alkenyl, halogen, $C_1$-$C_4$ haloalkyl, $C_1$-$C_4$ haloalkoxy, —CN, cycloalkyl, heterocycloalkyl, —O($C_1$-$C_4$ alkyl), —O-cycloalkyl, and —O-heterocycloalkyl.

8. The pharmaceutical composition of claim 1, wherein $R^5$ is 2-trifluoromethyl-pyridin-4-yl.

9. The pharmaceutical composition of claim 1, wherein $R^6$ is methyl.

10. The pharmaceutical composition of claim 1, wherein said compound is selected from the group consisting of:
- 2-(2-chloro-pyridin-4-yl)-4-methyl-4H-pyrazolo[1,5-a]quinazolin-5-one;
- 4-methyl 2-(2-methyl-pyridin-4-yl)-4H-pyrazolo[1,5-a]quinazolin-5-one;
- 2-(2-ethyl-pyridin-4-yl)-4-methyl-4H-pyrazolo[1,5-a]quinazolin-5-one;
- 2-(2-propyl-pyridin-4-yl)-4-methyl-4H-pyrazolo[1,5-a]quinazolin-5-one;
- 2-(2-cyclopropyl-pyridin-4-yl)-4-methyl-4H-pyrazolo[1,5-a]quinazolin-5-one;
- 2-(2-cyclobutyl-pyridin-4-yl)-4-methyl-4H-pyrazolo[1,5-a]quinazolin-5-one;
- 2-(2-cyclopentyl-pyridin-4-yl)-4-methyl-4H-pyrazolo[1,5-a]quinazolin-5-one;
- 2-(2-cyclohexyl-pyridin-4-yl)-4-methyl-4H-pyrazolo[1,5-a]quinazolin-5-one;
- 4-methyl-2-(2-vinyl-pyridin-4-yl)-4H-pyrazolo[1,5-a]quinazolin-5-one;
- 2-(2-isopropenyl-pyridin-4-yl)-4-methyl-4H-pyrazolo[1,5-a]quinazolin-5-one;
- 2-(2-isopropyl-pyridin-4-yl)-4-methyl-4H-pyrazolo[1,5-a]quinazolin-5-one;
- 4-(4-methyl-5-oxo-4,5-dihydro-pyrazolo[1,5-a]quinazolin-2-yl)-pyridine-2-carbonitrile;
- 2-(2-fluoro-pyridin-4-yl)-4-methyl-4H-pyrazolo[1,5-a]quinazolin-5-one;
- 2-(2-methoxy-pyridin-4-yl)-4-methyl-4H-pyrazolo[1,5-a]quinazolin-5-one;
- 2-(2-ethoxy-pyridin-4-yl)-4-methyl-4H-pyrazolo[1,5-a]quinazolin-5-one;
- 2-(2-isopropoxy-pyridin-4-yl)-4-methyl-4H-pyrazolo[1,5-a]quinazolin-5-one;
- 2-(2-cyclobutoxy-pyridin-4-yl)-4-methyl-4H-pyrazolo[1,5-a]quinazolin-5-one;
- 4-methyl-2-[2-(oxetan-3-yloxy)-pyridin-4-yl]-4H-pyrazolo[1,5-a]quinazolin-5-one;
- 2-(2-cyclopropylmethoxy-pyridin-4-yl)-4-methyl-4H-pyrazolo[1,5-a]quinazolin-5-one;
- 2-[2-(2-methoxy-ethoxy)-pyridin-4-yl]-4-methyl-4H-pyrazolo[1,5-a]quinazolin-5-one;
- 4-methyl-2-[2-(2,2,2-trifluoro-ethoxy)-pyridin-4-yl]-4H-pyrazolo[1,5-a]quinazolin-5-one;
- 4-methyl-2-[2-(2,2-difluoro-ethoxy)-pyridin-4-yl]-4H-pyrazolo[1,5-a]quinazolin-5-one;
- 2-[2-(2,2-difluoro-propoxy)-pyridin-4-yl]-4-methyl-4H-pyrazolo[1,5-a]quinazolin-5-one;
- 4-methyl-2-[2-(2,2,3,3,3-pentafluoro-propoxy)-pyridin-4-yl]-4H-pyrazolo[1,5-a]quinazolin-5-one;
- 4-methyl-2-[2-(2,2,2-trifluoro-1-trifluoromethyl-ethoxy)-pyridin-4-yl]-4H-pyrazolo[1,5-a]quinazolin-5-one;
- 4-methyl-2-(2-trifluoromethyl-pyridin-4-yl)-4H-pyrazolo[1,5-a]quinazolin-5-one;
- 4-methyl($D_3$)-2-(2-trifluoromethyl-pyridin-4-yl)-4H-pyrazolo[1,5-a]quinazolin-5-one;
- 4-ethyl-2-(2-trifluoromethyl-pyridin-4-yl)-4H-pyrazolo[1,5-a]quinazolin-5-one;
- 4-(2,2-difluoro-ethyl)-2-(2-trifluoromethyl-pyridin-4-yl)-4H-pyrazolo[1,5-a]quinazolin-5-one;
- 4-(2-methoxy-ethyl)-2-(2-trifluoromethyl-pyridin-4-yl)-4H-pyrazolo[1,5-a]quinazolin-5-one;
- 4-methyl-2-(2-difluoromethyl-pyridin-4-yl)-4H-pyrazolo[1,5-a]quinazolin-5-one;
- 2-[2-(1,1-difluoro-ethyl)-pyridin-4-yl]-4-methyl-4H-pyrazolo[1,5-a]quinazolin-5-one;
- 2-[2-(1,1-difluoro-ethyl)-pyridin-4-yl]-4-methyl($D_3$)-4H-pyrazolo[1,5-a]quinazolin-5-one;
- 7-methyl-2-(2-trifluoromethyl-pyridin-4-yl)-4H-pyrazolo[1,5-a]quinazolin-5-one;
- 7-chloro-2-(2-trifluoromethyl-pyridin-4-yl)-4H-pyrazolo[1,5-a]quinazolin-5-one;
- 7-methoxy-2-(2-trifluoromethyl-pyridin-4-yl)-4H-pyrazolo[1,5-a]quinazolin-5-one;
- 7-trifluoromethyl-2-(2-trifluoromethyl-pyridin-4-yl)-4H-pyrazolo[1,5-a]quinazolin-5-one;
- 7-fluoro-2-(2-trifluoromethyl-pyridin-4-yl)-4H-pyrazolo[1,5-a]quinazolin-5-one;
- 7-bromo-2-(2-trifluoromethyl-pyridin-4-yl)-4H-pyrazolo[1,5-a]quinazolin-5-one;
- 4-methyl-7-methylamino-2-(2-trifluoromethyl-pyridin-4-yl)-4H-pyrazolo[1,5-a]quinazolin-5-one;
- 4-methyl-7-methyl(D3)amino-2-(2-trifluoromethyl-pyridin-4-yl)-4H-pyrazolo[1,5-a]quinazolin-5-one;
- N-[4-methyl-5-oxo-2-(2-trifluoromethyl-pyridin-4-yl)-4,5-dihydro-pyrazolo[1,5-a]quinazolin-7-yl]-acetamide;
- 7-amino-4-methyl-2-(2-trifluoromethyl-pyridin-4-yl)-4H-pyrazolo[1,5-a]quinazolin-5-one;
- 7-dimethylamino-4-methyl-2-(2-trifluoromethyl-pyridin-4-yl)-4H-pyrazolo[1,5-a]quinazolin-5-one;
- 7-ethylamino-4-methyl-2-(2-trifluoromethyl-pyridin-4-yl)-4H-pyrazolo[1,5-a]quinazolin-5-one;
- 7-cyclobutylamino-4-methyl-2-(2-trifluoromethyl-pyridin-4-yl)-4H-pyrazolo[1,5-a]quinazolin-5-one;
- 4-methyl-7-morpholin-4-yl-2-(2-trifluoromethyl-pyridin-4-yl)-4H-pyrazolo[1,5-a]quinazolin-5-one;
- 7-hydroxy-4-methyl-2-(2-trifluoromethyl-pyridin-4-yl)-4H-pyrazolo[1,5-a]quinazolin-5-one;
- 7-ethoxy-4-methyl-2-(2-trifluoromethyl-pyridin-4-yl)-4H-pyrazolo[1,5-a]quinazolin-5-one;
- 7-(2-methoxy-ethoxy)-4-methyl-2-(2-trifluoromethyl-pyridin-4-yl)-4H-pyrazolo[1,5-a]quinazolin-5-one;
- 4-methyl-7-(2-morpholin-4-yl-ethoxy)-2-(2-trifluoromethyl-pyridin-4-yl)-4H-pyrazolo[1,5-a]quinazolin-5-one;
- 4-methyl-7-trifluoromethoxy-2-(2-trifluoromethyl-pyridin-4-yl)-4H-pyrazolo[1,5-a]quinazolin-5-one;
- 7-methanesulfonyl-4-methyl-2-(2-trifluoromethyl-pyridin-4-yl)-4H-pyrazolo[1,5-a]quinazolin-5-one;
- 8-methoxy-4-methyl-2-(2-trifluoromethyl-pyridin-4-yl)-4H-pyrazolo[1,5-a]quinazolin-5-one;
- 8-fluoro-4-methyl-2-(2-trifluoromethyl-pyridin-4-yl)-4H-pyrazolo[1,5-a]quinazolin-5-one;
- 8-chloro-4-methyl-2-(2-trifluoromethyl-pyridin-4-yl)-4H-pyrazolo[1,5-a]quinazolin-5-one;
- 4-methyl-8-trifluoromethyl-2-(2-trifluoromethyl-pyridin-4-yl)-4H-pyrazolo[1,5-a]quinazolin-5-one;
- 8-bromo-4-methyl-2-(2-trifluoromethyl-pyridin-4-yl)-4H-pyrazolo[1,5-a]quinazolin-5-one;
- 4-methyl-8-morpholin-4-yl-2-(2-trifluoromethyl-pyridin-4-yl)-4H-pyrazolo[1,5-a]quinazolin-5-one;
- 4-methyl-8-pyrrolidin-1-yl-2-(2-trifluoromethyl-pyridin-4-yl)-4H-pyrazolo[1,5-a]quinazolin-5-one;

4-methyl-8-methylamino-2-(2-trifluoromethyl-pyridin-4-yl)-4H-pyrazolo[1,5-a]quinazolin-5-one;
8-(4-methoxy-piperidin-1-yl)-4-methyl-2-(2-trifluoromethyl-pyridin-4-yl)-4H-pyrazolo[1,5-a]quinazolin-5-one;
8-(4-hydroxy-piperidin-1-yl)-4-methyl-2-(2-trifluoromethyl-pyridin-4-yl)-4H-pyrazolo[1,5-a]quinazolin-5-one;
8-dimethylamino-4-methyl-2-(2-trifluoromethyl-pyridin-4-yl)-4H-pyrazolo[1,5-a]quinazolin-5-one;
4-methyl-8-(4-methyl-piperazin-1-yl)-2-(2-trifluoromethyl-pyridin-4-yl)-4H-pyrazolo[1,5-a]quinazolin-5-one;
4-methyl-8-piperazin-1-yl-2-(2-trifluoromethyl-pyridin-4-yl)-4H-pyrazolo[1,5-a]quinazolin-5-one;
8-(4-hydroxymethyl-piperidin-1-yl)-4-methyl-2-(2-trifluoromethyl-pyridin-4-yl)-4H-pyrazolo[1,5-a]quinazoin-5-one;
8-(3-hydroxy-azetidin-1-yl)-4-methyl-2-(2-trifluoromethyl-pyridin-4-yl)-4H-pyrazolo[1,5-a]quinazolin-5-one;
8-(3-hydroxymethyl-azetidin-1-yl)-4-methyl-2-(2-trifluoromethyl-pyridin-4-yl)-4H-pyrazolo[1,5-a]quinazolin-5-one;
8-(3-hydroxy-pyrrolidin-1-yl)-4-methyl-2-(2-trifluoromethyl-pyridin-4-yl)-4H-pyrazolo[1,5-a]quinazolin-5-one;
8-(4-hydroxy-4-methyl-piperidin-1-yl)-4-methyl-2-(2-trifluoromethyl-pyridin-4-yl)-4H-pyrazolo[1,5-a]quinazolin-5-one;
4,8-dimethyl-2-(2-trifluoromethyl-pyridin-4-yl)-4H-pyrazolo[1,5-a]quinazolin-5-one;
8-cyclopropyl-4-methyl-2-(2-trifluoromethyl-pyridin-4-yl)-4H-pyrazolo[1,5-a]quinazolin-5-one;
8-cyclopentyl-4-methyl-2-(2-trifluoromethyl-pyridin-4-yl)-4H-pyrazolo[1,5-a]quinazolin-5-one;
4-methyl-5-oxo-2-(2-trifluoromethyl-pyridin-4-yl)-4,5-dihydro-pyrazolo[1,5-a]quinazoline-8-carbonitrile;
4-methyl-5-oxo-2-(2-trifluoromethyl-pyridin-4-yl)-4,5-dihydro-pyrazolo[1,5-a]quinazoline-8-carboxylic acid;
4-methyl-5-oxo-2-(2-trifluoromethyl-pyridin-4-yl)-4,5-dihydro-pyrazolo[1,5-a]quinazoline-8-carboxylic acid amide;
4-methyl-5-oxo-2-(2-trifluoromethyl-pyridin-4-yl)-4,5-dihydro-pyrazolo[1,5-a]quinazoline-8-carboxylic acid methylamide;
4-methyl-5-oxo-2-(2-trifluoromethyl-pyridin-4-yl)-4,5-dihydro-pyrazolo[1,5-a]quinazoline-8-carboxylic acid dimethylamide;
4-methyl-5-oxo-2-(2-trifluoromethyl-pyridin-4-yl)-4,5-dihydro-pyrazolo[1,5-a]quinazoline-8-carboxylic acid diethylamide;
4-methyl-8-(morpholine-4-carbonyl)-2-(2-trifluoromethyl-pyridin-4-yl)-4H-pyrazolo[1,5-a]quinazolin-5-one;
4-methyl-8-(pyrrolidine-1-carbonyl)-2-(2-trifluoromethyl-pyridin-4-yl)-4H-pyrazolo[1,5-a]quinazolin-5-one;
8-(2-hydroxy-ethoxy)-4-methyl-2-(2-trifluoromethyl-pyridin-4-yl)-4H-pyrazolo[1,5-a]quinazolin-5-one;
4-methyl-6-trifluoromethyl-2-(2-trifluoromethyl-pyridin-4-yl)-4H-pyrazolo[1,5-a]quinazolin-5-one;
6-fluoro-4-methyl-2-(2-trifluoromethyl-pyridin-4-yl)-4H-pyrazolo[1,5-a]quinazolin-5-one;
9-methoxy-4-methyl-2-(2-trifluoromethyl-pyridin-4-yl)-4H-pyrazolo[1,5-a]quinazolin-5-one;
7,8-dimethoxy-4-methyl-2-(2-trifluoromethyl-pyridin-4-yl)-4H-pyrazolo[1,5-a]quinazolin-5-one;
7,8-difluoro-4-methyl-2-(2-trifluoromethyl-pyridin-4-yl)-4H-pyrazolo[1,5-a]quinazolin-5-one;
8-fluoro-7-methoxy-4-methyl-2-(2-trifluoromethyl-pyridin-4-yl)-4H-pyrazolo[1,5-a]quinazolin-5-one;
8-(4-hydroxy-piperidin-1-yl)-7-methoxy-4-methyl-2-(2-trifluoromethyl-pyridin-4-yl)-4H-pyrazolo[1,5-a]quinazolin-5-one;
8-dimethylamino-7-fluoro-4-methyl-2-(2-trifluoromethyl-pyridin-4-yl)-4H-pyrazolo[1,5-a]quinazolin-5-one;
7-bromo-8-fluoro-4-methyl-2-(2-trifluoromethyl-pyridin-4-yl)-4H-pyrazolo[1,5-a]quinazolin-5-one;
7-bromo-8-methoxy-4-methyl-2-(2-trifluoromethyl-pyridin-4-yl)-4H-pyrazolo[1,5-a]quinazolin-5-one;
8-methoxy-4-methyl-7-methylamino-2-(2-trifluoromethyl-pyridin-4-yl)-4H-pyrazolo[1,5-a]quinazolin-5-one;
7-chloro-2-(2-chloro-pyridin-4-yl)-4-methyl-4H-pyrazolo[1,5-a]quinazolin-5-one;
7-chloro-2-(2-chloro-pyridin-4-yl)-4-methyl-4H-pyrazolo[1,5-a]quinazolin-5-one;
7-chloro-2-(2-Fluoro-pyridin-4-yl)-4-methyl-4H-pyrazolo[1,5-a]quinazolin-5-one;
7-chloro-4-methyl-2-[2-(2,2,2-trifluoro-ethoxy)-pyridin-4-yl]-4H-pyrazolo[1,5-a]quinazolin-5-one;
2-(2-chloro-pyridin-4-yl)-7-methoxy-4-methyl-4H-pyrazolo[1,5-a]quinazolin-5-one;
2-(2-cyclopropyl-pyridin-4-yl)-7-methoxy-4-methyl-4H-pyrazolo[1,5-a]quinazolin-5-one;
2-(2-fluoro-pyridin-4-yl)-7-methoxy-4-methyl-4H-pyrazolo[1,5-a]quinazolin-5-one;
7-methoxy-4-methyl-2-[2-(2,2,2-trifluoro-ethoxy)-pyridin-4-yl]-4H-pyrazolo[1,5-a]quinazolin-5-one;
4-methyl-2-(1-methyl-1H-pyrazol-4-yl)-4H-pyrazolo[1,5-a]quinazolin-5-one;
4-methyl-2-pyridin-4-yl-4H-pyrazolo[1,5-a]quinazolin-5-one;
2-(2-chloro-6-methyl-pyridin-4-yl)-4-methyl-4H-pyrazolo[1,5-a]quinazolin-5-one;
2-(2-cyclopropyl-6-methyl-pyridin-4-yl)-4-methyl-4H-pyrazolo[1,5-a]quinazolin-5-one;
2-(3-fluoro-pyridin-4-yl)-4-methyl-4H-pyrazolo[1,5-a]quinazolin-5-one;
2-(3-chloro-pyridin-4-yl)-4-methyl-4H-pyrazolo[1,5-a]quinazolin-5-one;
4-methyl-2-(3-methyl-pyridin-4-yl)-4H-pyrazolo[1,5-a]quinazolin-5-one;
8-(3-Hydroxy-azetidine-1-carbonyl)-4-methyl-2-(2-trifluoromethyl-pyridin-4-yl)-4H-pyrazolo[1,5-a]quinazolin-5-one;
8-(3-Hydroxy-propoxy)-4-methyl-2-(2-trifluoromethyl-pyridin-4-yl)-4H-pyrazolo[1,5-a]quinazolin-5-one;
2-(2-Cyclopropyl-pyridin-4-yl)-8-fluoro-4-methyl-4H-pyrazolo[1,5-a]quinazolin-5-one;
2-(2-Cyclopropyl-pyridin-4-yl)-8-(4-hydroxy-piperidin-1-yl)-4-methyl-4H-pyrazolo[1,5-a]quinazolin-5-one;
2-(2-Difluoromethyl-pyridin-4-yl)-8-fluoro-4-methyl-4H-pyrazolo[1,5-a]quinazolin-5-one;
2-(2-Difluoromethyl-pyridin-4-yl)-8-(4-hydroxy-piperidin-1-yl)-4-methyl-4H-pyrazolo[1,5-a]quinazolin-5-one;
2-(2-Cyclobutyl-pyridin-4-yl)-8-fluoro-4-methyl-4H-pyrazolo[1,5-a]quinazolin-5-one;
2-(2-Chloro-pyridin-4-yl)-8-fluoro-4-methyl-4H-pyrazolo[1,5-a]quinazolin-5-one;

2-(2-Chloro-pyridin-4-yl)-8-(4-hydroxy-piperidin-1-yl)-4-methyl-4H-pyrazolo[1,5-a]quinazolin-5-one;
7-Fluoro-8-(3-hydroxy-azetidin-1-yl)-4-methyl-2-(2-trifluoromethyl-pyridin-4-yl)-4H-pyrazolo[1,5-a]quinazolin-5-one;
7-Fluoro-4-methyl-8-(oxetan-3-yloxy)-2-(2-trifluoromethyl-pyridin-4-yl)-4H-pyrazolo[1,5-a]quinazolin-5-one;
3-[7-Fluoro-4-methyl-5-oxo-2-(2-trifluoromethyl-pyridin-4-yl)-4,5-dihydro-pyrazolo[1,5-a]quinazolin-8-ylamino]-propionitrile;
7-Fluoro-8-(2-hydroxymethyl-pyrrolidin-1-yl)-4-methyl-2-(2-trifluoromethyl-pyridin-4-yl)-4H-pyrazolo[1,5-a]quinazolin-5-one;
7-Fluoro-8-(7-hydroxymethyl-1-aza-spiro[3.5]non-1-yl)-4-methyl-2-(2-trifluoromethyl-pyridin-4-yl)-4H-pyrazolo[1,5-a]quinazolin-5-one;
8-(3-Hydroxy-piperidin-1-yl)-4-methyl-2-(2-trifluoromethyl-pyridin-4-yl)-4H-pyrazolo[1,5-a]quinazolin-5-one;
8-(2,6-Dimethyl-morpholin-4-yl)-4-methyl-2-(2-trifluoromethyl-pyridin-4-yl)-4H-pyrazolo[1,5-a]quinazolin-5-one;
8-(2-Hydroxy-2-methyl-propylamino)-4-methyl-2-(2-trifluoromethyl-pyridin-4-yl)-4H-pyrazolo[1,5-a]quinazolin-5-one; and
pharmaceutically acceptable salts and solvates thereof.

11. A pharmaceutical composition comprising the compound as defined in claim 2 or a pharmaceutically acceptable salt or solvate thereof, and a pharmaceutically acceptable excipient.

12. A method of treating a condition associated with altered glutamatergic signalling and/or functions, and/or a condition which can be affected by alteration of glutamate level or signalling, the method comprising the administration of the pharmaceutical composition of claim 1 to a subject in need of such treatment.

13. The method of claim 12, wherein the condition to be treated is selected from the group consisting of: epilepsy; dementias; parkinsonism and movement disorders; motor neuron disease or amyotrophic lateral sclerosis; neurodegenerative and/or hereditary disorders of the nervous system; disorders of the peripheral nervous system; multiple sclerosis and other demyelinating diseases of the nervous system; infantile cerebral palsy; paralytic syndromes including hemiplegia and hemiparesis; cerebrovascular disorders; migraine; headache; myoneural disorders; disorders of the eye and visual pathways; intracranial trauma/injury and their sequels; trauma/injury to nerves and spinal cord and their sequels; poisoning and toxic effects of nonmedicinal substances; accidental poisoning by drugs, medicinal substances and biologicals acting on the central, peripheral and autonomic system; neurological and psychiatric adverse effects of drugs, medicinal and biological substances; disturbance of sphincter control and sexual function; mental disorders; delirium and cognitive disorders; substance related disorders; schizophrenia and psychotic disorders; mood disorders; anxiety disorders; eating disorders; sleep disorders and sleep/wake disorders; medication-induced movement disorders; endocrine and metabolic diseases; acute and chronic pain; nausea and vomiting; irritable bowel syndrome; cancers; and autism spectrum disorders.

14. The method of claim 12, wherein the condition to be treated is selected from the group consisting of dementias, parkinsonism and movement disorders, acute or chronic pain, anxiety disorders, schizophrenia, mood disorders, endocrine or metabolic diseases, and cancers.

15. The method of claim 14, wherein said dementias are selected from the group consisting of: dementias of the Alzheimer's type (DAT); Alzheimer's disease; Pick's disease; vascular dementias; Lewy-body disease; dementias due to metabolic, toxic and deficiency diseases, including alcoholism, hypothyroidism, and vitamin B12 deficiency; AIDS-dementia complex; Creutzfeld-Jacob disease; and atypical subacute spongiform encephalopathy.

16. A method of treating Alzheimer's disease, the method comprising the administration of the pharmaceutical composition of claim 1 to a subject in need of such treatment.

17. The method of claim 12, wherein said subject is a human.

18. A method for identifying an agent that binds to metabotropic glutamate receptor 2 (mGluR2), comprising the following steps:
    (a) contacting mGluR2 with the compound of claim 2, wherein said compound is radio-labeled or fluorescence-labeled, under conditions that permit binding of the compound to mGluR2, thereby generating bound, labeled compound;
    (b) detecting a signal that corresponds to the amount of bound, labeled compound in the absence of test agent;
    (c) contacting the bound, labeled compound with a test agent;
    (d) detecting a signal that corresponds to the amount of bound labeled compound in the presence of test agent; and
    (e) comparing the signal detected in step (d) to the signal detected in step (b) to determine whether the test agent binds to mGluR2.

19. The compound of claim 2, wherein said compound is selected from the group consisting of:
    2-(2-chloro-pyridin-4-yl)-4-methyl-4H-pyrazolo[1,5-a]quinazolin-5-one;
    4-methyl 2-(2-methyl-pyridin-4-yl)-4H-pyrazolo[1,5-a]quinazolin-5-one;
    2-(2-ethyl-pyridin-4-yl)-4-methyl-4H-pyrazolo[1,5-a]quinazolin-5-one;
    2-(2-propyl-pyridin-4-yl)-4-methyl-4H-pyrazolo[1,5-a]quinazolin-5-one;
    2-(2-cyclopropyl-pyridin-4-yl)-4-methyl-4H-pyrazolo[1,5-a]quinazolin-5-one;
    2-(2-cyclobutyl-pyridin-4-yl)-4-methyl-4H-pyrazolo[1,5-a]quinazolin-5-one;
    2-(2-cyclopentyl-pyridin-4-yl)-4-methyl-4H-pyrazolo[1,5-a]quinazolin-5-one;
    2-(2-cyclohexyl-pyridin-4-yl)-4-methyl-4H-pyrazolo[1,5-a]quinazolin-5-one;
    4-methyl-2-(2-vinyl-pyridin-4-yl)-4H-pyrazolo[1,5-a]quinazolin-5-one;
    2-(2-isopropenyl-pyridin-4-yl)-4-methyl-4H-pyrazolo[1,5-a]quinazolin-5-one;
    2-(2-isopropyl-pyridin-4-yl)-4-methyl-4H-pyrazolo[1,5-a]quinazolin-5-one;
    4-(4-methyl-5-oxo-4,5-dihydro-pyrazolo[1,5-a]quinazolin-2-yl)-pyridine-2-carbonitrile;
    2-(2-fluoro-pyridin-4-yl)-4-methyl-4H-pyrazolo[1,5-a]quinazolin-5-one;
    2-(2-methoxy-pyridin-4-yl)-4-methyl-4H-pyrazolo[1,5-a]quinazolin-5-one;
    2-(2-ethoxy-pyridin-4-yl)-4-methyl-4H-pyrazolo[1,5-a]quinazolin-5-one;
    2-(2-isopropoxy-pyridin-4-yl)-4-methyl-4H-pyrazolo[1,5-a]quinazolin-5-one;
    2-(2-cyclobutoxy-pyridin-4-yl)-4-methyl-4H-pyrazolo[1,5-a]quinazolin-5-one;

4-methyl-2-[2-(oxetan-3-yloxy)-pyridin-4-yl]-4H-pyrazolo[1,5-a]quinazolin-5-one;
2-(2-cyclopropylmethoxy-pyridin-4-yl)-4-methyl-4H-pyrazolo[1,5-a]quinazolin-5-one;
2-[2-(2-methoxy-ethoxy)-pyridin-4-yl]-4-methyl-4H-pyrazolo[1,5-a]quinazolin-5-one;
4-methyl-2-[2-(2,2,2-trifluoro-ethoxy)-pyridin-4-yl]-4H-pyrazolo[1,5-a]quinazolin-5-one;
4-methyl-2-[2-(2,2-difluoro-ethoxy)-pyridin-4-yl]-4H-pyrazolo[1,5-a]quinazolin-5-one;
2-[2-(2,2-difluoro-propoxy)-pyridin-4-yl]-4-methyl-4H-pyrazolo[1,5-a]quinazolin-5-one;
4-methyl-2-[2-(2,2,3,3,3-pentafluoro-propoxy)-pyridin-4-yl]-4H-pyrazolo[1,5-a]quinazolin-5-one;
4-methyl-2-[2-(2,2,2-trifluoro-1-trifluoromethyl-ethoxy)-pyridin-4-yl]-4H-pyrazolo[1,5-a]quinazolin-5-one;
4-methyl-2-(2-trifluoromethyl-pyridin-4-yl)-4H-pyrazolo[1,5-a]quinazolin-5-one;
4-methyl($D_3$)-2-(2-trifluoromethyl-pyridin-4-yl)-4H-pyrazolo[1,5-a]quinazolin-5-one;
4-ethyl-2-(2-trifluoromethyl-pyridin-4-yl)-4H-pyrazolo[1,5-a]quinazolin-5-one;
4-(2,2-difluoro-ethyl)-2-(2-trifluoromethyl-pyridin-4-yl)-4H-pyrazolo[1,5-a]quinazolin-5-one;
4-(2-methoxy-ethyl)-2-(2-trifluoromethyl-pyridin-4-yl)-4H-pyrazolo[1,5-a]quinazolin-5-one;
4-methyl-2-(2-difluoromethyl-pyridin-4-yl)-4H-pyrazolo[1,5-a]quinazolin-5-one;
2-[2-(1,1-difluoro-ethyl)-pyridin-4-yl]-4-methyl-4H-pyrazolo[1,5-a]quinazolin-5-one;
2-[2-(1,1-difluoro-ethyl)-pyridin-4-yl]-4-methyl($D_3$)-4H-pyrazolo[1,5-a]quinazolin-5-one;
7-methyl-2-(2-trifluoromethyl-pyridin-4-yl)-4H-pyrazolo[1,5-a]quinazolin-5-one;
7-chloro-2-(2-trifluoromethyl-pyridin-4-yl)-4H-pyrazolo[1,5-a]quinazolin-5-one;
7-methoxy-2-(2-trifluoromethyl-pyridin-4-yl)-4H-pyrazolo[1,5-a]quinazolin-5-one;
7-trifluoromethyl-2-(2-trifluoromethyl-pyridin-4-yl)-4H-pyrazolo[1,5-a]quinazolin-5-one;
7-fluoro-2-(2-trifluoromethyl-pyridin-4-yl)-4H-pyrazolo[1,5-a]quinazolin-5-one;
7-bromo-2-(2-trifluoromethyl-pyridin-4-yl)-4H-pyrazolo[1,5-a]quinazolin-5-one;
4-methyl-7-methylamino-2-(2-trifluoromethyl-pyridin-4-yl)-4H-pyrazolo[1,5-a]quinazolin-5-one;
4-methyl-7-methyl(D3)amino-2-(2-trifluoromethyl-pyridin-4-yl)-4H-pyrazolo[1,5-a]quinazolin-5-one;
N-[4-methyl-5-oxo-2-(2-trifluoromethyl-pyridin-4-yl)-4,5-dihydro-pyrazolo[1,5-a]quinazolin-7-yl]-acetamide;
7-amino-4-methyl-2-(2-trifluoromethyl-pyridin-4-yl)-4H-pyrazolo[1,5-a]quinazolin-5-one;
7-dimethylamino-4-methyl-2-(2-trifluoromethyl-pyridin-4-yl)-4H-pyrazolo[1,5-a]quinazolin-5-one;
7-ethylamino-4-methyl-2-(2-trifluoromethyl-pyridin-4-yl)-4H-pyrazolo[1,5-a]quinazolin-5-one;
7-cyclobutylamino-4-methyl-2-(2-trifluoromethyl-pyridin-4-yl)-4H-pyrazolo[1,5-a]quinazolin-5-one;
4-methyl-7-morpholin-4-yl-2-(2-trifluoromethyl-pyridin-4-yl)-4H-pyrazolo[1,5-a]quinazolin-5-one;
7-hydroxy-4-methyl-2-(2-trifluoromethyl-pyridin-4-yl)-4H-pyrazolo[1,5-a]quinazolin-5-one;
7-ethoxy-4-methyl-2-(2-trifluoromethyl-pyridin-4-yl)-4H-pyrazolo[1,5-a]quinazolin-5-one;
7-(2-methoxy-ethoxy)-4-methyl-2-(2-trifluoromethyl-pyridin-4-yl)-4H-pyrazolo[1,5-a]quinazolin-5-one;
4-methyl-7-(2-morpholin-4-yl-ethoxy)-2-(2-trifluoromethyl-pyridin-4-yl)-4H-pyrazolo[1,5-a]quinazolin-5-one;
4-methyl-7-trifluoromethoxy-2-(2-trifluoromethyl-pyridin-4-yl)-4H-pyrazolo[1,5-a]quinazolin-5-one;
7-methanesulfonyl-4-methyl-2-(2-trifluoromethyl-pyridin-4-yl)-4H-pyrazolo[1,5-a]quinazolin-5-one;
8-methoxy-4-methyl-2-(2-trifluoromethyl-pyridin-4-yl)-4H-pyrazolo[1,5-a]quinazolin-5-one;
8-fluoro-4-methyl-2-(2-trifluoromethyl-pyridin-4-yl)-4H-pyrazolo[1,5-a]quinazolin-5-one;
8-chloro-4-methyl-2-(2-trifluoromethyl-pyridin-4-yl)-4H-pyrazolo[1,5-a]quinazolin-5-one;
4-methyl-8-trifluoromethyl-2-(2-trifluoromethyl-pyridin-4-yl)-4H-pyrazolo[1,5-a]quinazolin-5-one;
4-methyl-8-morpholin-4-yl-2-(2-trifluoromethyl-pyridin-4-yl)-4H-pyrazolo[1,5-a]quinazolin-5-one;
4-methyl-8-pyrrolidin-1-yl-2-(2-trifluoromethyl-pyridin-4-yl)-4H-pyrazolo[1,5-a]quinazolin-5-one;
4-methyl-8-methylamino-2-(2-trifluoromethyl-pyridin-4-yl)-4H-pyrazolo[1,5-a]quinazolin-5-one;
8-(4-methoxy-piperidin-1-yl)-4-methyl-2-(2-trifluoromethyl-pyridin-4-yl)-4H-pyrazolo[1,5-a]quinazolin-5-one;
8-(4-hydroxy-piperidin-1-yl)-4-methyl-2-(2-trifluoromethyl-pyridin-4-yl)-4H-pyrazolo[1,5-a]quinazolin-5-one;
8-dimethylamino-4-methyl-2-(2-trifluoromethyl-pyridin-4-yl)-4H-pyrazolo[1,5-a]quinazolin-5-one;
4-methyl-8-(4-methyl-piperazin-1-yl)-2-(2-trifluoromethyl-pyridin-4-yl)-4H-pyrazolo[1,5-a]quinazolin-5-one;
4-methyl-8-piperazin-1-yl-2-(2-trifluoromethyl-pyridin-4-yl)-4H-pyrazolo[1,5-a]quinazolin-5-one;
8-(4-hydroxymethyl-piperidin-1-yl)-4-methyl-2-(2-trifluoromethyl-pyridin-4-yl)-4H-pyrazolo[1,5-a]quinazoin-5-one;
8-(3-hydroxy-azetidin-1-yl)-4-methyl-2-(2-trifluoromethyl-pyridin-4-yl)-4H-pyrazolo[1,5-a]quinazolin-5-one;
8-(3-hydroxymethyl-azetidin-1-yl)-4-methyl-2-(2-trifluoromethyl-pyridin-4-yl)-4H-pyrazolo[1,5-a]quinazolin-5-one;
8-(3-hydroxy-pyrrolidin-1-yl)-4-methyl-2-(2-trifluoromethyl-pyridin-4-yl)-4H-pyrazolo[1,5-a]quinazolin-5-one;
8-(4-hydroxy-4-methyl-piperidin-1-yl)-4-methyl-2-(2-trifluoromethyl-pyridin-4-yl)-4H-pyrazolo[1,5-a]quinazolin-5-one;
4,8-dimethyl-2-(2-trifluoromethyl-pyridin-4-yl)-4H-pyrazolo[1,5-a]quinazolin-5-one;
8-cyclopropyl-4-methyl-2-(2-trifluoromethyl-pyridin-4-yl)-4H-pyrazolo[1,5-a]quinazolin-5-one;
8-cyclopentyl-4-methyl-2-(2-trifluoromethyl-pyridin-4-yl)-4H-pyrazolo[1,5-a]quinazolin-5-one;
4-methyl-5-oxo-2-(2-trifluoromethyl-pyridin-4-yl)-4,5-dihydro-pyrazolo[1,5-a]quinazoline-8-carbonitrile;
4-methyl-5-oxo-2-(2-trifluoromethyl-pyridin-4-yl)-4,5-dihydro-pyrazolo[1,5-a]quinazoline-8-carboxylic acid;
4-methyl-5-oxo-2-(2-trifluoromethyl-pyridin-4-yl)-4,5-dihydro-pyrazolo[1,5-a]quinazoline-8-carboxylic acid amide;
4-methyl-5-oxo-2-(2-trifluoromethyl-pyridin-4-yl)-4,5-dihydro-pyrazolo[1,5-a]quinazoline-8-carboxylic acid methylamide;

4-methyl-5-oxo-2-(2-trifluoromethyl-pyridin-4-yl)-4,5-dihydro-pyrazolo[1,5-a]quinazoline-8-carboxylic acid dimethylamide;
4-methyl-5-oxo-2-(2-trifluoromethyl-pyridin-4-yl)-4,5-dihydro-pyrazolo[1,5-a]quinazoline-8-carboxylic acid diethylamide;
4-methyl-8-(morpholine-4-carbonyl)-2-(2-trifluoromethyl-pyridin-4-yl)-4H-pyrazolo[1,5-a]quinazolin-5-one;
4-methyl-8-(pyrrolidine-1-carbonyl)-2-(2-trifluoromethyl-pyridin-4-yl)-4H-pyrazolo[1,5-a]quinazolin-5-one;
8-(2-hydroxy-ethoxy)-4-methyl-2-(2-trifluoromethyl-pyridin-4-yl)-4H-pyrazolo[1,5-a]quinazolin-5-one;
4-methyl-6-trifluoromethyl-2-(2-trifluoromethyl-pyridin-4-yl)-4H-pyrazolo[1,5-a]quinazolin-5-one;
6-fluoro-4-methyl-2-(2-trifluoromethyl-pyridin-4-yl)-4H-pyrazolo[1,5-a]quinazolin-5-one;
9-methoxy-4-methyl-2-(2-trifluoromethyl-pyridin-4-yl)-4H-pyrazolo[1,5-a]quinazolin-5-one;
7,8-dimethoxy-4-methyl-2-(2-trifluoromethyl-pyridin-4-yl)-4H-pyrazolo[1,5-a]quinazolin-5-one;
7,8-difluoro-4-methyl-2-(2-trifluoromethyl-pyridin-4-yl)-4H-pyrazolo[1,5-a]quinazolin-5-one;
8-fluoro-7-methoxy-4-methyl-2-(2-trifluoromethyl-pyridin-4-yl)-4H-pyrazolo[1,5-a]quinazolin-5-one;
8-(4-hydroxy-piperidin-1-yl)-7-methoxy-4-methyl-2-(2-trifluoromethyl-pyridin-4-yl)-4H-pyrazolo[1,5-a]quinazolin-5-one;
8-dimethylamino-7-fluoro-4-methyl-2-(2-trifluoromethyl-pyridin-4-yl)-4H-pyrazolo[1,5-a]quinazolin-5-one;
7-bromo-8-fluoro-4-methyl-2-(2-trifluoromethyl-pyridin-4-yl)-4H-pyrazolo[1,5-a]quinazolin-5-one;
7-bromo-8-methoxy-4-methyl-2-(2-trifluoromethyl-pyridin-4-yl)-4H-pyrazolo[1,5-a]quinazolin-5-one;
8-methoxy-4-methyl-7-methylamino-2-(2-trifluoromethyl-pyridin-4-yl)-4H-pyrazolo[1,5-a]quinazolin-5-one;
7-chloro-2-(2-chloro-pyridin-4-yl)-4-methyl-4H-pyrazolo[1,5-a]quinazolin-5-one;
7-chloro-2-(2-chloro-pyridin-4-yl)-4-methyl-4H-pyrazolo[1,5-a]quinazolin-5-one;
7-chloro-2-(2-Fluoro-pyridin-4-yl)-4-methyl-4H-pyrazolo[1,5-a]quinazolin-5-one;
7-chloro-4-methyl-2-[2-(2,2,2-trifluoro-ethoxy)-pyridin-4-yl]-4H-pyrazolo[1,5-a]quinazolin-5-one;
2-(2-chloro-pyridin-4-yl)-7-methoxy-4-methyl-4H-pyrazolo[1,5-a]quinazolin-5-one;
2-(2-cyclopropyl-pyridin-4-yl)-7-methoxy-4-methyl-4H-pyrazolo[1,5-a]quinazolin-5-one;
2-(2-fluoro-pyridin-4-yl)-7-methoxy-4-methyl-4H-pyrazolo[1,5-a]quinazolin-5-one;
7-methoxy-4-methyl-2-[2-(2,2,2-trifluoro-ethoxy)-pyridin-4-yl]-4H-pyrazolo[1,5-a]quinazolin-5-one;
4-methyl-2-(1-methyl-1H-pyrazol-4-yl)-4H-pyrazolo[1,5-a]quinazolin-5-one;
4-methyl-2-pyridin-4-yl-4H-pyrazolo[1,5-a]quinazolin-5-one;
2-(2-chloro-6-methyl-pyridin-4-yl)-4-methyl-4H-pyrazolo[1,5-a]quinazolin-5-one;
2-(2-cyclopropyl-6-methyl-pyridin-4-yl)-4-methyl-4H-pyrazolo[1,5-a]quinazolin-5-one;
2-(3-fluoro-pyridin-4-yl)-4-methyl-4H-pyrazolo[1,5-a]quinazolin-5-one;
2-(3-chloro-pyridin-4-yl)-4-methyl-4H-pyrazolo[1,5-a]quinazolin-5-one;
4-methyl-2-(3-methyl-pyridin-4-yl)-4H-pyrazolo[1,5-a]quinazolin-5-one;
8-(3-Hydroxy-azetidine-1-carbonyl)-4-methyl-2-(2-trifluoromethyl-pyridin-4-yl)-4H-pyrazolo[1,5-a]quinazolin-5-one;
8-(3-Hydroxy-propoxy)-4-methyl-2-(2-trifluoromethyl-pyridin-4-yl)-4H-pyrazolo[1,5-a]quinazolin-5-one;
2-(2-Cyclopropyl-pyridin-4-yl)-8-fluoro-4-methyl-4H-pyrazolo[1,5-a]quinazolin-5-one;
2-(2-Cyclopropyl-pyridin-4-yl)-8-(4-hydroxy-piperidin-1-yl)-4-methyl-4H-pyrazolo[1,5-a]quinazolin-5-one;
2-(2-Difluoromethyl-pyridin-4-yl)-8-fluoro-4-methyl-4H-pyrazolo[1,5-a]quinazolin-5-one;
2-(2-Difluoromethyl-pyridin-4-yl)-8-(4-hydroxy-piperidin-1-yl)-4-methyl-4H-pyrazolo[1,5-a]quinazolin-5-one;
2-(2-Cyclobutyl-pyridin-4-yl)-8-fluoro-4-methyl-4H-pyrazolo[1,5-a]quinazolin-5-one;
2-(2-Chloro-pyridin-4-yl)-8-fluoro-4-methyl-4H-pyrazolo[1,5-a]quinazolin-5-one;
2-(2-Chloro-pyridin-4-yl)-8-(4-hydroxy-piperidin-1-yl)-4-methyl-4H-pyrazolo[1,5-a]quinazolin-5-one;
7-Fluoro-8-(3-hydroxy-azetidin-1-yl)-4-methyl-2-(2-trifluoromethyl-pyridin-4-yl)-4H-pyrazolo[1,5-a]quinazolin-5-one;
7-Fluoro-4-methyl-8-(oxetan-3-yloxy)-2-(2-trifluoromethyl-pyridin-4-yl)-4H-pyrazolo[1,5-a]quinazolin-5-one;
3-[7-Fluoro-4-methyl-5-oxo-2-(2-trifluoromethyl-pyridin-4-yl)-4,5-dihydro-pyrazolo[1,5-a]quinazolin-8-ylamino]-propionitrile;
7-Fluoro-8-(2-hydroxymethyl-pyrrolidin-1-yl)-4-methyl-2-(2-trifluoromethyl-pyridin-4-yl)-4H-pyrazolo[1,5-a]quinazolin-5-one;
7-Fluoro-8-(7-hydroxymethyl-1-aza-spiro[3.5]non-1-yl)-4-methyl-2-(2-trifluoromethyl-pyridin-4-yl)-4H-pyrazolo[1,5-a]quinazolin-5-one;
8-(3-Hydroxy-piperidin-1-yl)-4-methyl-2-(2-trifluoromethyl-pyridin-4-yl)-4H-pyrazolo[1,5-a]quinazolin-5-one;
8-(2,6-Dimethyl-morpholin-4-yl)-4-methyl-2-(2-trifluoromethyl-pyridin-4-yl)-4H-pyrazolo[1,5-a]quinazolin-5-one;
8-(2-Hydroxy-2-methyl-propylamino)-4-methyl-2-(2-trifluoromethyl-pyridin-4-yl)-4H-pyrazolo[1,5-a]quinazolin-5-one; and pharmaceutically acceptable salts and solvates and prodrugs thereof.

20. The pharmaceutical composition of claim 1, wherein $R^3$ is selected from the group consisting of hydrogen, —F, —Cl, —I, —CN, —$NR^7R^8$, —$COOR^7$, —$SO_3H$, —$B(OH)_2$, —$CONR^7R^8$, —$COR^7$, —$SR^7$, —$SOR^7$, —$SO_2R^7$, —$SO_2NR^7R^8$, —$NR^7COR^8$, —$NR^7SO_2R^8$, —$OCOR^7$, —$NR^7C(O)NR^8R^9$, —$NR^7C(S)NR^8R^9$, —$NR^7COOR^8$, $C_1$-$C_4$ alkyl, $C_2$-$C_4$ alkenyl, cycloalkyl and heterocycloalkyl, wherein said $C_1$-$C_4$ alkyl and said $C_2$-$C_4$ alkenyl are each optionally substituted with one or more groups independently selected from the group consisting of halogen, —$CF_3$, —CN, —OH, —O($C_1$-$C_4$ alkyl), —$NH_2$, —NH($C_1$-$C_4$ alkyl) and —N($C_1$-$C_4$ alkyl)($C_1$-$C_4$ alkyl), and further wherein said cycloalkyl and said heterocycloalkyl are each optionally substituted with one or more groups independently selected from the group consisting of: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); and —N($C_1$-$C_4$ alkyl)($C_1$-$C_4$ alkyl).

21. The pharmaceutical composition of claim 3, wherein $R^3$ is selected from the group consisting of hydrogen, —F, —Cl, —I, $C_1$-$C_4$ haloalkyl, $C_1$-$C_4$ haloalkoxy, —CN, $C_1$-$C_4$ alkyl, cycloalkyl, heterocycloalkyl, —OH, —O($C_1$-$C_4$ alkyl), —O-cycloalkyl, —O-heterocycloalkyl, —$NH_2$, —NH($C_1$-$C_4$ alkyl), —N($C_1$-$C_4$ alkyl)($C_1$-$C_4$ alkyl), —NH-cycloalkyl, —N($C_1$-$C_4$ alkyl)-cycloalkyl, —NH-heterocycloalkyl, —N($C_1$-$C_4$ alkyl)-heterocycloalkyl, —CO-cycloalkyl, —CO-heterocycloalkyl, —CO—$NH_2$, —CO—NH($C_1$-$C_4$ alkyl), —CO—N($C_1$-$C_4$ alkyl)($C_1$-$C_4$ alkyl), —CO—NH-cycloalkyl, —CO—N($C_1$-$C_4$ alkyl)-cycloalkyl, —CO—NH-heterocycloalkyl, —CO—N($C_1$-$C_4$ alkyl)-heterocycloalkyl, —NH—CO-cycloalkyl, —N($C_1$-$C_4$ alkyl)-CO-cycloalkyl, —NH—CO-heterocycloalkyl, and —N($C_1$-$C_4$ alkyl)-CO-heterocycloalkyl, wherein said cycloalkyl, said heterocycloalkyl, the cycloalkyl moiety comprised in any of the aforementioned groups, and the heterocycloalkyl moiety comprised in any of the aforementioned groups are each optionally substituted with one or more groups independently selected from the group consisting of: $C_1$-$C_4$ alkyl; halogen; —$CF_3$; —CN; —OH; —O($C_1$-$C_4$ alkyl); $C_1$-$C_4$ alkyl substituted with one or more —OH groups; —$NH_2$; —NH($C_1$-$C_4$ alkyl); and —N($C_1$-$C_4$ alkyl)($C_1$-$C_4$ alkyl).

* * * * *